United States Patent
Chamberlain et al.

(10) Patent No.: US 10,167,485 B2
(45) Date of Patent: Jan. 1, 2019

(54) PRODUCTION OF VIRAL VECTORS

(71) Applicant: The Regents of the University of Michigan, Ann Arbor, MI (US)

(72) Inventors: Jeffrey S. Chamberlain, Seattle, WA (US); Dennis J. Hartigan-O'Connor, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 15/236,205

(22) Filed: Aug. 12, 2016

(65) Prior Publication Data

US 2017/0204431 A1    Jul. 20, 2017

Related U.S. Application Data

(63) Continuation of application No. 14/163,331, filed on Jan. 24, 2014, now Pat. No. 9,453,240, which is a continuation of application No. 12/884,027, filed on Sep. 16, 2010, now Pat. No. 8,637,313, which is a continuation of application No. 10/381,153, filed as application No. PCT/US01/29496 on Sep. 21, 2001, now Pat. No. 7,820,441.

(60) Provisional application No. 60/235,060, filed on Sep. 25, 2000.

(51) Int. Cl.

| C12N 15/861 | (2006.01) |
| C12N 5/10 | (2006.01) |
| C12N 7/01 | (2006.01) |
| C12N 15/11 | (2006.01) |
| C12N 15/34 | (2006.01) |
| A61K 39/235 | (2006.01) |
| C12N 15/86 | (2006.01) |

(52) U.S. Cl.
CPC .... *C12N 15/86* (2013.01); *C12N 2710/10043* (2013.01); *C12N 2710/10322* (2013.01); *C12N 2710/10343* (2013.01); *C12N 2710/10351* (2013.01); *C12N 2800/30* (2013.01); *C12N 2830/002* (2013.01); *C12N 2830/38* (2013.01)

(58) Field of Classification Search
None
See application file for complete search history.

(56) References Cited

U.S. PATENT DOCUMENTS

| 5,811,238 | A | 9/1998 | Stemmer et al. |
| 5,824,544 | A | 10/1998 | Armentano et al. |
| 5,919,676 | A | 7/1999 | Graham et al. |
| 5,932,210 | A | 8/1999 | Gregory et al. |
| 6,045,802 | A | 4/2000 | Schlom et al. |
| 6,057,158 | A | 5/2000 | Chamberlain et al. |
| 6,063,622 | A | 5/2000 | Chamberlain et al. |
| 6,083,750 | A | 7/2000 | Chamberlain et al. |
| 6,120,764 | A | 9/2000 | Graham et al. |
| 6,630,346 | B1 | 10/2003 | Morsy et al. |
| 7,820,441 | B2 | 10/2010 | Chamberlain et al. |
| 8,637,313 | B2 | 1/2014 | Chamberlain et al. |
| 9,453,240 | B2 | 9/2016 | Chamberlain et al. |
| 2004/0087029 | A1 | 5/2004 | Chamberlain et al. |
| 2010/0285065 | A1 | 11/2010 | Parrington et al. |
| 2011/0033926 | A1 | 2/2011 | Chamberlain et al. |

FOREIGN PATENT DOCUMENTS

| EP | 1016724 A2 | 7/2000 |
| WO | WO-9725446 A1 | 7/1997 |
| WO | WO-9813510 A1 | 4/1998 |
| WO | WO-0017377 A2 | 3/2000 |
| WO | WO-0018939 A1 | 4/2000 |
| WO | WO-0034494 A1 | 6/2000 |
| WO | WO-0046360 A1 | 8/2000 |
| WO | WO-03008649 A1 | 1/2003 |

OTHER PUBLICATIONS

Amalfitano, et al. (1997) Isolation and Characterization of Packaging Cell Lines That Coexpress the Adenovirus E1, DNA Polymerase, and Preterminal Proteins: Implications for Gene Therapy. Gene Ther. 4:258-263.

Amalfitano, et al. in Lucy J, and Brown S. (eds): Dystrophin: Gene, Protein, and Cell Biology (Cambridge University Press, 1997), Chpt. 1, 1-26.

Challberg, et al. Template requirements for the initiation of adenovirus DNA replication. Proc Natl Acad Sci U S A. Jan. 1984;81(1):100-4.

Graham. Covalently closed circles of human adenovirus DNA are infectious. EMBO J. Dec. 1, 1984;3(12):2917-22.

Hanahan. Studies on transformation of *Escherichia coli* with plasmids. J Mol Biol. Jun. 5, 1983;166(4):557-80.

Hartigan-O'Connor, et al. Efficient rescue of gutted adenovirus genomes allows rapid production of concentrated stocks without negative selection. Hum Gene Ther. Mar. 1, 2002;13(4):519-31.

Hartigan-O'Connor, et al. Improved production of gutted adenovirus in cells expressing adenovirus preterminal protein and DNA polymerase. J Virol 73;7835-7841 (1999a).

Hay. Origin of adenovirus DNA replication. Role of the nuclear factor I binding site in vivo. J Mol Biol. Nov. 5, 1985;186(1):129-36.

Hirt. Selective extraction of polyoma DNA from infected mouse cell cultures. J Mol Biol. Jun. 14, 1967;26(2):365-9.

Parks, et al. A helper-dependent adenovirus vector system: removal of helper virus by Cre-mediated excision of the viral packaging signal. Proc Natl Acad Sci U S A. Nov. 26, 1996;93(24):13565-70.

(Continued)

*Primary Examiner* — Maria Marvich
(74) *Attorney, Agent, or Firm* — Sheridan Ross P.C.

(57) ABSTRACT

The present invention relates to methods and compositions for the production of viral vectors. In particular, the present invention provides methods and compositions for faster, higher titer and higher purity production of viral vectors (e.g. adenoviral vectors). In some embodiments, the present invention provides gutted and helper viruses with identical or similar termini. In other embodiments, the present invention provides terminal protein linked adenoviral DNA. In certain embodiments, the present invention provides template extended adenoviral DNA.

21 Claims, 49 Drawing Sheets

Specification includes a Sequence Listing.

(56) References Cited

OTHER PUBLICATIONS

Pronk, et al. The adenovirus terminal protein influences binding of replication proteins and changes the origin structure. Nucleic Acids Res. May 25, 1993;21(10):2293-300.

Sargent et al, Activation of Adenoviral Gene Expression by Protein IX Is Not Required for Efficient Virus Replication. Journal of Virology, May 2004, p. 5032-5037.

Wright, et al. Dual-origin plasmids containing an amplifiable ColE1 ori; temperature-controlled expression of cloned genes. Gene. 1986;49(3):311-21.

Wu, et al. Examination of conditions affecting the efficiency of HVS-1 amplicon packaging. J Virol Methods. Mar. 1995;52(1-2):219-29.

Bewig, et al. (2000) Accelerated titering of adenoviruses. BioTechniques 28:871-873.

Ding, et al. Long-term efficacy after [E1-, polymerase-] adenovirus-mediated transfer of human acid-alpha-glucosidase gene into glycogen storage disease type II knockout mice. Hum Gene Ther 12;955-65 (2001).

Eo, et al. Prime-boost immunization with DNA vaccine: mucosal route of administration changes the rules. J Immunol 166;5473-9 (2001).

Hartigan-O'Connor, et al. Developments in gene therapy for muscular dystrophy. Microsc Res Tech 48;223-38 (2000).

Hauser, et al. Analysis of muscle creatine kinase regulatory elements in recombinant adenoviral vectors. Mol Ther 2;16-25 (2000).

Hirschowitz, et al. 2000. Murine dendritic cells infected with adenovirus vectors show signs of activation. Gene Ther 7:1112-1120.

Hodges, et al. (2000) Multiply deleted [E1, polymerase-, and pTP-] adenovirus vector persists despite deletion of the preterminal protein. J Gene Med 2:250-259.

Jonuleit, et al. 2000. Efficient transduction of mature CD83+ dendritic cells using recombinant adenovirus suppressed T cell stimulatory capacity. Gene Ther 7:249-254.

Kirk, et al. Gene-modified dendritic cells for use in tumor vaccines. Hum Gene Ther 11;797-806 (2000).

Luebke, et al. (2001) A Modified Adenovirus Can Transfect Cochlear Hair Cells In Vivo Without Compromising Cochlear Function. Gene Ther. 8:789-794.

Maione, et al. An improved helper-dependent adenoviral vector allows persistent gene expression after intramuscular delivery and overcomes preexisting immunity to adenovirus. Proc Natl Acad Sci U S A. May 22, 2001;98(11):5986-91. Epub May 15, 2001.

Maione, et al. Prolonged expression and effective readministration of erythropoietin delivered with a fully deleted adenoviral vector. Hum Gene Ther. Apr. 10, 2000;11(6):859-68.

Miller, et al. 2000. Intratumoral administration of adenoviral interleukin 7 gene-modified dendritic cells augments specific antitumor immunity and achieves tumor eradication. Hum Gene Ther 11:53-65.

Morelli, et al. 2000. Recombinant adenovirus induces maturation of dendritic cells via an NF- kappaB-dependent pathway. J Virol 74:9617-9628.

Qualikene, et al. Protease-deleted adenovirus vectors and complementing cell lines: potential applications of single-round replication mutants for vaccination and gene therapy. Human Gene Therapy Jun. 10, 2000;11(9):1341-53.

Sandig, et al. Optimization of the helper-dependent adenovirus system for production and potency in vivo. Proc Natl Acad Sci U S A. Feb. 1, 2000;97(3):1002-7.

Sullivan, et al. Development of a preventive vaccine for Ebola virus infection in primates. Nature 408;605-9 (2000).

Thomas, et al. Peripheral infection with adenovirus causes unexpected long-term brain inflammation in animals injected intracranially with first-generation, but not with high-capacity, adenovirus vectors: toward realistic long-term neurological gene therapy for chronic diseases. Proc Natl Acad Sci U S A 97;7482-7 (2000).

Tillman, et al. 2000. Adenoviral vectors targeted to CD40 enhance the efficacy of dendritic cell-based vaccination against human papillomavirus 16-induced tumor cells in a murine model. Cancer Res 60:5456-5463.

Wang, et al. Episomal segregation of the adenovirus enhancer sequence by conditional genome rearrangement abrogates late viral gene expression. J Virol. 2000; 74:11296-303.

Zhu, et al. (2000) Specific cytolytic T-cell responses to human CEA from patients immunized with recombinant avipox-CEA vaccine. Clin. Cancer Res. 6:24-33.

| Origin | Structure | |
|---|---|---|
| Natural or TP-primer-modified | ⬭CATCATCAATAA<br>　GTAGTAGTTATT | SEQ ID NO: 21<br>SEQ ID NO: 22 |
| Deproteinized or Hirt prep | Serine＼CATCATCAATAA<br>　　　GTAGTAGTTATT | SEQ ID NO: 21<br>SEQ ID NO: 22 |
| PacI | TAACATCATCAATAA<br>TAATTGTAGTAGTTATT | SEQ ID NO: 23<br>SEQ ID NO: 24 |
| FseI | CCATCATCAATAA<br>GGCCGGTAGTAGTTATT | SEQ ID NO: 25<br>SEQ ID NO: 26 |

B.

```
                12587                                17756
                  ↓                                    ↓
Wild-type:   GACGA GGCCGGCC TGGTC  ...  GGCAT GGCCGGCC ACGGC
             └─────────────────┘        └─────────────────┘
                SEQ ID NO: 27              SEQ ID NO: 28

ΔFseI.4:     GACGA AGCCGGCC TGGTC  ...  GGCAT GGCCGGCT ACGGC
             └─────────────────┘        └─────────────────┘
                SEQ ID NO: 29              SEQ ID NO: 30
```

C.

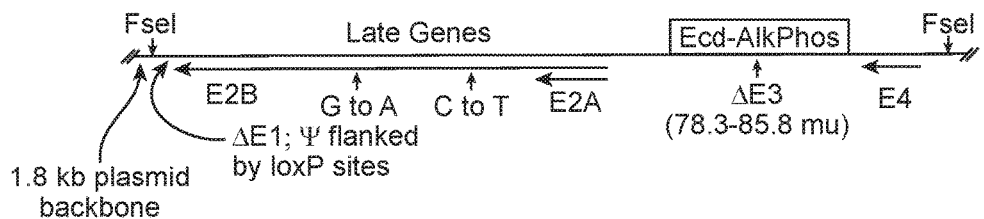

FIGURE 3
A.
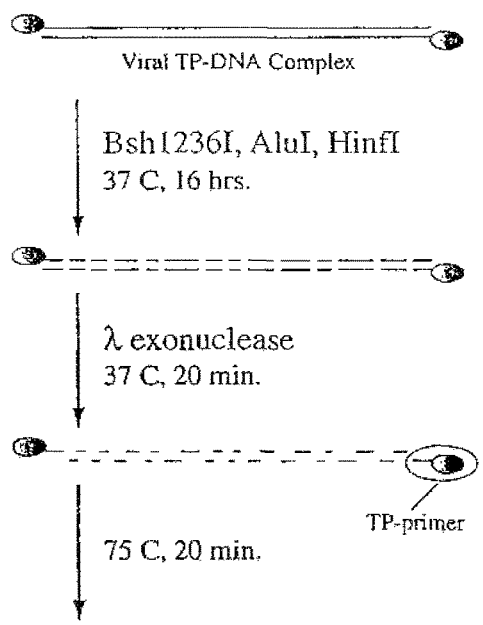
B.
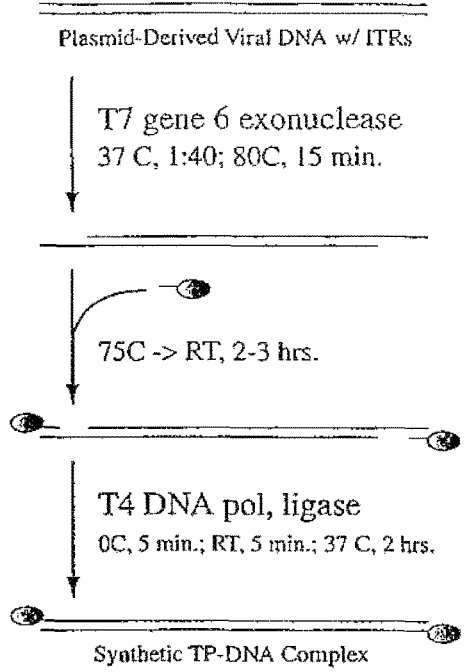

FIGURE 4
A.
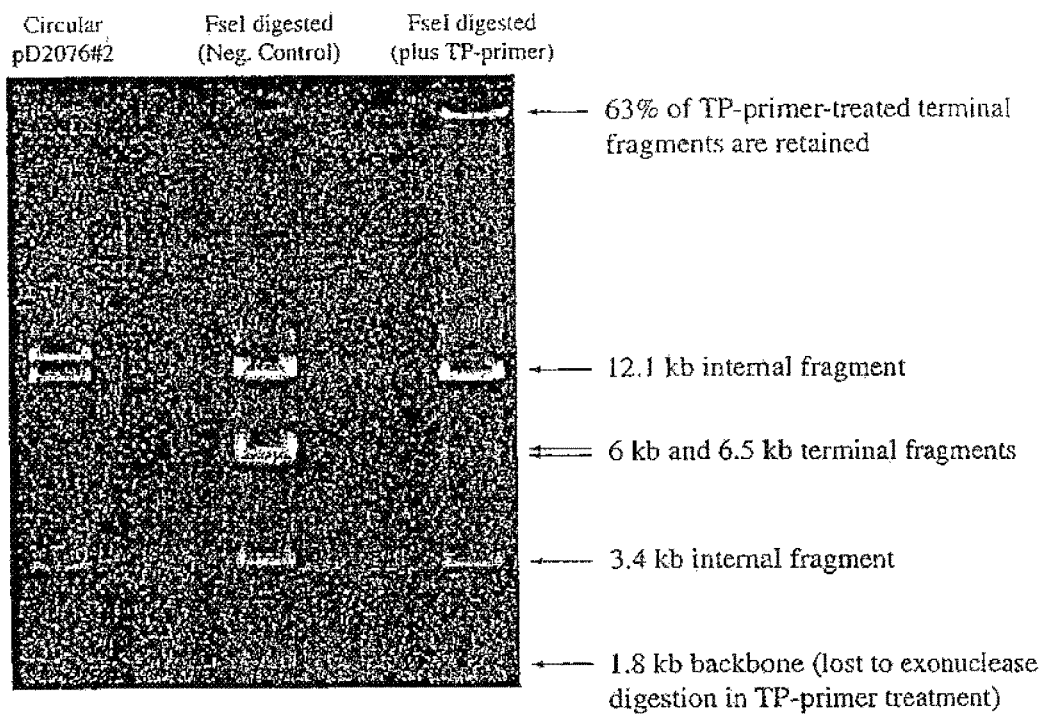
B.
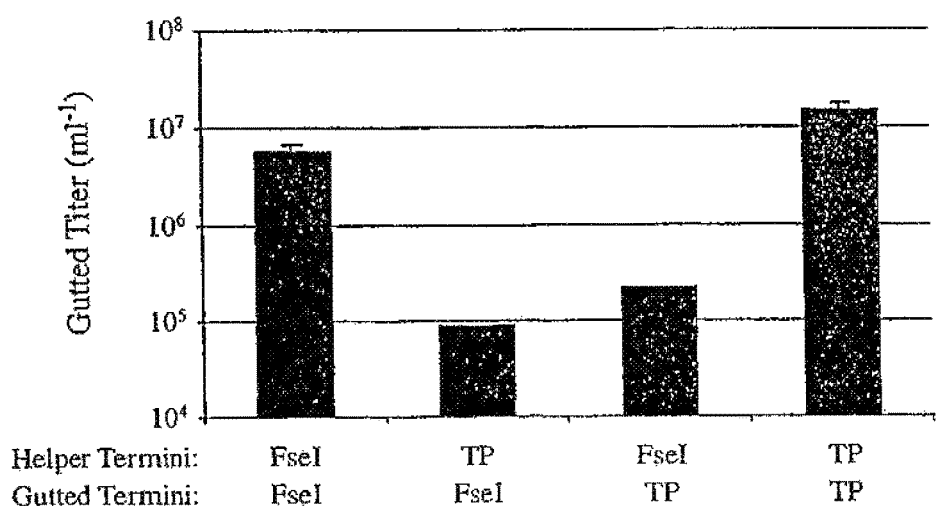

FIGURE 8 (SEQ ID NO:1) (+)lox(+)pol helper virus

```
CATCATCAATAATATACCTTATTTTGGATTGAAGCCAATATGATAATGAGGGGGTGGAGTTTGTGACGTGGCGCGG
GGCGTGGGAACGGGGCGGGTGACGTAGTAGTGTGGCGGAAGTGTGATGTTGCAAGTGTGGCGGAACACATGTATAA
CTTCGTATAATGTATGCTATACGAAGTTATACATGTAAGCGACGGATGTGGCAAAAGTGACGTTTTTGGTGTGCGC
CGGTGTACACAGGGAAGTGACAATTTTCGCGCGGTTTTAGGCGGATGTTGTAGTAAATTTGGGCGTAACCGAGTAAG
ATTTGGCCATTTTCGCGGGAAAACTGAATAAGAGGAAGTGAAATCTGAATAATTTTGTGTTACTCATAGCGCGTAA
TATTTGTCTAGGGAGATCTATAACTTCGTATAATGTATGCTATACGAAGTTATTACCGAAGAAATGGCTCGAGATC
TGCAAGGTGCTGAGGTACGATGAGACCCGCACCAGGTGCAGACCCTGCGAGTGTGGCGGTAAACATATTAGGAACC
AGCCTGTGATGCTGGATGTGACCGAGGAGCTGAGCCCGATCACTTGGTGCTGGCCTGCACCCGCGCTGAGTTTGG
CTCTAGCGATGAAGATACAGATTGAGGTACTGAAATGTGTGGGCGTGGCTTAAGGGTGGGAAAGAATATATAAGGT
GGGCGTCTTATGTAGTTTTGTATCTGTTTTGCAGCAGCCGCCGCCGCCATGAGCACCAACTCGTTTGATGGAAGCA
TTGTGAGCTCATATTTGACAACGCGCATGCCCCCATGGGCCGGGGTGCGTCAGAATGTGATGGGCTCCAGCATTGA
TGGTCGCCCCGTCCTGCCCGCAAACTCTACTACCTTGACCTACGAGACCGTGTCTGGAACGCCGTTGGAGACTGCA
GCCTCCGCGGCCGCTTCAGCCGCTGCAGCCACCGCCCGCGGATTGTGACTGACTTTGCTTTCCTGAGCCCGCTTG
CAAGCAGTGCAGCTTCCGGTTCATCCGCCCGCGATGACAAGTTGACGGCTCTTTTGGCACAATTGGATTCTTTGAC
CCCGGAACTTAATGTCGTTTCTCAGCAGCTGTTGGATCTGCGCCAGCAGGTTTCTGCCCTGAAGGCTTCCTCCGCT
CCCAATGCGGTTTAAAACATAAATAAAAAACCAGACTCTGTTTGGATTTGGATCAAGCAAGTGTCTTGCTGTCTTT
ATTTAGGGTTTTGCGCGCGCGGTAGGCCCGGGACCAGCGGTCTCGGTCGTTGAGGGTCCTGTGTATTTTTTCCAG
GACGTGGTAAAGGTGACTCTGGATGTTCAGATACATCGGCATAAGCCCGTCTCTGGGGTGGAGGTAGCACCACTGC
AGAGCTTCATGCTGCGGGGTGGTGTTGTAGATGATCCATAGCAGGAGCGCTGGGCGTGGTGCCTAAAAATGT
CTTTCAGTAGCAAGCTGATTGCCAGGGGCAGGCCCTTGGTGTAAGTGTTTACAAAGCGGTTAAGCTGGGATGGGTG
CATACGTGGGGATATGAGATGCATCTTGGACTGTATTTTAGGTTGGCTATGTTCCAGCCATATCCCTCCGGGA
TTCATGTTGTGCAGAACCACCAGCACAGTGTATCCGGTGCACTGGGAAATTTGTCATGTAGCTTAGAAGGAAATG
CGTGGAAGAACTTGGAGACGCCCTTGTCGACCTCCAAGATTTCCATGCATTCGTCCATAATGATGGCAATGGGCCC
ACGGGCCGGCGGCCTGGGCGAAGATATTTCTGGGATCACTAACGTCATAGTTGTGTTCCAGGATGAGATCGTCATAG
GCCATTTTTACAAAGCGCGGCGCAGGGTGCCAGACTGCGGTATAATGGTTCCATCCGCCCAGGGGCGTAGTTAC
CCTCACAGATTGCATTCCCACGCTTGAGTTCAGATGGGGGATCATGTCTACCTGCGGGCGGATGAAGAAAAC
GGTTTCCCGGGTAGGGGAGATCAGCTGGGAAGAAAGCAGGTTCCTGAGCAGCCTGCGACTTACCGCAGCCGGTGGGC
CCGTAAATCACACCTATTACCGGGTGCAACTGGTAGTTAAGAGAGCTGCAGCTGCCGTCATCCCTGAGCAGGGGGG
CCACTTCGTTAAGCATGTCCCTGACTCGCATGTTTTCCCTGACCAAATCCGCCAGAAGGCGCTCGCCGCCCAGCGA
TAGCAGTTCTTGCAAGGAAGCAAAGTTTTTCAACGGTTTGAGACCGTCCGCCGTAGGCATGCTTTTGAGCGTTTGA
CCAAGCAGTTCCAGGCGGTCCACAGCTCGGTCACCTGCTCTACGGCATCTCGATCCAGCATATCTCCTCGTTTCG
CGGGTTGGGCGGCTTTCGCTGTACGGCAGTAGTCGGTGCTCGTCCAGACGGGCCAGGGTCATGTCTTTCCACGGG
CGCAGGGTCCTCGTCAGCGTAGTCTGGGTCACGGTGAAGGGGTGCGCTCCGGGCTGCGCGCTGGCCAGGGTGCGCT
TGAGGCTGGTCCTGCTGGTGCTGAAGCGCTGCCGGTCTTCGCCCTGCGCGTCGGCCAGGTAGCATTTGACCATGGT
GTCATAGTCCAGCCTGTTGGGCGTGGCGGTGGCCCTTGGCCCTTGGACGGAGGCGCCGCACGAGGGCAG
TGCAGACTTTTGAGGGCGTAGAGCTTGGGCGCGAGAAATACCGATTCCGGGGAGTACGCATCCGCGCCGCAGGCCC
CGCAGACGGTCTCGCATTCCACGAGCCAGGCGAGCTCTGGCCGTTCGGGGTCAAAAACCAGGTTTCCCCCATGCTT
TTTGATCCGTTTCTTACCTCTGGTTCCATGAGCCGGTGTCCACGCTCGGTGACGAAAAGGCTGTCCGTGTCCCCG
TATACAGACTTGAGAGGCCTGTCCTCGAGCGGTGTTCCGCGGTCCTCCTCGTATAGAAACTGGGACCACTCTGAGA
CAAAGGCTCGCGTCCAGGCCAGCACGAAGGAGGCTAAGTGGGAGGGGTAGCGGTCGTTGTCCACTAGGGGGTCCAC
TCGCTCCAGGGTGTGAAGACACATGTCGCCCTCTTCGGCATCAAGGAAGGTGATTGGTTTGTAGGTGTAGGCCACG
TGACCGGGTGTTCCTGAAGGGGGGCTATAAAAGGGGGTGGGGCGCGTTCGTCCTCACTCTCTTCCGCATCGCTGT
CTGCGAGGGCCAGCTGTTGGGGTGAGTACTCCCTCTGGAAAGCGGGCATGACTTCTGCGCTAAGATTGTCAGTTTC
CAAAAACGAGGAGGATTTGATATTCACCTGGCCCGCGGTGATGCCTTTGACGGGTGGCCGCATCCATCGGTCAGAA
AAGACAATCTTTTGTTGTCAAGCTTGGTGGCAAACGACCCGTAGAGGGCGTTGGACAGCAACTTGGCGATGGAGC
GCAGGGTTTGGTTTTTGTCGCGATCGGCGCGCTCCTTGGCCGCGATGTTTAGCTGCACGTATTCGCGCGCAACGCA
CCGCCCATTCGGGAAGACGGTGGTCGCGCTCGTCGGGCACCAGGTGCACGCGCCAACCGCGGTTGTGCAGGGTGACA
AGGTCAACGCTGGTGGCTACCTCTCCGCGTAGGCGCTCGTTGGTCCAGCAGAGGCGGCCGCCCTTGCGCGAGCAGA
ATGGCGGTAGGGGGTCTAGCTGCGTCTCGTCCGGGGGTCTGCGTCCACGGTAAAGACCCCGGGCAGCAGGCGGCGC
GTCGAAGTAGTCTATCTTGCATCCTTGCAAGTCTAGCGCCTGCTGCCATGCGGGCGGCAAGCGCGCGGCTCGTAT
GGGTTGAGTGGGCACCCCATGGCATGGGGTGGGTGAGCGGCGGACGGCGTACATGCCGCAAATGTCGTAAACGTAGA
GGGGCTCTCTGAGTATTCCAAGATATGTAGGCGGTAGCATCTTCCACCGCGGATGCTCGGCGGCCACGTAATCGTATAG
TTCGTCGAGGGAGCGAGGAGGTCGGGACCGAGGTTGCTACGCGGCGGCTGCTCTGCTCGGAAGACTATCTGCCTG
AAGATGGCATGTGAGTTGGATGATATGGTTGGACGCTGGAAGACTTGAAGCTGGCGTCTGTGAGACCTACGGCGT
CACGCACGAAGGAGGCGTAGGAGTCGCGCAGCTTGTTGACCAGCTCGGCGGTGACCTGCACGTCTAGGCGCAGTA
GTCCAGGGTTTCCTTGATGATGTCATACTTATCCTGTCCCTTTTTTTCCACAGCTCGCGGTTGAGGACAAACTCT
TCGCGGTCTTTCCAGTACTCTTGGATCGGAAACCGTCGGCCTCCGAACGGTAAGAGCCTAGCATGTAGAACTGGT
TGACGGCCTGGTAGGCGCAGCATCCCTTTTCTACGGGTAGCGCGTATGCCTGCGCGGCCTTCCGGAGCGAGGTGTG
GGTGAGCGAAAGGTGTCCGTGCGGTTTTTGGAACGCGGATTTGGCAGGGCGAAGGTGACATGGTTGAAGAGTATCT
TCGCGGTCTTTCCAGTACTCTTGGATCGGAAACCGTCGGCCTCCGAACGGTAAGAGCCTAGCATGTAGAACTGGT
TTCCCGCGCGAGGCATAAAGTTGCGTGTGATGCGGAAGGGGTCCCGGCACCTCGGAACGGTTGTTAATTACCTGGGC
```

```
CTGCGCTGGGCCCCAAGCCGACGCGCCCTGGAGGCAGCTGGGGCCGGACCTGGGCTGGCGGTGGCACCCGCGCGCG
CTGGCAACGTCGGCGGCGTGGAGGAATATGACGAGGACGATGAGTACGAGCCAGAGGACGGCGAGTACTAAGCGGT
GATGTTTCTGATCAGATGATGCAAGACGCAACGGACCCGGCGGTGCGGGCGGCGCTGCAGAGCCAGCCGTCCGGCC
TTAACTCCACGGACGACTGGCGCCAGGTCATGGACCGCATCATGTCGCTGACTGCGCGCAATCCTGACGCGTTCCG
GCAGCAGCCGCAGGCCAACCGGCTCTCCGCAATTCTGGACGCGTGGTCCCGGCGCGCGCAAACCCCACGCACGAG
AAGGTGCTGGCGATCGTAAACGCGCTGGCCGAAAACAGGGCCATCCGCCCGACGAGGCCGGCCTGGTCTACGACG
CGCTGCTTCAGCGCGTGGCTCGTTACAACAGCGGCAACGTGCAGACCAACCTGGACCGGCTGGTGGGGATGTGCG
CGAGGCCGTGGCGCAGCGTGAGCGCGCGCAGCAGCAGGGCAACCTGGGCTCCATGGTTGCACTAAACGCCTTCCTG
AGTACACAGCCCGCCAACGTGCCGCGGGGACAGGAGGACTACACCAACTTTGTGAGCGCACTGCGGCTAATGGTGA
CTGAGACACCGCAAAGTGAGGTGTACCAGTCTGGGCCAGACTATTTTTCCAGACCAGTAGACAAGGCCTGCAGAC
CGTAAACCTGAGCCAGGCTTTCAAAAACTTGCAGGGGCTGTGGGGGGTGCGGGCTCCCACAGGCGACCGCGCGACC
GTGTCTAGCTTGCTGACGCCCAACTCGCGCCTGTTGCTGCTGCTAATAGCGCCTTCACGGACAGTGGCAGCGTGT
CCCGGGACACATACCTAGGTCACTTGCTGACACTGTACCGCGAGGCCATAGGTCAGGCGCATGTGGACGAGCATAC
TTTCCAGGAGATTACAAGTGTCAGCCGCGCGCTGGGCAGGAGGACACGGGCAGCCTGGAGGCAACCCTAAACTAC
CTGCTGACCAACCGGCGGCAGAAGATCCCCTCGTTGCACAGTTTAAACAGCGAGGAGGAGCGCATTTTGCGCTACG
TGCAGCAGACGCGTGAGCCTTAACCTGATGCGCGACGGGGCAACGCCCAGCGTGGCGCTGGACATGACCGCGCGCAA
CATGGAACCGGCATGTATGCCTCAAACCGGCCGTTTATCAACCGCCTAATGGACTACTTGCATCGCGCGGCCGCC
GTGAACCCCGAGTATTTCACCAATGCCATCTTGAACCGGCACTGGCTACCGCCCCTGGTTTCTACACCGGGGAT
TCGAGGTGCCCGAGGGTAACGATGGATTCCTCTGGACGACATAGACGACAGCGTGTTTCCCCGCAACCGCAGAC
CCTGCTAGAGTTGCAACAGCGCGAGCAGGCAGAGGCGGCGCTGCGAAAGGAAAGCTTCCGCAGGCCAAGCAGCTTG
TCCGATCTAGGCGCTGCGGCCCCGCGGTCAGATGCTAGTAGCCCATTTCCAAGCTTGATAGGGTCTCTTACCAGCA
CTCGCACCCACCCGCCCGCCCTGCTGGGCGAGGAGGAGTACCTAAACAACTCGCTGCTGCAGCCGCAGCGCGAAAA
AAACCTGCCTCCCGGCATTTCCCAACAACGGGATAGAGAGCCTAGTGGACAAGATGAGTAGATGGAAGACGTACGCG
CAGGAGCACAGGGACGTGCCAGGCCCGCGCCCGCCCACCCGTCGTCAAAGGCACGACCGTCAGCGGGGTCTGGTGT
GGGAGGACGATGACTCGGCAGACGACAGCAGCGTCCTGGATTTGGGAGGGAGTGGCAACCCGTTTGCGCACCTTCG
CCCCAGGCTGGGGACAATGTTTTAAAAAAAAAAAGCATGATGCAAAATAAAAAACTCACCAAGGCCATGGCACCG
AGCGGTTGGTTTCTTGTATTCCCCTTAGTATGCGGCGCGCGGCGATGTATGAGGAAGGTCCTCCTCCCTCCTACGA
GAGTGTGGTGAGCGCGGCGCCAGTGGCGGCGGCGCTGGGTTCTCCCTTCGATGCTCCCCTGGACCCGCCGTTTGTG
CCTCCGCGGTACCTGCGGCCTACCGGGGGAGAAACAGCATCCGTTACTCTGAGTTGGCACCCCTATTCGACACCA
CCCGTGTGTACCTGGTGGACAACAAGTCAACGGATGTGGCCTGAACTACCAGAACGACCACCAGCAACTTTCT
GACCACGGTCATTCAAAACAATGACTACAGCCGGGGAGGCAAGCACACACAGCCATCAATCTTGACGACCGGTCG
CACTGGGCGGCGACCTGAAAACCATCCTGCATACCAACATGCCAAATGTGAACGAGTTCATGTTTACCAATAAGT
TTAAGGCGCGGGTGATGGTGTCGCGCTTGCCTACTAAGGACAATCAGGTGGAGCTGAAATACGAGTGGGTGGAGTT
CACGCTGCCCGAGGGCAACTACTCCGAGACCATGACCATAGACCTTATGAACAACGCGATCGTGGAGCACTACTTG
AAAGTGGGCAGACAGAACGGGGTTCTGGAAAGCGACATCGGGGTAAAGTTTGACACCCGCAACTTCAGACTGGGGT
TTGACCCCGTCACTGGTCTTGTCATGCCTGGGGTATATACAAACGAAGCCTTCCATCCAGACATCATTTTGCTGCC
AGGATGCGGGGTGGACTTCACCCACAGCCGCCTGAGCAACTTGTTGGGCATCCGCAAGCGGCAACCCTTCCAGGAG
GGCTTTAGGATCACCTACGATGATCTGGAGGGTGGTAACATTCCCGCACTGTTGGATGTGGACGCCTACCAGGCGA
GCTTGAAAGATGACACCGAACGAGGGCGGGGTGGCGCAGGCGGCAGCAACGCAGTGGCAGCGGCGCGGAAGAGAA
CTCCAACGCGGCAGCCGCGGCAATGCAGCCGGTGAGGACATGAACGATCATGCCATTCGCGGCGACACCTTTGCC
ACACGGGCTGAGGAGAAGCGCGCTGAGGCCGAAGCAGCGGCCGAAGCTGCCGCCCCGCTGCGCAACCCGAGGTCG
AGAAGCCTCAGAAGAAACCGGTGATCAAACCCCTGACAGAGGACAGCAAGAAACGCAGTTACAACCTAATAAGCAA
TGACAGCACCTTCACCCAGTACCGCAGCTGGTACCTTGCATACAACTACGGCGACCCTCAGACCGGAATCCGCTCA
TGGACCCTGCTTTGCACTCCTGACGTAACCTGCGGCTCGGAGCAGGTCTACTGGTCGTTGCCAGACATGATGCAAG
ACCCCGTGACCTTCCGCTCCACGCGCCAGATCAGCAACTTTCCGGTGGTGGCGCCGAGCTGTTGCCCGTGCACTC
CAAGAGCTTCTACACACGACCAGGCCGTCTACTCCCAACTCATCCGCCAGTTTACCTCTCTGACCCACGTGTTCAAT
CGCTTTCCCGAGAACCAGATTTCTGCGCGCCCGCCACCCACCATCACCACCGTCAGTGAAAACGTTCCTGCTC
TCACAGATCACGGACGCTACCGCTGCGCAACAGCATCGGAGGAGTCCAGCGAGTGACCATTACTGACGCCGACACG
CCGCACCTGCCCCTACGTTTACAAGGCCCTGGGCATAGTCTCGCCGCGCGTGCTATCGAGCCGCACTTTTTGAGCA
AGCATGTCCATCCTTATATCGCCCAGCAATAACACAGGCTGGGGCCTGCGCTTCCCAAGCAAGATGTTTGGCGGGG
CCAAGAAGCGCTCCGACCAACACCCAGTGCGCGTGCGCGGGCACTACCGCGCGCCCTGGGGCGCGCACAAACGCGG
CCGCACTGGCGCACCACCGTCGATGACGCCATCGACGCGGTGGTGGAGGAGGCGCGCAACTACACGCCCACGCCG
CCACCAGTGTCCACAGTGGACGCGGCCATTCAGACCGGTGGTGCGCGGAGCCCGGCGCTATGCTAAAATGAAGAGAC
GGCGGAGCGGCGTAGCACGTCGCCACCGCCGCCGAACGCCACTGCCGCCCAACGCGCGGCGGCCCTGCTTAA
CCGCGCACGTCGCACCGGCCGCGGCCGGCCATGCGGGCCGCTCGAAGGCCTGGCCGCGGTATTGTCACTGTGCCC
CCCAGGTCCAGGCGACGAGCGGCCGCCGCAGCAGCCGCGGCCATTAGTGCTATGACTCAGGGTCGCAGGGCAACG
TGTATTGGGTCGCGACTCGGTTAGCGGCCTGCGCGTGCCCGTGCGCACCCGCCCCCGCGCAACTAGATTGCAAG
AAAAACTACTTAGACTCGTACTGTTGTATGTATCCAGCGGCGGCGGCGCAACGAAGCTATGTCCAAGCGCAAA
ATCAAAGAAGAGATGCTCCAGGTCATCGCGCCGGAGATCTATGGCCCCCCGAAGAAGGAAGAGCAGGATTACAAGC
CCCGAAAGCTAAAGCGGGTCAAAAAGAAAAAGAAAGATGATGATGATGAACTTGACGACGAGGTGGAACTGCTGCA
CGCTACCGCGCCCAGGCGACGGGTACAGTGGAAAGGTCGACGCGTAAAACGTGTTTTGCGACCCGGCACCACCGTA
```

FIGURE 8 (cont.)

```
GTCTTTACGCCCGGTGAGCGGTCCACCCGCACCTACAAGCGCGTGTATGATGAGGTGTACGGCGACGAGGACCTGC
TTGAGCAGGCCAACGAGCGCCTCGGGGAGTTTGCCTACGAAAGCGGCATAAGGACATGCTGGCGTTGCCGCTGGA
CGAGGGCAACCCAACACCTAGCCTAAAGCCCGTAACACTGCAGCAGGTGCTGCCCGCGCTTGCACCGTCCGAAGAA
AAGCGCGGCCTAAAGCGCGAGTCTGGTGACTTGGCACCCACCGTGCAGCTGATGGTACCCAAGCGCCAGCGACTGG
AAGATGTCTTGGAAAAAATGACCGTGGAACCTGGGCTGGAGCCCGAGGTCCGCGTGCGGCCAATCAAGCAGGTGGC
GCCGGGACTGGGCGTGCAGACCGTGGACGTTCAGATACCCACTACCAGTAGCACCAGTATTGCCACCGGCCACAGAG
GGCATGGAGACACAAACGTCCCCGGTTGCCTCAGCGGTGGCGGATGCCGCGGTGCAGGCGGTCGCTGCGGCCGCGT
CCAAGACCTCTACGGAGGTGCAAACGGACCCGTGGATGTTTCGCGTTTCAGCCCCCCGGCGCCCGGCCGGTTCGAG
GAAGTACGGCGCCGCCAGCGCGCTACTGCCCGAATATGCCCTACATCCTTCCATTGCGCCTACCCCCGGCTATCGT
GGCTACACCTACCGCCCCAGAAGCGAGCAACTACCCGACGCCGAACCACCACTGGAACCGCCGCCGTCGCC
GTCGCCAGCCCGTGCTGGCCCCGATTTCCGTGCGCAGGGTGGCTCGCGAAGGAGGCAGGACCCTGGTGCTGCCAAC
AGCGCGCTACCACCCCAGCATCGTTTAAAAGCCGGTCTTTGTGGTTCTTGCAGATATGGCCCTCACCTGCCGCCTC
CGTTTCCCGGTGCCGGGATCCGAGGAAGAATGCACCGTAGGAGGGCATGGCCGGCCACGGCCTGACGGGCGGCA
TGCGTCGTGCGCACCACCGGCGGCGGCGCGCGTGGCACCGTCGCATGCGCGGCGGTATCCTGCCCCTCCTTATTCC
ACTGATCGCCGCGGCGATTGGCGCCGTGCCCGGAATTGCATCCGTGGCCTTGCAGGCGCAGAGACACTGATTAAAA
ACAAGTTGCATGTGGAAAAATCAAAATAAAAGTCTGGACTCTCACGCTCGCTTGGTCCTGTAACTATTTTGTAGA
ATGGAAGACATCAACTTTGCGTCTCTGGCCCCGCGACACGGCTCGCGCCCGTTCATGGGAAACTGGCAAGATATCG
GCACCAGCAATATGAGCGGTGGCGCCTTCAGCTGGGGCTGCTGTGGAGCGGCATTAAAAATTTGGTTCCACCGT
TAAGAACTATGGCAGCAAGGCCTGGAACAGCAGCACAGGCCAGATGCTGAGGGATAAGTTGAAAGAGCAAAATTTC
CAACAAAAGGTCGTAGATGGCCTGGCCTCTGGCATTAGCGGGGTGGTGGACCTGGCCAACCAGGCAGTGCAAAATA
AGATTAACAGTAAGCTTGATCCCCGCCCTCCCGTAGAGGAGCCTCCACCGGCCGTGGAGACAGTGTCTCCAGAGGG
GCGTGGCGAAAAGCGTCCGCGCCCCGACAGGGAAGAAACTCTGGTGACGCAAATAGACGAGCCTCCCTCGTACGAG
GAGGCACTAAAGCAAGGCCTGCCCACCACCCGTCCCATCGCGCCCATGGCTACCGGAGTGCTGGGCCAGCACACAC
CCGTAACGCTGGACCTGCCTCCCCCGCCGACACCCAGCAGAAACCTGTGCTGCCAGGCCCGACCGCCGTTGTTGT
AACCCGTCCTAGCCGCGCGTCCCTGCGCTGCGCCGCCAGCGGTCCGCGATCGTTGCGGCCCGTAGCCAGTGGCAAC
TGGCAAAGCACACTGAACAGCATCGTGGGTCTGGGGGTGCAATCCCTGAAGCGCCGACGATGCTTCTGAATAGCTA
ACGTGTCGTATGTGTGTCATGTATGCGTCCATGTCGCCGCCAGAGGAGCTGCTGAGCCGCCGCGCGCCCGCTTTCC
AAGATGGCTACCCCTTCGATGATGCCGCAGTGGTCTTACATGCGACATCTCGGGCCAGGACGCCTCGGAGTACCTGA
GCCCCGGGCTGGTGCAGTTTGCCCGGCCACCGAGACGTACTTCAGCCTGAATAACAAGTTTAGAAACCCCACGGT
GGCGCCTACGCACGACGTGACCACAGACCGGTCCCAGCGTTTGACGCTGCGGTTCATCCCTGTGGACCGTGAGGAT
ACTGCGTACTCGTACAAGGCGCGGTTCACCCTAGCTGTGGGTGATAACCGTGTGCTGGACATGGCTTCCACGTACT
TTGACATCCGCGGCGTGCTGGACAGGGCCCTACTTTTAAGCCCTACTCTGGCACTGCCTACAACGCCTGGCTCC
CAAGGGTGCCCCAAATCCTTGCGAATGGGATGAAGCTGCTACTGCTCTTGAAATAAACCTAGAAGAAGAGGACGAT
GACAACGAAGACGAAGTAGACGAGCAAGCTGAGCAGCAAAAACTCACGTATTTCGGCAGGCGCCTATTCTGGTA
TAAATATTACAAAGGAGGGTATTCAAATAGGTGTCGAAGGTCAAACACCTAAATATGCCGATAAACATTTCAACC
TGAACCTCAAATAGGAGAATCTCAGTGGTACGAAACTGAAATTAATCATGCAGCTGGGAGAGTCCTTAAAAAGACT
ACCCCAATGAAACCATGTTACGGTTCATATGCAAAACCCACAAATGAAAATGGAGGGCAAGGCATTCTTGTAAAGC
AACAAAATGGAAAGCTAGAAAGTCAAGTGGAAATGCAATTTTTCTCAACTACTCAGGCGACCGCAGGCAATGGTGA
TAACTTGACTCCTAAAGTGGTATTGTACAGTGAAGATGTAGATATAGAAACCCCAGACACTCATATTTCTTACATG
CCCACTATTAAGGAAGGTAACTCACGAGAACTAATGGGCCAACAATCTATGCCCAACAGGCCTAATTACATTGCTT
TTAGGGACAATTTTATTGGTCTAATGTATTACAACAGCACGGGTAATATGGGTGTTCTGGCGGGCCAAGCATCGCA
GTTGAATGCTGTTGTAGATTTGCAAGACAGAAACACAGAGCTTTCATACCAGCTTTTGCTTGATTCCATTGGTGAT
AGAACCAGGTACTTTTCTATGTGGAATCAGGCTGTTGACAGCTATGATCCAGATGTTAGAATTATTGAAAATCATG
GAACTGAAGATGAACTTCCAAATTACTGCTTTCCACTGGGAGGTGTGATTAATACAGAGACTCTTACCAAGGTAAA
ACCTAAAACAGGTCAGGAAAATGGATGGAAAAAGATGCTACAGAATTTTCAGATAAAAATGAAATAAGAGTTGGA
AATAATTTTGCCATGGAAATCAATCTAAATGCCAACCTGTGGACAAATTTCCTGTACTCCAACATAGCGCTGTATT
TGCCCGACAAGCTAAAGTACAGTCCTTCCAACGTAAAAATTTCTGATAACCCAAACACCTACGACTACATGAACAA
GCGAGTGGTGGCTCCCGGGTTAGTGGACTGCTACATTAACCTTGGAGCACGCTGGTCCCTTGACTATATGGACAAC
GTCAACCCATTTAACCACCACCGCAATGCTGGCCTGCGCTACCGCTCAATGTTGCTGGGCAATGGTCGCTATGTGC
CCTTCCACATCCAGGTGCCTCAGAAGTTCTTTGCCATTAAAAACCTCCTTCTCCTGCCGGGCTCATACACCTACGA
GTGGAACTTCAGGAAGGATGTTAACATGGTTCTGCAGAGCTCCCTAGGAAATGACCTAAGGGTTGACGGAGCCAGC
ATTAAGTTTGATAGCATTTGCCTTTACGCCACCTTCTTCCCCATGGCCCACAACACCGCCTCCACGCTTGAGGCCA
TGCTTAGAAACGACACCAACGACCAGTCCTTTAACGACTATCTCTCCGCCGCCAACATGCTCTACCCTATACCCGC
CAACGCTACCAACGTGCCCATATCCATCCCCTCCCGCAACTGGCGGCTTTCCGCGGCTGGGCCTTCACGCGCTT
AAGACTAAGGAAACCCCATCACTGGGCTCGGGCTACGACCCTTATTACACCTACTCTGGCTCTATACCCTACCTAG
ATGGAACCTTTTACCTCAACCACACCACCTTTAAGAAGGTGGCCATTAACTTTGACTCTTCTGTCAGCTGGCCTGGCAA
TGACCGCCTGCTTACCCCAACGAGTTTGAAATTAAGCGCTCAGTTGACGGGGAGGGTTACAACGTTGCCCAGTGT
AACATGACCAAAGACTGGTTCCTGGTACAAATGCTAGCTAACTACAACATTGGCTACCAGGGCTTCTATATCCCAG
AGAGCTACAAGGACCGCATGTACTCCTTCTTTAGAAACTTCCAGCCCATGAGCCGTCAGGTGGTGGATGATACTAA
ATACAAGGACTACCAACAGGTGGGCATCCTACACCAACACAACAACTCTGGATTTGTTGGCTACCTTGCCCCACC
ATGCCGCGAAGGACAGGCCTACCCTGCTAACTTCCCCTATCCGCTTATAGGCAAGACCGCAGTTGACAGCATTACCC
```

FIGURE 8 (cont.)

AGAAAAAGTTTCTTTGCGATCGCACCCTTTGGCGCATCCCATTCTCCAGTAACTTTATGTCCATGGGCGCACTCAC
AGACCTGGGCCAAAACCTTCTCTACGCCAACTCCGCCCACGCGCTAGACATGACTTTTGAGGTGGATCCCATGGAC
GAGCCCACCCTTCTTTATGTTTTGTTTGAAGTCTTTGACGTGGTCCGTGTGCACCGGCCGCACCGCGGCGTCATCG
AAACCGTGTACCTGCGCACGCCCTTCTCGGCCGGCAACGCCACAACATAAAGAAGCAAGCAACATCAACAACAGCT
GCCGCCATGGGCTCCAGTGAGCAGGAACTGAAAGCCATTGTCAAAGATCTTGGTTGTGGGCCATATTTTTGGGCA
CCTATGACAAGCGCTTTCCAGGCTTTGTTTCTCCACACAAGCTCGCCTGCGCCATAGTCAATACGGCCGGTCGCGA
GACTGGGGCGTACACTGGATGGCCTTTGCCTGGAACCCGCACTCAAAAACATGCTACCTCTTTGAGCCCTTTGGC
TTTTCTGACCAGCGACTCAAGCAGGTTTACCAGTTTGAGTACGAGTCACTCCTGCGCCGTAGCGCCATTGCTTCTT
CCCCTCGACCGCTGTATAACGCTGGAAAAGTCCACCCAAAGCGTACAGGGGCCCAACTCGGCCGGCTGTGGACTATT
CTGCTGCATGTTTCTCCACGCCTTTGCCAACTGGCCCCAAACTCCCATGGATCACAACCCCACCATGAACCTTATT
ACCGGGGTACCCAACTCCATGCTCAACAGTCCCCAGGTACAGCCCACCCTGCGTCGCAACCAGGAACAGCTCTACA
GCTTCCTGGAGCGCCACTCGCCCTACTTCCGCAGCCACAGTGCGCAGATTAGGAGCGCCACTTCTTTTTGTCACTT
GAAAAACATGTAAAAATAATGTACTAGAGACACTTTCAATAAAGGCAAATGCTTTTATTTGTACACTCTCGGGTGA
TTATTTACCCCCACCCTTGCCGTCTGCGCCGTTTAAAAAATCAAAGGGTTCTGCCGCGCATCGCTATGCGCCACTG
GCAGGACACGTTGCGATACTGGTGTTAGTGCTCCACTTAAACTCAGGCACAACCATCCGCGGCAGCTCGCTGAA
GTTTTCACTCCACAGGCTGCGCACCATCACCAACGCGTTTAGCAGGTCGGGCGCCGATATCTTGAAGTCGCAGTTG
GGGCCTCCCGCCTGCGCGCGAGTTGCGATACACAGGGTTGCAGCACTGGAACACTATCAGCGCCGGGTGGTGCA
CGCTGGCCAGCACGCTCTTGTCGGAGATCAGATCCGCGTCCAGGTCCTCCGCGTTGCTCAGGGCGAACGGAGTCAA
CTTTGGTAGCTGCCTTCCCAAAAAGGGCGCGTGCCCAGGCTTTGAGTTGCACTCGCACCGTAGTGGCATCAAAAGG
TGACCGTGCCCGGTCTGGGCGTTAGGATACAGCGCCTGCATAAAAGCCTTGATCTGCTAAAAGCCACCTGAGCCT
TTGCGCCTTCAGAGAAGAACATGCCGCAAGACTTGCCGGAAAACTGATTGGCCGGACAGGCCGCGTCGTGCACGCA
GCACCTTGCGTCGGTGTTGGAGATCTGCACCACATTTCGGCCCCACCGGTTCTTCACGATCTTGGCCTTGCTAGAC
TGCTCCTTCAGCGCGCGCTGCCCGTTTTCGCTCGTCACATCCATTTCAATCACGTGCTCCTTATTTATCATAATGC
TTCCGTGTAGACACTTAAGCTCGCCTTCGATCTCAGCGCAGCGGTGCAGCCACAACGCGCAGCCCGTGGCTCGTG
ATGCTTGTAGGTCACCTCTGCAAACGACTGCAGGTACGCCTGCAGGAATCGCCCCATCATCGTCACAAAGGTCTTG
TTGCTGGTGAAGGTCAGCTGCAACCCGCGGTGCTCCTCGGTCCAGGTCTTGCATACGGCCGCCAGAGCTTCCA
CTTGGTCAGGCAGTAGTTTGAAGTTCGCCTTTAGATCGTTATCCACGTGGTACTTGTCCATCAGCGCGCGCAGC
CTCCATGCCCTTCTCCCACGCAGACACGATCGGCACACTCAGCGGGTTCATCACCGTAATTTCACTTTCCGCTTCG
CTGGGCTCTTCCTCTTCCTCTTGCGTCCGCATACCACGCGCCACTGGGTCGTCTTCATTCAGCCGCCGCACTGTGC
GCTTACCTCCTTTGCCATGCTTGATTAGCACCGGTGGGTTGCTGAAACCCACCATTTGTAGCGCCACATCTTCTCT
TTCTTCCTCGCTGTCCACGATTACCTCTGGTGATGGCGGGCGCTCGGCTTGGGAGAAGGGCGCTTCTTTTCTTC
TTGGGCGCAATGGCCAAATCCGCCGCCGAGGTCGATGGCCGCGGGCTGGGTGTGCGCGGCACCAGCGCGTCTTGTG
ATGAGTCTTCCTCGTCCTCGGACTCGATACGCCGCCTCATCGCTTTTTTGGGGCGCCCGGGGAGGCGCGGCGA
CGGGGACGGCGACGACACGTCCTCCATGGTTGGGGGACGTCGCGCCGCACCGGCGTCCGCGCTCGGGGGTGGTTCG
CGCTGCTCCTCTTCCCGACTGGCCATTTCCTTCTCCTATAGGCAGAAAAAGATCATGGAGTCAGTCGAGAAGAAGG
ACAGCCTAACCGCCCCCTCTGAGTTCGCCACCACCGCCTCCACCGATGCCGCCAACGCGCCTACCACCTTCCCCGT
CCAGGCACCCCGCTTGAGGAGGAGGAAGTGATTATCGAGCAGGACCCAGGTTTTGTAAGCGAAGACGACGAGGAC
CGCTCAGTACCAACAGAGGATAAAAAGCAAGACCAGGACAACGCAGAGGCAAACGAGGAACAAGTCGGGCGGGGG
ACGAAAGGCATGGCGACTACCTAGATGTGGAGACGACGTGCTGTTGAAGCATCTGCAGCGCCAGTGCGCCATTAT
CTGCGACGCGTTGCAAGAGCGCAGCGATGTGCCCCTCGCCATAGCGGATGTCAGCCTTGCCTACGAACGCCACCTA
TTCTCACCGCGCGTACCCCCCAAACGCCAAGAAAACGGCACATGCGAGCCCAACCCGCGCCTCAACTTCTACCCCG
TATTTGCCGTGCCAGAGGTGCTTGCCACCTATCACATCTTTTTCCAAAACTGCAAGATACCCCTATCCTGCCGTGC
CAACCGCAGCCGAGCGGACAAGCAGCTGGCCTTGCGGCAGGGCGCTGTCATACCTTGATATCGCCTCGCTCAACGAA
GTGCCAAAAATCTTTGAGGGTCTTGGACGCGACGAGAAGCGCGCGGCAAACGCTCTGCAACAGGAAAACAGCGAAA
ATGAAAGTCACTCTGGAGTGTTGGTGGAACTCGAGGGTGACAACGCGCGCCTAGCCGTACTAAAACGCAGCATCGA
GGTCACCCACTTTGCCTACCCGGCACTTAACCTACCCCGCCAAGGTCATGAGCACAGTCATGAGTGAGCTGATCGTG
CGCCGTGCGCAGCCCCTGGAGAGGGATGCAAATTTGCAAGAACAAACAGAGGAGGGCCTACCCGCAGTTGGCGACG
AGCAGCTAGCGCGCTGGCTTCAAACGCGCGAGCCTGCCGACTTGGAGGAGCGGACGCAAACTAATGATGGCCGCAGT
GCTCGTTACCGTGGAGCTTGAGTGCATGCAGCGGGTTCTTTGCTGACCCGGAGATGCAGCGCAAGCTAGAGGAAACA
TTGCACTACACCTTCGACAGGGCTACGTACGCCCAGGCCTGCAAGATCTCCAACGTGGAGCTCTGCAACCTGGTCT
CCTACCTTGGAATTTTGCACGAAAACCGCCTTGGGCAAAACGTGCTTCATTCCACGCTCAAGGGCGAGGCGCGCCG
CGACTACGTCCGCGACTGCGTTTACTTATTTCTATGCTACACCTGGCGACGGCCATGGGCGTTTGGCAGCAGTGC
TTGGAGGAGTGCAACCTCAAGGAGCTGCAGAAACTGCTAAAGCAAACTTGAAGGACCTATGGACGGCCTTCAACG
AGCGCTCCGTGGCCGCGCACCTGGCGGACATCATTTTCCCCGAACGCCTGCTTAAAACCCTGCAACAGGGTCTGCC
AGACTTCACCAGTCAAAGCATGTTGCAGAACTTTAGGAACTTTATCCTAGAGCGCTCAGGAATCTTGCCCGCCACC
TGCTGTGCACTTCCTAGCGACTTTGTGCCCATTAAGTACCGCGAATGCCCTCGGCCGCTTTGGGGCCACTGCTACC
TTCTGCAGCTAGCCAACTACCTTCCCTACCACTCTGACATAATGGAAGACGTGAGCGGTGACGGTCTACTGGAGTG
TCACTGTCGCTGCAACCCTATGCACCCCGCACCGCCTCCCTGGTTTGCAATTCGCAGCTGCTTAACGAAAGTCAAATT
ATCGGTACCTTTGAGCTGCAGGGTCCCTCGCCTGACGAAAAGTCCGCGGCTCCGGGGTTGAAACTCACTCCGGGGC
TGTGGACGTCGGCTTACCTTCGCAAATTTGTACCTGAGGACTACCACGCCCACGAGATTAGGTTCTACGAAGACCA
ATCCCGCCCGCCAAATGCGGAGCTTACCGCCTGCGTCATTACCCAGGGCCACATTCTTGGCCAATTGCAAGCCATC

FIGURE 8 (cont.)

```
AACAAAGCCGGCCAAGAGTTTCTGCTACGAAAGGGACGGGGGGTTTACTTGGACCCCCAGTCCGGCGAGGAGCTCA
ACCCAATCCCCCGCCGCCGCAGCCCTATCAGCAGCAGCCGCGGGCCCTTGCTTCCCAGGATGGCACCCAAAAAGA
AGCTGCAGCTGCCGCCGCCACCCACGGACGAGGAGGAATACTGGGACAGTCAGGCAGAGGAGGTTTTGGACGAGGA
GGAGGAGGACATGATGGAAGACTGGGAGAGCCTAGACGAGGAAGCTTCCGAGGTCGAAGAGGTGTCAGACGAAACA
CCGTCACCCTCGGTCGCATTCCCCTCGCCGGCGCCCCAGAAATCGGCAACCGGTTCCAGCATGGCTACAACCTCCG
CTCCTCAGGCGCCGCCGGCACTGCCCGTTCGCCGACCCAACCGTAGATGGGACACCACTGGAACCAGGGCCGGTAA
GTCCAAGCAGCCGCCGCCGTTAGCCCAAGAGCAACAACAGCGCCAAGGCTACCGGTCATGGCGCGGGCACAAGAAC
GCCATAGTTGCTTGCTTGCAAGACTGTGGGGCAACATCTCCTTCGCCCGCCGCTTTCTTCTCTACCATCACGGCG
TGGCCTTCCCCCGTAACATCCTGCATTACTACCGTCATCTCTACAGCCCATACTGCACCGGCGGCAGCGGCAGCGG
CAGCAACAGCAGCGGCCACACAGAAGCAAAGGCGACCGGATAGCAAGACTCTGACAAAGCCCAAGAAATCCACAGC
GGCGGCAGCAGCAGGAGGAGGAGCGCTGCGTCTGGCGCCCAACGAACCCGTATCGACCCGCGAGCTTAGAAACAGG
ATTTTTCCCACTCTGTATGCTATATTTCAACAGAGCAGGGCCAAGAACAAGAGCTGAAAATAAAAAACAGGTCTC
TGCGATCCCTCACCCGCAGCTGCCTGTATCACAAAAGCGAAGATCAGCTTCGGCGCACGCTGGAAGACGCGGAGGC
TCTCTTCAGTAAATACTGCGCGCTGACTCTTAAGGACTAGTTTCGCGCCCTTTCTCAAATTTAAGCGCGAAAACTA
CGTCATCTCCAGCCGGCCACACCCGGCGCCAGCACCTGTCGTCAGCGCCATTATGAGCAAGGAAATTCCCACGCCCT
ACATGTGGAGTTACCAGCCACAAATGGGACTTGCGGCTGGAGCTGCCCAAGACTACTCAACCCGAATAAACTACAT
GAGCGCGGGACCCCACATGATATCCGGGTCAACGGAATCCGCGCCCACCGAAACCGAATTCTCTTGGAACAGGCG
GCTATTACCACCACACCTCGTAATAACCTTAATCCCCGTAGTTGGCCCGCTGCCCTGGTGTACCAGGAAAGTCCCG
CTCCCACCACTGTGGTACTTCCCAGAGACGCCCAGGCCGAAGTTCAGATGACTAACTCAGCGGCGCAGCTTGCGGG
CGGCTTTCGTCACAGGGTGCGGTCGCCCGGCAGGGTATAACTCACCTGACAATCAGAGGCGAGGTATTCAGCTC
AACGACGAGTCGGTGAGCTCCTCGCTTGGTCTCCGTCGGACGGGACATTTCAGATCGGCGGCGCCGGCCGGTCCTT
CATTCACGCCTCGTCAGGCAATCCTAACTCTGCAGACCCTGGTCCTCTGAGCCGCGCTCTGGAGGCATTGGAACTCT
GCAATTTATTGAGGAGTTTGTGCCATCGGTCTACTTTAACCCCTTCTCGGGACCTCCGGCCACTATCCGGATCAA
TTTATTCCTAACTTTGACGCGGTAAAGGACTCGGCGGACGGCTACGACTGAATGTTAAGTGGAGAGGCAGAGCAAC
TGCGCCTGAAACACCTGGTCCACTGTCGCCGCCACAAGTGCTTGCCCGCGACTCCGGTGAGTTTTGCTACTTTGA
ATTGCCCGAGGATCATATCGAGGGCCCGGCGCACGGCGTCCGGCTTACCGCCCAGGGAGAGCTTGCCCGTAGCCTG
ATTCGGGAGTTTACCCAGCGCCCCCTGCTAGTTGAGCGGGACAGGGGACCCTGTGTTCTCACTGTGATTTGCAACT
GTCCTAACCTTGGATTACATCAAGATCCTCTAGTTAATTAACAGCTTGCATGCCTGCAGGTCGACGGGATCGGAGA
TCTCGGCCGCATATTAAGTGCATTGTTCTCGATACCGCTAAGTGCATTGTTCTCGTTAGCTCGATGGACAAGTGCA
TTGTTCTCTTGCTGAAAGCTCGATGGACAAGTGCATTGTTCTCTGCTGAAAGCTCGATGGACAAGTGCATTGTTC
TCTTGCTGAAAGCTCAGTACCCGGGAGTACCCTCGACCGCCGGAGTATAAATAGAGGCGCTTCGTCTACGGAGCGA
CAATTCAATTCAAACAAGCAAAGTGAACACGTCGCTAAGCGAAAGCTAAGCAAATAAACAAGCGCAGCTGAACAAG
CTAAACAATCTGCAGTAAAGTGCAAGTTAAAGTGAATCAATTAAAAGTAACCAGCAACCAAGTAAATCAACTGCAA
CTACTGAAATCTGCCAAGAAGTAAATTATTGAATACAAGAAGAGAACTCTGAATACTTTCAACAAGTTACCGAGAAA
GAAGAACTCACACAGCTAGCGTTTAAACTTAAGCTTCACCATGGTGGGGCCCTGCATGCTGCTGCTGCTGCTGC
TGCTGGGCCTGAGGCTACAGCTCTCCCTGGGCATCATCCTAGTTGAGGAGGAGAACCCGGACTTCTGGAACCGCGA
GGCAGCCGAGGCCCTGGGTGCCGCCAAGAAGCTGCAGCCTGCACAGACAGCCGCCAAGAACCTCATCATCTTCCTG
GGCGATGGGGTGGGGGTGTCTACGGTGACAGCTGCCAGGATCCTAAAAGGGCAGAAGAAGGACAAACTGGGGCCTG
AGATACCCCTGGCCATGGACCGCTTCCCATATGTGGCTCTGTCAAGACATACAATGTAGACAAACATGTGCCAGA
CAGTGGAGCCACAGCCACGGCCTACCTGTGCGGGGTCAAGGGCAACTTCCAGACCATTGGCTTGAGTGCAGCCGCC
CGCTTTAACCAGTGCAACACGACACGCGGCAACGAGGTCATCTCCGTGATGAATCGGCCAAGAAAGCAGGGAAGT
CAGTGGGAGTGGTAACCACCACACGAGTGCAGCACGCCCTGCCGCGGCACCTACGCCCACACGGTGAACCGCAA
CTGGTACTCGGACGCCGACGTGCCTGCCTGCCTCGGCCCAGGAGGGGTGCCAGGACATCGCTACGCAGCTCATCTCC
AACATGGACATTGACGTGATCCTAGGTGGGGGCCGAAAGTACATGTTTCGCATGGGAACCCCAGACCCTGAGTACC
CAGATGACTACAGCCAAGGTGGGACCAGGCTGGACGGGAAGAATCTGGTGCAGGAATGGCTGGCGAAGCACCAGGG
TGCCCGGTACGTGTGGAACCGCACTGAGCTCATGCGGGCTTCCCTGGACCCGTCTGTGGCCCATCTCATGGGTCTC
TTTGAGCCTGGAGACATGAAATACGAGATCCACCGAGACTCCACACTGGACCCCTCCCTGATGGAGATGACAGAGG
CTGCCCTGCGCCTGCTGAGCAGGAACCCCCGCGGCTTCTTCCTCTTCGTCGGAGGGTGGTCGCATCGACCATGGTCA
TCATGAAAGCAGGGCTTACCGGGCACTGACTGAGACGATCATGTTCGACGACGCCATTGAGAGGCGGGCCAGCTC
ACCAGCGAGGAGGACACGCTGAGCCTCGTCACTCGCCGACCACTCCCACGTCTTCTCCTTCGGAGGCTGCCCCTGC
GAGGGGGCTCCATCTTCGGGCTGGCCCCTGGCAAGGCCGGGGACAGGAAGGCCTACACGGTCCTCCTATACGGAAA
CGGTCCAGGCTATGTGCTCAAGGACGGCGCCCGGCCGGATGTTACCGAGAGCGAGACGCGGAGCCCCGAGTATCGG
CAGCAGTCAGCAGTGCCCCTGGACGAAGAGACCCACGCAGGCGAGGACGTGGCGGTGTTCGCGCGCGGCCCGCAGG
CGGCACCTGGTTCACGGCGTGCAGGAGCAGACCTTCATAGCGCACGTCATGGCCTTCGCCGCCTGCCTGGAGCCCTA
CACCGCCTGCGACCTGGCGCCCCCGCCGGCACCACCGACGCGCGCACCCGGGGCGGTCCGTGGTCCCCGCGTTG
CTTCCTCTGCTGGCCGGGACCCTGCTGCTGCTGGAGACGGCCACTGCTCCCTGAGTGTCCCGTCCCTGGGGCTCCT
GCTTCCCCATCCCGGAGTTCTCCTGCTCCCCGCCTCCTGTCGTCCTGCCTGGCCTCCAGCCCGAGTCGTCATCCCC
GGAGTCCCTATACAGAGGTCCTGCCATGGAACCTTCCCCCTCCCCGTGCGCTCTGGGGACTGCAGCCCATGACACCAA
ACCTGCCCCTTGGCTGCTCTCGGACTCCCTACCCCAACCCCAGGGACAGATCTGGCCAGATTTGTAAAACAAATAG
ATTTTAGGCCCAAAGATTATTTAAAGCATTGCCTGGAACGCAGTGAGTTTTTGTTAGAAAAGAGAATAATTCAAAG
TGGCATTGCTTTGCTTCTTATGTTAATTTGGTACAGACCTGTGGCTGAGTTTGCTCAAAGTATTCAGAGCAGAATT
```

FIGURE 8 (cont.)

GTGGAGTCGAAAGAGAGATTGGACAAAGAGTTTAGTTTGTCAGTGTATCAAAAAATGAAGTTTAATGTGGCTATGG
GAATTGGAGTTTTAGATTGGCTAAGAAACAGTGATGATGATGATGACAGCCAGGAAAATGCTGATAAAAATGA
AGATGGTGGGGAGAAGAACATGGAAGACTCAGGGCATGAAACAGGCATTGATTCACAGTCCCAAGGCTCATTTCAG
GCCCCTCAGTCCTCACAGTCTGTTCATGATCATAATCAGCCATACCACATTTGTAGAGGTTTTACTTGCTTTAAAA
AACCTCCCACACCTCCCCCTGAACCTGAAACATAAAATGAATGCAATTGTTGTTGTTAACTTGTTTATTGCAGCTT
ATAATGGTTACAAATAAAGCAATAGCATCACAAATTTCACAAATAAAGCATTTTTTTCACTGCATTCTAGTTGTGG
TTTGTCCAAACTCATCAATGTATCTTATCATGTCTGGATCCCCAGGAAGCTCCTCTGTGTCCTCATAAACCCTAAC
CTCCTCTACTTGAGAGGACATTCCAATCATAGGCTGCCCATCCACCCTCTGTGTCCTCCTGTTAATTAGGTCACTT
AACAAAAAGGAAATTGGGTAGGGGTTTTTCACAGACCGCTTTCTAAGGGTAATTTTAAAATATCTGGGAAGTCCCT
TCCACTGCTGTGTTCCAGAAGTGTTGGTAAACAGCCCCACAAATGTCAACAGCAGAAACATACAAGCTGTCAGCTTT
GCACAAGGGGCCCAACACCCTGCTCATCAAGAAGCACTGTGGTTGCTGTGTTAGTAATGTGCAAAACAGGAGGCACA
TTTTCCCCACCTGTGTAGGTTCCAAAATATCTAGTGTTTTCATTTTTACTTGGATCAGGAACCCAGCACTCCACTG
GATAAGCATTATCCTTATCCAAAACAGCCTTGTGGTCAGTGTTCATCTGCTGACTGCCAACTGTAGCATTTTTTGG
GGTTACAGTTTGAGCAGGATATTTGGTCCTGTAGTTTGCTAACACACCCTGCAGCTCCAAAGGTTCCCCACCAACA
GCAAAAAATGAAAATTTGACCCTTGAATGGGTTTTCCAGCACCATTTTCATGAGTTTTTTGTGTCCCTGAATGCA
AGTTTAACATAGCAGTTACCCCAATAACCTCAGTTTTAACAGTAACAGCTTCCCACATCAAAATATTTCCACAGGT
TAAGTCCTCATTTAAATTAGGCAAAGGAATTCCACTTCCCACTGCCTTGCTTCCGTCTCCCATTCAAACTTTTATC
AACTGACATTATTCTAAGTAAAATCCTCTTCATTATGTTGTCAGCAATCCATTGCTTGAAGGCCTGGCTCCCCAGA
ACCCCTCGACTGGTATGTCTTCTCCTAGAATACTCCAGAAGAAAAGGAGTGTATGAAGATAGTGACTGCACATTAA
AATGACTGAAACCATAGTAAATTAGGATGAGATTCTGGGCAGATAAACAGACAGCTGGCTAGGATCATTTTTTAT
GCCTTGGACTTCTTTGGCAATCTGTTGAAGCCTGACATTCCTCAGAATAATGTTTTAAAGCCCAACAATAAGACCC
TGTAGCACATATAATAAGTACTGCAGTTTTGAAGTAGTGATAAGCATAAATGATATTTGATATATTTATTATAAC
TGTAATGAGATGTGTACATATCTGTGACTTCATAGGTACTGATTGTACTACTGTGATTTTTTGCCTACTTTCAAA
ATGAAAGGAATGCTTAATTTCAGTTAGAGGTTAGTAAAGACAAATAGGTAATTTTCTTCTCCAGTGAAGAGCATG
GCGCCCCTTGCTATTCATGGACGCTTGCTTAAAGACTTGTACACAGGCTTGCTTTGTATCAAGCTATGACTTCCCC
TTACAGCCGATGATAGGTTTTTATTTGCACCTCCTTCGTGTACAAAGACAGTTTTGGTGGCTACGCCATCATTAAA
CTCATTATTATCATGCTTAAGCCTATAGATGTATCCAGTTCTTCTGTTACATAATTGAAGCTGTAGTGAATTGTCT
ATCTTAAACTGCATCGCTAACTGACTACATTTCACACTTCATTTGCTTCCAACATAGACTAACCTTCTTGGATGTC
CACTATTATTTGAACTTTTGAGATTTTTTTCCTATTTCTAATATCTTAAAATTTCAGAAGACTTAAAGTTTTGCA
ACTACAGGGCTCCATATAGACATCTAGCTTGAATTTATACACTTTCTTTCATTGATGTCCCTGGACTAAAAATGT
TAAATATTTCTAACCGCTGTACTTAAAGTCCATTACAAACGAAGACTACTGTTGTTAAGTTGAATAGGCATCTTAT
ATATTTTTCACCGGTGCAATAAATAACTTCTATTCCCTTCTAACATCTGCTTGCGTTGCACTGAGAGTACACTATT
GATTAGCAATAGGTTCGTGATTACAGCCCTTCTAATTAATTGTTAGGTTAACATATTATTCATAAAATATTATT
TTATTAATTTTTACTTGATTTGCTACTGGATGCTTAGAAATAGCTATGAGTATATTGGTAGAACCAGTACTTATAT
TTTATTACATTTTTACATTTCATAAAATTTAAGTGATATAAAAATCCTGAGGAAGTATGCCACAAAAGTGGTCTCA
GTGGAAATTTAAATATGTTAACATTTATTTTTAAAATGTAGCGTGAAATAGACAACTTTAAAAGCTCAGCTTAAA
AAAAACTCAAGGAAGCTGAACTTGACTTTTTAAAGCACTGAAGTGCAATATTTAATGTAGGTCAACATGTTTAAA
TGGGAAAATTTTTTTCCTAATTACAGCCAAATCCCTAGCTGTAATTAACTTAAAATTTGTATACTATTTCACAACA
GAGTCAGCATATACCACTTTCTTATAAAATTAGAAAGATCTAAAATTTTAGAGCGTTATTTGGTGAAACAGGCATAT
TGCTACATCTTTGTTTATAAATTATAATGTGCCTTTAGAGCCCAATAACAGATAACAAGATTTTGAAAATTCAGGT
GAATTAGAGTTATCAGAGGGAATGTTAATACACTCTATTCAAATACTATATGAGTAAGACATTTAAAATAGGAAAC
AATACTTTATATATTAAAAAAATTAATCTTCCAGTCGATTTAATCCACTTTATGAATTCATTTAAATCGATTTAA
ATTCGAATTAATTAACTAGAGTACCCGGGGATCTTATTCGCTTAACTAATAAAAAAAATAATAAAGCATCACTT
ACTTAAAATCAGTTAGCAAATTTCTGTCCAGTTTATTCAGCAGCACCTCCTTGCCCTCCTCCCAGCTCTGGTATTG
CAGCTTCCTCCTGGCTGCAAACTTTCTCCACAATCTAAATGGAATGTCAGTTTCCTCCTGTTCCTGTCCATCCGCA
CCCACTATCTTCATGTTGTTGCAGATGAAGCGCGCAAGACCGTCTGAAGATACCCTCAACCCCGTGTATCCATATG
ACACGGAAACCGGTCCTCCAACTGTGCCTTTTCTTACTCCTCCCTTTGTATCCCGCAATGGGTTTCAAGAGAGTCC
CCCTGGGGTACTCTCTTTGCGCCTATCCGAACCTCTAGTTACCTCCAATGGCATGCTTGCGCTCAAAATGGGCAAC
GGCCTCTCTCTGGACGAGGCCGGCAACCTTACCTCCCAAAATGTAACCACTGTGAGCCCACCTCTCAAAAAAACCA
AGTCAAACATAAACCTGGAAATATCTGCACCCCTCACAGTTACCTCAGAAGCCCTAACTGTGGCTGCCGCCGCACC
TCTAATGGTCGCGGGCAACACACTCACCATGCAATCACAGGCCCCGCTAACCGTGCACGACTCCAAACTTAGCATT
GCCACCCAAGGACCCCTCACAGTGTCAGAAGGAAAGCTAGCCCTGCAAACATCAGGCCCCCTCACCACCACCGATA
GCAGTACCCTTACTATCACTGCCTCACCCCTCTAACTACTGCCACTGGTAGCTTGGGCATTGACTTGAAAGAGCC
CATTTATACACAAAATGCGAAAACTAGGACTAAAGTACGGGGCTCCTTTGCATGTAACAGACGACCTAAACACTTTG
ACCGTAGCAACTGGTCCAGGTGTGACTATTAATAATACTTCCTTGCAAACTAAAGTTACTGGAGCCTTGGGTTTTG
ATTCACAAGGCAATATGCAACTTAATGTAGCAGGAGGACTAAGGATTGATTCTCAAAACAGACGCCTTATACTTGA
TGTTAGTTATCCGTTTGATGCTCAAAACCAACTAAATCTAAGACTAGGACAGGGCCCTCTTTTTATAAAGTCAGCC
CACAACTTGGATATTAACTACAACAAAGGCCTTTACTTGTTTACAGCTTCAAACAATTCCAAAAAGCTTGAGGTTA
ACCTAAGCACTGCCAAGGGGTTGATGTTTGACGCTACAGCCATAGCCATTAATGCAGGAGATGGGCTTGAATTTGG
TTCACCTAATGCACCAAACACAAATCCCCTCAAAACAAAATTGGCCATGGCCTAGATTTGATTCAAACAGGCT
ATGGTTCCTAAACTAGGAACTGGCCCTTAGTTTTGACAGCACAGGTGCCATTACAGTAGGAAACAAAAATAATGATA

FIGURE 8 (cont.)

```
AGCTAACTTTGTGGACCACACCAGCTCCATCTCCTAACTGTAGACTAAATGCAGAGAAAGATGCTAAACTCACTTT
GGTCTTAACAAAATGTGGCAGTCAAATACTTGCTACAGTTTCAGTTTTGGCTGTTAAAGGCAGTTTGGCTCCAATA
TCTGGAACAGTTCAAAGTGCTCATCTTATTATAAGATTTGACGAAAATGGAGTGCTACTAAACAATTCCTTCCTGG
ACCCAGAATATTGGAACTTTAGAAATGGAGATCTTACTGAAGGCACAGCCTATACAAACGCTGTTGGATTTATGCC
TAACCTATCAGCTTATCCAAAATCTCACGGTAAAACTGCCAAAAGTAACATTGTCAGTCAAGTTTACTTAAACGGA
GACAAAACTAAACCTGTAACACTAACCATTACACTAAACGGTACACAGGAAACAGGAGACACAACTCCAAGTGCAT
ACTCTATGTCATTTTCATGGGACTGGTCTGGCCACAACTACATTAATGAAATATTTGCCACATCCTCTTACACTTT
TTCATACATTGCCCAAGAATAAAGAATCGTTTGTGTTATGTTTCAACGTGTTTATTTTTCAATTGCAGAAAATTTC
AAGTCATTTTTCATTCAGTAGTATAGCCCCACCACCACATAGCTTATACAGATCACCGTACCTTAATCAAACTCAC
AGAACCCTAGTATTCAACCTGCCACCTTCCTCCAACACACAGAGTACACAGTCCTTTCTCCCCGGCTGGCCTTAA
AAAGCATCATATCATGGGTAACAGACATATTCTTAGGTGTTATATTCCACACGGTTTCCTGTCGAGCCAAACGCTC
ATCAGTGATATTAATAAACTCCCCGGGCAGCTCACTTAAGTTCATGTCGCTGTCCAGCTGCTGAGCCACAGGCTGC
TGTCCAACTTGCGGTTGCTTAACGGGCGGCGAAGGAGAAGTCCACGCCTACATGGGGGTAGAGTCATAATCGTGCA
TCAGGATAGGGCGGTGGTGCTGCAGCAGCGCGCGAATAAACTGCTGCCGCCGCCGCTCCGTCCTGCAGGAATACAA
CATGGCAGTGGTCTCCTCAGCGATGATTCGCACCGCCCGCAGCATAAGGCGCCTTGTCCTCCGGGCACAGCAGCGC
ACCCTGATCTCACTTAAATCAGCACAGTAACTGCAGCACGCACCACAATATTGTTCAAAATCCCACAGTGCAAGG
CGCTGTATCCAAAGCTCATGGCGGGGACCACAGAACCCACGTGGCCATCATACCACAAGCGCAGGTAGATTAAGTG
GCGACCCCTCATAAACACGCTGGACATAAACATTACCTCTTTTGGCATGTTGTAATTCACCACCTCCCGGTACCAT
ATAAACCTCTGATTAAACATGGCGCCATCCACCACCATCCTAAACCAGCTGGCCAAAACCTGCCCGCCGGCTATAC
ACTGCAGGGAACCGGGACTGGAACAATGACAGTGGAGAGCCCAGGACTCGTAACCATGGATCATCATGCTCGTCAT
GATATCAATGTTGGCACAACACAGGCACACGTGCATACACTTCCTCAGGATTACAAGCTCCTCCCGCGTTAGAACC
ATATCCCAGGGAACAACCCATTCCTGAATCAGCGTAAATCCCACACTGCAGGGAAGACCTCGCACGTAACTCACGT
TGTGCATTGTCAAAGTGTTACATTCGGGCAGCAGCGGATGATCCTCCAGTATGGTAGCGCGGGTTTCTGTCTCAAA
AGGAGGTAGACGATCCCTACTGTACGGAGTGCCGCCGAGACAACCGAGATCGTGTTGGTCGTAGTGTCATGCCAAAT
GGAACGCCGGACGTAGTCATATTTCCTGAAGCAAAACCAGGTGCGGGCGTGACAAACAGATCTGCGTCTCCGGTCT
CGCCGCTTAGATCGCTCTGTGTAGTAGTTGTAGTATATCCACTCTCTCAAAGCATCCAGGCGCCCCCTGGCTTCGG
GTTCTATGTAAACTCCTTCATGCGCCGCTGCCCTGATAACATCCACCACCGCAGAATAAGCCACACCCAGCCAACC
TACACATTCGTTCTGCGAGTCACACACGGGAGGAGCGGGAAGAGCTGGAAGAACCATGTTTTTTTTTTATTCCAA
AAGATTATCCAAAACCTCAAAATGAAGATCTATTAAGTGAACGCGCTCCCCTCCGGTGGCGTGGTCAAACTCTACA
GCCAAAGAACAGATAATGGCATTTGTAAGATGTTGCACAATGGCTTCCAAAAGGCAAACGGCCCTCACGTCCAAGT
GGACGTAAAGGCTAAACCCTTCAGGGTGAATCTCCTCTATAAACATTCCAGCACCTTCAACCATGCCCAAATAATT
CTCATCTCGCCACCTTCTCAATATATCTCTAAGCAAATCCCGAATATTAAGTCCGGCCATTGTAAAAATCTGCTCC
AGAGCGCCCTCCACCTTCAGCCTCAAGCAGCGAATCATGATTGCAAAAATTCAGGTTCCTCACAGACCTGTATAAG
ATTCAAAAGCAGAACATTAACAAAAATACCGCGATCCCGTAGGTCCCTTCGCAGGGCCAGCTGAACATAATCGTGC
AGGTCTGCACGGACCAGCGCGGCCACTTCCCCGCCAGGAACCTTGACAAAAGAACCCACACTGATTATGACACGCA
TACTCGGAGCTATGCTAACCAGCGTAGCCCGATGTAAGCTTTGTTGCATGGGCGGCGATATAAAATGCAAGGTGC
TGCTCAAAAATCAGGCAAAGCCTCGCGCAAAAAGAAAGCACATCGTAGTCATGCTCATGCAGATAAAGGCAGGT
AAGCTCCGGAACCACCACAGAAAAAGACACCATTTTTCTCTCAAACATGTCTGCGGGTTTCTGCATAAACACAAA
TAAAATAACAAAAAAACATTTAAACATTAGAAGCCTGTCTTACAACAGGAAAAACAACCCTTATAAGCATAAGACG
GACTACGGCCATGCCGGCGTGACCGTAAAAAAACTGGTCACCGTGATTAAAAAGCACCACCGACAGCTCCTCGGTC
ATGTCCGGAGTCATAATGTAAGACTCGGTAAACACATCAGGTTGATTCATCGGTCAGTGCTAAAAAGCGACCGAAA
TAGCCCGGGGGAATACATACCCGCAGGCGTAGAGACAACATTACAGCCCCCATAGGAGGTATAACAAAATTAATAG
GAGAGAAAACACATAAACACCTGAAAAACCCTCCTGCCTAGGCAAAATAGCACCCTCCCGCTCCAGAACAACATA
CAGCGCTTCACAGCGGCAGCCTAACAGTCAGCCTTACCAGTAAAAAGAAAACCTATTAAAAAAACACCACTCGAC
ACGGCACCAGCTCAATCAGTCACAGTGTAAAAAAGGGCCAAGTGCAGAGCGAGTATATATAGGACTAAAAAATGAC
GTAACGGTTAAAGTCCACAAAAAACACCCAGAAAACCGCACGCGAACCTACGCCCAGAAACGAAAGCCAAAAACC
CACAACTTCCTCAAATCGTCACTTCCGTTTTCCCACGTTACGTCACTTCCCATTTTAAGAAAACTACAATTCCCAA
CACATACAAGTTACTCCGCCCTAAAACCTACGTCACCCGCCCCGTTCCCACGCCCCGCGCCACGTCACAAACTCCA
CCCCCTCATTATCATATTGGCTTCAATCCAAAATAAGGTATATTATTGATGATG
```

FIGURE 9 (pBSX sequence, SEQ ID NO:12)

```
CTAAATTGTAAGCGTTAATATTTTGTTAAAATTCGCGTTAAATTTTTGTTAAATCAGCTCATTTTTTAACCAATAG
GCCGAAATCGGCAAAATCCCTTATAAATCAAAAGAATAGACCGAGATAGGGTTGAGTGTTGTTCCAGTTTGGAACA
AGAGTCCACTATTAAAGAACGTGGACTCCAACGTCAAAGGGCGAAAAACCGTCTATCAGGGCGATGGCCCACTACG
TGAACCATCACCCTAATCAAGTTTTTTGGGGTCGAGGTGCCGTAAAGCACTAAATCGGAACCCTAAAGGGAGCCCC
CGATTTAGAGCTTGACGGGGAAAGCCGGCGAACGTGGCGAGAAAGGAAGGGAAGAAAGCGAAAGGAGCGGGCGCTA
GGGCGCTGGCAAGTGTAGCGGTCACGCTGCGCGTAACCACCACACCCGCCGCGCTTAATGCGCCGCTACAGGGCGC
GTCCCATTCGCCATTCAGGCTGCGCAACTGTTGGGAAGGGCGATCGGTGCGGGCCTCTTCGCTATTACGCCAGCTG
GCGAAAGGGGGATGTGCTGCAAGGCGATTAAGTTGGGTAACGCCAGGGTTTTCCCAGTCACGACGTTGTAAAACGA
CGGCCAGTGAGCGCGCGTAATACGACTCACTATAGGGCGAATTGGAGCTTACGTATTAATTAAGGCGCGCGGTGG
CGGCCGCTCTAGAACTAGTGGATCCCCCGGGCTGCAGGAATTCGGCCGCCTAGGCCACGCGTAAGCTTATCGATAC
CGTCGACCTCGAGGGGGGGCCCGGTACCCAGCTTTTGTTCCCTTTAGTGAGGGTTAATTGCGCGCTTGGCGTAATC
ATGGTCATAGCTGTTTCCTGTGTGAAATTGTTATCCGCTCACAATTCCACACAACATACGAGCCGGAAGCATAAAG
TGTAAAGCCTGGGGTGCCTAATGAGTGAGCTAACTCACATTAATTGCGTTGCGCTCACTGCCCGCTTTCCAGTCGG
GAAACCTGTCGTGCCAGCTGCATTAATGAATCGGCCAACGCGCGGGGAGAGGCGGTTTGCGTATTGGGCGCTCTTC
CGCTTCCTCGCTCACTGACTCGCTGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAAAGGCCAGCAAAAGGCCAGGAACC
GTAAAAAGGCCGCGTTGCTGGCGTTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCCACTGGCAGCAGCC
ACTGGTAACAGGATTAGCAGAGCGAGGTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTGTTTGCAAGCAGCAGATTACGCGCAGAAAAAAAGGA
TCTCAAGAAGATCCTTTGATCTTTTCTACGGGGTCTGACGCTCAGTGGAACGAAAACTCACGTTAAGGGATTTTGG
TCATGAGATTATCAAAAAGGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTCAGCGATCTGTCTATTTCGT
TCATCCATAGTTGCCTGACTCCCCGTCGTGTAGATAACTACGATACGGGAGGGCTTACCATCTGGCCCCAGTGCTG
CAATGATACCGCGAGACCCACGCTCACCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGGCTT
CATTCAGCTCCGGTTCCCAACGATCAAGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCATGGTTATGGCAGCACTGCATAATTCT
CTTACTGTCATGCCATCCGTAAGATGCTTTTCTGTGACTGGTGAGTACTCAACCAAGTCATTCTGAGAATAGTGTA
TGCGGCGACCGAGTTGCTCTTGCCCGGCGTCAATACGGGATAATACCGCGCCACATAGCAGAACTTTAAAAGTGCT
CATCATTGGAAAACGTTCTTCGGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTGAGCAAAAACAGGAAGGCAAA
ATGCCGCAAAAAAGGGAATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAAACAAATAGGGGTTCCG
CGCACATTTCCCCGAAAAGTGCCAC
```

FIGURE 11 ΔFseI.4 (SEQ ID NO:9)

```
CATCATCAATAATATACCTTATTTTGGATTGAAGCCAATATGATAATGAGGGGGTGGAGTTTGTGACGTGGCGCGG
GGCGTGGGAACGGGGCGGGTGACGTAGTAGTGTGGCGGAAGTGTGATGTTGCAAGTGTGGCGGAACACATGTATAA
CTTCGTATAATGTATGCTATACGAAGTTATACATGTAAGCGACGGATGTGGCAAAAGTGACGTTTTTGGTGTGCGC
CGGTGTACACAGGAAGTGACAATTTTCGCGCGGTTTTAGGCGGATGTTGTAGTAAATTTGGGCGTAACCGAGTAAG
ATTTGGCCATTTTCGCGGGAAAACTGAATAAGAGGAAGTGAAATCTGAATAATTTTGTGTTACTCATAGCGCGTAA
TATTTGTCTAGGGAGATCTATAACTTCGTATAATGTATGCTATACGAAGTTATTACCGAAGAAATGGCTCGAGATC
TGGAAGGTGCTGAGGTACGATGAGACCCGCACCAGGTGCAGACCCTGCGAGTGTGGCGGTAAACATATTAGGAACC
AGCCTGTGATGCTGGATGTGACCGAGGAGCTGAGGCCCGATCACTTGGTGCTGGCCTGCACCCGCGCTGAGTTTGG
CTCTAGCGATGAAGATACAGATTGAGGTACTGAAATGTGTGGGCGTGGCTTAAGGGTGGGAAAGAATATATAAGGT
GGGGGTCTTATGTAGTTTTGTATCTGTTTTGCAGCAGCCGCCGCCGCCATGAGCACCAACTCGTTTGATGGAAGCA
TTGTGAGCTCATATTTGACAACGCGCATGCCCCCATGGGCGGGGGTGCGTCAGAATGTGATGGGCTCCAGCATTGA
TGGTCGCCCGTCCTGCCCGCAAACTCTACTACCTTGACCTACGAGACCGTGTCTGGAACGCCGTTGGAGACTGCA
GCCTCCGCCGCCGCTTCAGCCGCTGCAGCCACCGCCCGCGGATTGTGACTGACTTTGCTTTCCTGAGCCCGCTTG
CAAGCAGTGCAGCTTCCGTTCATCCGCCCGCGATGACAAGTTGACGGCTCTTTTGGCACAATTGGATTCTTTGAC
CCGGGAACTTAATGTCGTTTCTCAGCAGCTGTTGGATCTGCGCCAGCAGGTTTCTGCCCTGAAGGCTTCCTCCCT
CCCAATGCGGTTTAAAACATAAATAAAAAACCAGACTCTGTTTGGATTTGGATCAAGCAAGTGTCTTGCTGTCTTT
ATTTAGGGGTTTTGCGCGCGCGGTAGGCCCGGGACCAGCGGTCTCGGTCGTTGAGGGTCCTGTGTATTTTTTCCAG
GACGTGGTAAAGGTGACTCTGGATGTTCAGATACATGGGCATAAGCCCGTCTCTGGGGTGGAGGTAGCACCACTGC
AGAGCTTCATGCTGCGGGGTGGTGTTGTAGATGATCCAGTCGTAGCAGGAGCGCTGGGCGTGGTGCCTAAAAATGT
CTTTCAGTAGCAAGCTGATTGCCAGGGGCAGGCCCTTGGTGTAAGTGTTTACAAAGCGGTTAAGCTGGGATGGGTG
CATACGTGGGATATGAGATGCATCTTGGACTGTATTTTAGGTTGGCTATGTTCCCAGCCATATCCCTCCGGGGA
TTCATGTTGTGCAGAACCACCAGCACAGTGTATCCGGTGCACTTGGGAAATTTGTCATGTAGCTTAGAAGGAAATG
CGTGGAAGAACTTGGAGACGCCCTTGTGACCTCCAAGATTTTCCATGCATTCGTCCATAATGATGGCAATGGCCC
ACGGGCGGCGGCCTGGGCGAAGATATTTCTGGGATCACTAACGTCATAGTTGTGTTCCAGGATGAGATCGTCATAG
GCCATTTTTACAAAGCGCGGGCGGAGGGTGCCAGACTGCGGTATAATGGTTCCATCCGGCCCAGGGGCGTAGTTAC
CCTCACAGATTTGCATTTCCCACGCTTTGAGTTCAGATGGGGGATCATGTCTACCTGCGGGGCGATGAAGAAAAC
GGTTTCCGGGGTAGGGGAGATCAGCTGGGAAGAAAGCAGGTTCCTGAGCAGCTGCGACTTACCGCAGCCGGTGGGC
CCGTAAATCACACCTATTACCGGGTGCAACTGGTAGTTAAGAGAGCTGCAGCTGCCGTCATCCCTGAGCAGGGGGG
CCACTTCGTTAAGCATGTCCCTGACTCGCATGTTTCCCTGACCAAATCCGCCAGAAGGCGCTCGCCGCCCAGCGA
TAGCAGTTCTTGCAAGGAAGCAAAGTTTTTCAACGGTTTGAGACCGTCCGCCGTAGGCATGCTTTTGAGCGTTTGA
CCAAGCAGTTCCAGGCGGTCCCACAGCTCGGTCACCTGCTCTACGGCATCTCGATCCAGCATATCTCCTCGTTTCG
CGGGTTGGGGCGGCTTTCGCTGTACGGCAGTAGTCCGTGCTCGTCCAGACGGGCCAGGGTCATGTCTTTCCACGGG
CGCAGGGTCCTCGTCAGCGTAGTCTGGGTCACGGTGAAGGGGTGCGCTCCGGGCTGCGCGCTGGCCAGGGTGCGCT
TGAGGCTGGTCCTGCTGGTGCTGAAGCGCTGCCGGTCTTCGCCCTGCGCGTCGGCCAGGTAGCATTTGACCATGGT
GTCATAGTCCAGCCCCTCCGCGGCGTGGCCCTTGGCGCGCAGCTTGCCCTTGGAGGAGGCGCCGCACGAGGGCAG
TGCAGACTTTGAGGGCGTAGAGCTTGGGCGCGAGAAATACCGATTCGGGCGGAGTAGGCATCCGCGCCGCAGGCCC
CGCAGACGGTCTCGCATTCCACGAGCCAGGTGAGCTCTGCCGTTCGGGGTCAAAAACCAGGTTTCCCCCATGCTT
TTTGATGCGTTTCTTACCTCTGGTTTCCATGAGCCGGTGTCCACGCTCGGTGACGAAAAGGCTGTCCGTGTCCCG
TATACAGACTTGAGAGGCCTGTCCTCGAGCGGTGTTCCGCGGTCCTCCTCGTATAGAAACTCGGACCACTCTGAGA
CAAAGGCTCGCGTCCAGGCCAGCACGAAGGAGGCTAAGTGGAGGGGTAGCGGTCGTTGTCCACTAGGGGGTCCAC
TCGCTCCAGGGTGTGAAGACACATGTCGCCCTCTTCGGCATCAAGGAAGGTGATTGGTTTGTAGGTGTAGGCCACG
TGACCGGGTGTTCCTGAAGGGGGGCTATAAAAGGGGTGGGGGCGCGTTCGTCCTCACTCTCTTCCGCATCGCTGT
CTGCGAGGGCCAGCTGTTGGGGTGAGTACTCCCTCTGAAAAGCGGGCATGACTTCTGCGCTAAGATTGTCAGTTTC
CAAAAACGAGGAGGATTTGATATTCACCTGGCCCGCGGTGATGCCTTTGAGGGTGGCCGCATCCATCTGGTCAGAA
AAGACAATCTTTTTGTTGTCAAGCTTGGTGGCAAACGACCCGTAGAGGGCGTTGGACAGCAACTTGGCGATGGAGC
GCAGGGTTTGGTTTTTGTCGCGATCGGCGCGCTCCTTGGCCGCGATGTTTAGCTGCACGTATTCGCGCGCAACGCA
CCGCCATTCGGGAAAGACGGTGGTGCGCTCGTCGGGCACCAGGTGCACGCGCCAACGCGGTTGTGCAGGGTGACA
AGGTCAACGCTGGTGGCTACCTCTCCGCGTAGCGCTCGTTGGTCCAGCAGAGGCGGCCGCCCTTGCGCGAGCAGA
ATGGCGGTAGGGGTCTAGCTGCGTCTCGTCCGGGGGTCTGCGTCCACGGTAAAGACCCCGGGCAGCAGGCGCGC
GTCGAAGTAGTCTATCTTGCATCCTTGCAAGTCTAGCGCCTGCTGCCATGCGCGGGCGGCAAGCGCGCGCTCGTAT
GGGTTGAGTGGGGGACCCCATGGCATGGGTGGGTGAGCGCGGAGGCGTACATGCCGCAAATGTCGTAAACGTAGA
GGGGCTCTCTGAGTATTCCAAGATATGTAGGGTAGCATCTTCCACCGCGGATGCTGGCGCGCACGTAATCGTATAG
TTCGTGCCGAGGGAGCGAGGGAGGTCGGGACCGAGGTTGCTACGGCGGGCTGCTCTGCTCGGAAGACTATCTGCCTG
AAGATGGCATGTGAGTTGGATGATATGGTTGGACGCTGGAAGACGTTGAAGCTGGCGTCTGTGAGACCTACCGCGT
CACGCACGAAGGAGGCGTAGGAGTCGCGCAGCTTGTTGACCAGCTCGGCGGTGACCTGCACGTCTAGGGCGCAGTA
GTCCAGGGTTTCCTTGATGATGTCATACTTATCCTGTCCCTTTTTTTTCCACAGCTCGCGGTTGAGGACAAACTCT
TGCGCGTCTTTCCAGTACTCTTGGATCGGAAACCCGTCGGCCTCCGAACGGTAAGAGCCTAGCATGTAGAACTGGT
TGACGCCTGGTAGGCGCAGCATCCCTTTTCTACGGGTAGCGCGTATGCCTGCGCGGCCTTCCGGAGCGAGGTGTG
GGTGAGCGCAAAGGTGTCCCTGACCATGACTTTGAGGTACTGGTATTTGAAGTCAGTGTCGTCGCATCCGCCCTGC
TCCCAGAGCAAAAAGTCCGTGCGCTTTTTGGAACGCGGATTTGGCAGGGCGAAGGTGACATCGTTGAAGAGTATCT
TTCCCGCGCGAGGCATAAAGTTGCGTGTGATGCGGAAGGGTCCCGGCACCTCGGAACGGTTGTTAATTACCTGGGC
```

FIGURE 11 (cont.)

```
GGCGAGCACGATCTCGTCAAAGCCGTTGATGTTGTGGCCCACAATGTAAAGTTCCAAGAAGCGCGGGATGCCCTTG
ATGGAAGGCAATTTTTTAAGTTCCTCGTAGGTGAGCTCTTCAGGGGAGCTGAGCCCGTGCTCTGAAAGGGCCCAGT
CTGCAAGATGAGGGTTGGAAGCGACGAATGAGCTCCACAGGTCACGGGCCATTAGCATTTGCAGGTGGTCGCGAAA
CGTCCTAAACTGGCGACCTATGGCCATTTTTTCTGGGGTGATGCAGTAGAAGGTAAGCGGGTCTTGTTCCCAGCGG
TCCCATCCAAGGTTCGCGGCTAGGTCTCGCGCGGCAGTCACTAGAGGCTCATCTCCGCCGAACTTCATGACCAGCA
TGAAGGGCACGAGCTGCTTCCCAAAGGCCCCCATCCAAGTATAGGTCTCTACATCGTAGGTGACAAAGAGACGCTC
GGTGCGAGGATGCGAGCCGATCGGGAAGAACTGGATCTCCGCCACCAATTGGAGGAGTGGCTATTGATGTGGTGA
AAGTAGAAGTCCCTGCGACGGGCCGAACACTCGTGCTGGCTTTTGTAAAAACGTGCGCAGTACTGGCAGCGGTGCA
CGGGCTGTACATCCTGCACGAGGTTGACCTGACGACCGCGCACAAGGAAGCAGAGTGGGAATTTGAGCCCCTCGCC
TGCCGGGTTTGGCTGGTGGTCTTCTACTTCGGCTGCTTGTCCTTGACCGTCTGGCTGCTCGAGGGGAGTTACGGTG
GATCGGACCACCACGCCGCGCGAGCCCAAAGTCCAGATGTCCGCGCGCGGCGGTCGGAGCTTGATGACAACATCGC
GCAGATGGGAGCTGTCCATGGTCTGGAGCTCCGCGGCGTCAGGTCAGGCGGGAGCTCCTGCAGGTTTACCTCGCA
TAGACGGGTCAGGGCGCGGGCTAGATCCAGGTCATACCTAATTTCCAGGGGCTGGTTGGTGGCGGCGTCGATGGCT
TGCAAGAGGCCGCATCCCGCGGCGCGACTACGGTACCGCGCGGCGGGCGGTGGGCCGCGGGGGTGTCCTTGGATG
ATGCATCTAAAAGCGGTGACGCGGGCGAGCCCCCGGAGGTAGGGGGGGCTCCGGACCCGCCGGGAGAGGGGGCAGG
GGCACGTCGGCGCCGCGCGCGGGCAGGAGCTGGTGCTGCGCGCGTAGGTTGCTGGCGAACGCGACGACGCGGCGGT
TGATCTCCTGAATCTGGCGCCTCTGCGTGAAGACGACGGGCCCGGTGAGCTTGAGCCTGAAAGAGAGTTCGACAGA
ATCAATTTCGGTGTCGTTGACGGCGGCCTGGCGCAAAATCTCCTGCACGTCTCCTGAGTTGTCTTGATAGGCGATC
TCGGCCATGAACTGCTCGATCTCTTCCTCCTGGAGATCTCCGCGTCCGGCTCGCTCCACGGTGGCGGCGAGGTCGT
TGGAAATGCGGGCCATGAGCTGCGAGAAGGCGTTGAAGGCCTCCCTGCGTTCCAGACGCGGCTGTAGACCACGCCCC
TTCGGCATCGCGGGCGCGCATGACCACCTGCGCGAGATTGAGCTCCACGTGCCGGGCGAAGACGGCGTAGTTTCGC
AGGCGCTGAAAGAGGTAGTTGAGGGTGGTGGCGGTGTGTTCTGCCACGAAGAAGTACATAACCCAGCGTCGCAACG
TGGATTCGTTGATATCCCCAAGGCCTCAAGGCGCTCCATGGCCTCGTAGAAGTCCACGGCGAAGTTGAAAAACTG
GGAGTTGCGCGCCGACACGGTTAACTCCTCCTCCAGAAGACGGATGAGCTCGGCGACAGTGTCGCGCACCTCGCGC
TCAAAGGCTACAGGGGCCTCTTCTTCTTCTTCAATCTCCTCTTCCATAAGGGCCTCCCCTTCTTCTTCTTCTGGCG
GCGGTGGGGAGGGGGACACGGCGGCGACGACGGCGCACCGGGAGGCGGTCGACAAAGCGCTCGATCATCTCCCC
GCGGCGACGGCGCATGGTCTCGGTGACGGCGCGGCCGTTCTCGCGGGGGCGCAGTTGGAAGACGCCGCCCGTCATG
TCCCGGTTATGGGTTGGCGGGGGCTGCCATGCGGCAGGGATACGGCGCTAACGATGCATCTCAACAATTGTTGTG
TAGGTACTCCGCCGCCGAGGGACCTGAGCGAGTCCGCATCGACCGGATCGGAAAACCTCTCGAGAAAGGCGTCTAA
CCAGTCACAGTCGCAAGGTAGGCTGAGCACCGTGGCGGGCGGCAGCGGGCGGCGGTCGGGGTTGTTTCTGGCGGAG
GTGCTGCTGATGATGTAATTAAAGTAGGCGGTCTTGAGACGGCGGATGGTCGACAGAAGCACCATGTCCTTGGGTC
CGGCCTGCTGAATGCGCAGGCGGTCGGCCATGCCCCAGGCTTCGTTTTGACATCGCGCCAGGTCTTTGTAGTAGTC
TTGCATGAGCCTTTCTACCGGCACTTCTTCTTCTCCTTCCTCTTGTCCTGCATCTCTTGCATCTATCGCTGCCGCG
GCGGCGGAGTTTGGCCGTAGGTGGCGCCCTCTTCCTCCCATGCGTGTGACCCCGAAGCCCCTCATCGGCTGAAGCA
GGGCTAGGTCGGCGACAACGCGCTCGGCTAATATGGCCTGCTGCACCTGCGTGAGGGTAGACTGGAAGTCATCCAT
GTCCACAAAGCGGTGGTATGCGCCCGTGTTGATGGTGTAAGTGCAGTTGGCCATAACGGACCAGTTAACGGTCTGG
TGACCCGGCTGCGAGAGCTCGGTGTACCTGACACGCGAGTAAGCCCTCGAGTCAAATACGTAGTCGTTGCAAGTCC
GCACCAGGTACTGGTATCCCACCAAAAAGTGCGGCGGCGGCTGGCGGTAGAGGGGCCAGCGTAGGGTGGCCGGGGC
TCCGGGGGCGAGATCTTCCAACATAAGGCGATGATATCCGTAGATGTACCTGGACATCCAGGTGATGCCGCCGGCG
GTGGTGGAGGCGCGCGGAAAGTCGCGGACGCGGTTCCAGATGTTGCGCAGCGGCAAAAAGTGCTCCATGGTCGGGA
CGCTCTGGCCGGTCAGGCGCGCGCAATCGTTGACGCTCTACCGTGCAAAAGGAGAGCCTGTAAGCGGGCACTCTTC
CGTGGTCTGGTGGATAAATTCGCAAGGGTATCATGGCGGACGACGCGGGGTTCGAGCCCCGTATCCGGCCGTCCGCC
GTGATCCATGCGGTTACCGCCCGCGTGTCGAACCCAGGTGTGCGACGTCAGCAACGGGGAGTGCTCCTTTTGGC
TTCCTTCAGGCGCGGCGGCTGCTGCGCTAGCTTTTTTGGCCACTGGCCGCGCGCAGCGTAAGCGGTTAGGCTGGA
AAGCGAAAGCATTAAGTGGCTCGCTCCCTGTAGCCGGAGGGTTATTTTCCAAGGGTTGAGTCGCGGGACCCCCGGT
TCGAGTCTCGGACCGGCCGGACTGCGGCGAACGGGGTTTGCCTCCCCGTCATGCAAGACCCCGCTTGCAAATTCC
TCCGGAAACAGGGACCAGCCCCTTTTTTGCTTTTCCAGATGCATCCGGTGCTGCCGCAGATGCGCCCCCTCCTC
AGCAGCGGCAAGAGCAAGAGCAGCGGCAGACATGCAGGGCACCCTCCCCTCCTCCTACCGCGTCAGGAGGGCGAC
ATCCGCGGTTGACGCGGCAGCAGATGGTGATTACGAACCCCGCGGCGCCGGGCCCGGCACTACCTGGACTTGGAG
GAGGGCGAGGGCCTGGCGCGGCTAGGAGCGCCCTCTCCTGAGCGGTACCCAAGGGTGCAGCTGAAGCGTGATACGC
GTGAGGCGTACGTGCCGGGCAGAACCTGTTTCGCGACCCGCGAGGGAGAGGAGCCCGAGGAGATGCGGGATCGAAA
GTTCCACGCAGGGCGCGAGCTGCCGCATGGCCTGAATCGGCAGCGGTTGCTGCGCGAGGAGGACTTTGAGCCCGAC
GCGCGAACCGGGATTAGTCCCGCCGCGCACACGTGGCGGCCGCCGACCTGGTAACCGCATACGAGCAGACGGTGA
ACCAGGAGATTAACTTTCAAAAAAGCTTTAACAACCACGTGCGTACGCTTGTGGCGCGCGAGGAGGTGGCTATAGG
ACTGATGCATCTGTGGGACTTTGTAAGCGCGCTGGAGCAAAACCCAAATAGCAAGCCGCTCATGCGCAGCTGTTC
CTTATAGTGCAGCACAGCAGGGACAACGAGGCATTCAGGGATGCGCTGCTAAACATAGTAGAGCCCGAGGGCCGCT
GGCTGCTCGATTTGATAAACATCCTGCAGAGCATAGTGGTGCAGGAGCGCAGCTTGAGCCTGGCTGACAAGGTGGC
CGCCATCAACTATTCCATGCTTAGCCTGGGCAAGTTTTACGCCCGCAAGATATACCATACCCCTTACGTTCCCATA
GACAAGGAGGTAAAGATCGAGGGGTTCTACATGCGCATGGCGCTGAAGGTGCTTACCTTGAGCGACGACCTGGCCG
TTTATCGCAACGAGCGCATCCACAAGGCCGTGAGCGTGAGCCGGCGGCGCGAGCTCAGCGACGCGAGCTGATGCA
CAGCCTGCAAAGGGCCCTGGCTGGCACGGGCAGCGGCGATAGAGAGGCCGAGTCCTACTTTGACGCGGGCGCTGAC
```

FIGURE 11 (cont.)

```
CTGCGGTGGGCCCCAAGCCGACGCGCCCTGGAGGCAGCTGGGGCCGGACCTGGGCTGGCGGTGGCACCCGCGCGCG
CTGGCAACGTCGGCGGCGTGGAGGAATATGACGAGGACGATGAGTACGAGCCAGAGGACGGCGAGTACTAAGCGGT
GATGTTTCTGATCAGATGATGCAAGACGCAACGGACCCGGCGGTGCGGGCGGCGCTGCAGAGCCAGCCGTCCGGCC
TTAACTCCACGGACGACTGGCGCCAGGTCATGGACCGCATCATGTCGCTGACTGCGCGCAATCCTGACGCGTTCCG
GCAGCAGCCGCAGGCCAACCGGCTCTCCGCAATTCTGGAAGCGGTGGTCCCGGCGCGCGCAAACCCCACGCACGAG
AAGGTGCTGGCCGATCGTAAACGCGCTGGCCGAAAACAGGGCCATCCGGCCCGACGAAGCCGGCCTGGTCTACGACG
CGCTGCTTCAGCGCCTGGCTCGTTACAACAGCGGCAACGTGCAGACCAACCTGGACCGGCTGGTGGGGATGTGCG
CGAGGCCGTGGCGCAGCGTGAGCGCGCGCAGCAGCAGGGCAACCTGGGCTCCATGGTTGCACTAAACGCCTTCCTG
AGTACACAGCCCGCCAACGTGCCGCGGGGACAGGAGGACTACACCAACTTTGTGAGCGCACTGCGGCTAATGGTGA
CTGAGACACCGCAAAGTGAGGTGTACCAGTCTGGGCCAGACTATTTTTTCCAGACCAGTAGACAAGGCCTGCAGAC
CGTAAACCTGAGCCCAGGCTTTCAAAAACTTGCAGGGGCTGTGGGGGGTGCGGGCTCCCACAGGCGACGGCGCGACC
GTGTCTAGCTTGCTGACGCCCAACTCGCGCCTGTTGCTGCTGCTAATAGCGCCCTTCACGGACAGTGGCAGCGTGT
CCCCGGGACACATACCTAGGTCACTTGCTGACACTGTACCGCGAGGCCATAGGTCAGGCGCATGTGGACGAGCATAC
TTTCCAGGAGATTACAAGTGTCAGCCGCGCGCTGGGCAGGAGGACACGGGCAGCCTGGAGGCAACCCTAAACTAC
CTGCTGACCAACCGGCGGCAGAAGATCCCCTCGTTGCACAGTTTAAACAGCGAGGAGGAGCGCATTTTGCGCTACG
TGCAGCAGAGCGTGAGCCTTAACCTGATGCGCGACGGGGTAACGCCCAGCGTGGCGCTGGACATGACCGCGCGCAA
CATGGAACCGGGCATGTATGCCTCAAACCGGCCGTTTATCAACCGCCTAATGGACTACTTGCATCGCGCGGCCGCC
GTGAACCCCGAGTATTTCACCAATGCCATCTTGAACCCGCACTGGCTACCGCCCCTGGTTTCTACACCGGGGGAT
TCGAGGTGCCCGAGGGTAACGATGGATTCCTCTGGGACGACATAGACGACAGCGTGTTTCCCCGCAACCGCAGAC
CCTGCTAGAGTTGCAACAGCGCGAGCAGGCAGAGGCGGCGCTGCGAAAGGAAAGCTTCCGCAGGCCAAGCAGCTTG
TCCGATCTAGGCGCTGCGGCCCGCGGTCAGATGCTAGTAGCCCATTTCCAAGCTTGATAGGGTCTCTTACCAGCA
CTCGCACCACCCGCCCGCGCCTGCTGGGCGAGGAGGAGTACCTAAACAACTCGCTGCTGCAGCCGCAGCGCGAAAA
AAACCTGCCTCCGGCATTTCCCAACAACGGGATAGAGAGCCTAGTGGACAAGATGAGTAGATGGAAGACGTACGCG
CAGGAGCACAGGGACGTGCCAGGCCCGCGCCCGCCCACCCGTCGTCAAAGGCACGACCGTCAGCGGGGTCTGGTGT
GGGAGGACGATGACTCGGCAGACGACAGCAGCGTCCTGGATTTGGGAGGGAGTGGCAACCCGTTTGCGCACCTTCG
CCCCAGGCTGGGGAGAATGTTTAAAAAAAAAAAAGCATGATGCAAAATAAAAAAACTCACCAAGGCCATGCACCG
AGCGTTGGTTTCTTGTATTCCCCTTAGTATGCGGCGCGCGGCGATGTATGAGGAAGGTCCTCCTCCCTCCTACGA
GAGTGTGGTGAGCGCGGCGCCAGTGGCGGCGGCGCTGGGTTCTCCCTTCGATGCTCCCCTGGACCCGCCGTTTGTG
CCTCCGCGGTACCTGCGGCCTACCGGGGGAGAAACAGCATCCGTTACTCTGAGTTGGCACCCCTATTCGACACCA
CCCGTGTGTACCTGGTGGACAACAAGTCAACGGATGTGGCATCCTGAACTACCAGAACGACCACAGCAACTTTCT
GACCACGGTCATTCAAACAATGACTACAGCCGGGGGAGGCAAGCACACAGACCATCAATCTTGACGACCGGTCG
CACTGGGGCGGCGACCTGAAAACCATCCTGCATACCAACATGCCAAATGTGAACGAGTTCATGTTTACCAATAAGT
TTAAGGCGCGGGTGATGGTGTCGCGCTTGCCTACTAAGGACAATCAGGTGGAGCTGAAATACCAGTGGGTGGAGTT
CACGCTGCCCGAGGCAACTACTCCGAGACCATGACCATAGACCTTATGAACAACGCGATCGTGGAGCACTACTTG
AAAGTGGGCAGACAGAACGGGGTTCTGGAAAGCGACATCGGGGTAAAGTTTGACACCGGCAACTTCAGACTGGGGT
TTGACCCCGTCACTGGTCTTGTCATGCCTGGGGTATATACAAACGAAGCCTTCCATCCAGACATCATTTTGCTGCC
AGGATGCGGGGTGGACTTCACCCACAGCCGCCTGAGCAACTTGTTGGGCATCCGCAAGCGGCAACCCTTCCAGGAG
GGCTTTAGGATCACCTACGATGATCTGGAGGGTGGTAACATTCCCGCACTGTTGGATGTGGACGCCTACCAGGCGA
GCTTGAAAGATGACACCGAACAGGGCGGGGGTGGCGCAGGCGGCAGCAACAGCAGTGGCGGCGCGGAAGAGAA
CTCCAACGGCAGCCGCGGCAATGCAGGCGGTGGAGGACATGAACGATCATGCCATTCGCGGCGACACCTTTGCC
ACACGGGCTGAGGAGAAGCGCGCTGAGGCCGAAGCAGCGGCCGAAGCTGCCGCCCCGCTGCGCAACCCGAGGTCG
AGAAGCCTCAGAAGAAACCGGTGATCAAACCCCTGACAGAGGACAGCAAGAAACGCAGTTACAACCTAATAAGCAA
TGACAGCACCTTCACCCAGTACCGCAGCTGGTACCTTGCATACAACTACGGCGACCCTCAGACCGGAATCCGCTCA
TGGACCCTGCTTTGCACTCCTGACGTAACCTGCGGCTCGGAGCAGGTCTACTGGTCGTTGCCAGACATGATGCAAG
ACCCCCGTGACCTTCCGCTCCACGCGCCAGATCAGCAACTTTCCGGTGGTGGGCGCCGAGCTGTTGCCCGTGCACTC
CAAGAGCTTCTACAACGACCAGGCCGTCTACTCCCAACTCATCCGCCAGTTTACCTCTCTGACCCACGTGTTCAAT
CGCTTTCCCGAGAACCAGATTTTGGCGCGCCCGCCAGCCCCACCATCACCACCGTCAGTGAAAACGTTCCTGCTC
TCACAGATCACGGGACGCTACCGCTGCGCAACAGCATCGGAGAGTCCAGCGAGTGACCATTACTGACGCCAGACG
CCGCACCTGCCCCTACGTTTACAAGGCCCTGGGCATAGTCTGCCGCGACGGTCCTATCGAGCCGGCACTTTTTGAGCA
AGCATGTCCATCCTTATATCGCCCAGCCAATAACACAGGCTGGGGCCTGCGCTTCCCAAGCAAGATGTTTGGCGGGG
CCAAGGAGCGGCTCCGACCAACACCCAGTGCGCGTGCGCGGGCACTACCGCGCGCCCTGGGGCGCGCACAAACGCGG
CCGCACTGGCGCACCACCGTCGATGACGCCATCGACGCGGTGGTGGAGGAGGCGCGCAACTACACGCCCACGCCG
CCACCAGTGTCCACAGTGGACGCGGCCATTCAGACCGTGGTGCGCGGAGCCCGGCGCTATGCTAAAATGAAGAGAC
GGCGGAGGCGCGTAGCACGTCGCCACCGCCGCCGACCCGGCACTGCCGCCAACGCGCGGCGGCGGCCCTGCTTAA
CCGCGCACGTCGCACCGGCCGACGGGCGGCCATGCGGGCCGCTCGAAGGCTGGCCGCGGGTATTGTCACTGTGCCC
CCCAGGTCCAGGCGACGAGCGGCCGCCGCAGCAGCCGCGGCCATTAGTGCTATGACTCAGGGTCGCAGGGGCAACG
TGTATTGGGTGCGCGACTCGGTTAGCGGCCTGCGCGTGCCCGGTGCGCACCCGCCCCCGCGCAACTAGATTGCAAG
AAAAAACTACTTAGACTCGGTACTGTTGTATGTATCCAGCGGCGGCGCCGCAACGAAGCTATGTCCAAGCGCAAA
ATCAAAGAAGAGATGCTCCAGGTCATCGCGCCGGAGATCTATGGCCCCGAAGAAGGAAGAGCAGGATTACAAGC
CCCGAAAGCTAAAGCGGGTCAAAAAGAAAAAGAAAGATGATGATGATGAACTTGACGACGAGGTGGAACTGCTGCA
CGCTACCGCGCCCAGGCGACGCGTACAGTGGAAAGGTCGACGCGTAAAACGTGTTTTGCGACCCGGCACCACCGTA
```

FIGURE 11 (cont.)

```
GTCTTTACGCCCGGTGAGCGCTCCACCCGCACCTACAAGCGCGTGTATGATGAGGTGTACGGCGACGAGGACCTGC
TTGAGCAGGCCAACGAGCGCCTCGGGGAGTTTGCCTACGGAAAGCGGCATAAGGACATGCTGGCGTTGCCGCTGGA
CGAGGGCAACCCAACACCTAGCCTAAAGCCCGTAACACTGCAGCAGGTGCTGCCCGCGCTTGCACCGTCCGAAGAA
AAGCGCGGCCTAAAGCGCGAGTCTGGTGACTTGGCACCCACCGTGCAGCTGATGGTACCCAAGCGCCAGCGACTGG
AAGATGTCTTGGAAAAAATGACCGTGGAACCTGGGCTGGAGCCCGAGGTCCGCGTGCGGCCAATCAAGCAGGTGGC
GCCGGGACTGGGCGTGCAGACCGTGGACGTTCAGATACCCACTACCAGTAGCACCAGTATTGCCACCGCCACAGAG
GGCATGGAGACACAAACGTCCCCGGTTGCCTCAGCGGTGGCGGATGCCGCGGTGCAGGCGGTCGCTGCGGCCGCGT
CCAAGACCTCTACGGAGGTGCAAACGGACCCGTGGATGTTTCUCGTTTCAGCCCCCGGCGCCCGCGCGGTTCGAG
GAAGTACGGCGCCGCCAGCGCGCTACTGCCCGAATATGCCCTACATCCTTCCATTGCGCCTACCCCGGCTATCGT
GGCTACACCTACCGCCCAGAAGACGAGCAACTACCCGACGCCGAACCACCACTGGAACCCGCCGCCGCCGTCGCC
GTCGCCAGCCCGTGCTGGCCCCGATTTCCGTGCGCAGGGTGCTCGCGAAGGAGGCAGGACCCTGGTGCTGCCAAC
AGCGCGCTACCACCCCAGCATCGTTTAAAGCCGGTCTTTGTGGTTCTTGCAGATATGGCCCTCACCTGCCGCCTC
CGTTTCCCGGTGCCGGGATTCCGAGGAAGAATCCACCGTAGGAGGGGCATGGCCGGCTACGGCCTGACGGGCCGCA
TGCGTCGTGCGCACCACCGGCGGCGGCGCGCGTCGCACCGTCGCATGCGCGGCGGTATCCTGCCCCTCCTTATTCC
ACTGATCGCCGCGGCGATTGGCGCCGTGCCCGGAATTGCATCCGTGGCCTTGCAGGCGCAGAGACACTGATTAAAA
ACAAGTTGCATGTGGAAAAATCAAAATAAAAGTCTGGACTCTCACGCTCGCTTGGTCCTGTAACTATTTTGTAGA
ATGGAAGACATCAACTTTGCGTCTCTGGCCCCGCCGACACGGCTCGCGCCCGTTCATGGGAAACTGGCAAGATATCG
GCACCAGCAATATGAGCGGTCGCCCTTCAGCTGGGGCTCGCTGTGGAGCGGCATTAAAAATTTCGGTTCCACCGT
TAAGAACTATGGCAGCAAGGCCTGGAACAGCAGCACAGGCCAGATGCTGAGGGATAAGTTGAAAGAGCAAAATTTC
CAACAAAAGGTGGTAGATGGCCTGGCCTCTGGCATTAGCGGGGTGGTGGACCTGGCCAACCAGGCAGTGCAAAATA
AGATTAACAGTAAGCTTGATCCCCGCCCTCCCGTAGAGGAGCCTCCACCGGCCGTGGAGACAGTGTCTCCAGAGGG
GCGTGGCGAAAAGCGTCCGCGCCCCGACAGGGAAGAAACTCTGGTGACGCAAATAGACGAGCCTCCCTCGTACGAG
GAGGCACTAAAGCAAGGCCTGCCCACCACCCGTCCCATCGCGCCCATGGCTACCGGAGTGCTGGGCCAGCACACAC
CCGTAACGCTGGACCTGCCTCCCCCCGCCGACACCCAGCAGAAACCTGTGCTGCCAGGCCCGACCGCCGTTGTTGT
AACCCGTCCTAGCCGCGCGTCCCTGCGCCGGCGCCGCCAGCGGTCCGCGATCGTTGCGGCCCGTAGCCAGTGGCAAC
TGGCAAAGCACACTGAACAGCATCGTGGGTCTGGGGGTGCAATCCCTGAAGCGCCGACGATGCTTCTGAATAGCTA
ACGTGTCGTATGTGTCTCATGTATGCGTCCATGTCGCCGCCAGAGGAGCTGCTGAGCCGCCGCGCGCCCGCTTTCC
AAGATGGCTACCCCTTCGATGATGCCGCAGTGGTCTTACATGCACATCTCGGGCCAGGACGCCTCGGAGTACCTGA
GCCCCGGGCTGGTGCAGTTTGCCCGCGCACCGAGACGTACTTCAGCCTGAATAACAAGTTTAGAAACCCCACGGT
GGCGCCTACGCACGACGTGACCACAGACCGGTCCAGCGTTTGACGCTGCGGTTCATCCCTGTGGACCGTGAGGAT
ACTGCGTACTCGTACAAGGCGCGGTTCACCCTAGCTGTGGGTGATAACCGTGTGCTGGACATGGCTTCCACGTACT
TTGACATCCGCGGCGTGCTGGACAGGGGCCCTACTTTTAAGCCCTACTCTGGCACTGCCTACAACGCCCTGGCTCC
CAAGGGTGCCCCAAATCCTTGCGAATGGGATGAAGCTGCTACTGCTCTTGAAATAAACCTAGAAGAAGAGGACGAT
GACAACGAAGACGAAGTAGACGAGCAAGCTGAGCAGCAAAAAACTCACGTATTTGGGCAGGCGCCTTATTCTGGTA
TAAATATTACAAAGGAGGGTATTCAAATAGGTGTCGAAGGTCAAACACCTAAATATGCCGATAAAACATTTCAACC
TGAACCTCAAATAGGCAGAAATCTCAGTGGTACGAAACTGAAATTAATCATGCAGCTGGAGAGTCCTTAAAAAGACT
ACCCCAATGAAACCATGTTACGGTTCATATGCAAAACCCACAAATGAAAATGGAGGGCAAGGCATTCTTGTAAAGC
AACAAAATGGAAAGCTAGAAAGTCAAGTGGAAATGCAAGTTTTTCTCAACTACTGAGGCGACCGCAGGCAATGGTGA
TAACTTGACTCCTAAAGTGGTATTGTACAGTGAAGATGTAGATATAGAAACCCCAGACACTCATATTTCTTACATG
CCCACTATTAAGGAAGGTAACTCACGAGAACTAATGGGCCAACAATCTATGCCCAACAGGCCTAATTACATTGCTT
TTAGGGACAATTTTATTGGTCTAATGTATTACAACAGCACGGGTAATATGGGTGTTCTGGCGGGCCAAGCATCGCA
GTTGAATGCTGTTGTAGATTTGCAAGACAGAAACACAGAGCTTTCATACCAGCTTTTGCTTGATTCCATTGGTGAT
AGAACCAGGTACTTTTCTATGTGGAATCAGGCTGTTGACAGCTATGATCCAGATGTTAGAATTATTGAAAATCATG
GAACTGAAGATGAACTTCCAAATTACTGCTTTCCACTGGGAGGTGTGATTAATACAGAGACTCTTACCAAGGTAAA
ACCTAAAACAGGTCAGCAAAATGGATGGGAAAAGATGCTACAGAATTTTCAGATAAAAATGAAATAAGAGTTGGA
AATAATTTTGCCATGGAAATCAATCTAAATGCCAACCTGTGGAGAAATTTCCTGTACTCCAACATAGCGCTGTATT
TGCCCGACAAGCTAAAGTACAGTCCTTCCAACGTAAAAATTTCTGATAACCCAAACACCTACGACTACATGAACAA
GCGAGTGGTGGCTCCCGGGTTAGTGGACTGCTACATTAACCTTGGACTGGGTCCCTTGACTATATGGACAAC
GTCAACCCATTTAACCACCACCGCAATGCTGGCCTGCCTACCGCTCAATGTTGCTGGGCAATGGTCGCTATGTGC
CCTTCCACATCCAGGTGCCTCAGAAGTTCTTTGCCATTAAAAACCTCCTTCTCCTGCCGGGCTCATACACCTACGA
GTGGAACTTCAGGAAGGATGTTAACATGGTTCTGCAGAGCTCCCTAGGAAATGACCTAAGGGGTTGACGGAGCCAGC
ATTAAGTTTGATAGCATTTGCCTTTACGCCACCTTCTTCCCCATGGCCCACAACACCGCCTCCACGCTTGAGGCCA
TGCTTAGAAACGACACCAACGACCAGTCCTTTAAGCGACTATCTCTCCGCCGCCAACATGCTCTACCCTATACCGC
CAACGCTACCAACGTGCCCATATCCATCCCTCCCGCAACTGGGCGGCTTTCCGCGGCTGGGCCTTCACGGCGCTT
AAGACTAAGGAAACCCATCACTGGGCTCGGGCTACGACCCTTATTACACCTACTCTGGCTCTATACCCTACCTAG
ATGGAACCTTTTACCTCAACCACACCTTTAAGAAGGTGGCCATTACCTTTGACTCTTCTGTCAGCTGGCCTGGCAA
TGACCGCCTGCTTACCCCAACGAGTTTGAAATTAAGCGCTCAGTTGACGGGAGGGTTACAACGTTGCCCAGTGT
AACATGACCAAAGACTGGTTCCTGGTACAAATGCTAGCTAACTACAACATTGGCTACCAGGGCTTCTATATCCCAG
AGAGCTACAAGGACCCGCATGTACTCCTTCTTTAGAAACTTCCAGCCCATGAGCCGTGAGTGGTGGATGATACTAA
ATACAAGGACTACCAAGGTGGGCATGCTACACCAACACAACTCTGGATTTGTTGGCTACCTTGCCCCCACC
ATGCGCGAAGGACAGGCCTACCCTGCTAACTTCCCCTATCCGCTTATAGGCAAGACCGCAGTTGACAGCATTACCC
```

FIGURE 11 (cont.)

```
AGAAAAAGTTTCTTTGCGATCGCACCCTTTGGCGCATCCCATTCTCCAGTAACTTTATGTCCATGGGCGCACTCAC
AGACCTGGGCCAAAACCTTCTCTACGCCAACTCCGCCCACGCGCTAGACATGACTTTTGAGGTGGATCCCATGGAC
GAGCCCACCCTTCTTTATGTTTTGTTTGAAGTCTTTGACGTGGTCCGTGTGCACCGGCCGCACCGCGGCGTCATCG
AAACCGTGTACCTGCGCACGCCCTTCTCGGCCGGCACGCCACAACATAAAGAAGCAAGCAACATCAACAACAGCT
GCCGCCATGGGCTCCAGTGAGCAGGAACTGAAAGCCATTGTCAAAGATCTTGGTTGTGGGCCATATTTTTTGGGCA
CCTATGACAAGCGCTTTCCAGGCTTTGTTTCTCCACACAAGCTCGCCTGCGCCATAGTCAATACGGCCGGTCGCGA
GACTGGGGCGTACACTGGATGGCCTTTGCCTGGAACCCGCACTCAAAAACATGCTACCTCTTTGAGCCCTTTGGC
TTTTCTGACCAGCGACTCAAGCAGGTTTACCAGTTTGAGTACGAGTCACTCCTGCGCCGTAGCGCCATTGCTTCTT
CCCCCGACCGCTGTATAACGCTGGAAAAGTCCACCCAAAGCGTACAGGGGCCCAACTCGGCCGCCTGTGGACTATT
CTGCTGCATGTTTCTCCACGCCTTTGCCAACTGGCCCCAAACTCCCATGGATCACAACCCCACCATGAACCTTATT
ACCGGGGTACCCAACTCCATGCTCAACAGTCCCCAGGTACAGCCCACCCTGCGTCGCAACCAGGAACAGCTCTACA
GCTTCCTGGAGCGCCACTCGCCCTACTTCCGCAGCCACAGTGCGCAGATTAGGAGCGCCACTTCTTTTTGTCACTT
GAAAACATGTAAAATAATGTACTAGAGACACTTTCAATAAAGGCAAATGCTTTTATTTGTACACTCTCGGGTGA
TTATTTACCCCCACCCTTGCCGTCTGCGCCGTTTAAAAATCAAAGGGGTTCTGCCGCGCATCGCTATGCGCCACTG
GCAGGGACACGTTGCGATACTGGTGTTTAGTGCTCCACTTAAACTCAGGCACAACCATCCGCGGCAGCTCGGTGAA
GTTTTCACTCCACAGGCTGCGCACCATCACCAACGCGTTTAGCAGGTCGGGCGCCGATATCTTGAAGTCGCAGTTG
GGGCCTCCGCCCTGCGCGCGCGAGTTGCGATACACAGGGTTGCAGCACTGGAACACTATCAGCGCCGGGTGGTGCA
CGCTGGCCAGCACGCTCTTGTCGGAGATCAGATCCGCGTCCAGGTCCTCCGCGTTGCTCAGGGCGAACGGAGTCAA
CTTTGGTAGCTGCCTTCCCAAAAGGGCGCGTGCCCAGGCTTTGAGTTGCACTCGCACCGTAGTGGCATCAAAAGG
TGACCGTGCCCGGTCTGGGCGTTAGGATACAGCGCCTGCATAAAAGCCTTGATCTGCTTAAAAGCCACCTGAGCCT
TTGCGCCTTCAGAGAAGAACATGCCGCAAGACTTGCCGGAAAACTGATTGGCCGGACAGGCCGCGTCGTGCACGCA
GCACCTTGCGTCGGTGTTGGAGATCTGCACCACATTTCGGCCCCACCGGTTCTTCACGATCTTGGCCTTGCTAGAC
TGCTCCTTCAGCGCGCGCTGCCCGTTTTCGCTCGTCACATCCATTTCAATCACGTGCTCCTTATTTATCATAATGC
TTCCGTGTAGACACTTAAGCTCGCCTTCGATCTCAGCGCAGCGGTGCAGCCACAACGCGCAGCCCGTGGGCTCGTG
ATGCTTGTAGGTCACCTCTGCAAACGACTGCAGGTACGCCTGCAGGAATCGCCCCATCATCGTCACAAAGGTCTTG
TTGCTGGTGAAGGTCAGCTGCAACCCGCGGTGCTCCTCGTTGCATACGGCCGCCAGAGCTTCCA
CTTGGTCAGGCAGTAGTTTGAAGTTCGCCTTTAGATCGTTATCCACGTGGTACTTGTCCATCGCGCGCGCAGC
CTCCATGCCCTTCTCCCACGCAGACACGATCGGCACACTCAGCGGGTTCATCACCGTAATTTCACTTTCCGCTTCG
CTGGGCTCTTCCTCTTCCTCTTGCGTCCGCATACCACGCGCCACTGGGTCGTCTTCATTCAGCCGCCGCACTGTGC
GCTTACCTCCTTTGCCATGCTTGATTAGCACCGGTGGCTTGCTGAAACCCACCATTTGTAGCGCCACATCTTCTCT
TTCTTCCTCGCTGTCCACGATTACCTCTGGTGATGGCGGGCGCTCGGGCTTGGGAGAAGGGCGCTTCTTTTTCTTC
TTGGGCGCAATGGCCAAATCCGCCGCCGAGGTCGATGGCCGCGGGCTGGGTGTGCGCGGCACCAGCGCGTCTTGTG
ATGAGTCTTCCTCGTCCTCGGACTCGATCAGCCGCCTCATCCGCTTTTTTGGGGGCGCCCGGGGAGGCGGCGGCGA
CGGGGACGGGGACGACACGTCCTCCATGGTTGGGGGACGTCGCGCCGCACCGCGTCCGCGCTCGGGGGTGGTTTCG
CGCTGCTCCTCTTCCCGACTGGCCATTTCCTTCTCCTATAGGCAGAAAAAGATCATGGAGTCAGTCGGAGAAGAAGG
ACAGCCTAACCGCCCCCTCTGAGTTCGCCACCACCGGCCTCCACCGATGCCGCCAACGCGCCTACCACCTTCCCCGT
CGAGGCACCCCCGCTTGAGGAGGAGGAAGTGATTATCGAGCAGGACCCAGGTTTTGTAAGCGAAGACGACGAGGAC
CGCTCAGTACCAACAGAGGATAAAAAGCAAGACCAGGACAACGCAGAGGCAAACGAGGAACAAGTCGGGCGGGGGG
ACGAAAGGCATGGCGACTACCTAGATGTGGGAGACGACGTGCTGTTGAAGCATCTGCAGCGCCAGTGCGCCATTAT
CTGCGACGCGTTGCAAGAGCGCAGCGATGTGCCCCTCGCCATAGCGGATGTCAGCCTTGCCTACGAACGCCACCTA
TTCTCACCGCGCGTACCCCCCAAACGCCAAGAAAACGGCACATGCGAGCCCAACCCGCGCCTCAACTTCTACCCCG
TATTTCCGTGCCAGAGGTGCTTGCCACCTATCACATCTTTTTCCAAAACTGCAAGATACCCCTATCCTGCCGTGC
CAACCGCAGCCGAGCGGACAAGCAGCTGGCCTTGCGGCAGGGCGCTGTCATACCTGATATCGCCTCGCTCAACGAA
GTGCCAAAAATCTTTGAGGGTCTTGGACGCGACGAGAAGCGCGCGGCAAACGCTCTGCAACAGGAAAACAGCGAAA
ATGAAAGTCACTCTGGAGTGTTGGTGGAACTCGAGGGTGACAACGCGCGCCTAGCCGTACTAAAACGCAGCATCGA
GGTCACCCACTTTGCCTACCCGGCACTTAACCTACCCCCAAGGTCATGAGCACAGTCATGAGTGAGCTGATCGTG
CGCCGTGCCGCAGCCCCTGGAGAGGGATGCAAATTTGCAAGAACAAACAGAGGAGGGCCTACCCGCAGTTGGCGACG
AGCAGCTAGCGCGCTGGCTTCAAACGCGCGAGCCTGCCGACTTGGAGGAGCGACGCAAACTAATGATGGCCGCAGT
GCTCGTTACCGTGGAGCTTGAGTGCATGCAGCGGTTCTTTGCTGACCCCGAGATGCAGCGCAAGCTAGAGGAAACA
TTGCACTACACCTTTCGACAGGGCTACGTACGCCAGGCCTGCAAGATCTCCAACGTGGAGCTCTGCAACCTGGTCT
CCTACCTTGGAATTTTGCACGAAAACCGCCTTGGGCAAAACGTGCTTCATTCCACGCTCAAGGGCGAGGCGCGCCG
CGACTACGTCCGCGACTGCGTTTACTTATTTCTATGCTACACCTGGCAGACGGCCATGGCCGTTTGGCAGCAGTGC
TTGGAGGAGTGCAACCTCAAGGAGCTGCAGAAACTGCTAAAGCAAACTTGAAGGACCTATGGACGGCCTTCAACG
AGCGCTCCGTGGCCGCGCACCTGGCGGACATCATTTTCCCCGAACGCCTGCTTAAAACCCTGCAACAGGGTCTGCC
AGACTTCACCAGTCAAAGCATGTTGCAGAACTTTAGGAACTTTATCCTAGAGCGCTCAGGAATCTTGCCCGCCACC
TGCTGTGCACTTCCTAGCGACTTTGTGCCCATTAAGTACGCGAATGCCCTCCGCCGCTTTGGGGCCACTGCTACC
TTCTGCAGCTAGCCAACTACCTTGCCTACCACTCTGACATAATGGAAGACGTGAGCGGTGACGGTCTACTGGAGTG
TCACTGTCGCTGCAACCTATGCACCCCGCACCGCTCCCTGGTTTGCAATTCGCAGCTGCTTAACGAAAGTCAAATT
ATCGGTACCTTTGAGCTGCAGGGTCCCTCGCCTGACGAAAAGTCCGCGGCTCCGGGGTTGAAACTCACTCCGGGC
TGTGGACGTCGGCTTACCTTCGCAAATTTGTACCTGAGGACTACCACGCCCACGAGATTAGGTTCTACGAAGACCA
ATCCCGCCCGCCAAATGCGGAGCTTACCGCCTGCGTCATTACCCAGGGCCACATTCTTGGCCAATTGCAAGCCATC
```

FIGURE 11 (cont.)

```
AACAAAGCCCGCCAAGAGTTTCTGCTACGAAAGGGACGGGGGGTTTACTTGGACCCCCAGTCCGGCGAGGAGCTCA
ACCCAATCCCCCGCCGGCCGCAGCCCTATCAGCAGCAGCCGCGGGCCCTTGCTTCCCAGGATGGCACCCAAAAGA
AGCTGCAGCTGCCGCCGGCCACCCACGGACGAGGAGGAATACTGGGACAGTCAGGCAGAGGAGGTTTTGGACGAGCA
GGAGGAGGACATGATGGAAGACTGGGAGAGCCTAGACGAGGAAGCTTCCGAGGTCGAAGAGGTGTCAGACGAAACA
CCGTCACCCTCGGTCGCATTCCCCTCGCCGGCGCCCCAGAAATCGGCAACCGGTTCCAGCATGGCTACAACCTCCG
CTCCTCAGGCGCCGCCGGCACTGCCCGTTCGCCGACCCAACCGTAGATGGGACACCACTGGAACCAGGGCCGGTAA
GTCCAAGCAGCCGCCGCCGTTAGCCCAAGAGCAACAACAGCGCCAAGGCTACCGCTCATGGCGCGGGCACAAGAAC
GCCATAGTTGCTTGCTTGCAAGACTGTGGGGGCAACATCTCCTTCGCCLGCCGCTTTCTTCTCTACCATCACGGCG
TGGCCTTCCCCCGTAACATCCTGCATTACTACCGTCATCTCTACAGCCCATACTGCACCGGCGGCAGCGGCAGCGG
CAGCAACAGCAGCGGCCACACAGAAGCAAAGGCGACCGGATAGCAAGACTCTGACAAAGCCCAAGAAATCCACAGC
GGCGGCAGCAGCAGGAGGAGGAGCGCTGCGTCTGGCGCCCAACGAACCCGTATCGACCCGCGAGCTTAGAAACAGG
ATTTTTCCCACTCTGTATGCTATATTTCAACAGAGCAGGGGCCAAGAACAAGAGCTGAAAATAAAAAACAGGTCTC
TGCGATCCCTCACCCGCAGCTGCCTGTATCACAAAAGCGAAGATCAGCTTCGGCGACGCTGGAAGACGCGGAGGC
TCTCTTCAGTAAATACTGCGCGCTGACTCTTAAGGACTAGTTTCGCGCCCTTTCTCAAATTTAAGCGCGAAAACTA
CGTCATCTCCAGCGGCCACACCGGCGCCAGCACCTGTCGTCAGCGCCATTATGAGCAAGGAAATTCCCACGCCCT
ACATGTGGAGTTACCAGCCACAAATGGGACTTGCGGCTGGAGCTGCGCAAGACTACTCAACCCGAATAAACTACAT
GAGCGCGGGACCCCACATGATATCCCGGGTCAACGGAATCCGCGCCCACCGAAACCGAATTCTCTTGGAACAGGCG
GCTATTACCACCACACCTCGTAATAACCTTAATCCCCGTAGTTGGCCGGCTGCCCTGGTGTACCAGGAAAGTCCCG
CTCCCACCACTGTGGTACTTCCCAGAGATGCCCAGGCCGAAGTTCAGATGACTAACTCAGGGGCGCAGCTTGCGGG
CGGCTTTCGTCACAGGGTGCGGTCGCCCGGCCAGGGTATAACTCACCTGACAATCAGAGGCGAGGTATTCAGCTC
AACGACGAGTCGGTGAGCTCCTCGCTTGGTCTCCGTCCGGACGGGACATTTCAGATCGGCGGCGCCGGCCGTCCTT
CATTCACGCCTCGTCAGGCAATCCTAACTCTGCAGACCTCGTCCTCTGAGCCGCGCTCTGGAGGCATTGGAACTCT
GCAATTTATTGAGGAGTTTGTGCCATCGGTCTACTTTAACCCCTTCTCGGGACCTCCCGGCCACTATCCGGATCAA
TTTATTCCTAACTTTGACGCGGTAAAGGACTCGGCGGACGGCTACGACTGAATGTTAAGTGGAGAGGCAGAGCAAC
TGCGCCTGAAACACCTGGTCCACTGTCGCCGCCACAAGTGCTTTGCCCGCGACTCCGGTGAGTTTTGCTACTTTGA
ATTGCCGAGGATCATATCGAGGGCCCGGCGCACGGCGTCCGGCTTACCGCCCAGGGAGAGCTTGCCCGTAGCCTG
ATTGGGGAGTTTACCCAGCGCCCCTGCTAGTTGAGCGGGACAGGGGACCCTGTGTTCTCACTGTGATTTGCAACT
GTCCTAACCTTGGATTACATCAAGATCCTCTAGTTAATTAACAGCTTGCATGCCTGCAGGTCGACGGATCGGAGA
TCTCGGCCGCATATTAAGTGCATTGTTCTCGATACGCTAAGTGCATTGTTCTCGTTAGCTCGATGGACAAGTGCA
TTGTTCTCTTGCTGAAAGCTCGATGGACAAGTGCATTGTTCTCTTGCTGAAAGCTCGATGGACAAGTGCATTGTTC
TCTTGCTGAAAGCTCAGTACCCGGGAGTACCCTCGACCGCCGAGTATAAATAGAGGCGCTTCGTCTACGGAGCGA
CAATTCAATTCAAACAAGCAAAGTGAACACGTCGCTAAGCGAAAGCTAAGCAAATAAACAAGCGCAGCTGAACAAG
CTAAACAATCTGCAGTAAAGTGCAAGTTAAAGTGAATCAATTAAAAGTAACCAGCAACCAAGTAAATCAACTGCAA
CTACTGAAATCTGCCAAGAAGTAATTATTGAATACAAGAAGAGAACTCTGAATACTTTCAACAAGTTACCGAGAAA
GAAGAACTCACACACAGCTAGCGTTTAAACTTAAGCTTCACCATGGTGGGGCCCTGCATGCTGCTGCTGCTGCTGC
TGCTGGGCCTGAGGCTACAGCTCTCCCTGGGCATCATCCTAGTTGAGGAGGAGAACCCGGACTTCTGGAACCGCGA
GGCAGCCGAGGCCCTGGGTGCCGCCAAGAAGCTGCAGCCTGCACAGACAGCGCGCCAAGAACCTCATCATCTTCCTG
GGCGATGGGGTGGGGGTGTCTACGGTGACAGCTGCCAGGATCCTAAAAGGGCAGAAGAGGACAAACTGGGGCCTG
AGATACCCCTGGCCATGGACCGCTTCCCATATGTGGCTCTGTCCAAGACATACAATGTAGACAAACATGTGCCAGA
CAGTGGAGCCACAGCCACGGCCTACCTGTGCGGGGTCAAGGGCAACTTCCAGACCATTGGCTTGAGTGCAGCCGCC
CGCTTTAACCAGTGCAACACGACACGCGGCAACGAGGTCATCTCCGTGATGAATCGGGCCAAGAAAGCAGGGAAGT
CAGTGGGAGTGGTAACCACCACACGAGTGCAGCACGCCTCGCCAGCCGGCACCTACGCCCACACGGTGAACCGCAA
CTGGTACTCGGACGCCGACGTGCCTGCCTCGGCCCGCCAGGAGGGGTGCCAGGACATCGCTACGCAGCTCATCTCC
AACATGGACATTGACGTGATCCTAGGTGGGGGCCGAAAGTACATGTTTCGCATGGGAACCCCAGACCCTGAGTACC
CAGATGACTACAGCCAAGGTGGGACCAGGCTGACGGGAAGAATCTGGTGCAGGAATGGCTGGCGAAGCACCAGGG
TGCCCGGTACGTGTGGAACCGCACTGAGCTCATGCAGGCTTCCCTGGACCCGTCTGTGGCCCATCTCATGGGTCTC
TTTGAGCCTGGAGACATGAAATACGAGATCCACCGCGACTCCACACTGGACCCCTCCCTGATGGAGATGACAGAGG
CTGCCCTGCGCCTGCTGAGCAGGAACCCCCGGCCTTCTTCCTCTTCGTGGAGGGTGGTCGCATCGACCATGGTCA
TCATGAAAGCAGGCTTACCGGGCACTGACTGAGACGATCATGTTCGACGCCCATTGAGACGGCGGCCAGCTC
ACCAGCGAGGAGGACACGCTGAGCCTCGTCACTGCCGACCACTCCCACGTCTTCTCCTTCGGAGGCTGCCCCCTGC
GAGGGGCTCCATCTTCGGGCTGGCCCCTGGCAAGGCCCGGGACAGGAAGGCCTACACGGTCCTCCTATACGGAAA
CGGTCCAGGCTATGTGCTCAAGGACGGCGCCCGGCCGGATGTTACCGAGAGCGAGAGCGGGAGCCCCGAGTATCGG
CAGCAGTCAGCAGTGCCCCTGGACGAAGAGACCCACGCAGGCGAGGACGTGGCGGTGTTCGCGCGCGGCCCGCAGG
CGCACCTGGTTCACGGCGTGCAGGAGCAGACCTTCATAGCGCACGTCATGGCCTTCGCCGCCTGCCTGGAGCCCTA
CACCGCCTGCGACCTGGCGCCCCCGCCGGCACCACCGACGCCGCGCACCCGGGCGGTCCGTGGTCCCCGCGTTG
CTTCCTCTGCTGGCCGGGACCCTGCTGCTGCTGGAGACGGCCACTGCTCCCTGAGTGTCCCGTCCCTGGGCTCCT
GCTTCCCCATCCCGGAGTTCTCCTGCTCCCGGCCTCCTGTCGTCCTGCCTGGCCTCCAGCCCGGAGTCGTCATCCCC
GGAGTCCCTATACAGAGGTCCTGCCATGGAACCTTCCCCTCCCCGTGCGCTCTGGGGACTGAGCCCATGACACCAA
ACCTGCCCCTTGGCTGCTCTCGGACTCCCTACCCCAACCCCAGGGACAGATCTGGCCAGATTTGTAAAACAAATAG
ATTTTAGGCCCAAAGATTATTTAAAGCATTGCCTGGAACGCAGTGAGTTTTGTTAGAAAGAGAATAATTCAAAG
TGGCATTGCTTTGCTTCTTATGTTAATTTGGTACAGACCTGTGGCTGAGTTTGCTCAAAGTATTCAGAGCAGAATT
```

FIGURE 11 (cont.)

```
GTGGAGTGGAAAGAGAGATTGGACAAAGAGTTTAGTTTGTCAGTGTATCAAAAAATGAAGTTTAATGTGGCTATGG
GAATTGGAGTTTTAGATTGGCTAAGAAACAGTGATGATGATGATGAAGACAGCCAGGAAAATGCTGATAAAAATGA
AGATGGTCGGGAGAAGAACATGGAAGACTCAGGGCATGAAACAGGCATTGATTCACAGTCCCAAGGCTCATTTCAG
GCCCCTCAGTCCTCACAGTCTGTTCATGATCATAATCAGCCATACCACATTTGTAGAGGTTTTACTTGCTTTAAAA
AACCTCCCACACCTCCCCCTGAACCTGAAACATAAAATGAATGCAATTGTTGTTGTTAACTTGTTTATTGCAGCTT
ATAATGGTTACAAATAAAGCAATAGCATCACAAATTTCACAAATAAAGCATTTTTTTCACTGCATTCTAGTTGTGG
TTTGTCCAAACTCATCAATGTATCTTATCATGTCTGGATCCCCAGGAAGCTCCTCTGTGTCCTCATAAACCCTAAC
CTCCTCTACTTGAGAGGACATTCCAATCATAGGCTGCCCATCCACCCTCTGTGTCCTCCTGTTAATTAGGTCACTT
AACAAAAAGGAAATTGGGTAGGGGTTTTTCACAGACCGCTTTCTAAGGGTAATTTTAAATATCTGGGAAGTCCCT
TCCACTGCTGTGTTCCAGAAGTGTTGGTAAACAGCCCACAAATGTCAACAGCAGAAACATACAAGCTGTCAGCTTT
GCACAAGGGCCCAACACCCTGCTCATCAAGAAGCACTGTGGTTGCTGTGTTAGTAATGTGCAAAACAGGAGGCACA
TTTTCCCCACCTGTGTAGGTTCCAAAATATCTAGTGTTTCATTTTTACTTGGATCAGGAACCCAGCACTCCACTG
GATAAGCATTATCCTTATCCAAAACAGCCTTGTGGTCAGTGTTCATCTGCTGACTGTCAACTGTAGCATTTTTTGG
GGTTACAGTTTGAGCAGGATATTTGGTCCTGTAGTTTGCTAACACACCCTGCAGCTCCAAAGGTTCCCCACCAACA
GCAAAAAAATGAAAATTTGACCCTTGAATGGGTTTTCCAGCACCATTTTCATGAGTTTTTTGTGTCCCTGAATGCA
AGTTTAACATAGCAGTTACCCCAATAACCTCAGTTTTAACAGTAACAGCTTCCCACATCAAAATATTTCCACAGGT
TAAGTCCTCATTTAAATTAGGCAAAGGAATTCCACTTCCCACTGCCTTGCTTCCGTCTCCCATTCAAACTTTTATC
AACTGACATTATTCTAAGTAAAATCCTCTTCATTATGTTGTCAGCAATCCATTGCTTGAAGGCCTGGCTCCCAGA
ACCCCTCGACTGGTATGTCTTCTCCTAGAATACTCCAGAAGAAAAGGAGTGTATGAAGATAGTGACTGCACATTAA
AATGACTGAAACCATAGTAAATTAGGATGAGATTCTGGGCAGATAAACAGACAGCTGGCTAGGATCATTTTTTTAT
GCCTTGGACTTCTTTGGCAATCTGTTGAAGCCTGACATTCCTCAGAATAATGTTTTAAAGCCCAACAATAAGACCC
TGTAGCACATATAATAAGTACTGCAGTTTTGAAGTAGTGATAAGCATAAATGATATTTTGATATATTTATTATAAC
TGTAATGAGATGTACATATCTGTGACTTCATAGGTACTGATTGTACTGTGATTTTTTTGCCTACTTTCAAA
ATGAAAAGGAATGCTTAATTTCAGTTAGAGGTTAGTAAAGACAAATAGGTAATTTTCTTCTCCAGTGAAGAGCATG
GCGCCCCTTGCTATTCATGGACGCTTGCTTAAAGACTTGTACACAGGCTTGCTTTGTATCAACCTATGACTTCCCC
TTACAGCCGATGATAGGTTTTTATTTGCACCTCCTTCGTGTACAAAGACAGTTTTGGTGGCTACGCCATCATTAAA
CTCATTATTATCATGCTTAAGCCTATAGATGTATCCAGTTCTTCTGTTACATAATTGAAGCTGTAGTGAATTGTCT
ATCTTAAACTGCATCGCTAACTGACTACATTCACACTTCATTTGCTTCCAACATAGACTAACCTTCTTGGATGTC
CACTATTATTTGAACTTTTGAGATTTTTTTTCCTATTTCTAATATCTTAAAATTTCAGAAGACTTAAAGTTTTGCA
ACTACAGGGCTCCATATAGACATCTAGCTTGAATTTATACACTTTCTTTCATTGATGTCCCTGGACTAAAAAATGT
TAAATATTTCTAACCGCTGTACTTAAAGTCCATTACAAACGAAGACTACTGTTGTTAAGTTGAATAGGCATCTTAT
ATATTTTCACCGGTGCAATAAATAACTTCTATTCCCTTCTAACATCTGCTTGCGTTGCACTGAGAGTACACTATT
GATTAGCAATAGGTTCGTGATTACAGCCCTTCTATAATTAATTGTTAGGTTAACATATTATTCATAAAATATTATT
TTATTAATTTTTACTTGATTTGCTACTGGATGCTTAGAAATAGCTATGAGTATATTGGTAGAACCAGTACTTATAT
TTTATTACATTTTACATTTCATAAAATTTAAGTGATATAAAAATCCTGAGGAAGTATGCCACAAAAGTGGTCTCA
GTGGAAATTTAAATATGTTAACATTTATTTTTAAAATGTAGCGTGAAATAGACAACTTTAAAAGCTCAGCTTAAA
AAAAAACTCAAGGAAGCTGAACTTGACTTTTTAAAGCACTGAAGTGCAATATTTAATGTAGGTCAACATGTTAAA
TGGGAAAATTTTTTCCTAATTACAGCCAAATCCCTAGCTGTAATTAACTTAAAATTTGTATACTATTTCACAACA
GAGTCAGCATATACCACTTTCTTATAAAATTAGAAAGATCTAAAATTTAGAGGTCTTATTTGGTGAAACAGGCATAT
TGCTACATCTTTGTTTATAAATTATAATGTGCCTTTAGAGCCCAATAACAGATAACAAGATTTTGAAAATTCAGGT
GAATTAGAGTTATCAGAGGGAATGTTAATACACTCTATTCAAATACTATATGAGTAAGACATTTAAAAATAGGAAAC
AATACTTTATATATTAAAAAAAATTAATCTTCCAGTCGATTTAATCCACTTTATGAATTCATTTAAATCGATTTAA
ATTCGAATTAATTAACTAGAGTACCCGGGGATCTTATTCCCTTTAACTAATAAAAAAAATAATAAAGCATCACTT
ACTTAAAATCAGTTAGCAAATTTCTGTCCAGTTTATTCAGCAGCACCTCCTTGCCCTCCTCCCAGCTCTGGTATTG
CAGCTTCCTCCTGGCTGCAAACTTTCTCCACAATCTAAATGGAATGTCAGTTTCCTCCTGTTCCTGTCCATCCGCA
CCCACTATCTTCATGTTGTTGCAGATGAAGCGCGCAAGACCGTCTGAAGATACCTTCAACCCCGTGTATCCATATG
ACACGGAAACCGGTCCTCCAACTGTGCCTTTTCTTACTCCTCCCTTGTATCCCCAATGGGTTTCAAGAGAGTCC
CCCTGGGGTACTCTCTTTGCCGCTATCCGAACCTCCGAACCTGAATGGCATGCTTGCGCTCAAAATGGGCAAC
GGCCTCTCTCTGGACGAGGCCGGCAACCTTACCTCCCAAAATGTAACCACTGTGAGCCCACCTCTCAAAAAACCA
AGTCAAACATAAACCTGGAAATATCTGCACCCCTCACAGTTACCTCAGAAGCCCTAACTGTGGCTGCCGCCGCACC
TCTAATGGTCGCGGCAACACACTCACCATGCAATCACAGGCCCGCTAACCGTGCACGACTCCAAACTTAGCATT
GCCACCCAAGGACCCCTCACAGTGTCAGAAGGAAAGCTAGCCCTGCAAACATCAGGCCCCTCACCACCACCGATA
GCAGTACCCTTACTATCACTGCCTCACCCCCTCTAACTACTGCCACTGGTAGCTTGGGCATTGACTTGAAAGAGCC
CATTTATACACAAAATGGAAAACTAGGACTAAAGTACGGGGCTCCTTTGCATGTAACAGACGACCTAAACACTTTG
ACCGTAGCAACTGGTCCAGGTGTGACTATTAATAATACTTCCTTGCAAACTAAAGTTACTGGAGCCTTGGGTTTTG
ATTCACAAGGCAATGCAACTTAATGTAGCAGGAGGATTGATTCTCAAAACAGACGCCTTATACTTGA
TGTTAGTTATCCGTTTGATGCTCAAAACCAACTAAATCTAAGACTAGGACAGGGCCCTCTTTTTATAAACTCAGCC
CACAACTTGGATATTAACTACAACAAAGGCCTTTACTTGTTTACAGCTTCAAACAATTCCAAAAAGCTTGAGGTTA
ACCTAAGCACTGCCAAGGGGTTGATGTTTGACGCTACAGCCATAGCCATTAATGCAGGAGATGGGCTTGAATTTGG
TTCACCTAATGCACCAAACACAAATCCCCTCAAAACAAAATTTGGCCATGGCCTAGAATTTGATTCAAACAAGGCT
ATGGTTCCTAAACTAGGAACTGGCCTTAGTTTTGACAGCACAGGTGCCATTACAGTAGGAAACAAAAATAATGATA
```

FIGURE 11 (cont.)

```
AGCTAACTTTGTGGACCACACCAGCTCCATCTCCTAACTGTAGACTAAATGCAGAGAAAGATGCTAAACTCACTTT
GGTCTTAACAAAATGTGGCAGTCAAATACTTGCTACAGTTTCAGTTTTGGCTGTTAAAGGCAGTTTGGCTCCAATA
TCTGGAACAGTTCAAAGTGCTCATCTTATTATAAGATTTGACGAAAATGGAGTGCTACTAAACAATTCCTTCCTGG
ACCCAGAATATTGGAACTTTAGAAATGGAGATCTTACTGAAGGCACAGCCTATACAAACGCTGTTGGATTTATGCC
TAACCTATCAGCTTATCCAAAATCTCACGGTAAAACTGCCAAAAGTAACATTGTCAGTCAAGTTTACTTAAACGGA
GACAAAACTAAACCTGTAACACTAACCATTACACTAAACGGTACACAGGAAACAGGAGACACAACTCCAAGTGCAT
ACTCTATGTCATTTTCATGGGACTGGTCTGGCCACAACTACATTAATGAAATATTTGCCACATCCTCTTACACTTT
TTCATACATTGCCCAAGAATAAAGAATCGTTTGTGTTATGTTTCAACGTGTTTATTTTTCAATTGCAGAAAATTTC
AAGTCATTTTTCATTCAGTAGTATAGCCCCACCACCACATAGCTTATACAGATCACCGTACCTTAATCAAACTCAC
AGAACCCTAGTATTCAACCTGCCACCTCCCTCCCAACACACAGAGTACACAGTCCTTTCTCCCCGGCTGGCCTTAA
AAAGCATCATATCATGGGTAACAGACATATTCTTAGGTGTTATATTCCACACGGTTTCCTGTCGAGCCAAACGCTC
ATCAGTGATATTAATAAACTCCCGGGCAGCTCACTTAAGTTCATGTCGCTGTCCAGCTGCTGAGCCACAGGCTGC
TGTCCAACTTGCGGTTGCTTAACGGGCGGCGAAGGAGAAGTCCACGCCTACATGGGGGTAGAGTCATAATCGTGCA
TCAGGATAGGGCGGTGGTGCTGCAGCAGCGCGCGAATAAACTGCTGCCGCCGCCGCTCCGTCCTGCAGGAATACAA
CATGGCAGTGGTCTCCTCAGCGATGATTCGCACCGCCCGCAGCATAAGGCGCCTTGTCCTCCGGGCACAGCAGCGC
ACCCTGATCTCACTTAAATCAGCACAGTAACTGCAGCACAGCACCACAATATTGTTCAAAATCCCACAGTGCAAGG
CGCTGTATCCAAAGCTCATGGCGGGACCACAGAACCCACGTGGCCATCATACCACAAGCGCAGGTAGATTAAGTG
GCGACCCCTCATAAACACGCTGGACATAAACATTACCTCTTTTGGCATGTTGTAATTCACCACCTCCCGGTACCAT
ATAAACCTCTGATTAAACATGGCGCCATCCACCACCATCCTAAACCAGCTGGCCAAAACCTGCCCGCCGGCTATAC
ACTGCAGGGAACCGGGACTGGAACAATGACAGTGGAGAGCCCAGGACTCGTAACCATGGATCATCATGCTCGTCAT
GATATCAATGTTGGCACAACACAGGCACACGTGCATACACTTCCTCAGGATTACAAGCTCCTCCCGCGTTAGAACC
ATATCCCAGGGAACAACCCATTCCTGAATCAGCGTAAATCCCACACTGCAGGGAAGACCTCGCACGTAACTCACGT
TGTGCATTGTCAAAGTGTTACATTCGGGCAGCAGCGGATGATCCTCCAGTATGGTAGCGCGGGTTTCTGTCTCAAA
AGGAGGTAGACGATCCCTACTGTACGGAGTGCGCCGAGATCGTGTTGGTCGTAGTGTCATGCCAAAT
GGAACGCCGGACGTAGTCATATTTCCTGAAGCAAAACCAGGTGCGGGCGTGACAAACAGATCTGCGTCTCCGGTCT
CGCCGCTTAGATCGCTCTGTGTAGTAGTTGTAGTATATCCACTCTCTCAAAGCATCCAGGCGCCCCCTGGCTTCGG
GTTCTATGTAAACTCCTTCATGCGCCGCTGCCCTGATAACATCCACCACCGCAGAATAAGCCACACCCAGCCAACC
TACACATTCGTTCTGCCAGTCACACACGGGAGGAGCGGGAAGAGCTGGAAGAACCATGTTTTTTTTTTTATTCCAA
AAGATTATCCAAAACCTCAAAATGAAGATCTATTAAGTGAACGCGCTCCCCTCCGGTGGCGTGGTCAAACTCTACA
GCCAAAGAACAGATAATGGCATTTGTAAGATGTTGCACAATGGCTTCCAAAAGGCAAACGGCCCTCACGTCCAAGT
GGACGTAAAGGCTAAACCCTTCAGGGTGAATCTCCTCTATAAACATTCCAGCACCTTCAACCATGCCCAAATAATT
CTCATCTCGCCACCTTCTAATATATCTCTAAGCAAATCCCGAATATTAAGTCCGGCCATTGTAAAAATCTGCTCC
AGAGCGCCCTCCACCTTCAGCCTCAAGCAGCGAATCATGATTGCAAAAATTCAGGTTCCTCACAGACCTGTATAAG
ATTCAAAAGCGGACATTAACAAAAATACCGCGATCCCGTAGGTCCCTTCGCAGGGCCAGCTGAACATAATCGTGC
AGGTCTGCACGGACCAGCGCGGCCACTTCCCGCCAGGAACCTTGACAAAAGAACCCACACTGATTATGACACGCA
TACTCGGAGCTATGCTAACCAGCGTAGCCCCGATGTAAGCTTTGTTGCATGGGCGGCGATATAAAATGCAAGGTGC
TGCTCAAAAATCAGGCAAAGCCTCGCGCAAAAAGAAAGCACATCGTAGTCATGCTCATGCAGATAAAGGCAGGT
AAGCTCCGGAACCACCACAGAAAAAGACACCATTTTTCTCTCAAACATGTCTGCGGTTTCTGCATAAACACAAAA
TAAAATAACAAAAAACATTTAAACATTAGAAGCCTGTCTTACAACAGGAAAACAACCCTTATAAGCATAAGACG
GACTACGGCCATGCCGGCGTGACCGTAAAAAACTGGTCACGTGATTAAAAGCACCACCGACAGCTCCTCGGTC
ATGTCCGGAGTGCATAATGTAAGACTCGGTAAACACATCAGGTTGATTCATCGGTCAGTGCTAAAAAGCGACCGAAA
TAGCCCGGGGGAATACATACCCGCAGGCGTAGAGACAACATTACAGCCCCCATAGGAGGTATAACAAAATTAATAG
GAGAGAAAACACATAAACACCTGAAAAACCCTCCTGCCTAGGCAAAATAGCACCCTCCCGCTCCAGAACAACATA
CAGCGCTTCACAGCGGCAGCCTAACAGTCAGCCTTACCAGTAAAAAGAAAACCTATTAAAAAAACACCACTCGAC
ACGGCACCAGCTCAATCAGTCACAGTGTAAAAAAGGGCCAAGTGCAGAGCGAGTATATATAGGACTAAAAAATGAC
GTAACGGTTAAAGTCCACAAAAAACACCCAGAAAACCGCACGCGAACCTACGCCCAGAAACGAAAGCCAAAAAACC
CACAACTTCCTCAAATCGTCACTTCCGTTTTCCCACGTTACGTAACTTCCCATTTTAAGAAAACTACAATTCCCAA
CACATACAAGTTACTCCGCCCTAAAACCTACGTCACCCGCCCCGTTCCCACGCCCCGCGCCACGTCACAAACTCCA
CCGCCTCATTATCATATTGGCTTCAATCCAAAATAAGGTATATTATTGATGATG
```

FIGURE 13
TP-DNA Complex from (+)lox(+)pol Helper
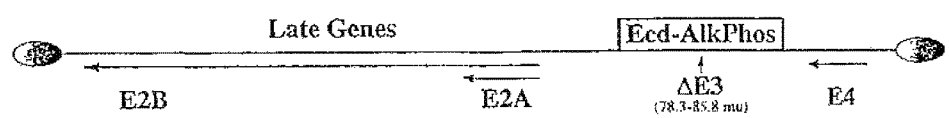
Deproteinized Hirt Prep DNA from ΔFseI.4
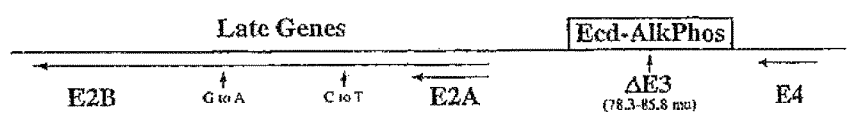
pD1940#3 or pD1940#6
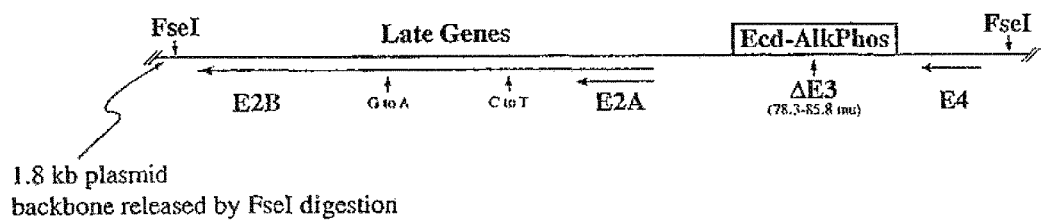
1.8 kb plasmid
backbone released by FseI digestion

FIGURE 14 pD1940 sequence (SEQ ID NO:13)

```
CTAAATTGTAAGCGTTAATATTTTGTTAAAATTCGGCCGGCCATCATCAATAATATACCTTATTTTGGATTGAAGC
CAATATGATAATGAGGGGGTGGAGTTTGTGACGTGGCGCGGGGCGTGGGAACGGGGCGGGTGACGTAGTAGTCTGG
CGGAAGTGTGATGTTGCAAGTGTGGCGGAACACATGTATAACTTCGTATAATGTATGCTATACGAAGTTATACATG
TAAGCGACGGATGTGGCAAAAGTGACGTTTTTGGTGTGCGCCGGTGTACACAGGAAGTGACAATTTTCGCGCGGTT
TTAGGCGGATGTTGTAGTAAATTTGGGCGTAACCGAGTAAGATTTGGCCATTTTCGCGGGAAAACTGAATAAGACG
AAGTGAAATCTGAATAATTTTGTGTTACTCATAGCGCGTAATATTTGTCTAGGGAGATCTATAACTTCGTATAATG
TATGCTATACGAAGTTATTACCGAAGAAATCGCTCGAGATCTGGAAGGTGCTGAGGTACGATGAGACCCGCACCAG
GTGCAGACCCTGCGAGTGTGGCGGTAAACATATTGGGAACCAGCCTGTGATGCTGGATGTGACCGAGGAGCTGAGG
CCCGATGAGTTGGTGCTGGCCTGCACCCGCGCTGAGTTTGGCTCTAGCGATGAAGATACAGATTGAGGTACTGAAA
TGTGTGGGCGTGGCTTAAGGGTGGGAAAGAATATATAAGGTGGGGGTCTTATGTAGTTTTGTATCTGTTTTGCAGC
AGCCGCCGCCGCCATGAGCACCAACTCGTTTGATGGAAGCATTGTGAGCTCATATTTGACAACGCGCATGCCCCCA
TGGGCCGGGGTGCGTCAGAATGTGATGGGCTCCAGCATTGATGGTCGCCCCGTCCTGCCCGCAAACTCTACTACCT
TGACCTACGAGACCGTGTCTGGAACGCCGTTGGAGACTTGCAGCCTCCGCCGCCGCTTCAGCCGCTGCAGCCACCGC
CCGCGGGATTGTGACTGACTTTGCTTTCCTGAGCCCGCTTGCAAGCAGTGCAGCTTCCCGTTCATCCGCCCGCGAT
GACAAGTTGACGGCTCTTTTGGCACAATTGGATTCTTTGACCCGGGAACTTAATGTCGTTTCTCAGCAGCTGTTGG
ATCTGCGCCAGCAGGTTTCTGCCCTGAAGGCTTCCTCCCCTCCCAATGCGGTTTAAAACATAAATAAAAAACCAGA
CTCTGTTTGGATTTGGATCAAGCAAGTGTCTTGCTGTCTTTATTAGGGGTTTTGCGCGCGCGGTAGGCCCGGGAC
CAGCGGTCTCGGTCGTTGAGGGTCCTGTGTATTTTTTCCAGGACGTGGTAAAGGTGACTCTGGATGTTCAGATACA
TGGGCATAAGCCCGTCTCTGGGGTGGAGGTAGCACCACTGCAGAGCTTCATGCTGCGGGGTGGTGTTGTAGATGAT
CCAGTCGTAGCAGGAGCGCTGGGCGTGGTGCCTAAAAATGTCTTTCAGTAGCAAGCTGATTGCCAGGGGCAGGCCC
TTGGTGTAAGTGTTTACAAAGCGGTTAAGCTGGGATGGGTGCATACGTGGGGATATGAGATGCATCTTGGACTGTA
TTTTTAGGTTGGCTATGTTCCCAGCCATATCCCTCGGGGATTCATGTTGTGCAGAACCACCAGCACAGTGTATCC
GGTGCACTTGGGAAATTTGTCATGTAGCTTAGAAGGAAATGCGTGGAAGAACTTGGAGACGCCCTTGTGACCTCCA
AGATTTTCCATGCATTCGTCCATAATGATGGCAATGGGCCCACGGCCGGCGGCCTGGGCGAAGATATTTCTGGGAT
CACTAACGTCATAGTTGTGTTCCAGGATGAGATCGTCATAGGCCATTTTTACAAAGCGCGGCGGAGGGTGCCAGA
CTGCCGTATAATGGTTCCATCCGGCCCAGGGGCGTAGTTACCCTCACAGATTTGCATTTCCCACGCTTTGAGTTCA
GATGGGGGGATCATGTCTACCTGCGGGCGATGAAGAAAACGGTTTCCGGGGTAGGGCAGATCAGCTGGGAGAAA
GCAGGTTCCTGAGCAGCTGCGACTTACCGCAGCCGGTGGGCCCGTAAATCACACCTATTACCGGGTGCAACTGGTA
GTTAAGAGAGCTGCAGCTGCCGTCATCCCTGAGCAGGGGGCCCACTTCGTTAAGCATGTCCCTGACTCGCATGTTT
TCCCTGACCAAATCCGCCAGAAGGCGCTCGCCGCCCAGCGATAGCAGTTCTTGCAAGGAAGCAAAGTTTTTCAACG
GTTTGAGACCGTCCGCGGTAGGCATGCTTTTGAGCGTTTGACCAAGCAGTTCCAGGCGGTCCCACAGCTCGGTCAC
CTGCTCTACGGCATCTCGATCCAGCATATCTCCTCGTTTCGCGGGTTGGGGCGGCTTTCGCTGTACGGCAGTAGTC
GGTGCTCGTCCAGACGGGCCAGGGTCATGTCTTTCCACGGGCGCAGGGTCCTCGTCAGCGTAGTCTGGGTCACGGT
GAAGGGGTGCGCTCCGGGCTGCGCGCTGGCCAGGGTGCGCTTGAGGCTGGTCCTGCTGGTGCTGAAGCGCTGCCGG
TCTTCGCCCTGCGCGTCGGCCAGGTAGCATTTGACCATGGTGTCATAGTCCAGCCCCTCCGCGGCGTGGCCCTTGG
CGCGCAGCTTGCCCTTGGAGGAGCGCGCCGCACGAGGGGCAGTGCAGACTTTTGAGGGCGTAGAGCTTGGGCGCGAG
AAATACCGATTCCGGGGAGTAGGCATCCGCGCCGCAGGCCCCGCAGACGGTCTCGCATTCCACGAGCCAGGTGAGC
TCTGGCCGTTCGGGGTCAAAAACCAGGTTTCCCCCATGCTTTTTGATGCGTTCTTACCTCTGGTTTCCATGAGCC
GGTGTCCACGCTCGGTGACGAAAAGGCTGTCCGTGTCCCGTATACAGACTTGAGAGGCCTGTCCTCGAGCGGTGT
TCCGCGGTCCTCCTCGTATAGAAACTCGGACCACTCTGAGACAAAGGCTCGCGTCCAGGCCAGCACGGAAGGAGGCT
AAGTGGGAGGGGTAGCGGTCGTTGTCCACTAGGGGGTCCACTCGCTCCAGGGTGTGAAGACACATGTCGCCCTCTT
CGGCATCAAGGAAGGTGATTGGTTTGTAGGTGTAGGCCACGTGACCGGGTGTTCCTGAAGGGGGGCTATAAAGGG
GGTGGGGGCGCGTTCGTCCTCACTCTCTTCCGCATCGCTGTCTGCGAGGGCCAGCTGTTGGGGTGAGTACTCCCTC
TGAAAAGCGGGCATGACTTCTGCGCTAAGATTGTCAGTTTCCAAAAACGAGGAGGATTGATATTCACCTGGCCCG
CGGTGATGCCTTTGAGGGTGGCCGCATCCATCTGGTCAGAAAGACAATCTTTTGTTGTCAAGCTTGGTGGCAAA
CGACCCGTAGAGGGCGTTGGACAGCAACTTGGCGATGGAGCGCAGGGTTTGGTTTTTGTCGCGATCGGCGCGCTCC
TTGGCCGCGATGTTTAGCTGCACGTATTCGCGCGCAACGCACCGCCATTCGGGAAAGACGGTGGTGCGCTCGTCGG
GCACCAGGTGCACGCGCCAACGCGGTTGTGCAGGGTGACAAGGTCAACGCTGGTGGCTACCTCTCCGCGTAGGCG
CTCGTTGGTCCAGCAGAGGCGGCCGCCCTTGCGCGAGCAGAATGGCGGTAGGGTCTAGCTGCGTCTCGTCCGGG
GGGTCTGCGTCCACGGTAAAGACCCCGGGCAGCAGGCGCGCGTCGAAGTAGTCTATCTTGCATCCTTGCAAGTCTA
GCGCCTGCTGCCATGCGCGGGCGGCAAGCGCGCGCTCGTATGGGTTGAGTGGGGGACCCCATGGCATGGGTGGGT
GAGCGCGGAGGCGTACATGCCGCAAATGTCGTAAACGTAGAGGGGCTCTCTGAGTATTCCAAGATATGTAGGGTAG
CATCTTCCACCGCGGATGCTGGCGCGCACGTAATCGTATAGTTCGTGCGAGGGAGCGAGGAGGTCGGGACCGAGGT
TGCTACGGCGGGCTGCTCTGCTCGGAAGACTATCTGCCTGAAGATGGCATGTGAGTTGGATGATATGGTTGGACG
CTGGAAGACGTTGAAGCTGGCGTCTGTGAGACCTACCGCGTCACGCACGAAGGAGGCGTAGGAGTCGCGCAGCTTG
TTGACCAGCTCGGCGGTGACCTGCACGTCTAGGGCGCAGTAGTCCAGGGTTTCCTTGATGATGTCATACTTATCCT
GTCCCTTTTTTTTCCACAGCTCGCGGTTGAGGACAAACTCTTCGCGGTCTTTCCAGTACTCTTGGATCGGAAACCC
GTCGGCCTCCGAACGGTAAGAGCCTAGCATGTAGAACTGGTTGACGGCCTGGTAGGCGCAGCATCCCTTTTCTACG
GGTAGCGCGTATCCTGCGCGGCCTTCCGGAGCGAGGTGTGGGTGAGCGCAAAGGTGTCCCTGACCATGACTTTGA
GGTACTGGTATTTGAAGTCAGTGTCGTCGCATCCGCCCTGCTCCCAGAGCAAAAAGTCCGTGCGCTTTTTGGAACG
CGGATTTGGCAGGGCGAAGGTGACATCGTTGAAGAGTATCTTTCCCGCGCGAGGCATAAAGTTGCGTGTGATGCGG
```

FIGURE 14 (cont.)

```
AAGGGTCCCGGCACCTCGGAACGGTTGTTAATTACCTGGGCGGCGAGCACGATCTCGTCAAAGCCGTTGATGTTGT
GGCCCACAATGTAAAGTTCCAAGAAGCGCGGGATGCCCTTGATGGAAGGCAATTTTTTAAGTTCCTCGTAGGTGAG
CTCTTCAGGGGAGCTGAGCCCGTGCTCTGAAAGGGCCCAGTCTGCAAGATGAGGGTTGGAAGCGACGAATGAGCTC
CACAGGTCACGGGCCATTAGCATTTGCAGGTGGTCGCGAAAGGTCCTAAACTGGCGACCTATGGCCATTTTTTCTG
GGGTGATGCAGTAGAAGGTAAGCGGGTCTTGTTCCCAGCGGTCCCATCCAAGGTTCGCGGCTAGGTCTCGCGCGGC
AGTCACTAGAGGCTCATCTCCGCCGAACTTCATGACCAGCATGAAGGGCACGAGCTGCTTCCCAAAGGCCCCCATC
CAAGTATAGGTCTCTACATCGTAGGTGACAAAGAGACGCTCGGTGCGAGGATGCGAGCCGATCGGGAAGAACTGGA
TCTCCCGCCACCAATTGGAGGAGTGGCTATTGATGTGGTGAAAGTAGAAGTCCCTGCGACGGGCCGAACACTCGTG
CTGGCTTTTGTAAAAACGTGCGCAGTACTGGCAGCGGTGCACGGGCTGTACATCCTGCACGAGGTTGACCTGACGA
CCGCGCACAAGGAAGCAGAGTGGGAATTTGAGCCCCTCGCCTGGCGGGTTTGGCTGGTGGTCTTCTACTTCGGCTG
CTTGTCCTTGACCGTCTGGCTGCTCGAGGGGAGTTACGGTGGATCGGACCACCACGCCGCGCGAGCCCAAAGTCCA
GATGTCCGCGCGCGGCGGTCGGAGCTTGATGACAACATCGCGCAGATGGGAGCTGTCCATGGTCTGGAGCTCCCGC
GGCGTCAGGTCAGGCGGGAGCTCCTGCAGGTTTACCTCGCATAGACGGGTCAGGGCGCGGGCTAGATCCAGGTGAT
ACCTAATTTCCAGGGGCTGGTTGGTGGCGGCGTCGATGGCTTGCAAGAGGCCGCATCCCCGCGGCGCGACTACGGT
ACCGCGCGGCGGCGGTGGGCCGCGGGGTGTCCTTCGATGATGCATCTAAAAGCGGTGACGCGGGCGAGCCCCCG
GAGGTAGGGGGGCTCCGGACCCGCCGGGAGACGGGGCAGGGCACGTCGGCGCCGCGCGCGGGCAGGAGCTGGTG
CTGCGCGCGTAGGTTGCTGGCGAACGCGACGACGCGGCGGTTGATCTCCTGAATCTGGCGCCTCTGCGTGAAGACG
ACGGGCCCGGTGAGCTTGAGCCTGAAAGAGAGTTCGACAGAATCAATTTCGGTGTCGTTGACGGCGGCCTGGCGCA
AAATCTCCTGCACGTCTCCTGAGTTGTCTTGATAGGCGATCTCGGCCATGAACTGCTCGATCTCTTCCTCCTGGAG
ATCTCCGCGTCCGGCTCGCTCCACGGTGGCGGCGAGGTCGTTGGAAATGCGGGCCATGAGCTGCGAGAAGGCGTTG
AGGCCTCCCTCGTTCCAGACGCGGCTGTAGACACGCCCCCTTCGGCATCGCGGGCGCGCATGACCACCTCGCGA
GATTGAGCTCCACGTGCCGGGCGAAGACGGCGTAGTTTCGCAGGCGCTGAAAGAGGTAGTTGAGGGTGGTGGCGGT
GTGTTCTGCCACGAAGAAGTACATAACCCAGCGTCGCAACGTGGATTCGTTGATATCCCCAAGGCCTCAAGGCGC
TCCATGGCCTCGTAGAAGTCCACGGCGAAGTTGAAAAACTGGGAGTTGCGCGCCGACACGGTTAACTCCTCCTCCA
GAAGACGGATGAGCTCGGCGACAGTGTCGCGCACCTCGCGCTCAAAGGCTACAGGGGCCTCTTCTTCTTCTTCAAT
CTCCTCTTCCATAAGGGCCTCCCCTTCTTCTTCTTCTGGCGGCGGTGGGGGAGGGGGGACACGCGGCGACGACGG
CGCACCGGGAGGCGGTCGACAAAGCGCTCGATCATCTCCCCGCGGCGACGGCGCATGGTCTCGGTGACGGCGCGGC
CGTTCTCGCGGGGCGCAGTTGGAAGACGCCGCCCGTCATGTCCGGTTATGGGTTGGCGGGGGGCTGCCATGCGG
CAGGGATACGGCGCTAACGATGCATCTCAACAATTGTTGTGTAGGTACTCCGCCGCCGAGGGACCTGAGCGAGTCC
GCATCGACCGGATCGGAAAACCTCTCGAGAAAGGCGTCTAACCAGTCACAGTCGCAAGGTAGGCTGAGCACCGTGG
CGGGCGGCAGCGGGCGGCGGTCGGGGTTGTTTCTGGCGGAGGTGCTGCTGATGATGTAATTAAAGTAGGCGGTCTT
GAGACGGCGGATGGTCGACAGAAGCACCATGTCCTTGGGTCCGGCCTGCTGAATGCGCAGGCGGTCGGCCATGCCC
CAGGCTTCGTTTTGACATCGGCCAGGTCTTTGTAGTAGTCGTTGCATGAGCCTTTCTACCGGCACTTCTTCTTCTC
CTTCCTCTTGTCCTGCATCTCTTGCATCTATCGCTCGGACGGCGGCGGAGTTTGGCCGTAGGTGGCGCCCTCTTCC
TCCCATGCGTGTGACCCCGAAGCCCCTCATCGGCTGAAGCAGGGCTAGGTCGGCGACAACGCGCTCGGCTAATATG
GCCTGCTGCACCTGCGTGAGGGTAGACTGGAAGTCATCCATGTCCACAAAGCGGTGGTATGCGCCCGTGTTGATGG
TGTAAGTGCAGTTGGCCATAACGGACCAGTTAACGGTCTGGTGACCCGGCTGCGAGAGCTCGGTGTACCTGAGACG
CGAGTAAGCCCTCGAGTCAAATACGTAGTCGTTGCAAGTCCGCACCAGGTACTGGTATCCCACCAAAAAGTGCGGC
GGCGGCTGGCGGTAGAGGGCCAGCGTAGGGTGGCCGGGGCTCCGGGGGCGAGATCTTCCAACATAAGGCGATGAT
ATCCGTAGATGTACCTGGACATCCAGGTGATGCCGGCGGCGGTGGTGGAGGCGCGCGGAAAGTCGCGGACGCGGTT
CCAGATGTTGCGCAGCGGCAAAAAGTGCTCCATGGTCGGACGCTCTGGCCGGTCAGGCGCGCGCAATCGTTGACG
CTCTACCGTGCAAAAGGAGAGCCTGTAAGCGGGCACTCTTCCGTGGTCTGGTGGATAAATTCGCAAGGGTATCATG
GCGGACGACCGGGGTTCGAGCCCCGTATCCGGCCGTCCGCCGTGATCCATGCGGTTACCGCCCGCGTGTCGAACCC
AGGTGTGCGACGTCAGACAACGGGGGAGTGCTCCTTTTGGCTTCCTTCCAGGCGCGGCGGCTGCTGCGCTAGCTTT
TTTGGCCACTGGCCGCGGCAGCGTAAGCGCTTAGGCTGGAAAGCGAAAGCATTAAGTGGCTCGCTCCCTGTAGCC
GGAGGGTTATTTCCAAGGGGTTGAGTCGCGGGACCCCCGGTTCGAGTCTCGGACCGGCCGGACTGCGGCGAACGGG
GGTTTGCCTCCCCGTCATGCAAGACCCCGCTTGCAAATTCCTCCGGAAACAGGGACGAGCCCCTTTTTTGCTTTTC
CCAGATGCATCCGGTGCTGCGGCAGATGCGCCCCCCTCCTCAGCAGCGGCAAGAGCAAGAGCAGCGGCAGACATGC
AGGGCACCCTCCCCTCCTCCTACCGCGTCAGGAGGGGCGACATCCGCGGTTGACGCGGCAGCAGATGGTGATTACG
AACCCCCGGCGCCGGCCCGGCACTACCTGGACTTGGAGGAGGGCGAGGGCCTGGCGCGGCTAGGAGCGCCCTC
TCCTGAGCGGTACCCAAGGGTGCAGCTGAAGCGTGATACGCGTGAGCGTACGTGCCGCGGCAGAACCTGTTTCGC
GACCGCGAGGGAGAGGAGCCCGAGGAGATGCGGGATCGAAAGTTCCACGCAGGGCGCGAGCTGCGGCATGGCCTGA
ATCGCGAGCGGTTGCTGCGCGAGGAGGACTTTGAGCCCGACGCGCGAACCCGGGATTAGTCCCGCGCGCACACGT
GGCGGCCGCCGACCTGGTAACCGCATACGAGCAGACGGTGAACCAGGAGATTAACTTTCAAAAAGCTTTAACAAC
CACGTGCCGTACGCTTGTGGCGCGCGAGGAGGTGGCTATAGGACTGATGCATCTGTGGGACTTTGTAAGCGCGCTGG
AGCAAAACCCAAATAGCAAGCGCGCTCATGGCGCAGCCTGTTCCTTATAGTGCAGCAGGACAACGAGGCATT
CAGGGATGCGCTGCTAAACATAGTAGCCCGAGGGCCGCTGGCTGCTCGATTTGATAAACATCCTGCAGAGCATA
GTGGTGCAGGAGCGCAGCTTGAGCCTGGCTGACAAGGCGCCGCCATCAACTATTCCATGCTTAGCCTGGGCAAGT
TTTACGCCCGCAAGATATACCATACCCCTTACGTTCCCATAGACAAGGAGGTAAAGATCGAGGGTTCTACATGCC
CATGGCGCTGAAGGTGCTTACCTTGAGCGACGACCTGGGCGTTTATCGCAACGAGCGCATCCACAAGGCCGTGAGC
GTGAGCCGGCGGCGCGAGCTCAGCGACCGCGAGCTGATGCACAGCCTGCAAAGGGCCCTGGCTGGCACGGGCAGCG
```

FIGURE 14 (cont.)

```
GCGATAGAGAGGCCGAGTCCTACTTTGACGCGGGCGCTGACCTGCGCTGGGCCCCAAGCCGACGCGCCCTGGAGGC
AGCTGGGGCCGGACCTGGGCTGGCGGTGGCACCCGCGCGCGCTGGCAACGTCGGCGGCGTGGAGGAATATGACGAG
GACGATGAGTACGAGCCAGAGGACGGCGAGTACTAAGCGGTGATGTTTCTGATCAGATGATGCAAGACGCAACGGA
CCCGGCGGTGCGGGCGGCGCTGCAGAGCCAGCCGTCCGGCCTTAACTCCACGGACGACTGGCGCCAGGTCATGGAC
CGCATCATGTCGCTGACTGCGCGCAATCCTGACGCGTTCCGGCAGCAGCCGCAGGCCAACCGGCTCTCCGGAATTC
TGGAAGCGGTGGTCCGGCGCGCGCAAACCCCACGCACGAGAAGGTGCTGGCGGATCGTAAACGCGCTGGCCGAAAA
CAGGGCCATCCGGCCCGACGAAGCCGGCCTGGTCTACGACGCGCTGCTTCAGCGCGTGGCTCGTTACAACAGCGGC
AACGTGCAGACCAACCTGGACCGGCTGGTGGGGGATGTGCGGAGGCCGTGGCGCAGCGTGAGCGCGCGCAGCAGC
AGGGCAACCTGGGCTCCATGGTTGCACTAAACGCCTTCCTGAGTACACAGCCCGCCAACGTGCCGCGGGACAGGA
GGACTACACCAACTTTGTGAGCGCACTGCGGCTAATGGTGACTGAGACACCGCAAAGTGAGGTGTACCAGTCTGGG
CCAGACTATTTTTTCCAGACCAGTAGACAAGGCCTGCAGACCGTAAACCTGAGCCAGGCTTTCAAAAACTTGCAGG
GGCTGTGGGGGTGCGGGCTCCCACAGGCGACCGCGCGACCGTGTCTAGCCTTGCTGACGCCCAACTCGCGCCTGTT
GCTGCTGCTAATAGCGCCCTTCACGGACAGTGGCAGCGTGTCCCGGGACACATACCTAGGTCACTTGCTGACACTG
TACCGCGAGGCCATAGGTCAGGCGCATGTGGACGAGCATACTTTCCAGGAGATTACAAGTGTCAGCCGCGCGCTGG
GGCAGGAGGACACGGGCAGCCTGGAGGCAACCCTAAACTACCTGCTGACCAACCGGCGGCAGAAGATCCCCTCGTT
GCACAGTTTAAACAGCGAGGAGGAGCGCATTTTGCGCTACGTGCAGCAGAGCGTGAGCCTTAACCTGATGCGCGAC
GGGGTAACGCCCAGCGTGGCGCTGGACATGACCGCGCGCAACATGGAACCGGGCATGTATGCCTCAAACCGGCCGT
TTATCAACCGCCTAATGGACTACTTGCATCGCGCGGCCGCCGTGAACCCCGAGTATTTCACCAATGCCATCTTGAA
CCCGCACTGGCTACCGCCCCCTGGTTTCTACACCGGGGATTCGAGGTGCCCGAGGGTAACGATGGATTCCTCTGG
GACGACATAGACGACGTGTTTTCCCCGCAACCGCAGACCCTGCTAGAGTTGCAACAGCGCGAGCAGGCAGAGG
CGGCGCTGCGAAAGCAAAGCTTCCGCAGGCCAAGCAGCTTGTCCGATCTAGGCGCTGCGGCCCCGCGGTCAGATGC
TAGTAGCCCATTTCCAAGCTTGATAGGGTCTCTTACCAGCACTCGCCACCACCCGCCCGCGCCTGCTGGGCGAGGAG
GAGTACCTAAACAACTCGCTGCTGCAGCCGCAGCGCGAAAAAAACCTGCCTCCGGCATTTCCCAACAACGGGATAG
AGAGCCTAGTGGACAAGATGAGTAGATGGAAGACGTACGCGCAGGAGCACAGGGACGTGCCAGGCCCGCGCCCGCC
CACCCGTCGTCAAAGGCACGACCGTCAGCGGGGTCTGGTGTGGGAGGACGATGACTCGGCAGACGACAGCAGCGTC
CTGGATTTGGGAGGGAGTGGCAACCCGTTTGCGCACCTTCGCCCCAGGCTGGGGAGAATGTTTTAAAAAAAAAAA
GCATGATGCAAAATAAAAAACTCACCAAGGCCATGGCACCGAGCGTTGGTTTTCTTGTATTCCCCTTAGTATGCGG
CGCGCGGCGATGTATGAGGAAGGTCCTCCTCCCTCCTACGAGAGTGTGGTGAGCGCGGCGCCAGTGGCGGCGGCGC
TGGGTTCTCCCTTCGATGCTCCCCTGGACCCGCCGTTTGTGCCTCCGCGGTACCTGCGGCCTACCGGGGGGAGAAA
CAGCATCCGTTACTCTGAGTTGGCACCCCTATTCGACACCACCCGTGTGTACCTGGTGGACAACAAGTCAACGGAT
GTGGCATCCCTGAACTACCAGAACGACCACAGCAACTTTCTGACCACGGTCATTCAAAACAATGACTACAGCCCGG
GGGAGGCAAGCACACAGACCATCAATCTTGACGACCGGTCGCACTGGGGCGGCGACCTGAAAACCATCCTGCATAC
CAACGCCCAAATGTGAACGAGTTCATGTTTACCAATAAGTTTAAGGCGCGGGTGATGCGTCGCGCTTGCTACT
AAGGACAATCAGGTGGAGCTGAAATACGAGTGGGTGGAGTTCACGCTGCCCGAGGGCAACTACTCCGAGACCATGA
CCATAGACCTTATGAACAACGCGATCGTGGAGCACTACTTGAAAGTGGGCAGACAGAACGGGGTTCTGGAAAGCGA
CATCGGGGTAAAGTTTGACACCCGCAACTTCAGACTGGGGTTTGACCCCGTCACTGGTCTTGTCATGCCTGGGGTA
TATACAAACGAAGCCTTCCATCCAGACATCATTTTGCTGCCAGGATGCGGGGTGGACTTCACCCACAGCCGCCTGA
GCAACTTGTTGGGCATCCGCAAGCGGCAACCCTTCCAGGAGGGCTTTAGGATCACCTACGATGATCTGGAGGGTGG
TAACATTCCCGCACTGTTGGATGTGGACGCCTACCAGGCGAGCTTGAAAGATGACACCGAACAGGGCGGGGGTGGC
GCAGGCGGCAGCAACAGCAGTGGCAGCGGCGCGGAAGAGAACTCCAACGCGGCAGCCGCGGCAATGCAGCCGGTGG
AGGACATGAACGATCATGCCATTCGCGGCGACACCTTTGCCACACGGGCTGAGGAGAAGCGCGCTGAGGCCGAAGC
AGCGGCCGAAGCTGCCGCCCCCCTGCGCAACCCGAGGTCGAGAAGCCTCAGAAGAAACCGGTGATCAAACCCCTG
ACAGAGGACAGCAAGAAACGCAGTTACAACCTAATAAGCAATGACAGCACCTTCACCCAGTACCGCAGCTGGTACC
TTGCATACAACTACGGCGACCCTCAGACCGGAATCCGCTCATGGACCCTGCTTTGCACTCCTGACGTAACCTGCGG
CTCGGAGCAGGTCTACTGGTCGTTGCCAGACATGATGCAAGACCCCGTGCACTCCAGAGCTTCTACAACGACCAGGCCGTCTACTCCC
AACTTTCCGGTGGTGGCCCGAGCGTGTTGCCCGTGCACTCCAGAGCTTCTACAACGACCAGGCCGTCTACTCCC
AACTCATCCGCCAGTTTACCTCTCTGACCCACGTGTTCAATCGCTTTCCCGAGAACCAGATTTTGGCGCGCCCGCC
AGCCCCCACCATCACCACCGTCAGTGAAAACGTTCCTGCTCTCACAGATCACGGACGCTACCGCTGCGCAACAGC
ATCGGAGGAGTCCAGCGAGTGACCATTACTGACGCCAGACGCCGCACCTGCCCCTACGTTTACAAGGCCCTGGGCA
TAGTCTCGCCGCGCGTCCTATCGAGCCGCACTTTTTGAGCAAGCATGTCCATCCTTATATCGCCCAGCAATAACAC
AGGCTGGGGCCTGCGCTTCCCAAGCAAGATGTTTGGCGGGGCCAAGAAGCGCTCCGACCAACACCCAGTGCGCGTG
CGCGGGCACTACCGCGCGCCCTGGGGCGCGCACAAACGCGGCCGCACTGGGCGCACCACCGTCGATGACGCCATCG
ACGCGGTGGTGGAGGAGGCGCGCAACTACACGCCCACGCCGCCACCAGTGTCCACAGTGGACGCGGCCATTCAGAC
CGTGGTGCGCGGAGCCCGGCGCTATGCTAAAATGAAGAGACGGCGGAGGCGCGTAGCACGTCGCCACCGCCGCCGA
CCCGGCACTGCCGCCCAACGCGCGGCGGCGGCCCTGCTTAACCGCGCACGTCGCACCGGCCGACGGGCGGCCATGC
GGGCCGCTCGAAGGCTGGCCGCGGGTATTGTCACTGTGCCCCCAGGTCCAGGCGACGAGCGGCCGCCGCAGCAGC
CGCGGCCATTAGTGCTATGACTCAGGGTCGCAGGGGCAACGTGTATTGGGTGCGCGACTCGGTTAGCGGCCTGCGC
GTGCCCGTGCGCACCCGCCCCCCGCGCAACTAGATTGCAAGAAAAAACTACTTAGACTGTACTGTTGTATGTATC
CAGCGGCGGCGGCGCGCAACGAAGCTATGTCCAAGCGCAAAATCAAAGAAGAGATGCTCCAGGTCATCGCGCCGGA
GATCTATGGCCCCCCGAAGAAGGAAGAGCAGGATTACAAGCCCCGAAAGCTAAAGCGGGTCAAAAAGAAAAAGAAA
GATGATGATGATGAACTTGACGACGAGGTGGAACTGCTGCACGCTACCGCGCCCAGGCGACGGGTACAGTGGAAAG
```

FIGURE 14 (cont.)

```
GTCGACGCGTAAAACGTGTTTTGCGACCCGGCACCACCGTAGTCTTTACGCCCGGTGAGCGCTCCACCCGCACCTA
CAAGCGCGTGTATGATGAGGTGTACGGCGACGAGGACCTGCTTGAGCAGGCCAACGAGCGCCTCGGGGAGTTTGCC
TACGGAAAGCGGCATAAGGACATGCTGGCGTTGCCGCTGGACGAGGGCAACCCAACACCTAGCCTAAAGCCCGTAA
CACTGCAGCAGGTGCTGCCCGCGCTTGCACCGTCCGAAGAAAAGCGCGGCCTAAAGCGCGAGTCTGGTGACTTGGC
ACCCACCGTGCAGCTGATGGTACCCAAGCGCCAGCGACTGGAAGATGTCTTGGAAAAAATGACCGTGGAACCTGGG
CTGGAGCCCGAGGTCCGCGTGCGGCCAATCAAGCAGGTGGCGCCGGGACTGGGCGTGCAGACCGTGGACGTTCAGA
TACCCACTACCAGTAGCACCAGTATTGCCACCGCCACAGAGGGCATGGAGACACAAACGTCCCCGGTTGCCTCAGC
GGTGGCGGATGCCGCGGTGCAGGCGGTCGCTGCGGCCGCGTCCAAGACCTCTACGGAGGTGCAAACGGACCCGTGG
ATGTTTCGCGTTTCAGCCCCCGGCGCCCGCGCGGTTCGAGGAAGTACGGCGCCGCCAGCGCGCTACTGCCCGAAT
ATGCCCTACATCCTTCCATTGCGCCTACCCCGGCTATCGTGGCTACACCTACCGCCCCAGAAGACGAGCAAGTAC
CCGACGCCGAACCACCACTGGAACCCGCCGCCGCCGTCGCCGTCGCCAGCCCGTGCTGGCCCCGATTTCCGTGCGC
AGGGTGGCTCGCGAAGGAGGCAGGACCCTGGTGCTGCCAACAGCGCGCTACCACCCCAGCATCGTTTAAAAGCCGG
TCTTTGTGGTTCTTGCAGATATGGCCCTCACCTGCCGCCTCCGTTTCCGGTGCCGGGATTCCGAGGAAGAATGCA
CCGTAGGAGGGGCATGGCCGGCTACGGCCTGACGGCGGCATGCGTCGTGCGCACCACCGGCGGCGGCGCGCGTCG
CACCGTCGCATGCGCCGCGGTATCCTGCCCCTCCTTATTCCACTGATCGCCGCGGCGATTGGCGCCGTGCCCGGAA
TTGCATCCGTGGCCTTGCAGGCGCAGAGACACTGATTAAAAACAAGTTGCATGTGGAAAAATCAAAATAAAAAGTC
TGGACTCTCACGCTCGCTTGGTCCTGTAACTATTTTGTAGAATGGAAGACATCAACTTTGCGTCTCTGGCCCCGCG
ACACGGCTCGCGCCCGTTCATGGAAACTGGCAAGATATCGGCACCAGCAATATGAGCGGTGGCGCCTTCAGCTGG
GGCTCCTGTGGAGCGGCATTAAAAATTTCGGTTCCACCGTTAAGAACTATGGCAGCAAGGCCTGGAACAGCAGCA
CAGGCCAGATGCTGAGGGATAAGTTGAAAGAGCAAAATTTCCAACAAAAGGTGGTAGATGGCCTGGCCTCTGGCAT
TAGCCGGGTGGTGGACCTGGCCAACCAGGCAGTGCAAAATAAGATTAACAGTAAGCTTGATCCCCGCCCTCCCGTA
GAGGAGCCTCCACCGGCCGTGGAGACAGTGTCTCCAGAGGGGCGTGGCGAAAAGCGTCCGCGCCCCGACAGGGAAG
AAACTCTGGTGACGCAAATAGACGAGCCTCCCTCGTACGAGGAGGCACTAAAGCAAGGCCTGCCCACCACCCGTCC
CATCGCCCCATGGCTACCGGAGTGCTGGGCCAGCACACACCCGTAACGCTGGACCTGCCTCCCCCCGCCGACACC
CAGCAGAAACCTGTGCTGCCAGGCCCGACCGCCGTTGTTGTAACCCGTCCTAGCCGCGCGTCCCTGCGCGCGCCG
CCAGCGGTCCGCGATCGTTGCGGCCCGTAGCCAGTGGCAACTGGCAAAGCACACTGAACAGCATCGTGGGTCTGGG
GGTGCAATCCCTGAAGCGCCGACGATGCTTCTGAATAGCTAACGTGTCGTATGTGTGTCATGTATGCGTCCATGTC
GCCGCCAGAGGAGCTGCTGAGCCGCCGCGCGCCCGCTTTCCAAGATGGCTACCCCTTCGATGATGCCGCAGTGGTC
TTACATGCACATCTCGGGCCAGGACGCCTCGGAGTACCTGAGCCCCGGGCTGGTGCAGTTTGCCCGCGCCACCGAG
ACGTACTTCAGCCTGAATAACAAGTTTAGAAACCCCACGGTGGCGCCTACGCACGACGTGACCACAGACCGGTCCC
AGCGTTTGACGCTGCGGTTCATCCCTGTGGACCGTGAGGATACTGCGTACTCGTACAAGGCGCGGTTCACCCTAGC
TGTGGGTGATAACCGTGTGCTCGACATGGCTTCCACGTACTTTGACATCCGCGGCGTGCTGGACAGGGGCCCTACT
TTTAAGCCCTACTCTGGCCACTGCCTACAACGCCCTGGCTCCCAAGGGGTGCCCCAAATCCTTGCGAATGGGATGAAG
CTGCTACTGCTCTTGAAATAAACCTAGAAGAAGAGGACGATGCAACGAAGACGAAGTAGACGAGCAAGCTGAGCA
GCAAAAAACTCACGTATTTGGGCAGGCGCCTTATTCTGGTATAAATATTACAAAGGAGGGTATTCAAATAGGTGTC
GAAGGTCAAACACCTAAATATGCCGATAAAACATTTCAACCTGAACCTCAAATAGGAGAATCTCAGTGGTACGAAA
CTGAAATTAATCATGCAGCTGGAGAGTCCTTAAAAAGACTACCCAATGAAACCATGTTACGGTTCATATGCAAA
ACCCACAAATGAAAATGGAGGGCAAGGCATTCTTGTAAAGCAACAAAATGGAAAGCTAGAAAGTCAAGTGGAAATG
CAATTTTTCTCAACTACTGAGGCGACCGCAGGCAATGGTGATAACTTGACTCCTAAAGTGGTATTGTACAGTGAAG
ATGTAGATATAGAAACCCCAGACACTCATATTTCTTACATGCCCACTATTAAGGAAGGTAACTCACGAGAACTAAT
GGGCCAACAATCTATGCCCAACAGGCCTAATTACATTGCTTTTAGGGACAATTTTATTGGTCTAATGTATTACAAC
AGCACGGGTAATATGGGTGTTCTGGCGGGCCAAGCATCGCAGTTGAATGCTGTTGTAGATTTGCAAGACAGAAACA
CAGAGCTTTCATACCAGCTTTTGCTTGCTTCCATTGGTGTGATAGAACCAGGTACTTTTCTATGTGGAATCAGGCTGT
TGACAGCTATGATCCAGATGTTAGAATTATTGAAAATCATGGAACTGAAGATGAACTTCCAAATTACTGCTTTCCA
CTGGGAGGTGTGATTAATACAGAGACTCTTACCAAGGTAAAACCTAAAACAGGTCAGGAAAATGGATGGGAAAAG
ATGGCTACAGAATTTTCAGATAAAAATGAAATAAGAGTTGGAAATAATTTTGCCATGGAAATCAATCTAAATGCCAA
CCTGTGGAGAAATTTCCTGTACTCCAACATAGCGCTGTATTTGCCCGACAAGCTAAAGTACAGTCCTTCCAACGTA
AAAATTTCTGATAACCCAAACACCTACGACTACATGAACAAGCGAGTGGTGGCTCCCGGGTTAGTGGACTGCTACA
TTAACCTTGGAGCACGCTGGTCCCTTGACTATATGGACAACGTCAACCCATTTAACCACCACCGCAATGCTGGCCT
GCGCTACCGCTCAATGTTGCTGGGCAATGGTCGCTATGTGCCCTTCCACATCCAGGTGCCTCAGAAGTTCTTTGCC
ATTAAAAACCTCCTTCTCCTGCCGGGCTCATACACCTACGAGTGGAACTTCAGGAAGGATGTTAACATGGTTCTGC
AGAGCTCCCTAGGGAAATGACCTAAGGGTTGACGGAGCCAGCATTAAGTTTGATAGCATTTGCCTTTACGCCACCTT
CTTCCCCCATGGCCCACAACACCGCCTCCACGCTTGAGGCCATGCTTAGAAACGACACCAACGACCAGTCCTTTAAC
GACTATCTCTCCGCCGCCAACATGCTCTACCCTATACCCGCCAACGCTACCAACGTGCCCATATCCATCCCCTCCC
GCAACTGGGCGGCTTTCCGCGGCTGGGCCTTCACGCGCCTTAAGACTAAGGAAACCCCATCACTGGGCTCGGCTA
CGACCCTTATTACACCTACTCTGGCTCTATACCCTACCTAGATGGAACCTTTACCTCAACCACACCTTTAAGAAG
GTGGCCATTACCTTTGACTCTTCTGTCAGCTGGCCTGGCAATGACCGCCTGCTTACCCCCAACGAGTTTGAAATTA
AGCGCTCAGTTGACGGGGAGGGTTACAACGTTGCCCAGTGTAACATGACCAAAGACTGGTTCCTGGTACAAATGCT
AGCTAACTACAACATTGGCTACCAGGGCTTCTATATCCCAGAGAGCTACAAGGACCGCATGTACTCCTTCTTTAGA
AACTTCCAGCCCATGAGCCGTCAGGTGGTGGATGATACTAAATACAAGGACTACCAACAGGTGGGCATCCTACACC
AACACAACAACTCTGGATTTGTTGGCTACCTTGCCCCCACCATGCGCGAAGGACAGGCCTACCCTGCTAACTTCCC
```

FIGURE 14 (cont.)

```
CTATCCGCTTATAGGCAAGACCGCAGTTGACAGCATTACCCAGAAAAAGTTTCTTTGCGATCGCACCCTTTGGCGC
ATCCCATTCTCCAGTAACTTTATGTCCATGGGCGCACTCACAGACCTGGGCCAAAACCTTCTCTACGCCAACTCCG
CCCACGCGCTAGACATGACTTTTGAGGTGGATCCCATGGACGAGCCCACCCTTCTTTATGTTTGTTTGAAGTCTT
TGACGTGGTCCGTGTGCACCGGCCGCACCGCGCGTCATCGAAACCGTGTACCTGCGCACGCCCTTCTCGGCCGGC
AACGCCACAACATAAAGAAGCAAGCAACATCAACAACAGCTGCCGCCATGGCTCCAGTGAGCAGGAACTGAAAGC
CATTGTCAAAGATCTTGGTTGTGGGCCATATTTTTTGGGCACCTATGACAAGCGCTTTCCAGGCTTTGTTTCTCCA
CACAAGCTCGCCTGCCGCATAGTCAATACGGCCGGTCGCGAGACTGGGGGCGTACACTGGATGCCTTTGCCTGGA
ACCCGCACTCAAAAACATGCTACCTCTTTGAGCCCTTTGGCTTTTCTGACCAGCGACTCAAGCAGGTTTACCAGTT
TGAGTACGAGTCACTCCTGCGCCGTAGCGCCATTGCTTCTTCCCCCGACCGCTGTATAACGCTGGAAAAGTCCACC
CAAAGCGTACAGGGGCCCAACTCGGCCGCCTGTGGACTATTCTGCTGCATGTTCTCCACGCCTTTGCCAACTGGC
CCCAAACTCCCATGGATCACAACCCCACCATGAACCTTATTACCGGGTACCCAACTCCATGCTCAACAGTCCCA
GGTACAGCCCACCCTGCGTCGCAACCAGGAACAGCTCTACAGCTTCCTGGAGCGCCACTCGCCCTACTTCCGCAGC
CACAGTGCGCAGATTAGGAGCGCCACTTCTTTTTGTCACTTGAAAAACATGTAAAAATAATGTACTAGAGACACTT
TCAATAAAGGCAAATGCTTTTATTTGTACACTCTCGGGTGATTATTTACCCCCACCCTTGCCGTCTGCGCCGTTTA
AAAATCAAAGGGGTTCTGCCGCGCATCGCTATGCGCCACTGGCAGGGACACGTTGCGATACTGGTGTTTAGTGCTC
CACTTAAACTCAGGCACAACCATCCGCGGCAGCTCGGTGAAGTTTTCACTCCCACAGGCTGCGCACCATCACCAACG
CGTTTAGCAGGTCGGGCGCCGATATCTTGAAGTCGCAGTTGGGGCCTCCGCCCTGCGCGCGAGTTGCGATACAC
AGGGTTGCAGCACTGGAACACTATCAGCGCCGGGTGGTGCACGCTGGCCAGCACGCTCTTGTCGGAGATCAGATCC
GCGTCCAGGTCCTCCGCGTTGCTCAGGCGAACGGAGTCAACTTTGGTAGCTGCCTTCCCAAAAAGGGCGCGTGCC
CAGGCTTTGAGTTGCACTCGCACCGTAGTGGCATCAAAAGGTGACCGTGCCGGTCTGGGCGTTAGGATACAGCGC
CTGCATAAAAGCCTTGATCTGCTTAAAAGCCACCTGAGCCTTTGCGCCTTCAGAGAAGAACATGCCGAAGACTTG
CCGGAAAACTGATTGGCCGGACAGGCCGCGTCGTGCACGCAGCACCTTGCGTCGGTGTTGGAGATCTGCACCACAT
TTCGGCCCCACCGGTTCTTCACGATCTTGGCCTTGCTAGACTGCTCCTTCAGCGCGCGCTGCCCGTTTCGCTCGT
CACATCCATTTCAATCACGTGCTCCTTATTTATCATAATGCTTCCGTGTAGACACTTAAGCTCGCCTTCGATCTCA
GCGCACGCGGTGCAGCCACAACGCGCAGCCCGTGGGCTCGTGATGCTTGTAGGTCACCTCTGCAAACGACTGCAGGT
ACGCCTGCAGGAATCGCCCCCATCATCGTCACAAAGGTCTTGTTGCTGGTGAAGGTCAGCTGCAACCCGCGGTGCTC
CTCGTTCAGCCAGGTCTTGCATACGGCCGCCAGAGCTTCCACTTGGTCAGGCAGTAGTTTGAAGTTCGCCTTTAGA
TCGTTATCCACGTGGTACTTGTCCATCAGCGCGCGCGCAGCCTCCATGCCCTTCTCCCACGCAGACACGATCGGCA
CACTCAGCGGGTTCATCACCGTAAATTTCACTTTCCGCTTCGCTGGGCTCTTCCTCTTCCTCTTGCGTCCGCATACC
ACGCGCCACTGGGTCGTCTTCATTCAGCCGCCGCACTGTGCGCTTACCTCCTTTGCCATGCTTGATTAGCACCGGT
GGGTTGCTGAAACCCACCATTTGTAGCGCCACATCTTCTCTTTCTTCCTCGCTGTCCACGATTACCTCTGGTGATG
GCGGGCGCTCGGGCTTGGGAGAAGGGCGCTTCTTTTTCTTCTTGGGCGCAATGGCCAAATCCGCCGCCGAGGTCGA
TGGCCGCGGCTGGGTGTGCGCGGCACCAGCGCGTCTTGTGATGAGTCTTCCTCGTCCTCGGACTCGATACGCCGC
CTCATCCGCTTTTTTGGGGGCGCCCGGGGAGGCGGCGGCGACGGGGACGGGGACGACACGTCCTCCATGGTTCGGG
GACGTCGCGCCGCCACCGCGTCCGCGCTCGGGGGTGGTTTCGCGCTGCTCCCGACTGGCGCCCATTTCCTTCTC
CTATAGGCAGAAAAAGATCATGGAGTCAGTCGAGAAGAAGGACAGCCTAACCGCCCCCTCTGAGTTCGCCACCACC
GCCTCCACCGATGCCGCCAACGCGCCTACCACCTTCCCCGTCGAGGCACCCCCCTTGAGGAGGAGGAAGTGATTA
TCGAGCAGGACCCAGGTTTTGTAAGCGAAGACGACGAGGACCGCTCAGTACCAACAGAGGATAAAAAGCAAGACCA
GGACAACGCAGAGGCAAACGAGGAACAAGTCGGCCGGGGGACGAAAGGCATGGCGACTACCTAGATGTGGGAGAC
GACGTGCTGTTGAAGCATCTGCAGCGCCAGTGCGCCATTATCTGCGACGCGTTGCAAGAGCGCAGCGATGTGCCCC
TCGCCATAGCGGATGTCAGCCTTGCCTACGAACGCCACCTATTCTCACCGCGCGTACCCCCAAACGCCAAGAAAA
CGGCACATGCGAGCCCAACCCGCGCCTCAACTTCTACCCCGTATTTGCCGTGCCAGAGGTGCTTGCCACCTATCAC
ATCTTTTTCCAAAACTGCAAGATACCCTATCCTGCCGTGCCAACCGCAGCCGAGCGGACAAGCAGCTGGCCTTGC
GGCAGGGCGCTGTCATACCTGATATCGCCTCGCTCAACGAAGTGCCAAAAATCTTTGAGGGTCTTGGACGCGACGA
GAAGCGCGCGGCAAACGCTCTGCAACAGGAAAACAGCGAAAATGAAAGTCACTCTGGAGTGTTGGTGGAACTCGAG
GGTGACAACGCGCGCCTAGCCGTACTAAAACGCAGCATCGAGGTCACCCACTTTGCCTACCCGGCACTTAACCTAC
CCCCCAAGGTCATGAGCACAGTCATGAGTGAGCTGATCGTGCGCCGTGCGCAGCCCCTGGAGAGGGATGCAAATTT
GCAAGAACAAACAGAGGAGGGCCTACCCGCAGTTGGCGACGAGCAGCTAGCGCGCTGGCTTCAAACGCGCGAGCCT
GCCGACTTGGAGGAGCGACGCAAACTAATGATGGCCGCAGTGCTCGTTACCGTGGAGCTTGAGTGCATGCAGCGGT
TCTTTGCTGACCCGGAGATGCAGCGCAAGCTAGAGGAAACATTGCACTACACCTTTCGACAGGGCTACGTACGCCA
GGCCTGCAAGATCTCCAACGTGGAGCTCTGCAACCTGGTCTCCTACCTTGGAATTTTGCACGAAAACCGCCTTGGG
CAAAACGTGCTTCATTCCACGCTCAAGGGCGAGGCGCGCCGCGACTACGTGCCGCGACTGCGTTTACTTATTTCTAT
GCTACACCTGGCAGACGGCCATGGGCGTTTGGCAGCAGTGCTTGGAGGAGTGCAACCTCAAGGAGCTGCAGAAACT
GCTAAAGCAAAACTTGAAGGACCTATGGACGCCTTCAACGAGCGCTCCGTGGCGCACCTGGCGGACATCATT
TTCCCCGAACGCCTGCTTAAAACCCTGCAACAGGGTCTGCCAGACTTCACCAGTCAAAGCATGTTGCAGAACTTTA
GGAACTTTATCCTAGAGCGCTCAGGAATCTTGCCCGCCACCTGCTGTGCACTTCCTAGCGACTTTGTGCCCATTAA
GTACCGCGAATGCCCTCCGCCGCTTTGGGGCCACTGCTACCTTCTGCAGCTAGCCAACTACCTTGCCTACCACTCT
GACATAATGGAAGACGTGAGCGGTGACGGTCTACTGGAGTGTCACTGTCGCTGCAACCTATGCACCCCGCACCGCT
CCCTGGTTTGCAATTCGCAGCTGCTTAACGAAAGTCAAATTATCGGTACCTTTGAGCTGCAGGTCCCTCGCCTGA
CGAAAAGTCCGCGGCTCCGGGGTTGAAACTCACTCCGGGCTGTGGACGTCGGCTTACCTTCGCAAATTTGTACCT
GAGGACTACCACGCCCACGAGATTAGGTTCTACGAAGACCAATCCCGCCCGCCAAATGCGGAGCTTACCGCCTGCG
```

FIGURE 14 (cont.)

```
TCATTACCCAGGGCCACATTCTTGGCCAATTGCAAGCCATCAACAAAGCCCGCCAAGAGTTTCTGCTACGAAAGGG
ACGGGGGGTTTACTTGGACCCCCAGTCCGGCGAGGAGCTCAACCCAATCCCCCCGCCGCCGCAGCCCTATCAGCAG
CAGCCGCGGGCCCTTGCTTCCCAGGATGGCACCCAAAAAGAAGCTGCAGCTGCCGCCGCCACCCACGGACGAGGAG
GAATACTGGGACAGTCAGGCACAGGAGGTTTTGGACGAGGAGGAGGAGGACATGATGGAAGACTGGGAGAGCCTAG
ACGAGGAAGCTTCCGAGGTCGAAGAGGTGTCAGACGAAACACCGTCACCCTCGGTCGCATTCCCCTCGCCGGCGCC
CCAGAAATCGGCAACCGGTTCCAGCATGGCTACAACCTCCGCTCCTCAGGCGCCGCCGGCACTGCCCGTTCGCCGA
CCCAACCGTAGATGGGACACCACTGGAACCAGGGCCGGTAAGTCCAAGCAGCCGCCGCCGTTAGCCCAAGAGCAAC
AACAGCGCCAAGGCTACCGCTCATGGCGCGGGCACAAGAACGCCATAGTTGCTTGCTTGCAAGACTGTGGGGGCAA
CATCTCCTTCGCCCGCCGCTTTCTTCTCTACCATCACGGCGTGGCCTTCCCCCGTAACATCCTGCATTACTACCGT
CATCTCTACAGCCCATACTGCACCGGCGGCAGCGGCAGCGGCAGCAACAGCAGCGGCCACACAGAAGCAAAGGCGA
CCGGATAGCAAGACTCTGACAAAGCCCAAGAAATCCACAGCGGCGGCAGCAGCAGGAGGAGCGCTGCGTCTGG
CGCCCAACGAACCCGTATCGACCCGCGAGCTTAGAACAGGATTTTCCCACTCTGTATGCTATATTTCAACAGAG
CAGGCGGCCAAGAACAAGAGCTGAAAATAAAAACAGGTCTCTGCGATCCCTCACCCGCAGCTGCCTGTATCACAAA
AGCGAAGATCAGCTTCGGCGCACGCTGGAAGACGCGGAGGCTCTCTTCAGTAAATACTGCGCGTGACTCTTAAGG
ACTAGTTTCGCGCCCTTTCTCAAATTTAAGCGCGAAAACTACGTCATCTCCAGCGGCCACACCCGGCGCCAGCACC
TGTCGTCAGCGCCATTATGAGCAAGGAAATTCCCACGCCCTACATGTGGAGTTACCAGCCACAAATGGGACTTGCG
GCTGGAGCTGCCCAAGACTACTCAACCCGAATAAACTACATGAGCGCGGGACCCCACATGATATCCCGGGTCAACG
GAATCCGCGCCCACCGAAACCGAATTCTCTTGGAACAGGCGGCTATTACCACCACACCTCGTAATAACCTTAATCC
CCGTAGTTGGCCCGCTGCCCTGGTGTACCAGGAAAGTCCCGCTCCCACCACTGTGGTACTTCCCAGAGACGCCCAG
GCCGAAGTTCAGATGACTAACTCAGGGGCGCAGCTTGCGGGCGGCTTTCGTCACAGGGTGCGGTCGCCCGGCAGG
GTATAACTCACCTGACAATCAGAGGGCGAGGTATTCAGCTCAACGACGAGTCGGTGAGCTCCTCGCTTGGTCTCCG
TCCGACGGGACATTTCAGATCGGCGGCGCCGGCCGTCCTTCATTCACGCCTCGTCAGGCAATCCTAACTCTGCAG
ACCTCGTCCTCTGAGCCGCGCTCTGGAGGCATTGGAACTCTGCAATTTATTGAGGAGTTTGTGCCATCGGTCTACT
TTAACCCCTTCTCGGGACCTCCCGGCCACTATCCGGATCAATTTATTCCTAACTTTGACGCGGTAAAGGACTCGGC
GGACGGCTACGACTGAATGTTAAGTGGAGAGGCAGAGCAACTGCGCCTGAAACACCTGGTCCACTGTCGCCGCCAC
AAGTGCTTTGCCCGCGACTCCGGTGAGTTTTGCTACTTTGAATTGCCCGAGGATCATATCGAGGGCCCGGCGCACG
GCGTCCGGCTTACCGCCCAGGGAGAGCTTGCCCGTAGCCTGATTCGGGAGTTTACCCAGCGCCCCCTGCTAGTTGA
GCGGGACAGGGGACCCTGTGTTCTCACTGTGATTTGCAACTGCCTAACCTTGGATTACATCAAGATCCTCTAGTT
AATTAACAGCTTGCATGCCTGCAGGTCGACGGATCGGGAGATCTCGGCCGCATATTAAGTGCATTGTTCTCGATAC
CGCTAAGTGCATTGTTCTCGTTAGCTCGATGGACAAGTGCATTGTTCTCTTGCTGAAAGCTCGATGGACAAGTGCA
TTGTTCTCTTGCTGAAAGCTCGATGGACAAGTGCATTGTTCTCTTGCTGAAAGCTCAGTACCCGGGAGTACCCTCG
ACCGCCGGAGTATAAATAGAGGCGCTTCGTCTACGGCGACAATTCAATTCAAACAAGCAAAGTGAACACGTCGC
TAAGCGAAAGCTAAGCAAATAAACAAGCGCAGCTGAACAAGCTAAACAATCTGCAGTAAAGTGCAAGTTAAAGTGA
ATCAATTAAAAGTAACCAGCAACCAAGTAAATCAACTGCAACTACTGAAATCTGCCAAGAAGTAATTATTGAATAC
AAGAAGAGAACTCTGAATACTTTCAACAAGTTACCGAGAAAGAAGAACTCACACACAGCTAGCGTTAAACTTAAG
CTTCACCATGGTGGGGCCCTGCATGCTGCTGCTGCTGCTGCTGGGCCTGAGGCTACAGCTCTCCCTGGGCATC
ATCCTAGTTGAGGAGGAGAACCCGGACTTCTGGAACCGCGAGGCAGCCGAGGCCCTGGGTGCCGCCAAGAAGCTGC
AGCCTGCACAGACAGCCGCCAAGAACCTCATCATCTTCCTGGGCGATGGGGTGGGGGTGTCTACGGTGACAGCTGC
CAGGATCCTAAAAGGGCAGAAGAAGGACAAACTGGGGCCTGAGATACCCTGGCCATGGACCGCTTCCCATATGTG
GCTCTGTCCAAGACATACAATGTAGACAAACATGTGCCAGACAGTGGAGCCACAGCCACCGGCCTACCTGTGCGGG
TCAAGGGCAACTTCCAGACCATTGGCTTGAGTGCAGCCGCCCGCTTTAACCAGTGCAACACGACACGCGGCAACGA
GGTCATCTCCGTGATGAATCGCGCCAAGAAAGCAGGCAAGTCAGTGGGAGTGGTAACCACCACACGAGTGCAGCAC
GCCTCGCCAGCCGGCACCTACGCCCACACGGTGAACCGCAACTGGTACTCGGACGCCGACGTGCCTGCCTCGGCCC
GCCAGGAGGGGTGCCAGGACATCGCTACGCAGCTCATCTCCAACATGGACATTGACGTGATCCTAGGTGGGGCCG
AAAGTACATGTTTCGCATGGGAACCCCAGACCCTGAGTACCCAGATGACTACAGCCAAGGTGGGACCAGGCTGGAC
GGGAAGAATCTGGTGCAGGAATGGCTGGCGAAGCACCAGGGTGCCCGGTACGTGTGGAACCGCACTGAGCTCATGC
GGGCTTCCCTGGACCCGTCTGTGGCCCATCTCATGGGTCTCTTTGAGCCTGGAGACATGAAATACCAGATCCACCG
AGACTCCACACTGGACCCCTCCCTGATGGAGATGACAGAGGCTGCCCTGCGCCTGCTGAGCAGGAACCCCGCGGC
TTCTTCCTCTTCGTGGAGGGTGGTCGCATCGACCATGGTCATCATGAAAGCAGGGCTTACCGGGCACTGACTGAGA
CGATCATGTTCGACGACGCCATTGAGAGGGCGGCCAGCTCACCAGCGAGGAGGACATTCGGCGAGCTCGTCACTGC
CGACCACTCCCACGTCTTCTCCTTCGGAGGCTGCCCCTGCAGGGGGCTCCATCTTCGGGCTGGCCCCTGGCAAG
GCCCGGGACAGGAAGGCCTACACGGTCCTCCTATACGGAAACGGTCCAGGCTATGTGCTCAAGGACGCGCCCGGC
CGGATGTTACCGAGAGCGAGAGCGGGAGCCCCGAGTATCGGCAGCAGTCAGCAGTGCCCCTGGACGAAGAGACCCA
CGCAGGCGAGGACGTGGCGGTGTTCGCGCGCGGCCCGCAGGCGCACCTGGTTCACGGCGTGCAGGAGCAGACCTTC
ATAGCGCACGTCATGGCCTTCGCCGCCTGCCTGGAGCCCTACACCGCCTGCGACCTGGCGCCCCCCGCCGGCACCA
CCGACGCCGCGCACCCGGGGCGGTCCGTGGTCCCCGCGTTGCTTCCTCTGCTGGCCGGGACCCTGCTGCTGCTGGA
GACGGCCACTGCTCCCTGAGTGTCCCGTCCCTGGGGCTCCTGCTTCCCCATCCCGGAGTTCTCCTGCTCCCCGCCT
CCTGTCGTCCTGCCTGGCCTCCAGCCCGAGTCGTCATCCCGGAGTCCCTATACAGAGGTCCTGCCATGGAACCTT
CCCCTCCCCGTCGCTCTGGGGACTGAGCCCATGACACCAAACCTGCCCCTTGGCTGCTCTCGGACTCCCTACCCC
AACCCCAGGGACAGATCTGGCCAGATTTGTAAAACAAATAGATTTTAGGCCCAAAGATTATTTAAAGCATTGCCTG
GAACGCAGTGAGTTTTTGTTAGAAAAGAGAATAAATTCAAAGTGGCATTGCTTTGCTTCTTATGTTAATTTGGTACA
```

FIGURE 14 (cont.)

```
GACCTGTGGCTGAGTTTGCTCAAAGTATTCAGAGCAGAATTGTGGAGTGGAAAGAGAGATTGGACAAAGAGTTTAG
TTTGTCAGTGTATCAAAAAATGAAGTTTAATGTGGCTATGGGAATTGGAGTTTTAGATTGGCTAAGAAACAGTGAT
GATGATGATGAAGACAGCCAGGAAAATGCTGATAAAAATGAAGATGGTGGGGAGAAGAACATGGAAGACTCAGGGC
ATGAAACAGGCATTGATTCACAGTCCCAAGGCTCATTTCAGGCCCCTCAGTCCTCACAGTCTGTTCATGATCATAA
TCAGCCATACCACATTTGTAGAGGTTTTACTTGCTTTAAAAAACCTCCCACACCTCCCCCTGAACCTGAAACATAA
AATGAATGCAATTGTTGTTGTTAACTTGTTTATTGCAGCTTATAATGGTTACAAATAAAGCAATAGCATCACAAAT
TTCACAAATAAAGCATTTTTTTCACTGCATTCTAGTTGTGGTTTGTCCAAACTCATCAATGTATCTTATCATGTCT
GGATCCCCAGGAAGCTCCTCTGTGTCCTCATAAACCTCCACCTCCTCTACTTGAGAGGGACATTCCAATCATAGGCT
GCCCATCCACCCTCTGTGTCCTCCTGTTAATTAGGTCACTTAACAAAAAGGALATTGGGTAGGGGTTTTTCACAGA
CCGCTTTCTAAGGGTAATTTTAAAATATCTGGGAAGTCCCTTCCACTGCTGTGTTCCAGAAGTGTTGGTAAACAGC
CCACAAATGTCAACAGCAGAAACATACAAGCTGTCAGCTTTGCACAAGGGCCCAACACCCTGCTCATCAAGAAGCA
CTGTGGTTGCTGTGTTAGTAATGTGCAAAACAGGAGGCACATTTTCCCCACCTGTGTAGGTTCCAAAATATCTAGT
GTTTTCATTTTTACTTGGATCAGGAACCAGCACTCCACTGGATAAGCATTATCCTTATCCAAAACAGCCTTGTGG
TCAGTGTTCATCTGCTGACTGTCAACTGTAGCATTTTTTGGGGTTACAGTTTGAGCAGGATATTTGGTCCTGTAGT
TTGCTAACACACCCTGCAGCTCCAAAGGTTCCCCACCAACAGCAAAAAAATGAAAATTTGACCCTTGAATGGGTTT
TCCAGCACCATTTTCATGAGTTTTTTGTGTCCCTGAATGCAAGTTTAACATAGCAGTTACCCCAATAACCTCAGTT
TTAACAGTAACAGCTTCCCACATCAAAATATTTCCACAGGTTAAGTCCTCATTTAAATTAGGCAAAGGAATTCCAC
TTCCCACTGCCTTGCTTCCGTCTCCCATTCAAACTTTTATCAACTGACATTATTCTAAGTAAAATCCTCTTCATTA
TGTTGTCAGCAATCCATTGCTTGAAGGCCTGGCTCCCCAGAACCCCTCGACTGGTATGTCTTCTCCTAGAATACTC
CAGAAGAAAAGGAGTGTATGAAGATAGTGACTGCACATTAAAATGACTGAAACCATAGTAAATAGGATGAGATTC
TGGGCAGATAAACAGACAGCTGGCTAGGATCATTTTTTTATGCCTTGGACTTCTTTGGCAATCTGTTGAAGCCTGA
CATTCCTCAGAATAATGTTTAAAGCCCAACAATAAGACCCTGTAGCACATATAATAAGTACTGCAGTTTTGAAGT
AGTGATAAGCATAAATGATATTTTGATATATTTATTATAACTGTAATGAGATGTGTACATATCTGTGACTTCATAG
GTACTGATTGTACTACTGTGATTTTTTGCCTACTTTCAAAATGAAAAGGAATGCTTAATTTCAGTTAGAGGTTAG
TAAAGACAAATAGGTAATTTTCTTCTCCAGTGAAGAGCATGGCGCCCCTTGCTATTCATGGACGCTTGCTTAAAGA
CTTGTACACAGGCTTGCTTTGTATCAACCTATGACTTCCCCTTACAGCCGATGATAGGTTTTATTTGCACCTCCT
TCGTGTACAAAGACAGTTTTGGTGGCTACGCCATCATTAAACTCATTATTATCATCCTTAAGCCTATAGATGTATC
CAGTTCTTCTGTTACATAATTGAAGCTGTAGTGAATTGTCTATCTTAAACTGCATCGCTAACTGACTACATTTCAC
ACTTCATTGCTTCCAACATAGACTAACCTTCTTGGATGTCCACTATTATTTGAACTTTTGAGATTTTTTTTCCTA
TTTCTAATATCTTAAAATTTCAGAAGACTTAAAGTTTTGCAACTACAGGGCTCCATATAGACATCTAGCTTGAATT
TATACACTTTCTTTCATTGATGTCCCTGGACTAAAAATGTTAAATATTTCTAACCGCTGTACTTAAAGTCCATTA
CAAACGAAGACTACTGTTGTTAAGTTGAATAGGCATCTTATATATTTTTCACCGGTGCAATAAATAACTTCTATTC
CCTTCTAACATCTGCTTGCGTTGCACTGAGAGTACACTATTGATTAGCAATAGGTTCGTGATTACAGCCCTTCTAT
AATTAATTGTTAGGTTAACATATTATTCATAAAATATTATTTATTAATTTTTACTTGATTTGCTACTGGATGCTT
AGAAATAGCTATGAGTATATTGGTAGAACCAGTACTTATATTTTATTACATTTTTACATTTCATAAAATTTAAGTG
ATATAAAAATCCTGAGGAAGTATGCCACAAAAGTGGTCTCAGTGGAAATTTAAATATGTTAACATTTATTTTTAAA
ATGTAGCGTGAAATAGACAACTTTAAAAGCTCAGCTTAAAAAAAAAACTCAAGCAAGCTGAACTTGACTTTTTAAA
GCACTGAAGTGCAATATTTAATGTAGGTCAACATGTTTAAATGGGAAAATTTTTTTCCTAATTACAGCCAAATCCC
TAGCTGTAATTAACTTAAAATTTGTATACTATTTCACAACAGAGTCAGCATATACCACTTTCTTATAAAATTAGAA
AGATCTAAAATTTTAGAGCTTATTTGGTGAAACAGGCATATTGCTACATCTTTGTTTATAAATTATAATGTGCCTT
TAGAGCCCAATAACAGATAACAAGATTTTGAAAATTCAGGTGAATTAGAGTTATCAGAGGGAATGTAATACACTC
TATTCAAATACTATATGAGTAAGACATTTAAAATAGGAAACAATACTTTATATATTAAAAAAAATTAATCTTCCAG
TCGATTTAATCCACTTTATGAATTCATTTAAATCGATTTAAATTCGAATTAATTAACTAGAGTACCCGGGGATCTT
ATTCCCTTTAACTAATAAAAAAAATAATAAAGCATCACTTACTTAAAATCAGTTAGCAAATTTCTGTCCAGTTTA
TTCAGCAGCACCTCCTTGCCCTGCTCCCAGCTCTGGTATTGCAGCTTCCTCCTGGCTGCAAACTTTCTCCACAATC
TAAATGGAATGTCAGTTTCCTCCTGTTCCTGTCCATCCGCACCCACTATCTTCATGTTGTTGCAGATGAAGCGCGC
AAGACCGTCTGAAGATACCTTCAACCCCGTGTATCCATATGACACGGAAACCGGTCCTCCAACTGTGCCTTTCTT
ACTCCTCCCTTTGTATCCCCCAATGGGTTTCAAGAGAGTCCCCCTGGGGTACTCTCTTTGCGCCTATCCGAACCTC
TAGTTACCTCCAATGGCATGCTTGCGCTCAAAATGGGCAACGGCCTCTCTCTGGACGAGGCCGGCAACCTTACCTC
CCAAAATGTAACCACTGTGAGCCCACCTCTCAAAAAACCAAGTCAAACATAAACCTGGAAATATCTGCACCCCTC
ACAGTTACCTCAGAAGCCCTAACTGTGGCTGCCGCGCACCTCTAATGGTCGCGGGCAACACACTCACCATGCAAT
CACAGGCCCGCTAACCGTGCACGACTCCAAACTTAGCATTGCCACCCAAGGACCCCTCACAGTGTCAGAAGGAAA
GCTAGCCCTGCAAACATCAGGCCCCCTCACCACCACCGGATAGCAGTACCCTTACTATCACTGCCTCACCCCTCTA
ACTACTGCCACTGGTAGCTTGGGCATTGACTTGAAAGAGCCATTTATACACAAAATGGAAAACTAGGACTAAAGT
ACGGGGCTCCTTTGCATGTAACAGACGACCTAAACACTTTGACCGTAGCAACTGGTCCAGGTGTGACTATTAATAA
TACTTCCTTGCAAACTAAAGTTACTGGAGCCTTGGGTTTGATTCACAAGGCAATATGCAACTTAATGTAGCAGGA
GGACTAAGGATTGATTCTCAAAACAGACGCCTTATACTTGATGTTAGTTATCCGTTTGATGCTCAAAACCAACTAA
ATCTAAGACTAGGACAGGGCCCTCTTTTTATAAACTCAGCCCACAACTTGGATATTAACTACAACAAAGGCCTTTA
CTTGTTTACAGCTTCAAACAATTCCAAAAGCTTGAGGTTAACCTAAGCACTGCCAAGGGGTTGATGTTTGACGCT
ACAGCCATAGCCATTAATGCAGGAGATGGGCTTGAATTTGGTTCACCTAATGCACCAAACACAAATCCCCTCAAAA
CAAAAATTGGCCATGGCCTAGAATTTGATTCAAACAAGGCTATGGTTCCTAAACTAGGAACTGGCCTTAGTTTTGA
```

FIGURE 14 (cont.)

```
CAGCACAGGTGCCATTACAGTAGGAAACAAAAATAATGATAAGCTAACTTTGTGGACCACACCAGCTCCATCTCCT
AACTGTAGACTAAATGCAGAGAAAGATGCTAAACTCACTTTGGTCTTAACAAAATGTGGCAGTCAAATACTTGCTA
CAGTTTCAGTTTTGGCTGTTAAAGGCAGTTTGGCTCCAATATCTGGAACAGTTCAAAGTGCTCATCTTATTATAAG
ATTTGACGAAAATGGAGTGCTACTAAACAATTCCTTCCTGGACCCAGAATATTGGAACTTTAGAAATGGAGATCTT
ACTGAAGGCACAGCCTATACAAACGCTGTTGGATTTATGCCTAACCTATCAGCTTATCCAAAATCTCACGGTAAAA
CTGCCAAAAGTAACATTGTCAGTCAAGTTTACTTAAACGGAGACAAAACTAAACCTGTAACACTAACCATTACACT
AAACGGTACACAGGAAACAGGAGACACAACTCCAAGTGCATACTCTATGTCATTTTCATGGGACTGGTCTGGCCAC
AACTACATTAATGAAATATTTGCCACATCCTCTTACACTTTTTCATACATTGCCCAAGAATAAAGAATCGTTTGTG
TTATGTTTCAACGTGTTTATTTTTCAATTGCAGAAAATTTCAAGTCATTTTTCATTCAGTAGTATAGCCCCACCAC
CACATAGCTTATACAGATCACCGTACCTTAATCAAACTCACAGAACCCTAGTATTCAACCTGCCACCTCCCTCCCA
ACACACAGAGTACACAGTCCTTTCTCCCCGGCTGGCCTTAAAAAGCATCATATCATGGGTAACAGACATATTCTTA
GGTGTTATATTCCACACGGTTTCCTGTCGAGCCAAACGCTCATCAGTGATATTAATAAACTCCCCGGGCAGCTCAC
TTAAGTTCATGTCGCTGTCCAGCTGCTGAGCCACAGGCTGCTGTCCAACTTGCGGTTGCTTAACGGGCGGCGAAGG
AGAAGTCCACGCCTACATGGGGTAGAGTCATAATCGTGCATCAGGATAGGCGGTGGTGCTGCAGCAGCGCGCCA
ATAAACTGCTGCCGCCGCCGCTCCGTCCTGCAGGAATACAACATGGCAGTGGTCTCCTCAGCGATGATTCGCACCG
CCCGCAGCATAAGGCGCCTTGTCCTCCGGGCACAGCAGCGCACCCTGATCTCACTTAAATCAGCACAGTAACTGCA
GCACAGCACCACAATATTGTTCAAAATCCCACAGTGCAAGGCGCTGTATCCAAAGCTCATGGCGGGACCACAGAA
CCCACGTGGCCATCATACCACAAGCGCAGGTAGATTAAGTGGCGACCCCTCATAAACACGCTGGACATAAACATTA
CCTCTTTTGGCATGTTGTAATTCACCACCTCCCGGTACCATATAAACCTCTGATTAAACATGGCGCCATCCACCAC
CATCCTAAACCAGCTGGCCAAAACCTGCCCGCCGGCTATACACTGCAGGGAACCGGGACTGGAACAATGACAGTGG
AGAGCCCAGGACTCGTAACCATGGATCATCATGCTCGTCATGATATCAATGTTGGCACAACACAGGCACACGTGCA
TACACTTCCTCAGGATTACAAGCTCCTCCCGCGTTAGAACCATATCCCAGGGAACAACCCATTCCTGAATCAGCGT
AAATCCCACACTGCAGGGAAGACCTCGCACGTAACTCACGTTGTGCATTGTCAAAGTGTTACATTCGGGCAGCAGC
GGATGATCCTCCAGTATGGTAGCGCGGGTTTCTGTCTCAAAAGGAGGTAGACGATCCCTACTGTACGGAGTGCGCC
GAGACAACCGAGATCGTGTTGGTCGTAGTGTCATGCCAAATGGAACGCCGGACGTAGTCATATTTCCTGAAGCAAA
ACCAGGTGCGGCGTGACAAACAGATCTGCGTCTCCGGTCTCGCCGCTTAGATCGCTCTGTGTAGTAGTTGTAGTA
TATCCACTCTCTCAAAGCATCCAGGCGCCCCCTGGCTTCGGGTTCTATGTAAACTCCTTCATGCGCCGCTGCCCTG
ATAACATCCACCACCGCAGAATAAGCCACACCCAGCCAACCTACACATTCTGTTCTGCGAGTCACACACGGGAGGAG
CGGGAAGAGCTGGAAGAACCCATGTTTTTTTTTTATTCCAAAAGATTATCCAAAACCTCAAAATGAAGATCTATTA
AGTGAACGCGCTCCCCTCCGGTGGCGTGGTCAAACTCTACAGCCAAAGAACAGATAATGGCATTTGTAAGATGTTG
CACAATGGCTTCCAAAAGGCAAACGGCCCTCACGTCCAAGTGGACGTAAAGGCTAAACCCTTCAGGGTGAATCTCC
TCTATAAACATTCCAGCACCTTCAACCATGCCCAAATAATTCTCATCTCGCCACCTTCTCAATATATCTCTAAGCA
AATCCCGAATATTAAGTCCGGCCATTGTAAAAATCTGCTCCAGAGCGCCCTCCACCTTCAGCCTCAAGCAGCGAAT
CATGATTGCAAAAATTCAGGTTCCTCACAGACCTGTATAAGATTCAAAAGCGGAACATTAACAAAAATACCGCGAT
CCCGTAGGTCCCTTCGCAGGGCCAGCTGAACATAATCGTGCAGGTCTGCACGGACCAGCGCGGCCACTTCCCCGCC
AGGAACCTTGACAAAAGAACCCACACTGATTATGACACGCATACTGGGAGCTATGCTAACCAGCGTAGCCCCGATG
TAAGCTTTGTTGCATGGGCGGCGATATAAAATGCAAGGTGCTCAAAAAATCAGGCAAAGCCTCGCGCAAAAAA
GAAAGCACATCGTAGTCATGCTCATGCAGATAAAGGCAGGTAAGCTCCGGAACCACCACAGAAAAAGACACCATTT
TTCTCTCAAACATGTCTGCGGGTTTCTGCATAAACACAAAATAAAATAACAAAAAAACATTTAAACATTAGAAGCC
TGTCTTACAACAGGAAAACAACCCTTATAAGCATAAGACGGACTACGGCCATGCCGGCGTGACCGTAAAAAAACT
GGTCACCGTGATTAAAAAGCACCACCGACAGCTCCTCGGTCATGTCCGGAGTCATAATGTAAGACTCGGTAAACAC
ATCAGGTTGATTCATCGGTCAGTGCTAAAAAGCGACCGAAATAGCCCGGGGAATACATACCCGCAGGCGTAGAGA
CAACATTACAGCCCCCATAGGAGGTATAACAAAATTAATAGGAGAGAAAAACACATAAACACCTGAAAAACCCTCC
TGCCTAGGCAAAATAGCACCCTCCCGCTCCAGAACAACATACAGCGCTTCACAGCGGCAGCCTAACAGTCAGCCTT
ACCAGTAAAAAGAAAACCTATTAAAAAAACACCACTCGACACGGCACCAGCTCAATCAGTCACAGTGTAAAAAG
GGCCAAGTGCAGAGCGAGTATATATAGGACTAAAAATGACGTAACGGTTAAAGTCCACAAAAAACACCCAGAAAA
CCGCACGCGAACCTACGCCCAGAAACGAAAGCCAAAAAACCCACAACTTCCTCAAATCGTCACTTCCGTTTTCCCA
CGTTACGTAACTTCCCATTTTAAGAAAACTACAATTCCCAACACATACAAGTTACTCCGCCCTAAAACCTACGTCA
CCCGCCCCGTTCCCACGCCCCGCGCCACGTCACAACTCCACCCCCTCATTATCATATTGGCTTCAATCCAAAATA
AGGTATATTATTGATGATGGCCGGCCGAATTGAATCAGGGGATAACGCAGGAAAGAACATGTGAGCAAAAGGCCAG
CAAAAGGCCAGGAACCGTAAAAGGCCGCGTTGCTGGCGTTTTTCCATAGGCTCCGCCCCCTGACGAGCATCACA
AAAATCGACGCTCAAGTCAGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAACCCGGTAAGACACGACTTATC
GCCACTGGCAGCAGCCACTGGTAACAGGATTAGCAGAGCGAGGTATGTAGGCGGTGCTACAGAGTTCTTGAAGTGG
TGGCCTAACTACGGCTACACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGCAAGCAGCAGATTAC
GCGCAGAAAAAAGGATCTCAAGAAGATCCTTTGATCTTTTCTACGGGGTCTGACGCTCAGTGGAACGAAAACTCA
CGTTAAGGGATTTTGGTCATGAGATTATCAAAAAGGATCTTCACCTAGATCCTTTTAAATTAAAAATGAAGTTTTA
AATCAATCTAAAGTATATATGAGTAAACTTGGTCTGACAGTTACCAATGCTTAATCAGTGAGGCACCTATCTCAGC
```

FIGURE 14 (cont.)

```
GATCTGTCTATTTCGTTCATCCATAGTTGCCTGACTCCCCGTCGTGTAGATAACTACGATACGGGAGGGCTTACCA
TCTGGCCCCAGTGCTGCAATGATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTATTAATTGTTGCCGGGAAGC
TAGAGTAAGTAGTTCGCCAGTTAATAGTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGTTACATGATCCCCATGTTGTGCAAAA
AAGCGGTTAGCTCCTTCGGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAGCGTTTCTGGGTGAGCA
AAAACAGGAAGGCAAAATGCCGCAAAAAAGGGAATAAGGGCGACACGGAAATGTTGAATACTCATACTCTTCCTTT
TTCAATATTATTGAAGCATTTATCAGGGTTATTGTCTCATGAGCGGATACATATTTGAATGTATTTAGAAAAATAA
ACAAATAGGGGTTCCGCGCACATTTCCCCGAAAAGTGCCAC
```

FIGURE 15 pD1962delBbsI-pIX (SEQ ID NO:14)

```
TCTAGAGTCGACCGGTCATGGCTGCGCCCGACACCCGCCAACACCCGCTGACGCGCCCTGACGGGCTTGTCTGCT
CCCGGCATCCGCTTACAGACAAGCTGTGACCGTCTCCGGGAGCTGCATGTGTCAGAGGTTTTCACCGTCATCACCG
AAACGCGCGAGGCAGCCGGATCATAATCAGCCATACCACATTTGTAGAGGTTTTACTTGCTTTAAAAAACCTCCCC
ACCTCCCCCTGAACCTGAAACATAAAATGAATGCAATTGTTGTTGTTAACTTGTTTATTGCAGCTTATAATGGTTA
CAAATAAAGCAATAGCATCACAAATTTCACAAATAAAGCATTTTTTTCACTGCATTCTAGTTGTGGTTTGTCCAAA
CTCATCAATGTATCTTATCATGTCTGGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGAATAAGGGCGACAC
GGAAATGTTGAATACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAAAGTGCCACCTGAC
GTCCATTGTTCATTCCACGGACAAAAACAGAGAAAGGAAACGACAGAGGCCAAAAAGCCTCGCTTTCAGCACCTGT
CGTTTCCTTTCTTTTCAGAGGGGTATTTTAAATAAAAACATTGGTTATGACGAAGAAGAACGAAACGCCTTAAAC
CGGAAAATTTTCATAAATAGCGAAAACCCGCGAGGTCGCGGCCCCGTAACCTGTCGGATCACCGGAAAGGACCCGT
AAAGTGATAATGATTATCATCTAGACTACATCGATGGGTCGTGCGCTCCTTTCGGTCGGGCGCTGCGGGTCGTGGG
GCGGGCGTCAGGCACCGGGCTTGCGGGTCATGCACCAGGTCGCGCGGTCCTTCGGGCACTCGACGTCGGCGGTGAC
GGTGAAGCCGAGCCGCTCGTAGAAGGGGAGGTTGCGGGGCGCGGAGGTCTCCAGGAAGGCGGGCACCCGGCGCGC
TCGGCCGCCTCCACTCCGGGGAGCACGACGGCGCTGCCCAGACCCTTGCCCTGGTGGTCGGGCGAGACGCCGACGG
TGGCCAGGAACCACGCGGGCTCCTTGGGCCGGTGCGGCGCCAGGAGGCCTTCCATCTGTTGCTGCGCGGCCAGCCG
GGAACCGCTCAACTCGGCCATGCGCGGGCCGATCTCGGCGAACACCGCCCCCGCTTCGACGCTCTCCGGCGTGGTC
CAGACCGCCACCGCGGCGCCGTCGTCCGCGACCCACACCTTGCCGATGTCGAGCCCGACGCGCGTGAGGAAGAGTT
CTTGCAGCTCGGTGACCCGCTCGATGTGGCGGTCCGGATCGACGGTGTGGCGCGTGGCGGGGTAGTCGGCGAACGC
GGCGGCGAGGGTGCGTACGGCCCTGGGGACGTCGTCGGGTGGCGAGGCGCACCGTGGGCTTGTACTCGGTCATG
GTAAGCTTGCTAGCAGCTGGTACCCAGCTTCTAGAGATCTGACGGTTCACTAAACGAGCTCTGCTTATATAGACCT
CCCACCGTACACGCCTACCGCCCATTTGCGTCAACGGGGCGGGGTTATTACGACATTTTGGAAAGTCCCGTTGATT
TTGGTGCCAAAACAAACTCCCATTGACGTCAATGGGGTGGAGACTTGGAAATCCCCGTGAGTCAAACCGCTATCCA
CGCCCATTGGTGTACTGCCAAAACCGCATCACCATGGTAATAGCGATGACTAATACGTAGATGTACTGCCAAGTAG
GAAAGTCCCGTAAGGTCATGTACTGGGCATAATGCCAGGCGGGCCATTTACCGTCATTGACGTCAATAGGGGGCGG
ACTTGGCATATGATACACTTGATGTACTGCCAAGTGGGCAGTTTACCGTAAATACTCCACCCATTGACGTCAATGG
AAAGTCCCTATTGGCGTTACTATGGGAACATACGTCATTATTGACGTCAATGGGCGGGGGTCGTTGGGCGGTCAGC
CAGGCGGGCCATTTACCGTAAGTTATGTAACGCGGAACTCCATATATGGGCTATGAACTAATGACCCCGTAATTGA
TTACTATTAATAACTAGTCAATAATCAATGTCAACATGGCGGTCATATTGGACATGAGCCAATATAAATGTACATA
TTATGATATAGATACAACGTATGCAATGGCCAATAGCCAATATTGATTTATGCTATATAACCAATGACTAATATGG
CTAATTGCCAATATTGATTCAATGTATAGATCTTCCATACCTACCAGTTCTGCGCCTGCAGCAATGCAACAACGTT
GCCCGGATCTGCGATGATAAGCTGTCAAACATGAGAATTGGTCCAGTAGCTTGGCGCCAGAAATCCGCGCGGTG
GTTTTTGGGGGTCGGGGGTGTTTGGCAGCCACAGACGCCCGGTGTTCGTGTCGCGCCAGTACATGCGGTCCATGCC
CAGGCCATCCAAAAACCATGGGTCTGTCTGCTCAGTCCAGTCGTGGACCAGACCCCACGCAACGCCCAAAATAATA
ACCCCCACGAACCATAAACCATTCCCATGGGGACCCCGTCCCTAACCCACGGGGCCAGTGGCTATGGCAGGGCC
TGCCGCCCGACGTTGGCTGCGAGCCCTGGGCCTTCACCCGAACTTGGGGGGTGGGGTGGGAAAAGGAAGAAACG
CGGGCGTATTGGCCCCAATGGGGTCTCGGTGGGGTATCGACAGAGTGCCAGCCCTGGGACCGAACCCCGCGTTTAT
GAACAAACGACCCAACACCCGTGCGTTTTATTCTGTCTTTTTATTGCCGTCATAGCGCGGGTTCCTTCCGGTATTG
TCTCCTTCCGTGTTTCAGTTAGCCTCCCCCATCTCCCTATTCCTTTGCCCTCGGACGAGTGCTGGGGCGTCGGTT
TCCACTATCGGCGAGTACTTCTACACAGCCATCGGTCCAGACGGCCGCGCTTCTGCGGGCGATTTGTGTACGCCCG
ACAGTCCCGGCTCCGGATCGGACGATTGCGTCGCATCGACCCTGCGCCCAAGCTGCATCATCGAAATTGCCGTCAA
CCAAGCTCTGATAGAGTTGGTCAAGACCAATGCGGAGCATATACGCCGGAGCCCGGCCGATCCTGCAAGCTCCGG
ATGCCTCCGCTCGAAGTAGCGCGTCTGCTGCTCCATACAAGCCAACCACGGCCTCCAGAAGAAGATGTTGGCGACC
TCGTATTGGGAATCCCCGAACATCGCCTCGCTCCAGTCAATGACCGCTGTTATGCGGCCATTGTCCGTCAGGACAT
TGTTGGAGCCGAAATCCGCGTGCACGAGGTGCCGGACTTCGGGGCAGTCCTCGGCCCAAAGCATCAGCTCATCGAG
AGCCTGCGCGACGGACGCACTGACGGTGTCGTCCATCACAGTTTGCCAGTGATACACATGGGGATCAGCAATCGCG
CATATGAAATCACGCCATGTAGTGTATTGACCGATTCCTTGCGGTCCGAATGGCCGAACCCGCTCGTCTGGCTAA
GATCGGCCGCAGCGCGCGCAAAACCCCTAAATAAAGACAGCAAGACACTTGCTTGATCCAAATCCAAACAGAGTCT
GGTTTTTTATTTATGTTTAAACCGCATTGGGAGGGGAGGAAGCCTTCAGGGCAGAAACCTGCTGGCGCAGATCCA
ACAGCTGCTGAGAAACGACATTAAGTTCCCGGGTCAAAGAATCCAATTGTGCCAAAAGAGCCGTCAACTTGTCATC
GCGGGCGGATGAACGGGAAGCTGCACTGCTTGCAAGCGGGCTCAGGAAAGCAAAGTCAGTCACAATCCCGCGGGCG
GTGGCTGCAGCGGCTGAAGCGGCGGCGGAGGCTGCAGTCTCCAACGGCGTTCCAGACACGGCTCTCGTAGGTCAAGG
TAGTAGAGTTTGCGGCGAGGACGGGCGACCATCAATGCTGGACCCCATCACATTCTGACGCACCCCGGCCCATGG
GGGCATGCGCGTTGTCAAATATGAGCTCACAATGCTTCCATCAAACGAGTTGGTGCTCATGGCGGCGGCGGCTGCT
GCAAAACAGATACAAAACTACATAAGACCCCCACCTTATATATTCTTTCCCACCCGGGATCTGCGGCACGCTGTTG
ACGCTGTTAAGCGGGTCGCTGCAGGGTCGCTCGGTGTTCGAGGCCACACGCGTCACCTTAATATGCGAAGTGGACC
TGGGACCGCGCCGCCCCGACTGCATCTGCGTGTTCGAATTCGCCAATGACAAGACGCTGGGCGGGTTTGTGTCAT
CATAGAACTAAAGACATGCAAATATATTTCTTCCGGGGACACCGCCAGCAAACGCGAGCAACGGGCCACGGGGATG
AAGCAGGGCATGGCGGCCCGACGCGCTGGGCTACGTCTTGCTGGCGTTCGCGACGCGAGGCTGGATGGCCTTCCCCA
TTATGATTCTTCTCGCTTCCGGCGGCATCGGGATGCCCGCGTTGCAGGCCATGCTGTCCAGGCAGGTAGATGACGA
```

FIGURE 15 (cont.)

CCATCAGGGACAGCTTCAAGGATCGCTCGCGGCTCTTACCAGCCTAACTTCGATCACTGGACCGCTGATCGTCACG
GCGATTTATGCCGCCTCGGCGAGCACATGGAACGGGTTGGCATGGATTGTAGGCGCCGCCCTATACCTTGTCTGCC
TCCCCGCGTTGCGTCGCGGTGCATGGAGCCGGGCCACCTCGACCTGAATGGAAGCCGGCGGCACCTCGCTAACGGA
TTCACCACTCCAAGAATTGGAGCCAATCAATTCTTGCGGAGAACTGTGAATGCGCAAACCAACCCTTGGCAGAACA
TATCCATCGCGTCCGCCATCTCCAGCAGCCGCACGCGGCGCAGCAAAAGGCCAGGAACCGTAAAAAGGCCGCGTTG
CTGGCGTTTTTCCATAGGCTCCGCCCCCTGACGAGCATCACAAAAATCGACGCTCAAGTCAGAGGTGGCGAAACC
CGACAGGACTATAAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGTTCAGCCCGACCGCTGCGCCTTATCCG
GTAACTATCGTCTTGAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGATCTCAAGAAGATCCTTT
GATCTTTTCTACGGGGTCTGACGCTCAGTGGAACGAAAACTCACGTTAAGGGATTTTGGTCATGAGATTATCAAAA
AGGATCTTCACCTAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATCCATAGTTGCCTG
ACTCCCCGTCGTGTAGATAACTACGATACGGGAGGGCTTACCATCTGGCCCCAGTGCTGCAATGATACCGCGAGAC
CCACGCTCACCGGCTCCAGATTTATCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGTAGTTCGCCAGTTAATAGTTTGCG
CAACGTTGTTGCCATTGCTGCAGGCATCGTGGTGTCACGCTCGTCGTTTGGTATGGCTTCATTCAGCTCCGGTTCC
CAACGATCAAGGCGAGTTACATGATCCCCCATGTTGTGCAAAAAAGCGGTTAGCTCCTTCGGTCCTCCGATCGTTG
TCAGAAGTAAGTTGGCCGCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTATGCGGCGACCGAGTTGC
TCTTGCCCGGCGTCAACACGGGATAATACCGCGCCACATAGCAGAACTTTAAAAGTGCTCATCATTGGAAAACGTT
CTTCGGGGCGAAAACTCTCAAGGATCTTACCGCTGTTGAGATCCAGTTCGATGTAACCCACTCGTGCACCCAACTG
ATCTTCAGCATCTTTTACTTTCACCAGCGTTTCTGGGTGAGCAAAAACAGGAAGGCAAAATGCCGCAAAAAAGGGA
ATAAGGGCGACACGGAAATGTTGAATACTCATACTCTTCCTTTTTCAATATTATTGAAGCATTTATCAGGGTTATT
GTCTCATGAGCGGATACATATTTGAATGTATTTAGAAAAATAAACAAATAGGGGTTCCGCGCACATTTCCCCGAAA
AGTGCCACCTGACGTCTAAGAAACCATTATTATCATGACATTAACCTATAAAAATAGGCGTATCACGAGGCCCTTC
CCGTAGTCTTCCTGGGCCCCTGGGAGGTACATGTCCCCCAGCATTGGTGTAAGAGCTTCAGCCAAGAGTTACACAT
AAAGGCAATGTTGTGTTGCAGTCCACAGACTGCAAAGTCTGCTCCAGGATGAAAGCCACTCAGTGTTGGCAAATGT
GCACATCCATTTATAAGGATGTCAACTACAGTCAGAGAACCCCTTTGTGTTTGGTCCCCCCCGTGTCACATGTGG
AACAGGGCCCAGTTGGCAAGTTGTACCAACCAACTGAAGGGATTACATGCACTGCCCCGCGAAGAAGGGGCAGAGA
TGCCGTAGTCAGGTTTAGTTCGTCCGGCGGCGGGGC

FIGURE 17 HAIX#3 (SEQ ID NO:15)

```
CTAAATTGTAAGCGTTAATATTTTGTTAAAATTCGGCCGGCCATCATCAATAATATACCTTATTTTGGATTGAAGC
CAATATGATAATGAGGGGGTGGAGTTTGTGACGTGGCGCGGGGCGTGGGAACGGGGCGGGTGACGTAGTAGTGTGG
CGGAAGTGTGATGTTGCAAGTGTGGCGGAACACATGTATAACTTCGTATAATGTATGCTATACGAAGTTATACATG
TAAGCGACGGATGTGGCAAAAGTGACGTTTTTGGTGTGCGCCGGTGTACACAGGAAGTGACAATTTTCGCGCGGTT
TTAGGCCGATGTTGTAGTAAATTTGGGCGTAACCGAGTAAGATTTGGCCATTTTCGCGGGAAAACTGAATAAGAGG
AAGTGAAATCTGAATAATTTTGTGTTACTCATAGCGCGTAATATTTGTCTAGGGAGATCAATTGGATTCTTTGACC
CGGGAACTTAATGTCGTTTCTCAGCAGCTGTTGGATCTGCGCCAGCAGGTTTCTGCCCTGAAGGCTTCCTCCCCTC
CCAATGCGGTTTAAAACATAAATAAAAAACCAGACTCTGTTTGGATTTGGATCAAGCAAGTGTCTTGCTGTCTTTA
TTTAGGGGTTTTGCGCGCGCGGTAGGCCCGGGACCAGCGGTCTCGGTCGTTGAGGGTCCTGTGTATTTTTTCCAGG
ACGTGGTAAAGGTGACTCTGGATGTTCAGATACATGGGCATAAGCCCGTCTCTGGGGTGGAGGTAGCACCACTGCA
GAGCTTCATGCTGCGGGTGGTGTTGTAGATGATCCAGTCGTAGCAGGAGCGCTGGGCGTGGTGCCTAAAAATGTC
TTTCAGTAGCAAGCTGATTGCCAGGGGCAGGCCCTTGGTGTAAGTGTTTACAAAGCGGTTAAGCTGGGATGGGTGC
ATACGTGGGGATATGAGATGCATCTTGGACTGTATTTTTAGGTTGGCTATGTTCCAGCCATATCCCTCCGGGGAT
TCATGTTGTGCAGAACCACCAGCACAGTGTATCCGGTGCACTTGGGAAATTTGTCATGTAGCTTAGAAGGAAATGC
GTGGAAGAACTTGGAGACGCCCTTGTGACCTCCAAGATTTTCCATGCATTCGTCCATAATGATGGCAATGGGCCCA
CGGGCGGCGGCCTGGGCGAAGATATTTCTGGGATCACTAACGTCATAGTTGTGTTCCAGGATGAGATCGTCATAGG
CCATTTTTACAAAGCGCGGCGGAGGGTGCCAGACTGCGGTATAATGGTTCCATCGGCCCAGGGGCGTAGTTACC
CTCACAGATTTGCATTTCCCACGCTTTGAGTTCAGATGGGGGATCATGTCTACCTGCGGGGCGATGAAGAAAACG
GTTTCCGGGTAGGGAGATCAGCTGGGAAGAAAGCAGGTTCCTGAGCAGCTGCGACTTACCGCAGCCGGTGGGCC
CGTAAATCACACCTATTACCGGTGCAACTGGTAGTTAAGAGAGCTGCAGCTGCCGTCATCCCTGAGCAGGGGGGC
CACTTCGTTAAGCATGTCCCTGACTCGCATGTTTTCCCTGACCAAATCCGCCAGAAGGCGCTCGCCGCCCAGCGAT
AGCAGTTCTTGCAAGGAAGCAAAGTTTTTCAACGGTTTGAGACCGTCCGCCGTAGGCATGCTTTTGAGCGTTTGAC
CAAGCAGTTCCAGGCGGTCCCACAGCTCGGTCACCTGCTCTACGGCATCTCGATCCAGCATATCTCCTCGTTTCGC
GGGTTGGGGCGGCTTTCGCTGTACGGCAGTAGTCGGTGCTCGTCCAGACGGGCCAGGGTCATGTCTTTCCACGGGC
GCAGGGTCCTCGTCAGCGTAGTCTGGGTCACGGTGAAGGGGTGCGCTCCGGGCTGCGCGCTGGCCAGGGTGCGCTT
GAGGCTGGTCCTGCTGGTGCTGAAGCGCTGCCGGTCTTCGCCCTGCGCGTCGGCCAGGTAGCATTTGACCATGGTG
TCATAGTCCAGCCCCTCGGCGGCGTGGCCCTTGGCGCGCAGCTTGCCCTTGGAGGAGGCGCCGCACGAGGGGCAGT
GCAGACTTTTGAGGGCGTAGAGCTTGGGCGCGAGAAATACCGATTCCGGGGAGTAGGCATCCGCGGCCGCAGGCCCC
GCAGACGGTCTCGCATTCCACGAGCCAGGTGAGCTCTGGCGTTCGGGGTCAAAAACCAGGTTTCCCCCATGCTTT
TTGATGCGTTTCTTACCTCTGGTTTCCATGAGCCGGTGTCCACGCTCGGTGACGAAAAGGCTGTCCGTGTCCCGT
ATACAGACTTGAGAGGCCTGTCCTCGAGCGGTGTTCCGCGGTCCTCCTCGTATAGAAACTCGGACCACTCTGAGAC
AAAGGCTCGCGTCCAGGCCAGCACGAAGGAGGCTAAGTGGGAGGGGTAGCGGTCGTTGTCCACTAGGGGGTCCACT
CGCTCCAGGGTGTGAAGACACATGTCGCCCTCTTCGGCATCAAGGAAGGTGATTGGTTTGTAGGTGTAGGCCACGT
GACCGGGTGTTCCTGAAGGGGGCTATAAAGGGGGTGGGGCGCGTTCGTCCTCACTCTCTTCCGCATCGCTGTC
TGCGAGGGCCAGCTGTTGGGGTGAGTACTCCCTCTGAAAAGCGGGCATGACTTCTGCGCTAAGATTGTCAGTTTCC
AAAAACGAGGAGGATTTGATATTCACCTGGCCCGCGGTGATGCCTTTGAGGGTGGCCGCATCCATCTGGTCAGAAA
AGACAATCTTTTTGTTGTCAAGCTTGGTGGCAAACGACCCGTAGAGGGCGTTGGACAGCAACTTGGCGATGGAGCG
CAGGGTTTGGTTTTTGTCGGCGATCGGCGCGCTCCTTGGCGCGATGTTTAGCTGCACGTATTCGCGCGCAACGCAC
CGCCATTCGGGAAAGACGGTGGTGCGCTCGTCGGGCACCAGGTGCACGCGCCAACCGCGGTTGTGCAGGGTGACAA
GGTCAACGCTGGTGGCTACCTCTCCGCGTAGGCGCTCGTTGGTCCAGCAGAGGCGGCCGCCCTTGCGCGAGCAGAA
TGGCGGTAGGGGGTCTAGCTGCGTCTCGTCCGGGGGTCTGCGTCCACGGTAAAGACCCCGGGCAGCAGGCGCGCG
TCGAAGTAGTCTATCTTGCATCCTTGCAAGTCTAGCGCCTGCTGCCATGCGCGGGCGGCAAGCGCGCTCGTATG
GGTTGAGTGGGGGACCCCATGGCATGGGGTGGGTGAGCGCGGAGGCGTACATGCCGCAAATGTCGTAAACGTAGAG
GGGCTCTCTGAGTATTCCAAGATATGTAGGGTAGCATCTTCCACCGCGGATGCTGGCGCGCACGTAATCGTATAGT
TCGTGCGAGGGAGCGAGGAGGTCGGGACCGAGGTTGCTACGGGCGGCTGCTCTGCTCGGAAGACTATCTGCCTGA
AGATGGCATGTGAGTTGGATGATATGGTTGGACGCTGGAAGACGTTGAAGCTGGCGTCTGTGAGACCTACCGCGTC
ACGCACGAAGGAGGCGTAGGAGTCGCGCAGCTTGTTGAGCCAGCTCGGCGGTGACCTGCACGTCTAGGGCGCAGTAG
TCCAGGGTTTCCTTGATGATGTCATACTTATCCTGTCCCTTTTTTTTCCACAGCTCGCGGTTGAGGACAAACTCTT
CGCGGTCTTTCCAGTACTCTTGGATCGGAAACCCGTCGGCCTCCGAACGGTAAGAGCCTAGCATGTAGAACTGGTT
GACGGCCTGGTAGGCGCAGCATCCCTTTTCTACGGGTAGCGCGTATGCCTGCGCGGCCTTCCGGAGCGAGGTGTGG
GTGAGCGCAAAGGTGTCCCTGACCATGACTTTGAGGTACTGGTATTTGAAGTCAGTGTCGTCGCATCCGCCCTGCT
CCCAGAGCAAAAAGTCCGTGCGCTTTTTGGAACGCGGATTTGGCAGGGCGAAGGTGACATCGTTGAAGAGTATCTT
TCCCGCGCGAGGCATAAAGTTGCGTGTGATGCGGAAGGGTCCCGGCACCTCGGAACGGTTGTTAATTACCTGGGCG
GCGAGCACGATCTCGTCAAAGCCGTTGATGTTGTGGCCCACAATGTAAAGTTCAAGAAGCGCGGGATGCCCTTGA
TGGAAGGCAATTTTTAAGTTCCTCGTAGGTGAGCTCTTCAGGGGAGCTGAGCCCGTGCTCTGAAAGGGCCCAGTC
TGCAAGATGAGGGTTGGAAGCGACGAATGAGCTCCACAGGTCACGGGCCATTAGCATTTGCAGGTGGTCGCGAAAG
GTCCTAAACTGGCGACCTATGCCATTTTTTCTGGGGTGATGCAGTAGAAGGTAAGCGGGTCTTGTTCCCAGCGGT
CCCATCCAAGGTTCGCGGCTAGGTCTCGCGGCGGCAGTCACTAGAGGCTCATCTCCGCCGAACTTCATGACCAGCAT
GAAGGGCACGAGCTGCTTCCCAAAGGCCCCCATCCAAGTATAGGTCTCTACATCGTAGGTGACAAAGAGACGCTCG
GTGCGAGGATGCGAGCCGATCGGGAAGAACTGGATCTCCCGCCACCAATTGGAGGAGTGGCTATTGATGTGGTGAA
AGTAGAAGTCCCTGCGACGGGCCGAACACTCGTGCTGGCTTTTGTAAAAACGTGCGCAGTACTGGCAGCGGTGCAC
```

FIGURE 17 (cont.)

```
GGGCTGTACATCCTGCACGAGGTTGACCTGACGACCGCGCACAAGGAAGCAGAGTGGGAATTTGAGCCCCTCGCCT
GGCGGGTTTGGCTGGTGGTCTTCTACTTCGGCTGCTTGTCCTTGACCGTCTGGCTGCTCGAGGGGAGTTACGGTGG
ATCGGACCACCACGCCGCGCGAGCCCAAAGTCCAGATGTCCGCGCGCGGCGGTCGGAGCTTGATGACAACATCGCG
CAGATGGGAGCTGTCCATGGTCTGGAGCTCCCGCGGCGTCAGGTCAGGCGGGAGCTCCTGCAGGTTTACCTCGCAT
AGACGGGTCAGGGCGCGGGCTAGATCCAGGTGATACCTAATTTCCAGGGGCTGGTTGGTGGCGGCGTCGATGGCTT
GCAAGAGGCCGCATCCCGCGGCGCGACTACGGTACCGCGCGGCGGGCGGTGGGCCGCGGGGGTGTCCTTGGATGA
TGCATCTAAAAGCGGTGACGCGGGCGAGCCCCGGAGGTAGGGGGGCTCCGGACCCGCCGGGAGAGGGGGCAGGG
GCACGTCGGCGCCGCGCGCGGGCAGGAGCTGGTGCTGCGCGCGTAGGTTGCTGGCGAACGCGACGACGCGGCGGTT
GATCTCCTGAATCTGGCGCCTCTGCGTGAAGACGACGGGCCCGGTGAGCTTGAGCGTGAAAGAGAGTTCGACAGAA
TCAATTTCGGTGTCGTTGACGGCGGCCTGGCGCAAAATCTCCTGCACGTCTCCTGAGTTGTCTTGATAGGCGATCT
CGGCCATGAACTGCTCGATCTCTTCCTCCTGGAGATCTCCGCGTCCGGCTCGCTCCACGGTGGCGGCGAGGTCGTT
GGAAATGCGGGCCATGAGCTGCGAGAAGGCGTTGAGGCCTCCCTCGTTCCAGACGCGGCTGTAGACCACGCCCCCT
TCGGCATCGCGGGCGCGCATGACCACCTGCGCGAGATTGAGCTCCACGTGCCGGGCGAAGACGGCGTAGTTTCGCA
GGCGCTGAAAGACGGTAGTTGAGGGTGGTGGCGGTGTGTTCTGCCACGAAGAAGTACATAACCCAGCGTCGCAACGT
GGATTCGTTGATATCCCCCAAGGCCTCAAGGCGCTCCATGGCCTCGTAGAAGTCCACGGCGAAGTTGAAAAACTGG
GAGTTGCGCGCCGACACGGTTAACTCCTCCTCCAGAAGACGGATGAGCTCGGCGACAGTGTCGCGCACCTCGCGCT
CAAAGGCTACAGGGGCCTCTTCTTCTTCTTCAATCTCCTCTTCCATAAGGGCCTCCCCTTCTTCTTCTTCTGGCGG
CGGTGGGGGAGGGGGACACGGCGGCGACGACGGCGCACCGGGAGGCGGTCGACAAAGCGCTCGATCATCTCCCCG
CGGCGACGGCGCATGGTCTCGGTGACGGCGCGGCCGTTCTCGCGGGGGCGCAGTTGGAAGACGCCGCCCGTCATGT
CCCGGTTATGGGTTGCCGGGGGGCTGCCATGCGGCAGGGATACGGCGTAACGATGCATCTCAACAATTGTTGTGT
AGGTACTCCGCCGCCGAGGGACCTGAGCGAGTCCGCATCGACCGGATCGGAAAAACCTCTCGAGAAAGGCGTCTAAC
CAGTCACAGTCGCAAGGTAGGCTGAGCACCGTGGCGGGCGGCAGCGGGCGGCGGTCGGGGTTGTTTCTGGCGGAGG
TGCTGCTGATGATGTAATTAAAGTAGGCGGTCTTGAGACGGCGGATGGTCGACAGAAGCACCATGTCCTTGGGTCC
GGCCTGCTGAATGCGCAGGCGGTCGGCCATGCCCCAGGCTTCGTTTTGACATCGGCGCAGGTCTTTGTAGTAGTCT
TGCATGAGCCTTTCTACCGGCACTTCTTCTTCTCCTTCCTCTTGTCCTGCATCTCTTGCATCTATCGCTGCGGCGG
CGGCGGAGTTTGGCCGTAGGTGGCGCCCTCTTCCTCCCATGCGTGTGACCCCGAAGCCCCTCATCGGCTGAAGCAG
GGCTAGGTCGGCGACAACGCGCTCGGCTAATATGGCCTGCTGCACCTGCGTGAGGGTAGACTGGAAGTCATCCATG
TCCACAAAGCGGTGGTATGCGCCCGTGTTGATGGTGTAAGTGCAGTTGGCCATAACGGACCAGTTAACGGTCTGGT
GACCCGGCTGCGAGAGCTCGGTGTACCTGAGACGCGAGTAAGCCCTCGAGTCAAATACGTAGTCGTTGCAAGTCCG
CACCAGGTACTGGTATCCCACCAAAAAGTGCGGCGGCGGCTGGCGGTAGAGGGGCCAGCGTAGGGTGGCGGGGCT
CCGGGGGCGAGATCTTCCAACATAAGGCGATGATATCCGTAGATGTACCTGGACATCCAGGTGATGCCGGCGGCGG
TGGTGGAGGCGCGCGGAAAGTCGCGGACGCGGTTCCAGATGTTGCGCAGCGGCAAAAAGTGCTCCATGGTCGGGAC
GCTCTGGCCGGTCAGGCGCGCGCAATCGTTGACGCTCTACCGTGCAAAAGGAGAGCCTGTAAGCGGGCACTCTTCC
GTGGTCTGGTGGATAAATTCGCAAGGGTATCATGGCGGACGACCGGGGTTCGAGCCCCGTATCCGGCCGTCCGCCG
TGATCCATGCGGTTACCGCCCGCGTGTCGAACCCAGGTGTGCGACGTCAGACAACGGGGGAGTGCTCCTTTTGGCT
TCCTTCCAGGCGCGGCGGCTGCTGCGCTAGCTTTTTTGGCCACTGGCCGCGCGCAGCGTAAGCGGTTAGGCTGGAA
AGCGAAAGCATTAAGTGGCTCGCTCCCTGTAGCCGGAGGGTTATTTTCCAAGGGTTGAGTCGCGGGACCCCCGGTT
CGAGTCTCGGACCGGCCGGACTGCGGCGAACGGGGGTTTGCCTCCCCGTCATGCAAGACCCCGCTTGCAAATTCCT
CCGGAAACAGGGACGAGCCCCTTTTTTGCTTTTCCCAGATGCATCCGGTGCTGCGGCAGATGCGCCCCCCTCCTCA
GCAGCGGCAAGAGCAAGAGCAGCGGCAGACATGCAGGGCACCCTCCCCTCCTCCTACCGCGTCAGGAGGGGCGACA
TCCGCGGTTGACGCGGCAGCAGATGGTGATTACGAACCCCGCGGCGCCGGGCCCGGCACTACCTGGACTTGGAGG
AGGGCGAGGGCCTGGCGCGGCTAGGAGCGCCCTCTCCTGAGCGGTACCCAAGGGTGCAGCTGAAGCGTGATACGCG
TGAGGCGTACGTGCCGCGGCAGAACCTGTTTCGCGACCGCGAGGGAGAGGAGCCCGAGGAGATGCGGGATCGAAAG
TTCCACGCAGGGCGCGAGCTGCGGCATGGCCTGAATCGCGAGCGGTTGCTGCGCGAGGAGGACTTTGAGCCCGACG
CGCGAACCGGGATTAGTCCCGCGCGCGCACACGTGGCGGCCGCCGACCTGGTAACCGCATACGAGCAGACGGTGAA
CCAGGAGATTAACTTTCAAAAAAGCTTTAACAACCACGTGCGTACGCTTGTGGCGCGCGAGGAGGTGGCTATAGGA
CTGATGCATCTGTGGGACTTTGTAAGCGCGCTGGAGCAAAACCCAAATAGCAAGCCGCTCATGGCGCAGCTGTTCC
TTATAGTGCAGCACAGCAGGGACAACGAGGCATTCAGGGATGCGCTGCTAAACATAGTAGAGCCCGAGGGCCGCTG
GCTGCTCGATTTGATAAACATCCTGCAGAGCATAGTGGTGCAGGAGCGCAGCTTGAGCCTGGCTGACAAGGTGGCC
GCCATCAACTATTCCATGCTTAGCCTGGGCAAGTTTTACGCCCGCAAGATATACCATACCCCTTACGTTCCCATAG
ACAAGGAGGTAAAGATCGAGGGGTTCTACATGCGCAGCGCTGAAGGTGCTTACCTTGAGCGACGACCTGGGCGT
TTATCGCAACGAGCGCATCCACAAGGCCGTGAGCGTGAGCGGCGGCGAGCTCAGCGACGCGGAGCTGATGCAC
AGCCTGCAAAGGGCCCTGGCTGGCACGGGCAGCGGCGATAGAGAGGCCGAGTCCTACTTTGACGCGGGCGCTGACC
TGCGCTGGCCCCAAGCCGACGCGCCCTGGAGGCAGCTGGGGCCGGACCTGGGCTGGCGGTGGCACCCGCGCGCGC
TGGCAACGTCGGCGGCGTGGAGGAATATGACGAGGACGATGAGTACGAGCCAGAGGACGGCGAGTACTAAGCGGTG
ATGTTTCTGATCAGATGATGCAAGACGCAACGGACCCGGCGGTGCGGCGGCGCTGCAGAGCCAGCCGTCCGGCCT
TAACTCCACGGACGACTGGCGCCAGGTCATGGACCGCATCATGTCGCTGACTGCGCGCAATCCTGACGCGTTCCGG
CAGCAGCCGCAGGCCAACCGGCTCTCCGCAATTCTGGAAGCGGTGGTCCCGGCGCGCGCAAACCCCACGCACGAGA
AGGTGCTGGCGATCGTAAACGCGCTGGCCGAAAACAGGGCCATCCGGCCCGACGAAGCCGGCCTGGTCTACGACGC
GCTGCTTCAGCGCGTGGCTCGTTACAACAGCGGCAACGTGCAGACCAACCTGGACCGGCTGGTGGGGGATGTGCGC
GAGGCCGTGGCGCAGCGTGAGCGCGCGCAGCAGCAGGGCAACCTGGGCTCCATGGTTGCACTAAACGCCTTCCTGA
```

FIGURE 17 (cont.)

```
GTACACAGCCCGCCAACGTGCCGCGGGGACAGGAGGACTACACCAACTTTGTGAGCGCACTGCGGCTAATGGTGAC
TGAGACACCGCAAAGTGAGGTGTACCAGTCTGGGCCAGACTATTTTTTCCAGACCAGTAGACAAGGCCTGCAGACC
GTAAACCTGAGCCAGGCTTTCAAAAACTTGCAGGGGCTGTGGGGGGTGCGGGCTCCCACAGGCGACCGCGCGACCG
TGTCTAGCTTGCTGACGCCCAACTCGCGCCTGTTGCTGCTGCTAATAGCGCCCTTCACGGACAGTGGCAGCGTGTC
CCGGGACACATACCTAGGTCACTTGCTGACACTGTACCGCGAGGCCATAGGTCAGGCGCATGTGGACGAGCATACT
TTCCAGGAGATTACAAGTGTCAGCCGCGCGCTGGGGCAGGAGGACACGGGCAGCCTGGAGGCAACCCTAAACTACC
TGCTGACCAACCGGCGGCAGAAGATCCCCTCGTTGCACAGTTTAAACAGCGAGGAGGAGCGCATTTTGCGCTACGT
GCAGCAGAGCGTGAGCCTTAACCTGATGCGCGACGGGGTAACGCCCAGCGTGGCGCTGGACATGACCGCGCGCAAC
ATGGAACCGGGCATGTATGCCTCAAACCGGCCGTTTATCAACCGCCTAATGGACTACTTGCATCGCGCGGCCGCCG
TGAACCCCGAGTATTTCACCAATGCCATCTTGAACCCGCACTGGCTACCGCCCCTGGTTTCTACACCGGGGATT
CGAGGTGCCCGAGGGTAACGATGGATTCCTCTGGGACACATAGACGACAGCGTGTTTTCCCCGCAACCGCAGACC
CTGCTAGAGTTGCAACAGCGCGAGCAGGCAGAGGCGGCGCTGCGAAAGGAAAGCTTCCGCAGGCCAAGCAGCTTGT
CCGATCTAGGCGCTGCGGCCCCGCGGTCAGATGCTAGTAGCCCATTTCCAAGCTTGATAGGGTCTCTTACCAGCAC
TCGCACCACCCGCCCGCGCCTGCTGGGCGAGGAGGAGTACCTAAACAACTCGCTGCTGCAGCCGCAGCGCGAAAAA
AACCTGCCTCCGGCATTTCCCAACAACGGGATAGAGAGCCTAGTGGACAAGATGAGTAGATGGAAGACGTACGCGC
AGGAGCACAGGGACGTGCCAGGCCCGCGCCCGCCCACCCGTCGTCAAAGGCACGACCGTCAGCGGGGTCTGGTGTG
GGAGGACGATGACTCGGCAGACGACAGCAGCGTCCTGGATTTGGGAGGGAGTGGCAACCCGTTTGCGCACCTTCGC
CCCAGGCTGGGGAGAATGTTTTAAAAAAAAAAAAGCATGATGCAAAATAAAAAACTCACCAAGGCCATGGCACCGA
GCGTTGGTTTTCTTGTATTCCCCTTAGTATGCGGCGCGCGGCGATGTATGAGGAAGGTCCTCCTCCCTCCTACGAG
AGTGTGGTGAGCGCGGCGCCAGTGGCGGCGGCGCTGGGTTCTCCCTTCGATGCTCCCCTGGACCCGCCGTTTGTGC
CTCCGCGGTACCTGCGGCCTACCGGGGGGAGAAACAGCATCCGTTACTCTGAGTTGGCACCCCTATTCGACACCAC
CCGTGTGTACCTGGTGGACAACAAGTCAACGGATGTGGCATCCCTGAACTACCAGAACGACCACAGCAACTTTCTG
ACCACGGTCATTCAAAACAATGACTACAGCCGGGGCAGGCAAGCACACAGACCATCAATCTTGACGACCGGTCGC
ACTGGGGCGGCGACCTGAAAACCATCCTGCATACCAACATGCCAAATGTGAACGAGTTCATGTTTACCAATAAGTT
TAAGGCGCGGGTGATGGTGTCGCGCTTGCCTACTAAGGACAATCAGGTGGAGCTGAAATACGAGTGGGTGGAGTTC
ACGCTGCCCGAGGGCAACTACTCCGAGACCATGACCATAGACCTTATGAACAACGCGATCGTGGAGCACTACTTGA
AAGTGGGCAGACAGAACGGGTTCTGGAAAGCGACATCGGGGTAAAGTTTGACACCCGCAACTTCAGACTGGGGTT
TGACCCCGTCACTGGTCTTGTCATGCCTGGGGTATATACAAACGAAGCCTTCCATCCAGACATCATTTTGCTGCCA
GGATGCGGGGTGGACTTCACCCACCAGCCCGCTGAGCAACTTGTTGGGCATCCGCAAGCGGCAACCCTTCCAGGAGG
GCTTTAGGATCACCTACGATGATCTGGAGGGTGGTAACATTCCCGCACTGTTGGATGTGGACGCCTACCAGGCGAG
CTTGAAAGATGACACCGAACAGGGCGGGGGTGGCGCAGGCGGCAGCAACAGCAGTGGCAGCGGCGCGGAAGAGAAC
TCCAACGCGGCAGCCGCGGCAATGCAGCCGGTGGAGGACATGAACGATCATGCCATTCGCGGCGACACCTTTGCCA
CACGGGCTGAGGAGAAGCGCGCTGAGGCCGAAGCAGCGGCCGAAGCTGCCGCCCCCGCTGCGCAACCCGAGGTCGA
GAAGCCTCAGAAGAAACCGGTGATCAAACCCCTGACAGAGGACAGCAAGAAACGCAGTTACAACCTAATAAGCAAT
GACAGCACCTTCACCCAGTACCGCAGCTGGTACCTTGCATACAACTACGGCGACCCTCAGACCGGAATCCGCTCAT
GGACCCTGCTTTGCACTCCTGACGTAACCTGCGGCTCGGAGCAGGTCTACTGGTCGTTGCCAGACATGATGCAAGA
CCCCGTGACCTTCCGCTCCACGCGCCAGATCAGCAACTTTCGGTGGTGGGCGCCGAGCTGTTGCCCGTGCACTCC
AAGAGCTTCTACAACGACCAGGCCGTCTACTCCCAACTCATCCGCCAGTTTACCTCTCTGACCCACGTGTTCAATC
GCTTTCCGAGAACCAGATTTTGGCGCGCCCGCCAGCCCCCACCATCACCACCGTCAGTGAAAACGTTCCTGCTCT
CACAGATCACGGGACGCTACGCTGCGCAACAGCATCGGAGGAGTCCAGCGAGTGACCATTACTGACGCCAGACGC
CGCACCTGCCCCTACGTTTACAAGGCCCTGGGCATAGTCTCGCCGCGCGTCCTATCGAGCCGCACTTTTTGAGCAA
GCATGTCCATCCTTATATCGCCCAGCAATAACACAGGCTGGGGCCTGCGCTTCCCAAGCAAGATGTTTGCGGGGC
CAAGAAGCGCTCCGACCAACACCCAGTGCGCGGTGCGCGGGCACTACCGCGCGCCCTGGGGCGCGCACAAACGCGGC
CGCACTGGGCGCACCACCGTCGATGACGCCATCGACGCGGTGGTGGAGGAGGCGCGCAACTACACGCCCACGCCGC
CACCAGTGTCCACAGTGGACGCGCGGCCATTCAGACCGTGGTCGCGGACCTGCCGCCCAACGCGGCGGCGCCTGCTTAAC
GCGCACGTCGCACCGGCCGACGGGCGGCCATGCGGGCCGCTCGAAGGCTGGCCGCGGGTATTGTCACTGTGCCCC
CCAGGTCCAGGCGACGAGCGGCCGCCGCAGCAGCCGCGGCCATTAGTGCTATGACTCAGGGTCGCAGGGGCAACGT
GTATTGGGTGCGCGACTCGGTTAGCGGCCTGCGCGTGCCCGTGCGCACCCGCCCCCGCGCAACTAGATTGCAAGA
AAAAACTACTTAGACTCGTACTGTTGTATGTATCCAGCGGCGGCGGCGCGCAACGAAGCTATGTCCAAGCGCAAAA
TCAAAGAAGAGATGCTCCAGGTCATCGCGCCGGAGATCTATGGCCCCCCGAAGAAGGAAGAGCAGGATTACAAGCC
CCGAAAGCTAAAGCGGGTCAAAAAGAAAAAGAAAGATGATGATGATGAACTTGACGACGAGGTGGAACTGCTGCAC
GCTACCGCCGCCCAGGCGACGGGTACAGTGGAAAGGTCGACGCGTAAAACGTGTTTGCGACCCGGCACCACCGTAG
TCTTTACGCCCGGTGAGCGCTCCACCCGCACCTACAGCGCGTGTATGATGAGGTGTACGGCGACGAGGACCTGCT
TGAGCAGGCCAACGAGCGCCTCGGGGAGTTTGCCTACGGAAAGCGGCATAAGGACATGCTGGCGTTGCCGCTGGAC
GAGGGCAACCCAACACCTAGCCTAAAGCCCGTAACACTGCAGCAGGTGCTGCCCGCGCTTGCACCGTCCGAAGAAA
AGCGCGGCCTAAAGCGCGAGTCTGGTGACTTGGCACCCACCGTGCAGCTGATGGTACCCAAGCGCCAGCGACTGGA
AGATGTCTTGGAAAAAATGACCGTGGAACCTGGGCTGGAGCCCGAGGTCCGCGTGCGGCCAATCAAGCAGGTGGCG
CCGGGACTGGGCGTGCAGACCGTGGACGTTCAGATACCCACTACCAGTAGCACCAGTATTGCCACCGCCACAGAGG
GCATGGAGACACAAACGTCCCCGGTTGCCTCAGCGGTGGCGATGCCGCGGTGCAGGCGGTCGCTGCGGCCGCGTC
CAAGACCTCTACGGAGGTGCAAACGGACCCCGTGGATGTTTCGCGTTTCAGCCCCCCGGCGCCCGCGCGGTTCGAGG
```

FIGURE 17 (cont.)

```
AAGTACGGCGCCGCCAGCGCGCTACTGCCCGAATATGCCCTACATCCTTCCATTGCGCCTACCCCCGGCTATCGTG
GCTACACCTACCGCCCCAGAAGACGAGCAACTACCCGACGCCGAACCACCACTGGAACCCGCCGCCGCCGTCGCCG
TCGCCAGCCCGTGCTGGCCCCGATTTCCGTGCGCAGGGTGGCTCGCGAAGGAGGCAGGACCCTGGTGCTGCCAACA
GCGCGCTACCACCCCAGCATCGTTTAAAAGCCGGTCTTTGTGGTTCTTGCAGATATGGCCCTCACCTGCCGCCTCC
GTTTCCCGGTGCCGGGATTCCGAGGAAGAATGCACCGTAGGAGGGCATGGCCGGCTACGGCCTGACGGGCGGCAT
GCGTCGTGCGCACCACCGGCGGCGGCGCGCGTCGCACCGTCGCATGCGCGGCGGTATCCTGCCCCTCCTTATTCCA
CTGATCGCCGCGGCGATTGGCGCCGTGCCCGGAATTGCATCCGTGGCCTTGCAGGCGCAGAGACACTGATTAAAAA
CAAGTTGCATGTGGAAAAATCAAAATAAAAAGTCTGGACTCTCACGCTCGCTTGGTCCTGTAACTATTTTGTAGAA
TGGAAGACATCAACTTTGCGTCTCTGGCCCCGCGACACGGCTCGCGCCCGTTCATGGGAAACTGGCAAGATATCGG
CACCAGCAATATGAGCGGTGGCGCCTTCAGCTGGGGCTCGCTGTGGAGCGGCATTAAAAATTTCGGTTCCACCGTT
AAGAACTATGGCAGCAAGGCCTGGAACAGCAGCACAGGCCAGATGCTGAGGGATAAGTTGAAAGAGCAAATTTCC
AACAAAAGGTGGTAGATGGCCTGGCCTCTGGCATTAGCGGGGTGGTGGACCTGGCCAACCAGGCAGTGCAAAATAA
GATTAACAGTAAGCTTGATCCCCGCCCTCCCGTAGAGGAGCCTCCACCGGCCGTGGAGACAGTGTCTCCAGAGGG
CGTGGCGAAAAGCGTCCGCGCCCCGACAGGGAAGAAACTCTGGTGACGCAAATAGACGAGCCTCCCTCGTACGAGG
AGGCACTAAAGCAAGGCCTGCCCACCACCCGTCCCATCGCGCCCATGGCTACCGGAGTGCTGGGCCAGCACACACC
CGTAACGCTGGACCTGCCTCCCCCCGCCGACACCCAGCAGAAACCTGTGCTGCCAGGCCCGACCGCCGTTGTTGTA
ACCCGTCCTAGCCGCGCGTCCCTGCGCCGCGCCGCCAGCGGTCCGCGATCGTTGCGGCCCGTAGCCAGTGGCAACT
GGCAAAGCACACTGAACAGCATCGTGGGTCTGGGGGTGCAATCCCTGAAGCGCCGACGATGCTTCTGAATAGCTAA
CGTGTCGTATGTGTGTCATGTATGCGTCCATGTGCGCCAGAGGAGCTGCTGAGCCGCCGCGCGCCCGCTTTCCA
AGATGGCTACCCCTTCGATGATGCGCAGTGGTCTTACATGCACATCTCGGGCCAGGACGCCTCGGAGTACCTGAG
CCCCGGGCTGGTGCAGTTTGCCCGCGCCACCGAGACGTACTTCAGCCTGAATAACAAGTTTAGAAACCCCACGGTG
GCGCCTACGCACGACGTGACCACAGACCGGTCCCAGCGTTTGACGCTGCGGTTCATCCCTGTGGACCGTGAGGATA
CTGCGTACTCGTACAAGGCGCGGTTCACCCTAGCTGTGGGTGATAACCGTGTGCTGGACATGGCTTCCACGTACTT
TGACATCCGCGGCGTGCTGGACAGGGGCCCTACTTTTAAGCCCTACTCTGGCACTGCCTACAACGCCCTGGCTCCC
AAGGGTGCCCCAAATCCTTGCGAATGGGATGAAGCTGCTACTGCTCTTGAAATAAACCTAGAAGAAGAGGACGATG
ACAACGAAGACGAAGTAGACGAGCAAGCTGAGCAGCAAAAAACTCACGTATTTGGGCAGGCGCCTTATTCTGGTAT
AAATATTACAAAGGAGGGTATTCAAATAGGTGTCGAAGGTCAAACACCTAAATATGCCGATAAAACATTTCAACCT
GAACCTCAAATAGGAGAATCTCAGTGGTACGAAACTGAAATTAATCATGCAGCTGGGAGAGTCCTTAAAAAGACTA
CCCCAATGAAACCATGTTACGGTTCATATGCAAAACCCACAAATGAAAATGGAGGGCAAGGCATTCTTGTAAAGCA
ACAAAATGGAAAGCTAGAAAGTCAAGTGGAAATGCAATTTTTCTCAACTACTGAGGCGACCGCAGGCAATGGTGAT
AACTTGACTCCTAAAGTGGTATTGTACAGTGAAGATGTAGATATAGAAACCCCAGACACTCATATTTCTTACATGC
CCACTATTAAGGAAGGTAACTCACGAGAACTAATGGGCCAACAATCTATGCCCAACAGGCCTAATTACATTGCTTT
TAGGGACAATTTTATTGGTCTAATGTATTACAACAGCACGGGTAATATGGGTGTTCTGGCGGGCCAAGCATCGCAG
TTGAATGCTGTTGTAGATTTGCAAGACAGAAACACAGAGCTTTCATACCAGCTTTTGCTTGATTCCATTGGTGATA
GAACCAGGTACTTTTCTATGTGGAATCAGGCTGTTGACAGCTATGATCCAGATGTTAGAATTATTGAAAATCATGG
AACTGAAGATGAACTTCCAAATTACTGCTTTCCACTGGGAGGTGTGATTAATACAGAGACTCTTACCAAGGTAAAA
CCTAAAACAGGTCAGGAAAATGGATGGGAAAAAGATGCTACAGAATTTTCAGATAAAAATGAAATAAGAGTTGGAA
ATAATTTTGCCATGGAAATCAATCTAAATGCCAACCTGTGGAGAAATTTCCTGTACTCCAACATAGCGCTGTATTT
GCCCGACAAGCTAAAGTACAGTCCTTCCAACGTAAAATTTCTGATAACCCAAACACCTACGACTACATGAACAAG
CGAGTGGTGGCTCCCGGGTTAGTGGACTGCTACATTAACCTTGGAGCACGCTGGTCCCTTGACTATATGGACAACG
TCAACCCATTTAACCACCACGCAATGCTGGCCTGCGCTACCGCTCAATGTTGCTGGGCAATGGTCGCTATGTGCC
CTTCCACATCCAGGTGCCTCAGAAGTTCTTTGCCATTAAAAACCTCCTTCTCCTGCCGGGCTCATACACCTACGAG
TGGAACTTCAGGAAGGATGTTAACATGGTTCTGCAGAGCTCCCTAGGAAATGACCTAAGGGTTGACGGAGCCAGCA
TTAAGTTTGATAGCATTTGCCTTTACGCCACCTTCTTCCCCATGGCCCACAACACCGCCTCCACGCTTGAGGCCAT
GCTTAGAAACGACACCAACGACCAGTCCTTTAACGACTATCTCTCCGCCGCCAACATGCTCTACCCTATACCCGCC
AACGCTACCAACGTGCCCATATCCATCCCCTCCCGCAACTGGGCGGCTTTCCGCGGCTGGGCCTTCACGCGCCTTA
AGACTAAGGAAACCCCATCACTGGGCTCGGCTACGACCCTTATTACACCTACTCTGGCTCTATACCCTACCTAGA
TGGAACCTTTTACCTCAACCACACCTTTAAGAAGGTGGCCATTACCTTTGACTCTTCTGTCAGCTGGCCTGGCAAT
GACCGCCTGCTTACCCCCAACGAGTTTGAAATTAAGCGCTCAGTTGACGGGGAGGGTTACAACGTTGCCCAGTGTA
ACATGACCAAAGACTGGTTCCTGGTACAAATGCTAGCTAACTACAACATTGGCTACCAGGGCTTCTATATCCCAGA
GAGCTACAAGGACCGCATGTACTCCTTCTTTAGAAACTTACAGCCCATGAGCCGTCAGGTGGTGGATGATACTAAA
TACAAGGACTACCAACAGGTGGGCATCCTACACCAACAACAACTCTGGATTTGTTGGCTACCTTGCCCCCACCA
TGCGCGAAGGACAGGCCTACCCTGCTAACTTCCCCTATCCGCTTATAGGCAAGACCGCAGTTGACAGCATTACCCA
GAAAAAGTTTCTTTGCGATCGCACCCTTTGGCGCATCCCATTCTGCAGTAACTTTATGTCCATGGGCGCACTCACA
GACCTGGGCCAAAACCTTCTCTACGCCAACTCCGCCCACGCGCTAGACATGACTTTTGAGGTGGATCCCATGGACG
AGCCCACCCTTCTTTATGTTTTGTTTGAAGTCTTTGACGTGGTCCGTGTGCACCGGCCGCACCGCGGCGTCATCGA
AACCGTGTACCTGCGCACGCCCTTCTCGGCCGGCAACGCCACAACATAAAGAAGCAAGCAACATCAACAACAGCTG
CCGCCATGGGCTCCAGTGAGCAGGAACTGAAAGCCATTGTCAAAGATCTTGGTTGTGGGCCATATTTTTTGGGCAC
CTATGACAAGCGCTTTCCAGGCTTTGTTTCTCCACACAAGCTCGCCTGCGCCATAGTCAATACGGCCGGTCGCGAG
ACTGGGGCGTACACTGGATGGCCTTTGCCTGGAACCCGCACTCAAAAACATGCTACCTCTTTGAGCCCTTTGGCT
TTTCTGACCAGCGACTCAAGCAGGTTTACCAGTTTGAGTACGAGTCACTCCTGCGCCGTAGCGCCATTGCTTCTTC
```

FIGURE 17 (cont.)

```
CCCCGACCGCTGTATAACGCTGGAAAAGTCCACCCAAAGCGTACAGGGGCCCAACTCGGCCGCCTGTGGACTATTC
TGCTGCATGTTTCTCCACGCCTTTGCCAACTGGCCCCAAACTCCCATGGATCACAACCCCACCATGAACCTTATTA
CCGGGGTACCCAACTCCCATGCTCAACAGTCCCCAGGTACAGCCCACCCTGCGTCGCAACCAGGAACAGCTCTACAG
CTTCCTGGAGCGCCACTCGCCCTACTTCCGCAGCCACAGTGCGCAGATTAGGAGCGCCACTTCTTTTTGTCACTTG
AAAAACATGTAAAAATAATGTACTAGAGACACTTTCAATAAAGGCAAATGCTTTTATTTGTACACTCTCGGGTGAT
TATTTACCCCCACCCTTGCCGTCTGCGCCGTTTAAAAATCAAAGGGGTTCTGCCGCGCATCGCTATGCGCCACTGG
CAGGGACACGTTGCGATACTGGTGTTTAGTGCTCCACTTAAACTCAGGCACAACCATCCGCGGCAGCTCGGTGAAG
TTTTCACTCCACAGGCTGCGCACCATCACCAACGCGTTTAGCAGGTCGGGCGCCGATATCTTGAAGTCGCAGTTCG
GGCCTCCGCCCTGCGCGCGCGAGTTGCGATACACAGGGTTGCAGCACTGGAACACTATCAGCGCCGGGTGGTGCAC
GCTGGCCAGCACGCTCTTGTCGGAGATCAGATCCGCGTCCAGGTCCTCCGCGTTGCTCAGGGCGAACGGAGTCAAC
TTTGGTAGCTGCCTTCCCAAAAAGGGCGCGTGCCCAGGCTTTGAGTTGCACTCGCACCGTAGTGGCATCAAAAGGT
GACCGTGCCCGGTCTGGGCGTTAGGATACAGCGCCTGCATAAAAGCCTTGATCTGCTTAAAAGCCACCTGAGCCTT
TGCGCCTTCAGAGAAGAACATGCCGCAAGACTTGCCGGAAAACTGATTGGCCGGACAGGCCGCGTCGTGCACGCAG
CACCTTGCGTCGGTGTTGGAGATCTGCACCACATTTCGGCCCCACCGGTTCTTCACGATCTTGGCCTTGCTAGACT
GCTCCTTCAGCGCGCGCTGCCCGTTTTCGCTCGTCACATCCATTTCAATCACGTGCTCCTTATTTATCATAATGCT
TCCGTGTAGACACTTAAGCTCGCCTTCGATCTCAGCGCAGCGGTGCAGCCACAACGCGCAGCCCGTGGGCTCGTGA
TGCTTGTAGGTCACCTCTGCAAACGACTGCAGGTACGCCTGCAGGAATCGCCCATCATCGTCACAAAGGTCTTGT
TGCTGGTGAAGGTCAGCTGCAACCCGCGGTGCTCCTCGTTCAGCCAGGTCTTGCATACGGCCGCCAGAGCTTCCAC
TTGGTCAGGCAGTAGTTTGAAGTTCGCCTTTAGATCGTTATCCACGTGGTACTTGTCCATCAGCGCGCGCGCAGCC
TCCATGCCCTTCTCCCACGCAGACACGATCGGCACACTCAGCGGGTTCATCACCGTAATTTCACTTTCCGCTTCGC
TGGGCTCTTCCTCTTCCTCTTGGCGTCCGCATACCACGCGCCACTGGGTCGTCTTCATTCAGCCGCCGCACTGTGCG
CTTACCTCCTTTGCCATGCTTGATTAGCACCGGTGGGTTGCTGAAACCCACCATTTGTAGCGCCACATCTTCTCTT
TCTTCCTCGCTGTCCACGATTACCTCTGGTGATGGCGGGCGCTCGGGCTTGGGAGAAGGGCGCTTCTTTTTCTTCT
TGGGCGCAATGGCCAAATCCGCCGCCGAGGTCGATGGCCGCGGCTGGGTGTGCGCGGCACCAGCGCGTCTTGTGA
TGAGTCTTCCTCGTCCTCGGACTCGATACGCCGCCTCATCCGCTTTTTTGGGGGCGCCCGGGGAGGCGGCGGCGAC
GGGGACGGGGACGACACGTCCTCCATGGTTGGGGACGTCGCGCCGCACCGCGTCCGCGCTCGGGGGTGGTTTCGC
GCTGCTCCTCTTCCCGACTGGCCATTTCCTTCTCCTATAGGCAGAAAAGATCATGGAGTCAGTCGAGAAGAAGGA
CAGCCTAACCGCCCCTCTGAGTTCGCCACCACCGCCTCCACCGATGCCGCCAACGCGCCTACCACCTTCCCCGTC
GAGGCACCCCGCTTGAGGAGGAGGAAGTGATTATCGAGCAGGACCCAGGTTTTGTAAGCGAAGACGACGAGGACC
GCTCAGTACCAACAGAGGATAAAAAGCAAGACCAGGACAACGCAGAGGCAAACGAGGAACAAGTCGGGCGGGGGA
CGAAAGGCATGGCGACTACCTAGATGTGGGAGACGACGTGCTGTTGAAGCATCTGCAGCGCCAGTGCGCCATTATC
TGCGACGCGTTGCAAGAGCGCAGCGATGTGCCCCTCGCCATACGGATGTCAGCCTTGCCTACGAACGCCACCTAT
TCTCACCGCGCGTACCCCCAAACGCCAAGAAAACGCACATGCGAGCCCAACCGCGCGCCTCAACTTCTACCCCGT
ATTTGCCGTGCCAGAGGTGCTTGCCACCTATCACATCTTTTTCCAAAACTGCAAGATACCCCTATCCTGCCGTGCC
AACCCAGCCGAGCGGACAAGCAGCTGGCCTTGCGGCAGGGCGCTGTCATACCTGATATCGCCTCGCTCAACGAAG
TGCCAAAAATCTTTGAGGGTCTTGGACGCGACGAGAAGCGCGCGGCAAACGCTCTGCAACAGGAAAACAGCGAAAA
TGAAAGTCACTCTGGAGTGTTGGTGGAACTCGAGGGTGACAACGCGCGCCTAGCCGTACTAAAACGCAGCATCGAG
GTCACCCACTTTGCCTACCCGGCACTTAACCTACCCCCCAAGGTCATGAGCACAGTCATGAGTGAGCTGATCGTGC
GCCGTGCGCAGCCCCTGGAGAGGGATGCAAATTTGCAAGAACAAACAGAGGAGGGCCTACCCGCAGTTGGCGACGA
GCAGCTAGCGCGCTGGCTTCAAACGCGCGAGCCTGCCGACTTGGAGGAGCGACGCAAACTAATGATGGCCGCAGTG
CTCGTTACCGTGGAGCTTGAGTGCATGCAGCGGTTCTTTGCTGACCCGGAGATGCAGCGCAAGCTAGAGGAAACAT
TGCACTACACCTTTCGACAGGGCTACGTACGCCAGGCCTGCAAGATCTCCAACGTGGAGCTCTGCAACCTGGTCTC
CTACCTTGGAATTTTGCACGAAAACCGCCTTGGGCAAAACGTGCTTCATTCCACGCTCAAGGGCGAGGCGCGCCGC
GACTACGTCCGCGACTGCGTTTACTTATTTCTATGCTACACCTGGCAGACGGCCATGGGCGTTTGGCAGCAGTGCT
TGGAGGAGTGCAACCTCAAGGAGCTGCAGAAACTGCTAAAGCAAAACTTGAAGGACCTATGGACGGCCTTCAACGA
GCGCTCCGTGGCCGCGCACCTGGCGGACATCATTTTCCCCGAACGCCTGCTTAAAACCCTGCAACAGGGTCTGCCA
GACTTCACCAGTCAAAGCATGTTGCAGAACTTTAGGAACTTTATCCTAGAGCGCTCAGGAATCTTGCCCGCCACCT
GCTGTGCACTTCCTAGCGACTTTGTGCCCATTAAGTACCGCGAATGCCCTCCGCCGCTTTGGGGCCACTGCTACCT
TCTGCAGCTAGCCAACTACCTTGCCTACCACTCTGACATAATGGAAGACGTGAGCGGTGACGGTCTACTGGAGTGT
CACTGTCGCTGCAACCTATGCACCCCGCACCGCTCCCTGGTTTGCAATTCGCAGCTGCTTAACGAAAGTCAAATTA
TCGGTACCTTTGAGCTGCAGGGTCCCTCGCCTGACGAAAAGTCCGCGGCTCCGGGGTTGAAACTCACTCCGGGGCT
GTGGACGTCGGCTTACCTTCGCAAATTTGTACCTGAGGACTACCACGCCCACGAGATTAGGTTCTACGAAGACCAA
TCCCGCCCGCCAAATGCGGAGCTTACCGCCTGCGTCATTACCCAGGCCCACATTCTTGGCCAATTGCAAGCCATCA
ACAAAGCCCGCCAAGAGTTTCTGCTACGAAAGGGACGGGGGGTTTACTTGGACCCCAGTCCGGCGAGGAGCTCAA
CCCAATCCCCCCGCCGCCGCAGCCCTATCAGCAGCAGCCGCGGGCCCTTGCTTCCCAGGATGGCACCCAAAAAGAA
GCTGCAGCTGCCGCCGCCACCCACGGACGAGGAGGAATACTGGGACAGTCAGGCAGAGGAGGTTTTGGACGAGGAG
GAGGAGGACATGATGGAAGACTGGAGAGCCTAGACGAGGAAGCTTCCGAGGTCGAAGAGGTGTCAGACGAAACAC
CGTCACCCTCGGTCGCATTCCCCTCGCCGGCGCCCCAGAAATCGGCAACCGGTTCCAGCATGGCTACAACCTCCGC
TCCTCAGGCGCCGCCGGCACTGCCCGTTCGCCGACCCAACCGTAGATGGGACACCACTGGAACCAGGGCCGGTAAG
TCCAAGCAGCCGCCGCCGTTAGCCCAAGAGCAACAACAGCGCCAAGGCTACCGCTCATGGCGCGGGCACAAGAACG
CCATAGTTGCTTGCTTGCAAGACTGTGGGGCAACATCTCCTTCGCCCGCCGCTTTCTTCTCTACCATCACGGCGT
```

FIGURE 17 (cont.)

```
GGCCTTCCCCCGTAACATCCTGCATTACTACCGTCATCTCTACAGCCCATACTGCACCGGCGGCAGCGGCAGCGGC
AGCAACAGCAGCGGCCACACAGAAGCAAAGGCGACCGGATAGCAAGACTCTGACAAAGCCCAAGAAATCCACAGCG
GCGCAGCAGCAGGAGGAGGAGCGCTGCGTCTGGCGCCCAACGAACCCGTATCGACCCGCGAGCTTAGAAACAGGA
TTTTTCCCACTCTGTATGCTATATTTCAACAGAGCAGGGGCCAAGAACAAGAGCTGAAAATAAAAAACAGGTCTCT
GCGATCCCTCACCCGCAGCTGCCTGTATCACAAAAGCGAAGATCAGCTTCGGCGCACGCTGGAAGACGCGGAGGCT
CTCTTCAGTAAATACTGCGCGCTGACTCTTAAGGACTAGTTCGCGCCCTTTCTCAAATTTAAGCGCGAAAACTAC
GTCATCTCCAGCGGCCACACCCGGCGCCAGCACCTGTCGTCAGCGCCATTATGAGCAAGGAAATTCCCACGCCCTA
CATGTGGAGTTACCAGCCACAAATGGGACTTGCGGCTGGAGCTGCCCAAGACTACTCAACCCGAATAAACTACATG
AGCGCGGGACCCCACATGATATCCCGGGTCAACGGAATCCGCGCCCACCGAAACCGAATTCTCTTGGAACAGGCGG
CTATTACCACCACACCTCGTAATAACCTTAATCCCCGTAGTTGGCCCGCTGCCCTGGTGTACCAGGAAAGTCCCGC
TCCCACCACTGTGGTACTTCCCAGAGACGCCCAGGCCGAAGTTCAGATGACTAACTCAGGGGCGCAGCTTGCGGGC
GGCTTTCGTCACAGGGTGCGGTCGCCCGGGCAGGGTATAACTCACCTGACAATCAGAGGGCGAGGTATTCAGCTCA
ACGACGAGTCGGTGAGCTCCTCGCTTGGTCTCCGTCCGACGGGACATTTCAGATCGGCGGCGCCGGCCGTCCTTC
ATTCACGCCTCGTCAGGCAATCCTAACTCTGCAGACCTCGTCCTCTGAGCCGCGCTCTGGAGGCATTGGAACTCTG
CAATTTATTGAGGAGTTTGTGCCATCGGTCTACTTTAACCCCTTCTCGGGACCTCCCGGCCACTATCCGGATCAAT
TTATTCCTAACTTTGACGCGGTAAAGGACTCGGCGGACGGCTACGACTGAATGTTAAGTGGAGAGGCAGAGCAACT
GCGCCTGAAACACCTGGTCCACTGTCGCCGCCACAAGTGCTTTGCCCGCGACTCCGGTGAGTTTTGCTACTTTGAA
TTGCCCGAGGATCATATCGAGGGCCCGGCGCACGGCGTCCGGCTTACCGCCCAGGGAGAGCTTGCCCGTAGCCTGA
TTCGGAGTTTACCCAGCGCCCCCTGCTAGTTGAGCGGGACAGGGGACCCTGTGTTCTCACTGTGATTTGCAACTG
TCCTAACCTTGGATTACATCAAGATCCTCTAGTTAATTAACAGCTTGCATGCCTGCAGGTCGACGGATCGGGAGAT
CTCGGCCGCATATTAAGTGCATTGTTCTCGATACCGCTAAGTGCATTGTTCTCGTTAGCTCGATGGACAAGTGCAT
TGTTCTCTTGCTGAAAGCTCGATGGACAAGTGCATTGTTCTCTTGCTGAAAGCTCGATGGACAAGTGCATTGTTCT
CTTGCTGAAAGCTCAGTACCCGGGAGTACCCTCGACCGCCGGAGTATAAATAGAGGCGCTTCGTCTACGGAGCGAC
AATTCAATTCAAACAAGCAAAGTGAACACGTCGCTAAGCGAAAGCTAAGCAAATAAACAAGCGCAGCTGAACAAGC
TAAACAATCTGCAGTAAAGTGCAAGTTAAAGTGAATCAATTAAAAGTAACCAGCAACCAAGTAAATCAACTGCAAC
TACTGAAATCTGCCAAGAAGTAATTATTGAATACAAGAAGAGAACTCTGAATACTTTCAACAAGTTACCGAGAAAG
AAGAACTCACACACAGCTAGCGTTTAAACTTAAGCTTCACCATGGTGGGGCCCTGCATGCTGCTGCTGCTGCTGCT
GCTGGGCCTGAGGCTACAGCTCTCCCTGGGCATCATCCTAGTTGAGGAGGAGAACCCGGACTTCTGGAACCGCGAG
GCAGCCGAGGCCCTGGGTGCCGCCAAGAAGCTGCAGCCTGCACAGACAGCCGCCAAGAACCTCATCATCTTCCTGG
GCGATGGGGTGGGGGTGTCTACGGTGACAGCTGCCAGGATCCTAAAAGGGCAGAAGAAGGACAAACTGGGGCCTGA
GATACCCCTGGCCATGGACCGCTTCCCATATGTGGCTCTGTCCAAGACATACAATGTAGACAAACATGTGCCAGAC
AGTGGAGCCACAGCCACCGGCCTACCTGTGCGGGGTCAAGGGCAACTTCCAGACCATTGGCTTGAGTGCAGCCGCC
GCTTTAACCAGTGCAACGCGACGCGGCAACGAGGTCATCTCCGGTGATGAATCGGGCCAAGAAAGCAGGCAAGTC
AGTGGGAGTGGTAACCACCACACGAGTGCAGCACGCCTCGCCAGCCGGCACCTACGCCCACACGGTGAACCGCAAC
TGGTACTCGGACGCCGACGTGCCTGCCTCGGCCCGCCAGGAGGGGTGCCAGGACATCGCTACGCAGCTCATCTCCA
ACATGGACATTGACGTGATCCTAGGTGGGGGCCGAAAGTACATGTTTCGCATGGGAACCCCAGACCCTGAGTACCC
AGATGACTACAGCCAAGGTGGGACCAGGCTGGACGGGAAGAATCTGGTGCAGGAATGGCTGGCGAAGCACCAGGGT
GCCCGGTACGTGTGGAACCGCACTGAGCTCATGCGGGCTTCCCTGGACCCGTCTGTGGCCCATCTCATGGGTCTCT
TTGAGCCTGGAGACATGAAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCGCATCGACCATGGTCAT
CATGAAAGCAGGGCTTACCGGGCACTGACTGAGACGATCATGTTCGACGACGCCATTGAGAGGGCGGGCCAGCTCA
CCAGCGAGGAGGACACGCTGAGCCTCGTCACTGCCGACCACTCCCACGTCTTCTCCTTCGGAGGCTGCCCCCTGCG
AGGGGGCTCCATCTTCGGGCTGGCCCCTGGCAAGGCCCGGGACAAGGCCTACACGGTCCTCCTATACGGAAAC
GGTCCAGGCTATGTGCTCAAGGACGGCGCCCGGCCGGATGTTACCGAGAGCGAGAGCGGGAGCCCCGAGTATCGC
AGCAGTCAGCAGTGCCCCTGGACGAAGAGACCCACGCAGGCGAGGACGTGGCGGTGTTCGCGCGGCCCGCAGGC
GCACCTGGTTCACGGCGTGCAGGAGCAGACCTTCATAGCGCACGTCATGGCCTTCGCCGCCTGCCTGGAGCCCTAC
ACCGCCTGCGACCTGGCGCCCCCGCCGGCACCACCGACGCGCGCACCCGGGGCGGTCCGTGGTCCCGCGTTGC
TTCCTCTGCTGGCCGGGACCCTGCTGCTGCTGGAGACGGCCACTGCTCCCTGAGTGTCCCGTCCCTGGGGCTCCTG
CTTCCCCATCCCGGAGTTCTCCTGCTCCCCGCCTCCTGTCGTCCTGCCTGGCCTCCAGCCCGAGTCGTCATCCCG
GAGTCCCTATACAGAGGTCCTGCCATGGAACCTTCCCCTCCCGTGCGCTCTGGGGACTGAGCCCATGACACCAAA
CCTGCCCCTTGGCTGCTCTCGGACTCCCTACCCCAACCCCAGGGACAGATCTGGCCAGATTTGTAAAACAAATAGA
TTTTAGGCCCAAAGATTATTTAAAGCATTGCCTGGAACGCAGTGAGTTTTTGTTAGAAAAGAGAATAATTCAAAGT
GGCATTGCTTTGCTTCTTATGTTAATTTGGTACAGACCTGTGGCTGAGTTTGCTCAAAGTATTCAGAGCAGAATTG
TGGAGTGGAAAGAGACGATTGGACAAAGAGTTTAGTTTGTCAGTGTATCAAAAAATGAAGTTTAATGTGGCTATGGG
AATTGGAGTTTTAGATTGGCTAAGAAACAGTGATGATGATGATGAAGACAGCCAGGAAAATGCTGATAAAAATGAA
GATGGTGGGGAGAAGAACATGGAAGACTCAGGGCATGAAACAGGCATTGATTCACAGTCCCAAGGCTCATTTCAGG
CCCCTCAGTCCTCACAGTCTGTTCATGATCATAATCAGCCATACCACATTTGTAGAGGTTTTACTTGCTTTAAAAA
ACCTCCCACACCTCCCCCTGAACCTGAAACATAAAATGAATGCAATTGTTGTTGTTAACTTGTTTATTGCAGCTTA
TAATGGTTACAAATAAAGCAATAGCATCACAAATTTCACAAATAAAGCATTTTTTTCACTGCATTCTAGTTGTGGT
TTGTCCAAACTCATCAATGTATCTTATCATGTCTGGATCCCCAGGAAGCTCCTCTGTGTCCTCATAAACCCTAACC
TCCTCTACTTGAGAGGACATTCCAATCATAGGCTGCCCATCCACCCTCTGTGTCCTCCTGTTAATTAGGTCACTTA
```

FIGURE 17 (cont.)

```
ACAAAAAGGAAATTGGGTAGGGGTTTTTCACAGACCGCTTTCTAAGGGTAATTTTAAAATATCTGGGAAGTCCCTT
CCACTGCTGTGTTCCAGAAGTGTTGGTAAACAGCCCACAAATGTCAACAGCAGAAACATACAAGCTGTCAGCTTTG
CACAAGGGCCCAACACCCTGCTCATCAAGAAGCACTGTGGTTGCTGTGTTAGTAATGTGCAAAACAGGAGGCACAT
TTTCCCCACCTGTGTAGGTTCCAAAATATCTAGTGTTTTCATTTTTACTTGGATCAGGAACCCAGCACTCCACTGG
ATAAGCATTATCCTTATCCAAAACAGCCTTGTGGTCAGTGTTCATCTGCTGACTGTCAACTGTAGCATTTTTTGGG
GTTACAGTTTCAGCAGGATATTTGGTCCTGTAGTTTGCTAACACACCCTGCAGCTCCAAAGGTTCCCCACCAACAG
CAAAAAAATGAAAATTTGACCCTTGAATGGGTTTTCAGCACCATTTCATGAGTTTTTGTGTCCCTGAATGCAA
GTTAACATAGCAGTTACCCCAATAACCTCAGTTTTAACAGTAACAGCTTCCCACATCAAAATATTTCCACAGGTT
AAGTCCTCATTTAAATTAGGCAAAGGAATTCCACTTCCCACTGCCTTGCTTCCGTCTCCCATTCAAACTTTTATCA
ACTGACATTATTCTAAGTAAAATCCTCTTCATTATGTTGTCAGCAATCCATTGCTTGAAGGCCTGGCTCCCCAGAA
CCCCTCGACTGGTATGTCTTCTCCTAGAATACTCCAGAAGAAAGGAGTGTATGAAGATAGTGACTGCACATTAAA
ATGACTGAAACCATAGTAAATTAGGATGAGATTCTGGGCAGATAAACAGACAGCTGGCTAGGATCATTTTTTTATG
CCTTGGACTTCTTTGGCAATCTGTTGAAGCCTGACATTCCTCAGAATAATGTTTTAAAGCCCAACAATAAGACCCT
GTAGCACATATAATAAGTACTGCAGTTTTGAAGTAGTGATAAGCATAAATGATATTTTGATATATTTATTATAACT
GTAATGAGATGTGTACATATCTGTGACTTCATAGGTACTGATTGTACTACTGTGATTTTTTGCCTACTTTCAAAA
TGAAAAGGAATGCTTAATTTCAGTTAGAGGTTAGTAAAGACAAATAGGTAATTTTCTTCTCCAGTGAAGAGCATGG
CGCCCCTTGCTATTCATGGACGCTTGCTTAAAGACTTGTACACAGGCTTGCTTTGTATCAACCTATGACTTCCCCT
TACAGCCGATGATAGGTTTTTATTTGCACCTCCTTCGTGTACAAAGACAGTTTTGGTGGCTACGCCATCATTAAAC
TCATTATTATCATGCTTAAGCCTATAGATGTATCCAGTTCTTCTGTTACATAATTGAAGCTGTAGTGAATTGTCTA
TCTTAAACTGCATCGCTAACTGACTACATTTCACACTTCATTTGCTTCCAACATAGACTAACCTTCTTGGATGTCC
ACTATTATTTGAACTTTTGAGATTTTTTTTCCTATTTCTAATATCTTAAAATTTCAGAAGACTTAAAGTTTTGCAA
CTACAGGGCTCCATATAGACATCTAGCTTGACTTGAATTTATACACTTTCTTTCATTGATGTCCCTGGACTAAAAATGTT
AAATATTTCTAACCGCTGTACTTAAAGTCCATTACAAACGAAGACTACTGTTGTTAAGTTGAATAGGCATCTTATA
TATTTTTCACCGGTGCAATAAATAACTTCTATTCCCTTCTAACATCTGCTTGCGTTGCACTGAGAGTACACTATTG
ATTAGCAATAGGTTCGTGATTACAGCCCTTCTATAATTAATTGTTAGGTTAACATATTATTCATAAAATATTATTT
TATTAATTTTTACTTGATTTGCTACTGGATGCTTAGAAATAGCTATGAGTATATTGGTAGAACCAGTACTTATATT
TTATTACATTTTACATTTCATAAAATTTAAGTGATATAAAAATCCTGAGGAAGTATGCCACAAAAGTGGTCTCAG
TGGAAATTTAAATATGTTAACATTTATTTTTAAAATGTAGCGTGAAATAGACAACTTTAAAAGCTCAGCTTAAAAA
AAAAACTCAAGGAAGCTGAACTTGACTTTTTAAAGCACTGAAGTGCAATATTTAATGTAGGTCAACATGTTTAAAT
GGGAAATTTTTTTCCTAATTACAGCCAAATCCCTAGCTGTAATTAACTTAAAATTTGTATACTATTTCACAACAG
AGTCAGCATATACCACTTTCTTATAAAATTAGAAAGATCTAAAATTTTAGAGCTTATTTGGTGAAACAGCATATT
GCTACATCTTTGTTTATAAATTATAATGTGCCTTTAGAGCCCAATAACAGATAACAAGATTTTGAAAATTCAGGTG
AATTAGAGTTATCAGAGGGAATGTTAATACACTCTATTCAAATACTATATGAGTAAGACATTTAAAATAGGAAACA
ATACTTTATATATTAAAAAAATTAATCTTCCAGTCGATTTAATCCACTTTATGAATTCATTTAAATCGATTTAAA
TTCGAATTAATTAACTAGAGTACCCGGGGATCTTATTCCCTTTAACTAATAAAAAAAATAATAAAGCATCACTTA
CTTAAAATCAGTTAGCAAATTTCTGTCCAGTTTATTCAGCAGCACCTCCTTGCCCTCCTCCCAGCTCTGGTATTGC
AGCTTCCTCCTGGCTGCAAACTTTCTCCACAATCTAAATGGAATGTCAGTTTCCTCCTGTTCCTGTCCATCCGCAC
CCACTATCTTCATGTTGTTGCAGATGAAGCGCGCAAGACCGTCTGAAGATACCTTCAACCCCGTGTATCCATATGA
CACGGAAACCGGTCCTCCAACTGTGCCTTTTCTTACTCCTCCCTTTGTATCCCCCAATGGGTTTCAAGAGAGTCCC
CCTGGGGTACTCTCTTTGCGCCTATCCGAACCTCTAGTTACCTCCAATGGCATGCTTGCGCTCAAAATGGGCAACG
GCCTCTCTCTGGACGAGGCCGGCAACCTTACCTCCCAAAATGTAACCACTGTGAGCCCACCTCTCAAAAAAACCAA
GTCAAACATAAACCTGGAAATATCTGCACCCCTCACAGTTACCTCAGAAGCCCTAACCTGTGGCTGCCGCCGCACCT
CTAATGGTCGCGGCAACACACTCACCATGCAATCACAGGCCCCGCTAACCGTGCACGACTCCAAACTTAGCATTG
CCACCCAAGGACCCCTCACAGTGTCAGAAGGAAAGCTAGCCCTGCAAACATCAGGCCCCCTCACCACCACCGATAG
CAGTACCCTTACTATCACTGCCTCACCCCCTCTAACTACTGCCACTGGTAGCTTGGGCATTGACTTGAAAGAGCCC
ATTTATACACAAAATGGAAAACTAGGACTAAAGTACGGGGCTCCTTTGCATGTAACAGACGACCTAAACACTTTGA
CCGTAGCAACTGGTCCAGGTGTGACTATTAATAATACTTCCTTGCAAACTAAAGTTACTGGAGCCTTGGGTTTTGA
TTCACAAGGCAATATGCAACTTAATGTAGCAGGAGGACTAAGGATTGATTCTCAAAACAGACGCCTTATACTTGAT
GTTAGTTATCCGTTTGATGCTCAAAACCAACTAAATCTAAGACTAGGACAGGGCCCTCTTTTTATAAACTCAGCCC
ACAACTTGGATATTAACTACAACAAAGGCCTTTACTTGTTTACAGCTTCAAACAATTCCAAAAAGCTTGAGGTTAA
CCTAAGCACTGCCAAGGGGTTGATGTTTGACGCTACAGCCATAGCCATTAATGCAGGAGATGGGCTTGAATTTGGT
TCACCTAATGCACCAAACACAAATCCCCTCAAAACAAAAATTGGCCATGGCCTAGAATTTGATTCAAACAAGGCTA
TGGTTCCTAAACTAGGAACTGGCCTTAGTTTTGACAGCACAGGTGCCATTACAGTAGGAAACAAAATAATGATAA
GCTAACTTTGTGGACCACACCAGCTCCATCTCCTAACTGTAGACTAAATGCAGAGAAAGATGCTAAACTCACTTTG
GTCTTAACAAAATGTGGCAGTCAAATACTTGCTACAGTTTCAGTTTTGGCTGTTAAAGGCAGTTTGGCTCCAATAT
CTGGAACAGTTCAAAGTGCTCATCTTATTATAAGATTTGACGAAAATGGAGTGCTACTAAACAATTCCTTCCTGGA
CCCGAATATTGGAACTTTAGAAATGGAGATCTTACTGAAGGCACAGCCTATACAAACGCTGTTGGATTTATGCCT
AACCTATCAGCTTATCCAAAATCTCACGGTAAAACTGCCAAAAGTAACATTGTCAGTCAAGTTTACTTAAACGGAG
ACAAAACTAAACCTGTACAACTAACCATTACACTAAACGGTACACAGGGAAACAGGAGACACAACTCCAAGTGCATA
CTCTATGTCATTTCATGGGACTGGTCTGGCCACAACTACATTAATGAAATATTTGCCACATCCTCTTACACTTTT
TCATACATTGCCCAAGAATAAAGAATCGTTTGTGTTATGTTTCAACGTGTTTATTTTTCAATTGCAGAAAATTTCA
```

FIGURE 17 (cont.)

```
AGTCATTTTTCATTCAGTAGTATAGCCCCACCACCACATAGCTTATACAGATCACCGTACCTTAATCAAACTCACA
GAACCCTAGTATTCAACCTGCCACCTCCCTCCCAACACACAGAGTACACAGTCCTTTCTCCCCGGCTGGCCTTAAA
AAGCATCATATCATGGGTAACAGACATATTCTTAGGTGTTATATTCCACACGGTTTCCTGTCGAGCCAAACGCTCA
TCAGTGATATTAATAAACTCCCCGGGCAGCTCACTTAAGTTCATGTCGCTGTCCAGCTGCTGAGCCACAGGCTGCT
GTCCAACTTGCGGTTGCTTAACGGGCGGCGAAGGAGAAGTCCACGCCTACATGGGGGTAGAGTCATAATCGTGCAT
CAGGATAGGGCGGTGGTGCTGCAGCAGCGCGCGAATAAACTGCTGCCGCCGCCGCTCCGTCCTGCAGGAATACAAC
ATGGCAGTGGTCTCCTCAGCGATGATTCGCACCGCCCGCAGCATAAGGCGCCTTGTCCTCCGGGCACAGCAGCGCA
CCCTGATCTCACTTAAATCAGCACAGTAACTGCAGCACAGCACCACAATATTGTTCAAAATCCCACAGTGCAAGGC
GCTGTATCCAAAGCTCATGGCGGGGACCACAGAACCCACGTGGCCATCATACCACAAGCGCAGGTAGATTAAGTGG
CGACCCCTCATAAACACGCTGGACATAAACATTACCTCTTTTGGCATGTTGTAATTCACCACCTCCCGGTACCATA
TAAACCTCTGATTAAACATGGCGCCATCCACCACCATCCTAAACCAGCTGGCCAAAACCTGCCCGCCGGCTATACA
CTGCAGGGAACCGGGACTGGAACAATGACAGTGGAGAGCCCAGGACTCGTAACCATGGATCATCATGCTCGTCATG
ATATCAATGTTGGCACAACACAGGCACACGTGCATACACTTCCTCAGGATTACAAGCTCCTCCCGCGTTAGAACCA
TATCCAGGGAACAACCCATTCCTGAATCAGCGTAAATCCCACACTGCAGGGAAGACCTCGCACGTAACTCACGTT
GTGCATTGTCAAAGTGTTACATTCGGGCAGCAGCGGATGATCCTCCAGTATGGTAGCGCGGGTTTCTGTCTCAAAA
GGAGGTAGACGATCCCTACTGTACGGAGTGCGCCGAGACAACCGAGATCGTGTTGGTCGTAGTGTCATGCCAAATG
GAACGCCGGACGTAGTCATATTTCCTGAAGCAAAACCAGGTGCGGGCGTGACAAACAGATCTGCGTCTCCGGTCTC
GCCGCTTAGATCGCTCTGTGTAGTAGTTGTAGTATATCCACTCTCTCAAAGCATCCAGGCGCCCCTGGCTTCGGG
TTCTATGTAAACTCCTTCATGCGCCGCTGCCCTGATAACATCCACCACCGCAGAATAAGCCACACCCAGCCAACCT
ACACATTCGTTCTGCGAGTCACACACGGGAGGAGCGGGAAGAGCTGGAAGAACCATGTTTTTTTTTTATTCCAAA
AGATTATCCAAAACCTCAAAATGAAGATCTATTAAGTGAACGCGCTCCCCTCCGGTGGCGTGGTCAAACTCTACAG
CCAAAGAACAGATAATGGCATTTGTAAGATGTTGCACAATGGCTTCCAAAAGGCAAACGGCCCTCACGTCCAAGTG
GACGTAAAGGCTAAACCCTTCAGGGTGAATCTCCTCTATAAACATTCCAGCACCTTCAACCATGCCCAAATAATTC
TCATCTCGCCACCTTCTCAATATATCTCTAAGCAAATCCCGAATATTAAGTCCGGCCATTGTAAAAATCTGCTCCA
GAGCGCCCTCCACCTTCAGCCTCAAGCAGCGAATCATGATTGCAAAAATTCAGGTTCCTCACAGACCTGTATAAGA
TTCAAAAGCGGAACATTAACAAAAATACCGCGATCCCGTAGGTCCCTTCGCAGGGCCAGCTGAACATAATCGTGCA
GGTCTGCACGGACCAGCGCGGCCACTTCCCCGCCAGGAACCTTGACAAAAGAACCCACACTGATTATGACACGCAT
ACTCGGAGCTATGCTAACCAGCGTAGCCCCGATGTAAGCTTTGTTGCATGGGCGGCGATATAAAATGCAAGGTGCT
GCTCAAAAAAATCAGGCAAAGCCTCGCGCAAAAAGAAAGCACATCGTAGTCATGCTCATGCAGATAAAGGCAGGTA
AGCTCCGGAACCACCACAGAAAAAGACACCATTTTTCTCTCAAACATGTCTGCGGGTTTCTGCATAAACACAAAAT
AAAATAACAAAAAAACATTTAAACATTAGAAGCCTGTCTTACAACAGGAAAAACAACCCTTATAAGCATAAGACGG
ACTACGGCCATGCCGGCCGTGACCGTAAAAAAACTGGTCACCGTGATTAAAAAGCACCACCGACAGCTCCTCGGTCA
TGTCCGGAGTCATAATGTAAGACTCGGTAAACACATCAGGTTGATTCATCGGTCAGTGCTAAAAAGCGACCGAAAT
AGCCCGGGGAATACATACCCGCAGGCGTAGAGACAACATTACAGCCCCCATAGGAGGTATAACAAAATTAATAGG
AGAGAAAAACACATAAACACCTGAAAAACCCTCCTGCCTAGGCAAAATAGCACCCTCCCGCTCCAGAACAACATAC
AGCGCTTCACAGCGGCAGCCTAACAGTCAGCCTTACCAGTAAAAAAGAAAACCTATTAAAAAAACACCACTCGACA
CGGCACCAGCTCAATCAGTCACAGTGTAAAAAAGGGCCAAGTGCAGAGCGAGTATATATAGGACTAAAAAATGACG
TAACGGTTAAAGTCCACAAAAAACACCCAGAAAACCGCACGCGAACCTACGCCCAGAAACGAAAGCCAAAAAACCC
ACAACTTCCTCAAATCGTCACTTCCGTTTTCCCACGTTACGTAACTTCCCATTTTAAGAAAACTACAATTCCCAAC
ACATACAAGTTACTCCGCCCTAAAACCTACGTCACCCGCCCCGTTCCCACGCCCCGCGCCACGTCACAAACTCCAC
CCCCTCATTATCATATTGGCTTCAATCCAAAATAAGGTATATTATTGATGATGGCCGGCCGAATTGAATCAGGGGA
TAACGCAGGAAGAACATGTGAGCAAAAGGCCAGCAAAAGGCCAGGAACCGTAAAAAGGCCGCGTTGCTGGCGTTT
TTCCATAGGCTCCGCCCCCTGACGAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGGACAGTATTTGGTATC
TGGCTCTGCTGAAGCCAGTTACCTTCGGAAAAGAGTTGGTAGCTCTTGATCCGGCAAACAAACCACCGCTGGTA
GCGGTGGTTTTTTTGTTTGCAAGCAGCAGATTACGCGCAGAAAAAAGGATCTCAAGAAGATCCTTTGATCTTTTC
TACGGGGTCTGACGCTCAGTGGAACGAAAACTCACGTTAAGGGATTTTGGTCATGAGATTATCAAAAGGATCTTC
ACCTAGATCCTTTTAAATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCACGCTCA
CCGGCTCCAGATTTATCAGCAATAAACCAGCCAGCCGGAAGGGCCGAGCGCAGAAGTGGTCCTGCAACTTTATCCG
CCTCCATCCAGTCTATTAATTGTTGCCGGGAAGCTAGAGTAAGTAGTTCGCCAGTTAATAGTTTGCGCAACGTTGT
TGCCATTGCTACAGGCATCGTGGTGTCACGCTCGTCGTTTGGTATGGCTTCATTCAGCTCCGGTTCCCAACGATCA
AGGCGAGTTACATGATCCCCCATGTTGTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCATGCCATCCGTAAGATG
CTTTTCTGTGACTGGTGAGTACTCAACCAAGTCATTCTGAGAATAGTGTATGCGGCGACCGAGTTGCTCTTGCCCG
GCGTCAATACGGGATAATACCGCGCCACATAGCAGAACTTTAAAAGTGCTCATCATTGGAAAACGTTCTTCGGGGC
```

FIGURE 17 (cont.)

```
GAAAACTCTCAAGGATCTTACCGCTGTTGAGATCCAGTTCGATGTAACCCACTCGTGCACCCAACTGATCTTCAGC
ATCTTTTACTTTCACCAGCGTTTCTGGGTGAGCAAAAACAGGAAGGCAAAATGCCGCAAAAAGGGAATAAGGGCG
ACACGGAAATGTTGAATACTCATACTCTTCCTTTTTCAATATTATTGAAGCATTTATCAGGGTTATTGTCTCATGA
GCGGATACATATTTGAATGTATTTAGAAAAATAAACAATAGGGGTTCCGCGCACATTTCCCCGAAAAGTGCCAC
```

FIGURE 18

SEQ ID NO:17 (Ad2 preterminal protein)
MALSVNDCARLTGQSVPTMEHFLPLRNIWNRVRDFPRASTTAAGITWMSRYIYGYHRLMLEDLA
PGAPATLRWPLYRQPPPHFLVGYQYLVRTCNDYVFDSRAYSRLRYTELSQPGHQTVNWSVMANC
TYTINTGAYHRFVDMDDFQSTLTQVQQAILAERVVADLALLQPMRGFGVTRMGGRGRHLRPNSA
AAVAIDARDAGQEEGEEEVPVERLMQDYYKDLRRCQNEAWGMADRLRIQQAGPKDMVLLSTIR
RLKTAYFNYIISSTSARNNPDRHPLPPATVLSLPCDCDWLDAFLERFSDPVDADSLRSLGGGVPTQQ
LLRCIVSAVSLPHGSPPPTHNRDMTGGVFQLRPRENGRAVTETMRRRRGEMIERFVDRLPVRRRRR
RVPPPPPPPEEEEEGEALMEEEIEEEEAPVAFEREVRDTVAELIRLLEEELTVSARNSQFFNFAVDFY
EAMERLEALGDINESTLRRWVMYFFVAEHTATTLNYLFQRLRNYAVFARHVELNLAQVVMRAR
DAEGGVVYSRVWNEGGLNAFSQLMARISNDLAATVERAGRGDLQEEEIEQFMAEIAYQDNSGDV
QEILRQAAVNDTEIDSVELSFRFKLTGPVVFTQRRQIQEINRRVVAFASNLRAQHQLLPARGADVPL
PPLPAGPEPPLPPGARPRHRF*

SEQ ID NO:18 (Ad2 terminal protein)
VFQLRPRENGRAVTETMRRRRGEMIERFVDRLPVRRRRRRVPPPPPPPEEEEEGEALMEEEIEEEEA
PVAFEREVRDTVAELIRLLEEELTVSARNSQFFNFAVDFYEAMERLEALGDINESTLRRWVMYFFV
AEHTATTLNYLFQRLRNYAVFARHVELNLAQVVMRARDAEGGVVYSRVWNEGGLNAFSQLMA
RISNDLAATVERAGRGDLQEEEIEQFMAEIAYQDNSGDVQEILRQAAVNDTEIDSVELSFRFKLTGP
VVFTQRRQIQEINRRVVAFASNLRAQHQLLPARGADVPLPPLPAGPEPPLPPGARPRHRF*

SEQ ID NO:19 (Ad5 preterminal protein)
MALSVNDCARLTGQSVPTMEHFLPLRNIWNRVRDFPRASTTAAGITWMSRYIYGYHRLMLEDLA
PGAPATLRWPLYRQPPPHFLVGYQYLVRTCNDYVFDSRAYSRLRYTELSQPGHQTVNWSVMANC
TYTINTGAYHRFVDMDDFQSTLTQVQQAILAERVVADLALLQPMRGFGVTRMGGRGRHLRPNSA
AAAAIDARDAGQEEGEEEVPVERLMQDYYKDLRRCQNEAWGMADRLRIQQAGPKDMVLLSTIR
RLKTAYFNYIISSTSARNNPDRRPLPPATVLSLPCDCDWLDAFLERFSDPVDADSLRSLGGGVPTQQ
LLRCIVSAVSLPHGSPPPTHNRDMTGGVFQLRPRENGRAVTETMRRRRGEMIERFVDRLPVRRRRR
RVPPPPPPPEEEEGEALMEEEIEEEEAPVAFEREVRDTVAELIRLLEEELTVSARNSQFFNFAVDFY
EAMERLEALGDINESTLRRWVMYFFVAEHTATTLNYLFQRLRNYAVFARHVELNLAQVVMRAR
DAEGGVVYSRVWNEGGLNAFSQLMARISNDLAATVERAGRGDLQEEEIEQFMAEIAYQDNSGDV
QEILRQAAVNDTEIDSVELSFRLKLTGPVVFTQRRQIQEINRRVVAFASNLRAQHQLLPARGADVP
LPPLPAGPEPPLPPGARPRHRF*

SEQ ID NO:20 (Ad5 terminal protein)
VFQLRPRENGRAVTETMRRRRGEMIERFVDRLPVRRRRRRVPPPPPPPEEEEGEALMEEEIEEEEA
PVAFEREVRDTVAELIRLLEEELTVSARNSQFFNFAVDFYEAMERLEALGDINESTLRRWVMYFFV
AEHTATTLNYLFQRLRNYAVFARHVELNLAQVVMRARDAEGGVVYSRVWNEGGLNAFSQLMA
RISNDLAATVERAGRGDLQEEEIEQFMAEIAYQDNSGDVQEILRQAAVNDTEIDSVELSFRLKLTGP
VVFTQRRQIQEINRRVVAFASNLRAQHQLLPARGADVPLPPLPAGPEPPLPPGARPRHRF*

SEQUENCE LISTING

```
<160> NUMBER OF SEQ ID NOS: 34

<210> SEQ ID NO 1
<211> LENGTH: 36154
<212> TYPE: DNA
<213> ORGANISM: Artificial Sequence
<220> FEATURE:
<223> OTHER INFORMATION: Synthetic

<400> SEQUENCE: 1
catcatcaat aatataccett attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtat aacttcgtat aatgtatgct atacgaagtt     180
atacatgtaa gcgacggatg tggcaaaagt gacgttttg gtgtgcgccg gtgtacacag     240
gaagtgacaa ttttcgcgcg gttttaggcg gatgttgtag taaatttggg cgtaaccgag     300
taagatttgg ccattttcgc gggaaaactg aataagagga agtgaaatct gaataatttt     360
gtgttactca tagcgcgtaa tatttgtcta gggagatcta taacttcgta taatgtatgc     420
tatacgaagt tattaccgaa gaaatggctc gagatctgga aggtgctgag gtacgatgag     480
acccgcacca ggtgcagacc ctgcgagtgt ggcggtaaac atattaggaa ccagcctgtg     540
atgctggatg tgaccgagga gctgaggccc gatcacttgg tgctggcctg cacccgcgct     600
gagtttggct ctagcgatga agatacagat tgaggtactg aaatgtgtgg gcgtggctta     660
agggtgggaa agaatatata aggtgggggt cttatgtagt tttgtatctg ttttgcagca     720
gccgccgccg ccatgagcac caactcgttt gatggaagca ttgtgagctc atatttgaca     780
acgcgcatgc ccccatgggc cggggtgcgt cagaatgtga tgggctccag cattgatggt     840
cgccccgtcc tgcccgcaaa ctctactacc ttgacctacg agaccgtgtc tggaacgccg     900
ttggagactg cagcctccgc cgccgcttca gccgctgcag ccaccgcccg cgggattgtg     960
```

```
actgactttg ctttcctgag cccgcttgca agcagtgcag cttcccgttc atccgcccgc    1020
gatgacaagt tgacggctct tttggcacaa ttggattctt tgacccggga acttaatgtc    1080
gtttctcagc agctgttgga tctgcgccag caggtttctg ccctgaaggc ttcctcccct    1140
cccaatgcgg tttaaaacat aaataaaaaa ccagactctg tttggatttg gatcaagcaa    1200
gtgtcttgct gtctttattt aggggttttg cgcgcgcggt aggcccggga ccagcggtct    1260
cggtcgttga gggtcctgtg tattttttcc aggacgtggt aaaggtgact ctggatgttc    1320
agatacatgg gcataagccc gtctctgggg tggaggtagc accactgcag agcttcatgc    1380
tgcggggtgg tgttgtagat gatccagtcg tagcaggagc gctgggcgtg gtgcctaaaa    1440
atgtctttca gtagcaagct gattgccagg ggcaggccct tggtgtaagt gtttacaaag    1500
cggttaagct gggatgggtg catacgtggg gatatgagat gcatcttgga ctgtattttt    1560
aggttggcta tgttcccagc catatccctc cggggattca tgttgtgcag aaccaccagc    1620
acagtgtatc cggtgcactt gggaaatttg tcatgtagct tagaaggaaa tgcgtggaag    1680
aacttggaga cgcccttgtg acctccaaga ttttccatgc attcgtccat aatgatggca    1740
atgggcccac gggcggcggc ctgggcgaag atatttctgg gatcactaac gtcatagttg    1800
tgttccagga tgagatcgtc ataggccatt tttacaaagc gcgggcggag ggtgccagac    1860
tgcggtataa tggttccatc cggcccaggg gcgtagttac cctcacagat ttgcatttcc    1920
cacgctttga gttcagatgg ggggatcatg tctacctgcg gggcgatgaa gaaaacggtt    1980
tccggggtag gggagatcag ctgggaagaa agcaggttcc tgagcagctg cgacttaccg    2040
cagccggtgg gcccgtaaat cacacctatt accgggtgca actggtagtt aagagagctg    2100
cagctgccgt catccctgag caggggggcc acttcgttaa gcatgtccct gactcgcatg    2160
ttttccctga ccaaatccgc cagaaggcgc tcgccgccca gcgatagcag ttcttgcaag    2220
gaagcaaagt ttttcaacgg tttgagaccg tccgccgtag gcatgctttt gagcgtttga    2280
ccaagcagtt ccaggcggtc ccacagctcg gtcacctgct ctacggcatc tcgatccagc    2340
atatctcctc gtttcgcggg ttggggcggc tttcgctgta cggcagtagt cggtgctcgt    2400
ccagacgggc cagggtcatg tctttccacg ggcgcagggt cctcgtcagc gtagtctggg    2460
tcacggtgaa ggggtgcgct ccgggctgcg cgctggccag ggtgcgcttg aggctggtcc    2520
tgctggtgct gaagcgctgc cggtcttcgc cctgcgcgtc ggccaggtag catttgacca    2580
tggtgtcata gtccagcccc tccgcggcgt ggcccttggc gcgcagcttg cccttggagg    2640
aggcgccgca cgaggggcag tgcagacttt tgagggcgta gagcttgggc gcgagaaata    2700
ccgattccgg ggagtaggca tccgcgccgc aggccccgca gacggtctcg cattccacga    2760
gccaggtgag ctctggccgt tcggggtcaa aaaccaggtt tccccatgcc tttttgatgc    2820
gtttcttacc tctggtttcc atgagccggt gtccacgctc ggtgacgaaa aggctgtccg    2880
tgtccccgta tacagacttg agaggcctgt cctcgagcgg tgttccgcgg tcctcctcgt    2940
atagaaactc ggaccactct gagacaaagg ctcgcgtcca ggccagcacg aaggaggcta    3000
agtgggaggg gtagcggtcg ttgtccacta gggggtccac tcgctccagg gtgtgaagac    3060
acatgtcgcc ctcttcggca tcaaggaagg tgattggttt gtaggtgtag ccacgtgac    3120 cgggtgttcc tgaagggggg ctataaaagg gggtgggggc gcgttcgtcc tcactctctt    3180
ccgcatcgct gtctgcgagg gccagctgtt ggggtgagta ctccctctga aaagcgggca    3240
tgacttctgc gctaagattg tcagtttcca aaaacgagga ggatttgata ttcacctggc    3300
ccgcggtgat gcctttgagg gtggccgcat ccatctggtc agaaaagaca atcttttttgt    3360
```

```
tgtcaagctt ggtggcaaac gacccgtaga gggcgttgga cagcaacttg gcgatggagc   3420
gcagggtttg gttttttgtcg cgatcggcgc gctccttggc cgcgatgttt agctgcacgt   3480
attcgcgcgc aacgcaccgc cattcggaa agacggtggt gcgctcgtcg gcaccaggt   3540 gcacgcgcca accgcggttg tgcagggtga caaggtcaac gctggtggct acctctccgc   3600
gtaggcgctc gttggtccag cagaggcggc cgcccttgcg cgagcagaat ggcggtaggg   3660
ggtctagctg cgtctcgtcc gggggtctg cgtccacggt aaagacccg ggcagcaggc   3720 gcgcgtcgaa gtagtctatc ttgcatcctt gcaagtctag cgcctgctgc catgcgcggg   3780
cggcaagcgc gcgctcgtat gggttgagtg ggggaccca tggcatgggg tgggtgagcg   3840
cggaggcgta catgccgcaa atgtcgtaaa cgtagagggg ctctctgagt attccaagat   3900
atgtagggta gcatcttcca ccgcggatgc tggcgcgcac gtaatcgtat agttcgtgcg   3960
agggagcgag gaggtcggga ccgaggttgc tacgggcggg ctgctctgct cggaagacta   4020
tctgcctgaa gatggcatgt gagttggatg atatggttgg acgctggaag acgttgaagc   4080
tggcgtctgt gagacctacc gcgtcacgca cgaaggaggc gtaggagtcg cgcagcttgt   4140
tgaccagctc ggcggtgacc tgcacgtcta gggcgcagta gtccagggtt tccttgatga   4200
tgtcatactt atcctgtccc ttttttttcc acagctcgcg gttgaggaca aactcttcgc   4260
ggtctttcca gtactcttgg atcggaaacc cgtcggcctc cgaacggtaa gagcctagca   4320
tgtagaactg gttgacggcc tggtaggcgc agcatccctt ttctacgggt agcgcgtatg   4380
cctgcgcggc cttccggagc gaggtgtggg tgagcgcaaa ggtgtccctg accatgactt   4440
tgaggtactg gtatttgaag tcagtgtcgt cgcatccgcc ctgctcccag agcaaaaagt   4500
ccgtgcgctt tttggaacgc ggatttggca gggcgaaggt gacatcgttg aagagtatct   4560
ttcccgcgcg aggcataaag ttgcgtgtga tgcggaaggg tcccggcacc tcggaacggt   4620
tgttaattac ctgggcggcg agcacgatct cgtcaaagcc gttgatgttg tggcccacaa   4680
tgtaaagttc caagaagcgc gggatgccct tgatggaagg caattttta agttcctcgt   4740 aggtgagctc ttcaggggag ctgagcccgt gctctgaaag ggcccagtct gcaagatgag   4800
ggttggaagc gacgaatgag ctccacaggt cacgggccat tagcatttgc aggtggtcgc   4860
gaaaggtcct aaactggcga cctatggcca ttttttctgg ggtgatgcag tagaaggtaa   4920
gcgggtcttg ttcccagcgg tcccatccaa ggttcgcggc taggtctcgc gcggcagtca   4980
ctagaggctc atctccgccg aacttcatga ccagcatgaa gggcacgagc tgcttcccaa   5040 aggccccat ccaagtatag gtctctacat cgtaggtgac aaagagacgc tcggtgcgag   5100
gatgcgagcc gatcgggaag aactggatct cccgccacca attggaggag tggctattga   5160
tgtggtgaaa gtagaagtcc ctgcgacggg ccgaacactc gtgctggctt ttgtaaaaac   5220
gtgcgcagta ctggcagcgg tgcacgggct gtacatcctg cacgaggttg acctgacgac   5280
cgcgcacaag gaagcagagt gggaatttga gcccctcgcc tggcgggttt ggctggtggt   5340
cttctacttc ggctgcttgt ccttgaccgt ctggctgctc gagggagtt acggtggatc   5400 ggaccaccac gccgcgcgag cccaaagtcc agatgtccgc gcgcggcggt cggagcttga   5460
tgacaacatc gcgcagatgg gagctgtcca tggtctggag ctcccgcggc gtcaggtcag   5520
gcgggagctc ctgcaggttt acctcgcata gacgggtcag ggcgcgggct agatccaggt   5580
gatacctaat ttccaggggc tggttggtgg cggcgtcgat ggcttgcaag aggccgcatc   5640
cccgcggcgc gactacggta ccgcgcggcg ggcggtgggc cgcgggggtg tccttggatg   5700
```

```
atgcatctaa aagcggtgac gcgggcgagc ccccggaggt agggggggct ccggacccgc    5760
cgggagaggg ggcaggggca cgtcggcgcc gcgcgcgggc aggagctggt gctgcgcgcg    5820
taggttgctg gcgaacgcga cgacgcggcg gttgatctcc tgaatctggc gcctctgcgt    5880
gaagacgacg ggcccggtga gcttgagcct gaaagagagt tcgacagaat caatttcggt    5940
gtcgttgacg gcggcctggc gcaaaatctc ctgcacgtct cctgagttgt cttgataggc    6000
gatctcggcc atgaactgct cgatctcttc ctcctggaga tctccgcgtc cggctcgctc    6060
cacggtggcg gcgaggtcgt tggaaatgcg ggccatgagc tgcgagaagg cgttgaggcc    6120
tccctcgttc cagacgcggc tgtagaccac gcccccttcg gcatcgcggg gcgcatgac     6180 cacctgcgcg agattgagct ccacgtgccg ggcgaagacg gcgtagtttc gcaggcgctg    6240
aaagaggtag ttgagggtgg tggcggtgtg ttctgccacg aagaagtaca taacccagcg    6300
tcgcaacgtg gattcgttga tatccccaa ggcctcaagg cgctccatgg cctcgtagaa     6360
gtccacggcg aagttgaaaa actgggagtt gcgcgccgac acggttaact cctcctccag    6420
aagacggatg agctcggcga cagtgtcgcg cacctcgcgc tcaaaggcta cagggggcctc   6480 ttcttcttct tcaatctcct cttccataag ggcctcccct tcttcttctt ctggcggcgg    6540 tggggaggg gggacacggc ggcgacgacg gcgcaccggg aggcggtcga caaagcgctc     6600
gatcatctcc ccgcggcgac ggcgcatggt ctcggtgacg gcgcggccgt tctcgcgggg    6660
gcgcagttgg aagacgccgc ccgtcatgtc ccggttatgg gttggcgggg ggctgccatg    6720
cggcagggat acggcgctaa cgatgcatct caacaattgt tgtgtaggta ctccgccgcc    6780
gagggacctg agcgagtccg catcgaccgg atcggaaaac ctctcgagaa aggcgtctaa    6840
ccagtcacag tcgcaaggta ggctgagcac cgtggcgggc ggcagcgggc ggcggtcggg    6900
gttgtttctg gcggaggtgc tgctgatgat gtaattaaag taggcggtct tgagacggcg    6960
gatggtcgac agaagcacca tgtccttggg tccggcctgc tgaatgcgca ggcggtcggc    7020
catgccccag gcttcgtttt gacatcggcg caggtctttg tagtagtctt gcatgagcct    7080
ttctaccggc acttcttctt ctccttcctc ttgtcctgca tctcttgcat ctatcgctgc    7140
ggcggcggcg gagtttggcc gtaggtggcg ccctcttcct cccatgcgtg tgaccccgaa    7200
gcccctcatc ggctgaagca gggctaggtc ggcgacaacg cgctcggcta atatggcctg    7260
ctgcacctgc gtgagggtag actgaagtc atccatgtcc acaaagcggt ggtatgcgcc     7320
cgtgttgatg gtgtaagtgc agttggccat aacggaccag ttaacggtct ggtgacccgg    7380
ctgcgagagc tcggtgtacc tgagacgcga gtaagccctc gagtcaaata cgtagtcgtt    7440
gcaagtccgc accaggtact ggtatcccac caaaaagtgc ggcggcggct ggcggtagag    7500
gggccagcgt agggtggccg gggctccggg ggcgagatct tccaacataa ggcgatgata    7560
tccgtagatg tacctggaca tccaggtgat gccggcggcg gtggtggagg cgcgcggaaa    7620
gtcgcggacg cggttccaga tgttgcgcag cggcaaaaag tgctccatgg tcgggacgct    7680
ctggccggtc aggcgcgcgc aatcgttgac gctctaccgt gcaaaaggag agcctgtaag    7740
cgggcactct tccgtggtct ggtggataaa ttcgcaaggg tatcatggcg gacgaccggg    7800
gttcgagccc cgtatccggc cgtccgccgt gatccatgcg gttaccgccc gcgtgtcgaa    7860
cccaggtgtg cgacgtcaga caacggggga gtgctccttt tggcttcctt ccaggcgcgg    7920
cggctgctgc gctagctttt ttggccactg gccgcgcgca gcgtaagcgg ttaggctgga    7980
aagcgaaagc attaagtggc tcgctccctg tagccggagg gttatttcc aagggttgag     8040 tcgcgggacc cccggttcga gtctcggacc ggccggactg cggcgaacgg gggtttgcct    8100
```

```
ccccgtcatg caagaccccg cttgcaaatt cctccggaaa cagggacgag cccctttttt      8160
gcttttccca gatgcatccg gtgctgcggc agatgcgccc ccctcctcag cagcggcaag      8220
agcaagagca gcggcagaca tgcagggcac cctcccctcc tcctaccgcg tcaggagggg      8280
cgacatccgc ggttgacgcg gcagcagatg gtgattacga accccgcgg cgccgggccc       8340 ggcactacct ggacttggag gagggcgagg gcctggcgcg gctaggagcg ccctctcctg      8400
agcggtaccc aagggtgcag ctgaagcgtg atacgcgtga ggcgtacgtg ccgcggcaga      8460
acctgtttcg cgaccgcgag ggagaggagc ccgaggagat gcgggatcga aagttccacg      8520
cagggcgcga gctgcggcat ggcctgaatc gcgagcggtt gctgcgcgag gaggactttg      8580
agcccgacgc gcgaaccggg attagtcccg cgcgcgcaca cgtggcggcc gccgacctgg      8640
taaccgcata cgagcagacg gtgaaccagg agattaactt tcaaaaaagc tttaacaacc      8700
acgtgcgtac gcttgtggcg cgcgaggagg tggctatagg actgatgcat ctgtgggact      8760 tgtaagcgc gctggagcaa aacccaaata gcaagccgct catggcgcag ctgttcctta      8820
tagtgcagca cagcagggac aacgaggcat tcagggatgc gctgctaaac atagtagagc      8880
ccgagggccg ctggctgctc gatttgataa acatcctgca gagcatagtg gtgcaggagc      8940
gcagcttgag cctggctgac aaggtggccg ccatcaacta ttccatgctt agcctgggca      9000
agttttacgc ccgcaagata taccataccc cttacgttcc catagacaag gaggtaaaga      9060 tcgagggggtt ctacatgcgc atggcgctga aggtgcttac cttgagcgac gacctgggcg      9120
tttatcgcaa cgagcgcatc cacaaggccg tgagcgtgag ccggcggcgc gagctcagcg      9180
accgcgagct gatgcacagc ctgcaaaggg ccctggctgg cacgggcagc ggcgatagag      9240
aggccgagtc ctactttgac gcgggcgctg acctgcgctg gccccaagcc cgacgcgccc      9300
tggaggcagc tggggccgga cctgggctgg cggtggcacc cgcgcgcgct ggcaacgtcg      9360
gcggcgtgga ggaatatgac gaggacgatg agtacgagcc agaggacggc gagtactaag      9420
cggtgatgtt tctgatcaga tgatgcaaga cgcaacggac ccggcggtgc gggcggcgct      9480
gcagagccag ccgtccggcc ttaactccac ggacgactgg cgccaggtca tggaccgcat      9540
catgtcgctg actgcgcgca atcctgacgc gttccggcag cagccgcagg ccaaccggct      9600
ctccgcaatt ctggaagcgg tggtcccggc gcgcgcaaac cccacgcacg agaaggtgct      9660
ggcgatcgta aacgcgctgg ccgaaaacag ggccatccgg cccgacgagg ccggcctggt      9720
ctacgacgcg ctgcttcagc gcgtggctcg ttacaacagc ggcaacgtgc agaccaacct      9780
ggaccggctg gtgggggatg tgcgcgaggc cgtggcgcag cgtgagcgcg cgcagcagca      9840
gggcaacctg ggctccatgg ttgcactaaa cgccttcctg agtacacagc ccgccaacgt      9900
gccgcgggga caggaggact acaccaactt tgtgagcgca ctgcgggctaa tggtgactga      9960 gacaccgcaa agtgaggtgt accagtctgg gccagactat ttttccaga ccagtagaca      10020 aggcctgcag accgtaaacc tgagccaggc tttcaaaaac ttgcagggc tgtgggggt       10080 gcgggctccc acaggcgacc gcgcgaccgt gtctagcttg ctgacgccca actcgcgcct      10140
gttgctgctg ctaatagcgc ccttcacgga cagtggcagc gtgtcccggg acacataccg      10200
aggtcacttg ctgacactgt accgcgaggc cataggtcag gcgcatgtgg acgagcatac      10260
tttccaggag attacaagtg tcagccgcgc gctggggcag gaggacacgg gcagcctgga      10320
ggcaacccta aactacctgc tgaccaaccg gcggcagaag atcccctcgt tgcacagttt      10380
aaacagcgag gaggagcgca ttttgcgcta cgtgcagcag agcgtgagcc ttaacctgat      10440
```

-continued

```
gcgcgacggg gtaacgccca gcgtggcgct ggacatgacc gcgcgcaaca tggaaccggg   10500
catgtatgcc tcaaaccggc cgtttatcaa ccgcctaatg gactacttgc atcgcgcggc   10560
cgccgtgaac cccgagtatt tcaccaatgc catcttgaac ccgcactggc taccgccccc   10620
tggtttctac accgggggat tcgaggtgcc cgagggtaac gatggattcc tctgggacga   10680
catagacgac agcgtgtttt ccccgcaacc gcagaccctg ctagagttgc aacagcgcga   10740
gcaggcagag gcgcgcgctg caaaggaaag cttccgcagg ccaagcagct tgtccgatct   10800
aggcgctgcg gccccgcggt cagatgctag tagcccattt ccaagcttga tagggtctct   10860
taccagcact cgcaccaccc gcccgcgcct gctgggcgag gaggagtacc taaacaactc   10920
gctgctgcag ccgcagcgcg aaaaaaacct gcctccggca tttcccaaca acgggataga   10980
gagcctagtg gacaagatga gtagatggaa gacgtacgcg caggagcaca gggacgtgcc   11040
aggcccgcgc ccgcccaccc gtcgtcaaag gcacgaccgt cagcggggtc tggtgtggga   11100
ggacgatgac tcggcagacg acagcagcgt cctggatttg ggagggagtg gcaacccgtt   11160
tgcgcacctt cgccccaggc tggggagaat gttttaaaaa aaaaaagca tgatgcaaaa   11220
taaaaactc accaaggcca tggcaccgag cgttggtttt cttgtattcc ccttagtatg   11280
cggcgcgcgg cgatgtatga ggaaggtcct cctccctcct acgagagtgt ggtgagcgcg   11340
gcgccagtgg cggcggcgct gggttctccc ttcgatgctc ccctggaccc gccgtttgtg   11400
cctccgcggt acctgcggcc taccgggggg agaaacagca tccgttactc tgagttggca   11460
cccctattcg acaccacccg tgtgtacctg gtggacaaca agtcaacgga tgtggcatcc   11520
ctgaactacc agaacgacca cagcaacttt ctgaccacgg tcattcaaaa caatgactac   11580
agcccggggg aggcaagcac acagaccatc aatcttgacg accggtcgca ctgggcggc   11640
gacctgaaaa ccatcctgca taccaacatg ccaaatgtga acgagttcat gtttaccaat   11700
aagtttaagg cgcgggtgat ggtgtcgcgc ttgcctacta aggacaatca ggtggagctg   11760
aaatacgagt gggtggagtt cacgctgccc gagggcaact actccgagac catgaccata   11820
gaccttatga caacgcgat cgtggagcac tacttgaaag tgggcagaca gaacggggtt   11880
ctggaaagcg acatcgggt aaagtttgac acccgcaact tcagactggg gtttgacccc   11940
gtcactggtc ttgtcatgcc tggggtatat acaaacgaag ccttccatcc agacatcatt   12000
ttgctgccag gatgcgggt ggacttcacc cacagccgcc tgagcaactt gttgggcatc   12060
cgcaagcggc aacccttcca ggagggcttt aggatcacct acgatgatct ggagggtggt   12120
aacattcccg cactgttgga tgtggacgcc taccaggcga gcttgaaaga tgacaccgaa   12180
cagggcgggg gtggcgcagg cggcagcaac agcagtggca gcggcgcgga agagaactcc   12240
aacgcggcag ccgcggcaat gcagccggtg gaggacatga acgatcatgc cattcgcggc   12300
gacacctttg ccacacgggc tgaggagaag cgcgctgagg ccgaagcagc ggccgaagct   12360
gccgcccccg ctgcgcaacc cgaggtcgag aagcctcaga agaaaccggt gatcaaaccc   12420
ctgacagagg acagcaagaa acgcagttac aacctaataa gcaatgacag caccttcacc   12480
cagtaccgca gctggtacct tgcatacaac tacggcgacc ctcagaccgg aatccgctca   12540
tggaccctgc tttgcactcc tgacgtaacc tgcggctcgg agcaggtcta ctggtcgttg   12600
ccagacatga tgcaagaccc cgtgaccttc cgctccacgc gccagatcag caactttccg   12660
gtggtgggcg ccgagctgtt gcccgtgcac tccaagagct ctacaacga ccaggccgtc   12720
tactcccaac tcatccgcca gtttaccttct ctgacccacg tgttcaatcg ctttcccgag   12780
aaccagattt tggcgcgccc gccagccccc accatcacca ccgtcagtga aaacgttcct   12840
```

```
gctctcacag atcacgggac gctaccgctg cgcaacagca tcggaggagt ccagcgagtg   12900
accattactg acgccagacg ccgcacctgc ccctacgttt acaaggccct gggcatagtc   12960
tcgccgcgcg tcctatcgag ccgcactttt tgagcaagca tgtccatcct tatatcgccc   13020
agcaataaca caggctgggg cctgcgcttc caagcaaga tgtttggcgg ggccaagaag   13080
cgctccgacc aacaccagt gcgcgtgcgc gggcactacc gcgcgccctg gggcgcgcac   13140
aaacgcggcc gcactgggcg caccaccgtc gatgacgcca tcgacgcggt ggtggaggag   13200
gcgcgcaact acacgcccac gccgccacca gtgtccacag tggacgcggc cattcagacc   13260
gtggtgcgcg gagcccggcg ctatgctaaa atgaagagac ggcggaggcg cgtagcacgt   13320
cgccaccgcc gccgacccgg cactgccgcc caacgcgcgg cggcggccct gcttaaccgc   13380
gcacgtcgca ccgccgacg ggcggccatg cgggccgctc gaaggctggc cgcgggtatt   13440
gtcactgtgc cccccaggtc caggcgacga gcggccgccg cagcagccgc ggccattagt   13500
gctatgactc agggtcgcag gggcaacgtg tattgggtgc gcgactcggt tagcggcctg   13560
cgcgtgcccg tgcgcacccg ccccccgcgc aactagattg caagaaaaaa ctacttagac   13620
tcgtactgtt gtatgtatcc agcggcggcg gcgcgcaacg aagctatgtc caagcgcaaa   13680
atcaaagaag agatgctcca ggtcatcgcg ccggagatct atggcccccc gaagaaggaa   13740
gagcaggatt acaagcccg aaagctaaag cgggtcaaaa agaaaaagaa agatgatgat   13800
gatgaacttg acgacgaggt ggaactgctg cacgctaccg cgcccaggcg acgggtacag   13860
tggaaaggtc gacgcgtaaa acgtgttttg cgacccggca ccaccgtagt ctttacgccc   13920
ggtgagcgct ccacccgcac ctacaagcgc gtgtatgatg aggtgtacgg cgacgaggac   13980
ctgcttgagc aggccaacga gcgcctcggg gagtttgcct acggaaagcg gcataaggac   14040
atgctggcgt tgccgctgga cgagggcaac ccaacaccta gcctaaagcc cgtaacactg   14100
cagcaggtgc tgcccgcgct tgcaccgtcc gaagaaaagc gcggcctaaa gcgcgagtct   14160
ggtgacttgg cacccaccgt gcagctgatg gtacccaagc gccagcgact ggaagatgtc   14220
ttggaaaaaa tgaccgtgga acctgggctg gagcccgagg tccgcgtgcg gccaatcaag   14280
caggtggcgc cgggactggg cgtgcagacc gtggacgttc agatacccac taccagtagc   14340
accagtattg ccaccgccac agagggcatg gagacacaaa cgtccccggt tgcctcagcg   14400
gtggcggatc ccgcggtgca ggcggtcgct gcggccgcgt ccaagacctc tacggaggtg   14460
caaacggacc cgtggatgtt tcgcgtttca gcccccggc gcccgcgcgg ttcgaggaag   14520
tacggcgccc ccagcgcgct actgcccgaa tatgccctac atccttccat tgcgcctacc   14580
cccggctatc gtggctacac ctaccgcccc agaagacgag caactacccg acgccgaacc   14640
accactggaa cccgccgccg ccgtcgccgt cgccagcccg tgctggcccc gatttccgtg   14700
cgcagggtgg ctcgcgaagg aggcaggacc ctggtgctgc aacagcgcg ctaccacccc   14760 agcatcgttt aaaagccggt cttgtggtt cttgcagata tggccctcac ctgccgcctc   14820
cgtttcccgg tgccgggatt ccgaggaaga atgcaccgta ggagggcat ggccggccac   14880 ggcctgacgg gcggcatgcg tcgtgcgcac caccggcggc ggcgcgcgtc gcaccgtcgc   14940
atgcgcggcg gtatcctgcc cctccttatt ccactgatcg ccgcggcgat tggcgccgtg   15000
cccggaattg catccgtggc cttgcaggcg cagagacact gattaaaaac aagttgcatg   15060
tggaaaaatc aaaataaaaa gtctggactc tcacgctcgc ttggtcctgt aactattttg   15120
tagaatggaa gacatcaact ttgcgtctct ggccccgcga cacggctcgc gcccgttcat   15180
```

```
gggaaactgg caagatatcg gcaccagcaa tatgagcggt ggcgccttca gctgggctc    15240
gctgtggagc ggcattaaaa atttcggttc caccgttaag aactatggca gcaaggcctg   15300
gaacagcagc acaggccaga tgctgaggga taagttgaaa gagcaaaatt ccaacaaaa    15360
ggtggtagat ggcctggcct ctggcattag cggggtggtg gacctggcca accaggcagt   15420
gcaaaataag attaacagta agcttgatcc ccgccctccc gtagaggagc ctccaccggc   15480
cgtggagaca gtgtctccag aggggcgtgg cgaaaagcgt ccgcgccccg cagggaaga    15540
aactctggtg acgcaaatag acgagcctcc ctcgtacgag gaggcactaa agcaaggcct   15600
gcccaccacc cgtcccatcg cgcccatggc taccggagtg ctgggccagc acacaccgt    15660
aacgctggac ctgcctcccc ccgccgacac ccagcagaaa cctgtgctgc caggcccgac   15720
cgccgttgtt gtaacccgtc ctagccgcgc gtccctgcgc cgcgccgcca gcggtccgcg   15780
atcgttgcgg cccgtagcca gtggcaactg gcaaagcaca ctgaacagca tcgtgggtct   15840
gggggtgcaa tccctgaagc gccgacgatg cttctgaata gctaacgtgt cgtatgtgtg   15900
tcatgtatgc gtccatgtcg ccgccagagg agctgctgag ccgccgcgcg cccgctttcc   15960
aagatggcta cccccttcgat gatgccgcag tggtcttaca tgcacatctc gggccaggac   16020
gcctcggagt acctgagccc cgggctggtg cagtttgccc gcgccaccga gacgtacttc   16080
agcctgaata caagtttag aaaccccacg gtggcgccta cgcacgacgt gaccacagac   16140
cggtcccagc gtttgacgct gcggttcatc cctgtggacc gtgaggatac tgcgtactcg   16200
tacaaggcgc ggttcaccct agctgtgggt gataaccgtg tgctggacat ggcttccacg   16260
tactttgaca tccgcggcgt gctggacagg ggccctactt ttaagcccta ctctggcact   16320
gcctacaacg ccctggctcc caagggtgcc ccaaatcctt gcgaatggga tgaagctgct   16380
actgctcttg aaataaacct agaagaagag gacgatgaca acgaagacga agtagacgag   16440
caagctgagc agcaaaaaac tcacgtattt gggcaggcgc cttattctgg tataaatatt   16500
acaaaggagg gtattcaaat aggtgtcgaa ggtcaaacac ctaaatatgc cgataaaaca   16560
tttcaacctg aacctcaaat aggagaatct cagtggtacg aaactgaaat taatcatgca   16620
gctgggagag tccttaaaaa gactacccca atgaaaccat gttacggttc atatgcaaaa   16680
cccacaaatg aaaatggagg gcaaggcatt cttgtaaagc aacaaaatgg aaagctagaa   16740
agtcaagtgg aaatgcaatt tttctcaact actgaggcga ccgcaggcaa tggtgataac   16800
ttgactccta aagtggtatt gtacagtgaa gatgtagata tagaaacccc agacactcat   16860
atttcttaca tgcccactat taaggaaggt aactcacgag aactaatggg ccaacaatct   16920
atgcccaaca ggcctaatta cattgctttt agggacaatt ttattggtct aatgtattac   16980
aacagcacgg gtaatatggg tgttctggcg ggccaagcat cgcagttgaa tgctgttgta   17040
gatttgcaag acagaaacac agagctttca taccagcttt tgcttgattc cattggtgat   17100
agaaccaggt acttttctat gtggaatcag gctgttgaca gctatgatcc agatgttaga   17160
attattgaaa atcatggaac tgaagatgaa cttccaaatt actgctttcc actgggaggt   17220
gtgattaata cagagactct taccaaggta aaacctaaaa caggtcagga aaatggatgg   17280
gaaaagatg ctacagaatt ttcagataaa atgaaataa gagttggaaa taattttgcc   17340
atggaaatca atctaaatgc caacctgtgg agaaatttcc tgtactccaa catagcgctg   17400
tatttgcccg acaagctaaa gtacagtcct tccaacgtaa aaatttctga taacccaaac   17460
acctacgact acatgaacaa gcgagtggtg gctcccgggt tagtggactg ctacattaac   17520
cttggagcac gctggtccct tgactatatg gacaacgtca acccatttaa ccaccaccgc   17580
```

```
aatgctggcc tgcgctaccg ctcaatgttg ctgggcaatg gtcgctatgt gcccttccac   17640
atccaggtgc ctcagaagtt ctttgccatt aaaaacctcc ttctcctgcc gggctcatac   17700
acctacgagt ggaacttcag gaaggatgtt aacatggttc tgcagagctc cctaggaaat   17760
gacctaaggg ttgacggagc cagcattaag tttgatagca tttgcccttta cgccaccttc   17820 ttccccatgg cccacaacac cgcctccacg cttgaggcca tgcttagaaa cgacaccaac   17880
gaccagtcct ttaacgacta tctctccgcc gccaacatgc tctaccctat acccgccaac   17940
gctaccaacg tgcccatatc catcccctcc cgcaactggg cggctttccg cggctgggcc   18000
ttcacgcgcc ttaagactaa ggaaacccca tcactgggct cgggctacga cccttattac   18060
acctactctg gctctatacc ctacctagat ggaaccttt acctcaacca cacctttaag   18120
aaggtggcca ttacctttga ctcttctgtc agctggcctg gcaatgaccg cctgcttacc   18180
cccaacgagt ttgaaattaa gcgctcagtt gacggggagg gttacaacgt tgcccagtgt   18240
aacatgacca aagactggtt cctggtacaa atgctagcta actacaacat tggctaccag   18300
ggcttctata tcccagagag ctacaaggac cgcatgtact ccttctttag aaacttccag   18360
cccatgagcc gtcaggtggt ggatgatact aaatacaagg actaccaaca ggtgggcatc   18420
ctacaccaac acaacaactc tggatttgtt ggctaccttg ccccaccat gcgcgaagga   18480 caggcctacc ctgctaactt cccctatccg cttataggca agaccgcagt tgacagcatt   18540
acccagaaaa agtttctttg cgatcgcacc ctttggcgca tcccattctc cagtaacttt   18600
atgtccatgg gcgcactcac agacctgggc caaaaccttc tctacgccaa ctccgcccac   18660
gcgctagaca tgacttttga ggtggatccc atggacgagc ccacccttct ttatgttttg   18720
tttgaagtct ttgacgtggt ccgtgtgcac cggccgcacc gcggcgtcat cgaaaccgtg   18780
tacctgcgca cgcccttctc ggccggcaac gccacaacat aaagaagcaa gcaacatcaa   18840
caacagctgc cgccatgggc tccagtgagc aggaactgaa agccattgtc aaagatcttg   18900
gttgtgggcc atatttttg gcacctatg acaagcgctt ccaggctttt gtttctccac    18960
acaagctcgc ctgcgccata gtcaatacgg ccggtcgcga gactgggggc gtacactgga   19020
tggcctttgc ctggaacccg cactcaaaaa catgctacct ctttgagccc tttggcttt    19080 ctgaccagcg actcaagcag gtttaccagt ttgagtacga gtcactcctg cgccgtagcg   19140
ccattgcttc ttccccccgac cgctgtataa cgctggaaaa gtccacccaa agcgtacagg   19200
ggcccaactc ggccgcctgt ggactattct gctgcatgtt tctccacgcc tttgccaact   19260
ggccccaaac tcccatggat cacaaccccca ccatgaacct tattaccggg gtacccaact   19320
ccatgctcaa cagtccccag gtacagccca ccctgcgtcg caaccaggaa cagctctaca   19380
gcttcctgga gcgccactcg ccctacttcc gcagccacag tgcgcagatt aggagcgcca   19440
cttctttttg tcacttgaaa aacatgtaaa aataatgtac tagagacact ttcaataaag   19500
gcaaatgctt ttatttgtac actctcgggt gattatttac ccccacccct gccgtctgcg   19560
ccgtttaaaa atcaaagggg ttctgccgcg catcgctatg cgccactggc agggacacgt   19620
tgcgatactg gtgtttagtg ctccacttaa actcaggcac aaccatccgc ggcagctcgg   19680
tgaagttttc actccacagg ctgcgcacca tcaccaacgc gtttagcagg tcgggcgccg   19740
atatcttgaa gtcgcagttg gggcctccgc cctgcgcgcg cgagttgcga tacacagggt   19800
tgcagcactg gaacactatc agcgccgggt ggtgcacgct ggccagcacg ctcttgtcgg   19860
agatcagatc cgcgtccagg tcctccgcgt tgctcagggc gaacggagtc aactttggta   19920
```

```
gctgccttcc caaaaagggc gcgtgcccag gctttgagtt gcactcgcac cgtagtggca   19980
tcaaaaggtg accgtgcccg gtctgggcgt taggatacag cgcctgcata aaagccttga   20040
tctgcttaaa agccacctga gcctttgcgc cttcagagaa gaacatgccg caagacttgc   20100
cggaaaactg attggccgga caggccgcgt cgtgcacgca gcaccttgcg tcggtgttgg   20160
agatctgcac cacatttcgg ccccaccggt tcttcacgat cttggccttg ctagactgct   20220
ccttcagcgc gcgctgcccg ttttcgctcg tcacatccat ttcaatcacg tgctccttat   20280
ttatcataat gcttccgtgt agacacttaa gctcgccttc gatctcagcg cagcggtgca   20340
gccacaacgc gcagcccgtg ggctcgtgat gcttgtaggt cacctctgca aacgactgca   20400
ggtacgcctg caggaatcgc cccatcatcg tcacaaaggt cttgttgctg gtgaaggtca   20460
gctgcaaccc gcggtgctcc tcgttcagcc aggtcttgca tacggccgcc agagcttcca   20520
cttggtcagg cagtagtttg aagttcgcct ttagatcgtt atccacgtgg tacttgtcca   20580
tcagcgcgcg cgcagcctcc atgcccttct cccacgcaga cacgatcggc acactcagcg   20640
ggttcatcac cgtaatttca ctttccgctt cgctgggctc ttcctcttcc tcttgcgtcc   20700
gcataccacg cgccactggg tcgtcttcat tcagccgccg cactgtgcgc ttacctcctt   20760
tgccatgctt gattagcacc ggtgggttgc tgaaacccac catttgtagc gccacatctt   20820
ctctttcttc ctcgctgtcc acgattacct ctggtgatgg cgggcgctcg ggcttgggag   20880
aagggcgctt cttttcttc ttgggcgcaa tggccaaatc cgccgccgag gtcgatggcc   20940
gcgggctggg tgtgcgcggc accagcgcgt cttgtgatga gtcttcctcg tcctcggact   21000
cgatacgccg cctcatccgc tttttgggg gcgcccgggg aggcggcggc gacggggacg   21060
gggacgacac gtcctccatg gttggggac gtcgcgccgc accgcgtccg cgctcggggg   21120
tggtttcgcg ctgctcctct tcccgactgg ccatttcctt ctcctatagg cagaaaagaa   21180
tcatggagtc agtcgagaag aaggacagcc taaccgcccc ctctgagttc gccaccaccg   21240
cctccaccga tgccgccaac gcgcctacca ccttccccgt cgaggcaccc ccgcttgagg   21300
aggaggaagt gattatcgag caggacccag gttttgtaag cgaagacgac gaggaccgct   21360
cagtaccaac agaggataaa aagcaagacc aggacaacgc agaggcaaac gaggaacaag   21420
tcgggcgggg ggacgaaagg catggcgact acctagatgt gggagacgac gtgctgttga   21480
agcatctgca gcgccagtgc gccattatct gcgacgcgtt gcaagagcgc agcgatgtgc   21540
ccctcgccat agcggatgtc agccttgcct acgaacgcca cctattctca ccgcgcgtac   21600
cccccaaacg ccaagaaaac ggcacatgcg agcccaaccc gcgcctcaac ttctaccccg   21660
tatttgccgt gccagaggtg cttgccacct atcacatctt tttccaaaac tgcaagatac   21720
ccctatcctg ccgtgccaac cgcagccgag cggacaagca gctggccttg cggcagggcg   21780
ctgtcatacc tgatatcgcc tcgctcaacg aagtgccaaa aatctttgag ggtcttggac   21840
gcgacgagaa gcgcgcggca aacgctctgc aacaggaaaa cagcgaaaat gaaagtcact   21900
ctggagtgtt ggtggaactc gagggtgaca acgcgcgcct agccgtacta aaacgcagca   21960
tcgaggtcac ccactttgcc tacccggcac ttaacctacc ccccaaggtc atgagcacag   22020
tcatgagtga gctgatcgtg cgccgtgcgc agccctgga gggatgca aatttgcaag   22080 aacaaacaga ggagggccta cccgcagttg gcgacgagca gctagcgcgc tggcttcaaa   22140
cgcgcgagcc tgccgacttg gaggagcgac gcaaactaat gatggccgca gtgctcgtta   22200
ccgtggagct tgagtgcatg cagcggttct ttgctgaccc ggagatgcag cgcaagctag   22260
aggaaacatt gcactacacc tttcgacagg gctacgtacg ccaggcctgc aagatctcca   22320
```

```
acgtggagct ctgcaacctg gtctcctacc ttggaatttt gcacgaaaac cgccttgggc  22380
aaaacgtgct tcattccacg ctcaagggcg aggcgcgccg cgactacgtc cgcgactgcg  22440
tttacttatt tctatgctac acctggcaga cggccatggg cgtttggcag cagtgcttgg  22500
aggagtgcaa cctcaaggag ctgcagaaac tgctaaagca aaacttgaag gacctatgga  22560
cggccttcaa cgagcgctcc gtggccgcgc acctggcgga catcattttc cccgaacgcc  22620
tgcttaaaac cctgcaacag gtctgccag acttcaccag tcaaagcatg ttgcagaact  22680
ttaggaactt tatcctagag cgctcaggaa tcttgcccgc cacctgctgt gcacttccta  22740
gcgactttgt gcccattaag taccgcgaat gccctccgcc gctttggggc cactgctacc  22800
ttctgcagct agccaactac cttgcctacc actctgacat aatggaagac gtgagcggtg  22860
acggtctact ggagtgtcac tgtcgctgca acctatgcac cccgcaccgc tcctggtttt  22920
gcaattcgca gctgcttaac gaaagtcaaa ttatcggtac ctttgagctg cagggtccct  22980
cgcctgacga aaagtccgcg gctccggggt tgaaactcac tccggggctg tggacgtcgg  23040
cttaccttcg caaatttgta cctgaggact accacgccca cgagattagg ttctacgaag  23100
accaatcccg cccgccaaat gcggagctta ccgcctgcgt cattacccag gccacattc  23160
ttggccaatt gcaagccatc aacaaagccc gccaagagtt tctgctacga aagggacggg  23220
gggtttactt ggaccccag tccggcgagg agctcaaccc aatcccccg ccgccgcagc  23280
cctatcagca gcagccgcgg gcccttgctt cccaggatgg cacccaaaaa gaagctgcag  23340
ctgccgccgc cacccacgga cgaggaggaa tactgggaca gtcaggcaga ggaggttttg  23400
gacgaggagg aggaggacat gatggaagac tgggagagcc tagacgagga agcttccgag  23460
gtcgaagagg tgtcagacga aacaccgtca ccctcggtcg cattcccctc gccgcgccc  23520
cagaaatcgg caaccggttc cagcatggct acaacctccg ctcctcaggc gccgccggca  23580
ctgcccgttc gccgacccaa ccgtagatgg gacaccactg gaaccagggc cggtaagtcc  23640
aagcagccgc cgccgttagc ccaagagcaa caacagcgcc aaggctaccg ctcatggcgc  23700
gggcacaaga acgccatagt tgcttgcttg caagactgtg ggggcaacat ctccttcgcc  23760
cgccgctttc ttctctacca tcacggcgtg gccttccccc gtaacatcct gcattactac  23820
cgtcatctct acagcccata ctgcaccggc ggcagcggca gcggcagcaa cagcagcggc  23880
cacacagaag caaaggcgac cggatagcaa gactctgaca aagcccaaga atccacagc  23940
ggcggcagca gcaggaggag gagcgctgcg tctggcgccc aacgaacccg tatcgacccg  24000
cgagcttaga aacaggattt ttcccactct gtatgctata tttcaacaga gcaggggcca  24060
agaacaagag ctgaaaataa aaaacaggtc tctgcgatcc ctcacccgca gctgcctgta  24120
tcacaaaagc gaagatcagc ttcggcgcac gctggaagac gcggaggctc tcttcagtaa  24180
atactgcgcg ctgactctta aggactagtt tcgcgccctt tctcaaattt aagcgcgaaa  24240
actacgtcat ctccagcggc cacacccggc gccagcacct gtcgtcagcg ccattatgag  24300
caaggaaatt cccacgccct acatgtggag ttaccagcca caaatgggac ttgcggctgg  24360
agctgcccaa gactactcaa cccgaataaa ctacatgagc gcgggacccc acatgatatc  24420
ccgggtcaac ggaatccgcg cccaccgaaa ccgaattctc ttggaacagg cggctattac  24480
caccacacct cgtaataacc ttaatcccg tagttggccc gctgccctgg tgtaccagga  24540
aagtcccgct cccaccactg tggtacttcc cagagacgcc caggccgaag ttcagatgac  24600
taactcaggg gcgcagcttg cgggcggctt tcgtcacagg gtgcggtcgc ccgggcaggg  24660
```

```
tataactcac ctgacaatca gagggcgagg tattcagctc aacgacgagt cggtgagctc    24720
ctcgcttggt ctccgtccgg acgggacatt tcagatcggc ggcgccggcc gtccttcatt    24780
cacgcctcgt caggcaatcc taactctgca gacctcgtcc tctgagccgc gctctggagg    24840
cattggaact ctgcaattta ttgaggagtt tgtgccatcg gtctacttta accccttctc    24900
gggacctccc ggccactatc cggatcaatt tattcctaac tttgacgcgg taaaggactc    24960
ggcggacggc tacgactgaa tgttaagtgg agaggcagag caactgcgcc tgaaacacct    25020
ggtccactgt cgccgccaca agtgctttgc ccgcgactcc ggtgagtttt gctactttga    25080
attgcccgag gatcatatcg agggcccggc gcacggcgtc cggcttaccg cccagggaga    25140
gcttgcccgt agcctgattc gggagtttac ccagcgcccc ctgctagttg agcgggacag    25200
gggaccctgt gttctcactg tgatttgcaa ctgtcctaac cttggattac atcaagatcc    25260
tctagttaat taacagcttg catgcctgca ggtcgacgga tcgggagatc tcggccgcat    25320
attaagtgca ttgttctcga taccgctaag tgcattgttc tcgttagctc gatggacaag    25380
tgcattgttc tcttgctgaa agctcgatgg acaagtgcat tgttctcttg ctgaaagctc    25440
gatggacaag tgcattgttc tcttgctgaa agctcagtac ccgggagtac cctcgaccgc    25500
cggagtataa atagaggcgc ttcgtctacg gagcgacaat tcaattcaaa caagcaaagt    25560
gaacacgtcg ctaagcgaaa gctaagcaaa taaacaagcg cagctgaaca agctaaacaa    25620
tctgcagtaa agtgcaagtt aaagtgaatc aattaaaagt aaccagcaac caagtaaatc    25680
aactgcaact actgaaatct gccaagaagt aattattgaa tacaagaaga gaactctgaa    25740
tactttcaac aagttaccga gaaagaagaa ctcacacaca gctagcgttt aaacttaagc    25800
ttcaccatgg tggggccctg catgctgctg ctgctgctgc tgctgggcct gaggctacag    25860 ctctcccctgg gcatcatcct agttgaggag gagaacccgg acttctggaa ccgcgaggca    25920
gccgaggccc tgggtgccgc caagaagctg cagcctgcac agacagccgc caagaacctc    25980
atcatcttcc tgggcgatgg ggtggggtg tctacggtga cagctgccag gatcctaaaa    26040
gggcagaaga aggacaaact ggggcctgag ataccctgg ccatggaccg cttcccatat    26100
gtggctctgt ccaagacata caatgtagac aaacatgtgc cagacagtgg agccacagcc    26160
acggcctacc tgtgcgggt caagggcaac ttccagacca ttggcttgag tgcagccgcc    26220
cgctttaacc agtgcaacac gacacgcggc aacgaggtca tctccgtgat gaatcgggcc    26280
aagaaagcag ggaagtcagt gggagtggta accaccacac gagtgcagca cgcctcgcca    26340
gccggcacct acgcccacac ggtgaaccgc aactggtact cggacgccga cgtgcctgcc    26400
tcggcccgcc aggaggggtg ccaggacatc gctacgcagc tcatctccaa catggacatt    26460
gacgtgatcc taggtgggg ccgaaagtac atgtttcgca tgggaacccc agaccctgag    26520
tacccagatg actacagcca aggtgggacc aggctggacg ggaagaatct ggtgcaggaa    26580
tggctggcga agcaccaggg tgcccggtac gtgtggaacc gcactgagct catgcgggct    26640
tccctggacc cgtctgtggc ccatctcatg ggtctctttg agcctggaga catgaaatac    26700
gagatccacc gagactccac actggacccc tccctgatgg agatgacaga ggctgccctg    26760
cgcctgctga gcaggaaccc ccgcggcttc ttcctcttcg tggagggtgg tcgcatcgac    26820
catggtcatc atgaaagcag ggcttaccgg gcactgactg agacgatcat gttcgacgac    26880
gccattgaga gggcgggcca gctcaccagc gaggaggaca cgctgagcct cgtcactgcc    26940
gaccactccc acgtcttctc cttcggaggc tgccccctgc gagggggctc catcttcggg    27000
ctggcccctg gcaaggcccg ggacaggaag gcctacacgg tcctcctata cggaaacggt    27060
```

```
ccaggctatg tgctcaagga cggcgcccgg ccggatgtta ccgagagcga gagcgggagc   27120
cccgagtatc ggcagcagtc agcagtgccc ctggacgaag agacccacgc aggcgaggac   27180
gtggcggtgt tcgcgcgcgg cccgcaggcg cacctggttc acggcgtgca ggagcagacc   27240
ttcatagcgc acgtcatggc cttcgccgcc tgcctggagc cctacaccgc ctgcgacctg   27300
gcgccccccg ccggcaccac cgacgccgcg cacccggggc ggtccgtggt ccccgcgttg   27360
cttcctctgc tggccgggac cctgctgctg ctggagacgg ccactgctcc ctgagtgtcc   27420
cgtccctggg gctcctgctt ccccatcccg gagttctcct gctccccgcc tcctgtcgtc   27480
ctgcctggcc tccagcccga gtcgtcatcc ccggagtccc tatacagagg tcctgccatg   27540
gaaccttccc ctccccgtgc gctctgggga ctgagcccat gacaccaaac ctgccccttg   27600
gctgctctcg gactccctac cccaacccca gggacagatc tggccagatt tgtaaaacaa   27660
atagatttta ggcccaaaga ttatttaaag cattgcctgg aacgcagtga gttttgtta   27720 gaaaagagaa taattcaaag tggcattgct ttgcttctta tgttaatttg gtacagacct   27780
gtggctgagt ttgctcaaag tattcagagc agaattgtgg agtggaaaga gagattggac   27840
aaagagttta gtttgtcagt gtatcaaaaa atgaagttta atgtggctat gggaattgga   27900
gttttagatt ggctaagaaa cagtgatgat gatgatgaag acagccagga aaatgctgat   27960
aaaaatgaag atggtgggga gaagaacatg gaagactcag ggcatgaaac aggcattgat   28020
tcacagtccc aaggctcatt tcaggcccct cagtcctcac agtctgttca tgatcataat   28080
cagccatacc acatttgtag aggttttact tgctttaaaa aacctcccac acctcccct   28140 gaacctgaaa cataaaatga atgcaattgt tgttgttaac ttgtttattg cagcttataa   28200
tggttacaaa taaagcaata gcatcacaaa tttcacaaat aaagcatttt ttcactgca   28260 ttctagttgt ggtttgtcca aactcatcaa tgtatcttat catgtctgga tccccaggaa   28320
gctcctctgt gtcctcataa accctaacct cctctacttg agaggacatt ccaatcatag   28380
gctgcccatc caccctctgt gtcctcctgt taattaggtc acttaacaaa aaggaaattg   28440
ggtaggggtt tttcacagac cgcttttctaa gggtaatttt aaaatatctg ggaagtccct   28500
tccactgctg tgttccagaa gtgttggtaa acagcccaca aatgtcaaca gcagaaacat   28560
acaagctgtc agctttgcac aagggcccaa caccctgctc atcaagaagc actgtggttg   28620
ctgtgttagt aatgtgcaaa acaggaggca cattttcccc acctgtgtag gttccaaaat   28680
atctagtgtt ttcattttta cttggatcag gaacccagca ctccactgga taagcattat   28740
ccttatccaa aacagccttg tggtcagtgt tcatctgctg actgtcaact gtagcatttt   28800
ttggggttac agtttgagca ggatatttgg tcctgtagtt tgctaacaca ccctgcagct   28860
ccaaaggttc cccaccaaca gcaaaaaaat gaaaatttga cccttgaatg ggttttccag   28920
caccattttc atgagttttt tgtgtccctg aatgcaagtt taacatagca gttaccccaa   28980
taacctcagt tttaacagta acagcttccc acatcaaaat atttccacag gttaagtcct   29040
catttaaatt aggcaaagga attccacttc ccactgcctt gcttccgtct cccattcaaa   29100
cttttatcaa ctgacattat tctaagtaaa atcctcttca ttatgttgtc agcaatccat   29160
tgcttgaagg cctggctccc cagaaccct cgactggtat gtcttctcct agaatactcc   29220
agaagaaaag gagtgtatga agatagtgac tgcacattaa aatgactgaa accatagtaa   29280
attaggatga gattctgggc agataaacag acagctggct aggatcattt ttttatgcct   29340
tggacttctt tggcaatctg ttgaagcctg acattcctca gaataatgtt ttaaagccca   29400
```

```
acaataagac cctgtagcac atataataag tactgcagtt ttgaagtagt gataagcata    29460
aatgatattt tgatatattt attataactg taatgagatg tgtacatatc tgtgacttca    29520
taggtactga ttgtactact gtgattttt tgcctacttt caaaatgaaa aggaatgctt    29580
aatttcagtt agaggttagt aaagacaaat aggtaatttt cttctccagt gaagagcatg    29640
gcgccccttg ctattcatgg acgcttgctt aaagacttgt acacaggctt gctttgtatc    29700
aacctatgac ttccccttac agccgatgat aggtttttat ttgcacctcc ttcgtgtaca    29760
aagacagttt tggtggctac gccatcatta aactcattat tatcatgctt aagcctatag    29820
atgtatccag ttcttctgtt acataattga agctgtagtg aattgtctat cttaaactgc    29880
atcgctaact gactacattt cacacttcat ttgcttccaa catagactaa ccttcttgga    29940
tgtccactat tatttgaact tttgagattt ttttcctat ttctaatatc ttaaaatttc    30000
agaagactta aagttttgca actacagggc tccatataga catctagctt gaatttatac    30060
actttctttc attgatgtcc ctggactaaa aaatgttaaa tatttctaac cgctgtactt    30120
aaagtccatt acaaacgaag actactgttg ttaagttgaa taggcatctt atatattttt    30180
caccggtgca ataaataact tctattccct tctaacatct gcttgcgttg cactgagagt    30240
acactattga ttagcaatag gttcgtgatt acagcccttc tataattaat tgttaggtta    30300
acatattatt cataaaatat tattttatta attttactt gatttgctac tggatgctta    30360
gaaatagcta tgagtatatt ggtagaacca gtacttatat tttattacat ttttacattt    30420
cataaaattt aagtgatata aaaatcctga ggaagtatgc cacaaaagtg gtctcagtgg    30480
aaatttaaat atgttaacat ttattttaa aatgtagcgt gaaatagaca actttaaaag    30540
ctcagcttaa aaaaaaaact caaggaagct gaacttgact ttttaaagca ctgaagtgca    30600
atatttaatg taggtcaaca tgtttaaatg ggaaaatttt tttcctaatt acagccaaat    30660
ccctagctgt aattaactta aaatttgtat actatttcac aacagagtca gcatatacca    30720
cttttcttata aaattagaaa gatctaaaat tttagagctt atttggtgaa acaggcatat    30780
tgctacatct ttgtttataa attataatgt gcctttagag cccaataaca gataacaaga    30840
ttttgaaaat tcaggtgaat tagagttatc agagggaatg ttaatacact ctattcaaat    30900
actatatgag taagacattt aaaataggaa acaatacttt atatattaaa aaaaattaat    30960
cttccagtcg atttaatcca ctttatgaat tcatttaaat cgatttaaat tcgaattaat    31020
taactagagt acccggggat cttattccct ttaactaata aaaaaaaata ataaagcatc    31080
acttacttaa aatcagttag caaatttctg tccagtttat tcagcagcac ctccttgccc    31140
tcctcccagc tctggtattg cagcttcctc ctggctgcaa actttctcca caatctaaat    31200
ggaatgtcag tttcctcctg ttcctgtcca tccgcaccca ctatcttcat gttgttgcag    31260
atgaagcgcg caagaccgtc tgaagatacc ttcaaccccg tgtatccata tgacacggaa    31320
accggtcctc caactgtgcc tttctcttact cctcccttg tatcccccaa tgggtttcaa    31380
gagagtcccc ctggggtact ctctttgcgc ctatccgaac tctagttac ctccaatggc    31440
atgcttgcgc tcaaaatggg caacggcctc tctctggacg aggccggcaa ccttacctcc    31500
caaaatgtaa ccactgtgag cccacctctc aaaaaaacca agtcaaacat aaacctggaa    31560
atatctgcac ccctcacagt tacctcagaa gccctaactg tggctgccgc cgcacctcta    31620
atggtcgcgg gcaacacact caccatgcaa tcacaggccc cgctaaccgt gcacgactcc    31680
aaacttagca ttgccacccca aggacccctc acagtgtcag aaggaaagct agccctgcaa    31740
acatcaggcc ccctcaccac caccgatagc agtaccctta ctatcactgc ctcacccct    31800
```

```
ctaactactg ccactggtag cttgggcatt gacttgaaag agcccattta tacacaaaat    31860
ggaaaactag gactaaagta cggggctcct ttgcatgtaa cagacgacct aaacactttg    31920
accgtagcaa ctggtccagg tgtgactatt aataatactt ccttgcaaac taaagttact    31980
ggagccttgg gttttgattc acaaggcaat atgcaactta atgtagcagg aggactaagg    32040
attgattctc aaaacagacg ccttatactt gatgttagtt atccgtttga tgctcaaaac    32100
caactaaatc taagactagg acagggccct cttttatata actcagccca caacttggat    32160
attaactaca acaaaggcct ttacttgttt acagcttcaa acaattccaa aaagcttgag    32220
gttaacctaa gcactgccaa gggggttgatg tttgacgcta cagccatagc cattaatgca    32280
ggagatgggc ttgaatttgg ttcacctaat gcaccaaaca caaatcccct caaaacaaaa    32340
attggccatg gcctagaatt tgattcaaac aaggctatgg ttcctaaact aggaactggc    32400
cttagttttg acagcacagg tgccattaca gtaggaaaca aaaataatga taagctaact    32460
ttgtggacca caccagctcc atctcctaac tgtagactaa atgcagagaa agatgctaaa    32520
ctcactttgg tcttaacaaa atgtggcagt caaatacttg ctacagtttc agttttggct    32580
gttaaaggca gtttggctcc aatatctgga acagttcaaa gtgctcatct tattataaga    32640
tttgacgaaa atggagtgct actaaacaat tccttcctgg acccagaata ttggaacttt    32700
agaaatggag atcttactga aggcacagcc tatacaaacg ctgttggatt tatgcctaac    32760
ctatcagctt atccaaaatc tcacggtaaa actgccaaaa gtaacattgt cagtcaagtt    32820
tacttaaacg gagacaaaac taaacctgta acactaacca ttacactaaa cggtacacag    32880
gaaacaggag acacaactcc aagtgcatac tctatgtcat tttcatggga ctggtctggc    32940
cacaactaca ttaatgaaat atttgccaca tcctcttaca cttttctcata cattgcccaa    33000 gaataaagaa tcgtttgtgt tatgtttcaa cgtgtttatt tttcaattgc agaaaatttc    33060
aagtcatttt tcattcagta gtatagcccc accaccacat agcttataca gatcaccgta    33120
ccttaatcaa actcacagaa ccctagtatt caacctgcca cctccctccc aacacacaga    33180
gtacacagtc ctttctcccc ggctggcctt aaaaagcatc atatcatggg taacagacat    33240
attcttaggt gttatattcc acacggtttc ctgtcgagcc aaacgctcat cagtgatatt    33300
aataaactcc ccgggcagct cacttaagtt catgtcgctg tccagctgct gagccacagg    33360
ctgctgtcca acttgcggtt gcttaacggg cggcgaagga gaagtccacg cctacatggg    33420
ggtagagtca taatcgtgca tcaggatagg gcggtggtgc tgcagcagcg cgcgaataaa    33480
ctgctgccgc cgccgctccg tcctgcagga atacaacatg gcagtggtct cctcagcgat    33540
gattcgcacc gcccgcagca taaggcgcct tgtcctccgg gcacagcagc gcaccctgat    33600
ctcacttaaa tcagcacagt aactgcagca cagcaccaca atattgttca aaatcccaca    33660
gtgcaaggcg ctgtatccaa agctcatggc ggggaccaca gaacccacgt ggccatcata    33720
ccacaagcgc aggtagatta agtggcgacc cctcataaac acgctggaca taaacattac    33780
ctcttttggc atgttgtaat tcaccacctc ccggtaccat ataaacctct gattaaacat    33840
ggcgccatcc accaccatcc taaaccagct ggccaaaacc tgcccgccgg ctatacactg    33900
cagggaaccg ggactggaac aatgacagtg gagagcccag gactcgtaac catggatcat    33960
catgctcgtc atgatatcaa tgttggcaca acacaggcac acgtgcatac acttcctcag    34020
gattacaagc tcctcccgcg ttagaaccat atcccaggga caacccatt cctgaatcag    34080 cgtaaatccc acactgcagg gaagacctcg cacgtaactc acgttgtgca ttgtcaaagt    34140
```

```
gttacattcg ggcagcagcg gatgatcctc cagtatggta gcgcgggttt ctgtctcaaa    34200
aggaggtaga cgatccctac tgtacggagt gcgccgagac aaccgagatc gtgttggtcg    34260
tagtgtcatg ccaaatggaa cgccggacgt agtcatattt cctgaagcaa aaccaggtgc    34320
gggcgtgaca aacagatctg cgtctccggt ctcgccgctt agatcgctct gtgtagtagt    34380
tgtagtatat ccactctctc aaagcatcca ggcgccccct ggcttcgggt tctatgtaaa    34440
ctccttcatg cgccgctgcc ctgataacat ccaccaccgc agaataagcc acacccagcc    34500
aacctacaca ttcgttctgc gagtcacaca cgggaggagc gggaagagct ggaagaacca    34560
tgttttttt tttattccaa aagattatcc aaaacctcaa aatgaagatc tattaagtga    34620
acgcgctccc ctccggtggc gtggtcaaac tctacagcca agaacagat aatggcattt     34680
gtaagatgtt gcacaatggc ttccaaaagg caaacggccc tcacgtccaa gtggacgtaa    34740
aggctaaacc cttcagggtg aatctcctct ataaacattc cagcaccttc aaccatgccc    34800
aaataattct catctcgcca ccttctcaat atatctctaa gcaaatcccg aatattaagt    34860
ccggccattg taaaaatctg ctccagagcg ccctccacct tcagcctcaa gcagcgaatc    34920
atgattgcaa aaattcaggt tcctcacaga cctgtataag attcaaaagc ggaacattaa    34980
caaaatacc gcgatcccgt aggtcccttc gcagggccag ctgaacataa tcgtgcaggt     35040
ctgcacggac cagcgcggcc acttccccgc caggaacctt gacaaaagaa cccacactga    35100
ttatgacacg catactcgga gctatgctaa ccagcgtagc cccgatgtaa gctttgttgc    35160
atgggcggcg atataaaatg caaggtgctg ctcaaaaaat caggcaaagc ctcgcgcaaa    35220
aaagaaagca catcgtagtc atgctcatgc agataaaggc aggtaagctc cggaaccacc    35280
acagaaaaag acaccatttt tctctcaaac atgtctgcgg gtttctgcat aaacacaaaa    35340
taaaataaca aaaaaacatt taaacattag aagcctgtct tacaacagga aaacaaccc     35400
ttataagcat aagacggact acggccatgc cggcgtgacc gtaaaaaaac tggtcaccgt    35460
gattaaaaag caccaccgac agctcctcgg tcatgtccgg agtcataatg taagactcgg    35520
taaacacatc aggttgattc atcggtcagt gctaaaaagc gaccgaaata gcccggggga    35580
atacataccc gcaggcgtag agacaacatt acagccccca taggaggtat aacaaaatta    35640
ataggagaga aaacacata aacacctgaa aaaccctcct gcctaggcaa aatagcaccc     35700
tcccgctcca gaacaacata cagcgcttca cagcggcagc ctaacagtca gccttaccag    35760
taaaaagaa aacctattaa aaaaacacca ctcgacacgg caccagctca atcagtcaca     35820
gtgtaaaaaa gggccaagtg cagagcgagt atatatagga ctaaaaaatg acgtaacggt    35880
taaagtccac aaaaaacacc cagaaaaccg cacgcgaacc tacgcccaga aacgaaagcc    35940
aaaaaaccca caacttcctc aaatcgtcac ttccgttttc ccacgttacg tcacttccca    36000
ttttaagaaa actacaattc ccaacacata caagttactc cgccctaaaa cctacgtcac    36060
ccgcccccgtt cccacgcccc gcgccacgtc acaaactcca cccctcatt atcatattgg     36120
cttcaatcca aaataaggta tattattgat gatg                                 36154
```

<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
cggaattcgg atccagcgac cgcgagctga t                                    31

<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3
cggaattcag ccggcttcgt cgggccggat ggc                                  33

<210> SEQ ID NO 4
<211> LENGTH: 32
<212> TYPE: DNA
<213> ORGANISM: Artificial Sequence
<220> FEATURE:
<223> OTHER INFORMATION: Synthetic

<400> SEQUENCE: 4
cgcggatccg ccggctacgg cctgacgggc gg                                   32

<210> SEQ ID NO 5
<211> LENGTH: 28
<212> TYPE: DNA
<213> ORGANISM: Artificial Sequence
<220> FEATURE:
<223> OTHER INFORMATION: Synthetic

<400> SEQUENCE: 5
cggaattcac acacatacga cacgttag                                        28

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
cggaattcgg ccggccatca tcaataatat ac                                   32

<210> SEQ ID NO 7
<211> LENGTH: 43
<212> TYPE: DNA
<213> ORGANISM: Artificial Sequence
<220> FEATURE:
<223> OTHER INFORMATION: Synthetic

<400> SEQUENCE: 7
cggtcgattc aattgctggc aagcttcggc cctagacaaa tat                       43

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
ctatgctaac cagcgtagc                                                  19

<210> SEQ ID NO 9
<211> LENGTH: 36154
<212> TYPE: DNA
<213> ORGANISM: Artificial Sequence
<220> FEATURE:

<223> OTHER INFORMATION: Synthetic

<400> SEQUENCE: 9

```
catcatcaat aatatacctt attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtat aacttcgtat aatgtatgct atacgaagtt   180
atacatgtaa gcgacggatg tggcaaaagt gacgttttg gtgtgcgccg gtgtacacag    240
gaagtgacaa ttttcgcgcg gttttaggcg gatgttgtag taaatttggg cgtaaccgag   300
taagatttgg ccattttcgc gggaaaactg aataagagga agtgaaatct gaataatttt   360
gtgttactca tagcgcgtaa tatttgtcta gggagatcta taacttcgta taatgtatgc   420
tatacgaagt tattaccgaa gaaatggctc gagatctgga aggtgctgag gtacgatgag   480
acccgcacca ggtgcagacc ctgcgagtgt ggcggtaaac atattaggaa ccagcctgtg   540
atgctgatg tgaccgagga gctgaggccc gatcacttgg tgctggcctg cacccgcgct    600
gagtttggct ctagcgatga agatacagat tgaggtactg aaatgtgtgg gcgtggctta   660
agggtgggaa agaatatata aggtgggggt cttatgtagt tttgtatctg ttttgcagca   720
gccgccgccg ccatgagcac caactcgttt gatggaagca ttgtgagctc atatttgaca   780
acgcgcatgc ccccatgggc cggggtgcgt cagaatgtga tgggctccag cattgatggt   840
cgccccgtcc tgcccgcaaa ctctactacc ttgacctacg agaccgtgtc tggaacgccg   900
ttggagactg cagcctccgc cgccgcttca gccgctgcag ccaccgcccg cgggattgtg   960
actgactttg ctttcctgag cccgcttgca agcagtgcag cttcccgttc atccgcccgc  1020
gatgacaagt tgacggctct tttggcacaa ttggattctt tgacccggga acttaatgtc  1080
gtttctcagc agctgttgga tctgcgccag caggtttctg ccctgaaggc ttcctcccct  1140
cccaatgcgg tttaaaacat aaataaaaaa ccagactctg tttggatttg gatcaagcaa  1200
gtgtcttgct gtctttattt aggggttttg cgcgcgcgt aggcccggga ccagcggtct   1260
cggtcgttga gggtcctgtg tattttttcc aggacgtggt aaaggtgact ctggatgttc  1320
agatacatgg gcataagccc gtctctgggg tggaggtagc accactgcag agcttcatgc  1380
tgcggggtgg tgttgtagat gatccagtcg tagcaggagc gctgggcgtg gtgcctaaaa  1440
atgtctttca gtagcaagct gattgccagg ggcaggccct tggtgtaagt gtttacaaag  1500
cggttaagct gggatgggtg catacgtggg gatatgagat gcatcttgga ctgtattttt  1560
aggttggcta tgttcccagc catatccctc cggggattca tgttgtgcag aaccaccagc  1620
acagtgtatc cggtgcactt gggaaattg tcatgtagct tagaaggaaa tgcgtggaag   1680
aacttggaga cgcccttgtg acctccaaga ttttccatgc attcgtccat aatgatggca  1740
atgggcccac gggcggcggc ctgggcgaag atatttctgg gatcactaac gtcatagttg  1800
tgttccagga tgagatcgtc ataggccatt tttacaaagc gcgggcggag ggtgccagac  1860
tgcggtataa tggttccatc cggcccaggg gcgtagttac cctcacagat ttgcatttcc  1920
cacgctttga gttcagatgg ggggatcatg tctacctgcg gggcgatgaa gaaaacggtt  1980
tccggggtag gggagatcag ctgggaagaa agcaggttcc tgagcagctg cgacttaccg  2040
cagccggtgg gcccgtaaat cacacctatt accgggtgca actggtagtt aagagagctg  2100
cagctgccgt catccctgag cagggggggcc acttcgttaa gcatgtccct gactcgcatg  2160
ttttccctga ccaaatccgc cagaaggcgc tcgccgccca gcgatagcag ttcttgcaag  2220
gaagcaaagt ttttcaacgg ttttgagaccg tccgccgtag gcatgctttt gagcgtttga  2280
```

```
ccaagcagtt ccaggcggtc ccacagctcg gtcacctgct ctacggcatc tcgatccagc    2340
atatctcctc gtttcgcggg ttggggcggc tttcgctgta cggcagtagt cggtgctcgt    2400
ccagacgggc cagggtcatg tctttccacg ggcgcagggt cctcgtcagc gtagtctggg    2460
tcacggtgaa ggggtgcgct ccgggctgcg cgctggccag ggtgcgcttg aggctggtcc    2520
tgctggtgct gaagcgctgc cggtcttcgc cctgcgcgtc ggccaggtag catttgacca    2580
tggtgtcata gtccagcccc tccgcggcgt ggcccttggc gcgcagcttg cccttggagg    2640
aggcgccgca cgaggggcag tgcagacttt tgagggcgta gagcttgggc gcgagaaata    2700
ccgattccgg ggagtaggca tccgcgccgc aggccccgca gacggtctcg cattccacga    2760
gccaggtgag ctctggccgt tcggggtcaa aaaccaggtt tcccccatgc ttttttgatgc    2820 gtttcttacc tctggtttcc atgagccggt gtccacgctc ggtgacgaaa aggctgtccg    2880
tgtccccgta tacagacttg agaggcctgt cctcgagcgg tgttccgcgg tcctcctcgt    2940
atagaaactc ggaccactct gagacaaagg ctcgcgtcca ggccagcacg aaggaggcta    3000
agtgggaggg gtagcggtcg ttgtccacta ggggtccac tcgctccagg gtgtgaagac    3060
acatgtcgcc ctcttcggca tcaaggaagg tgattggttt gtaggtgtag ccacgtgac    3120 cgggtgttcc tgaaggggg ctataaaagg gggtggggc gcgttcgtcc tcactctctt    3180
ccgcatcgct gtctgcgagg gccagctgtt ggggtgagta ctccctctga aaagcgggca    3240
tgacttctgc gctaagattg tcagtttcca aaaacgagga ggatttgata ttcacctggc    3300
ccgcggtgat gcctttgagg gtggccgcat ccatctggtc agaaaagaca atcttttttgt    3360 tgtcaagctt ggtggcaaac gacccgtaga gggcgttgga cagcaacttg gcgatggagc    3420
gcagggtttg gttttttgtcg cgatcggcgc gctccttggc cgcgatgttt agctgcacgt    3480
attcgcgcgc aacgcaccgc cattcgggaa agacggtggt gcgctcgtcg ggcaccaggt    3540
gcacgcgcca accgcggttg tgcagggtga caaggtcaac gctggtggct acctctccgc    3600
gtaggcgctc gttggtccag cagaggcggc cgcccttgcg cgagcagaat ggcggtaggg    3660
ggtctagctg cgtctcgtcc gggggtctg cgtccacggt aaagaccccg ggcagcaggc    3720
gcgcgtcgaa gtagtctatc ttgcatcctt gcaagtctag cgcctgctgc catgcgcggg    3780
cggcaagcgc gcgctcgtat gggttgagtg ggggacccca tggcatgggg tgggtgagcg    3840
cggaggcgta catgccgcaa atgtcgtaaa cgtagagggg ctctctgagt attccaagat    3900
atgtagggta gcatcttcca ccgcggatgc tggcgcgcac gtaatcgtat agttcgtgcg    3960
agggagcgag gaggtcggga ccgaggttgc tacgggcggg ctgctctgct cggaagacta    4020
tctgcctgaa gatggcatgt gagttggatg atatggttgg acgctggaag acgttgaagc    4080
tggcgtctgt gagacctacc gcgtcacgca cgaaggaggc gtaggagtcg cgcagcttgt    4140
tgaccagctc ggcggtgacc tgcacgtcta gggcgcagta gtccagggtt tccttgatga    4200
tgtcatactt atcctgtccc ttttttttcc acagctcgcg gttgaggaca aactcttcgc    4260 ggtcttttcca gtactcttgg atcggaaacc cgtcggcctc cgaacggtaa gagcctagca    4320
tgtagaactg gttgacggcc tggtaggcgc agcatcccct ttctacgggt agcgcgtatg    4380
cctgcgcggc cttccggagc gaggtgtggg tgagcgcaaa ggtgtccctg accatgactt    4440
tgaggtactg gtatttgaag tcagtgtcgt cgcatccgcc ctgctcccag agcaaaaagt    4500
ccgtgcgctt tttggaacgc ggatttgcgca gggcgaaggt gacatcgttg aagagtatct    4560
ttcccgcgcg aggcataaag ttgcgtgtga tgcggaaggg tcccggcacc tcggaacggt    4620
```

```
tgttaattac ctgggcggcg agcacgatct cgtcaaagcc gttgatgttg tggcccacaa    4680
tgtaaagttc caagaagcgc gggatgccct tgatggaagg caattttttta agttcctcgt    4740 aggtgagctc ttcaggggag ctgagcccgt gctctgaaag ggcccagtct gcaagatgag    4800
ggttggaagc gacgaatgag ctccacaggt cacgggccat tagcatttgc aggtggtcgc    4860
gaaaggtcct aaactggcga cctatggcca tttttctgg ggtgatgcag tagaaggtaa    4920
gcgggtcttg ttcccagcgg tcccatccaa ggttcgcggc taggtctcgc gcggcagtca    4980
ctagaggctc atctccgccg aacttcatga ccagcatgaa gggcacgagc tgcttcccaa    5040
aggcccccat ccaagtatag gtctctacat cgtaggtgac aaagagacgc tcggtgcgag    5100
gatgcgagcc gatcgggaag aactggatct cccgccacca attggaggag tggctattga    5160
tgtggtgaaa gtagaagtcc ctgcgacggg ccgaacactc gtgctggctt ttgtaaaaac    5220
gtgcgcagta ctggcagcgg tgcacgggct gtacatcctg cacgaggttg acctgacgac    5280
cgcgcacaag gaagcagagt gggaatttga gcccctcgcc tggcgggttt ggctggtggt    5340
cttctacttc ggctgcttgt ccttgaccgt ctggctgctc gaggggagtt acggtggatc    5400
ggaccaccac gccgcgcgag cccaaagtcc agatgtccgc gcgcggcggt cggagcttga    5460
tgacaacatc gcgcagatgg gagctgtcca tggtctggag ctcccgcggc gtcaggtcag    5520
gcgggagctc ctgcaggttt acctcgcata gacgggtcag ggcgcgggct agatccaggt    5580
gatacctaat ttccaggggc tggttggtgg cggcgtcgat ggcttgcaag aggccgcatc    5640
cccgcggcgc gactacggta ccgcgcggcg ggcggtgggc cgcggggtg tccttggatg    5700 atgcatctaa aagcggtgac gcgggcgagc ccccggaggt aggggggct ccggacccgc    5760 cgggagaggg ggcaggggca cgtcggcgcc gcgcgcgggc aggagctggt gctgcgcgcg    5820
taggttgctg gcgaacgcga cgacgcgcg gttgatctcc tgaatctggc gcctctgcgt    5880
gaagacgacg ggcccggtga gcttgagcct gaaagagagt tcgacagaat caatttcggt    5940
gtcgttgacg gcgcctggc gcaaaatctc ctgagttgt cttgataggc    6000 gatctcggcc atgaactgct cgatctcttc ctcctggaga tctccgcgtc cggctcgctc    6060
cacggtggcg gcgaggtcgt tggaaatgcg ggccatgagc tgcagaagg cgttgaggcc    6120 tccctcgttc cagacgcggc tgtagaccac gccccttcg gcatcgcggg cgcgcatgac    6180
cacctgcgcg agattgagct ccacgtgccg ggcgaagacg gcgtagttc gcaggcgctg    6240 aaagaggtag ttgagggtgg tggcggtgtg ttctgccacg aagaagtaca taacccagcg    6300
tcgcaacgtg gattcgttga tatccccaa ggcctcaagg cgctccatgg cctcgtagaa    6360
gtccacggcg aagttgaaaa actgggagtt gcgcgccgac acggttaact cctcctccag    6420
aagacggatg agctcggcga cagtgtcgcg cacctcgcgc tcaaaggcta caggggcctc    6480
ttcttcttct tcaatctcct cttccataag ggcctcccct tcttcttctt ctggcggcgg    6540
tgggggaggg gggacacggc ggcgacgacg gcgcaccggg aggcggtcga caaagcgctc    6600
gatcatctcc ccgcggcgac ggcgcatggt ctcggtgacg gcgcggccgt tctcgcgggg    6660
gcgcagttgg aagacgccgc ccgtcatgtc ccggttatgg gttggcgggg ggctgccatg    6720
cggcagggat acgcgctaa cgatgcatct caacaattgt tgtgtaggta ctccgccgcc    6780
gagggacctg agcgagtccg catcgaccgg atcggaaaac ctctcgagaa aggcgtctaa    6840
ccagtcacag tcgcaaggta ggctgagcac cgtggcgggc ggcagcgggc ggcggtcggg    6900
gttgtttctg gcgaggtgc tgctgatgat gtaattaaag taggcggtct tgagacggcg    6960
gatggtcgac agaagcacca tgtccttggg tccggcctgc tgaatgcgca ggcggtcggc    7020
```

| | |
|---|---|
| catgccccag gcttcgtttt gacatcggcg caggtctttg tagtagtctt gcatgagcct | 7080 |
| ttctaccggc acttcttctt ctccttcctc ttgtcctgca tctcttgcat ctatcgctgc | 7140 |
| ggcggcggcg gagtttggcc gtaggtggcg ccctcttcct cccatgcgtg tgaccccgaa | 7200 |
| gccccctcatc ggctgaagca gggctaggtc ggcgacaacg cgctcggcta atatggcctg | 7260 |
| ctgcacctgc gtgagggtag actggaagtc atccatgtcc acaaagcggt ggtatgcgcc | 7320 |
| cgtgttgatg gtgtaagtgc agttggccat aacggaccag ttaacggtct ggtgacccgg | 7380 |
| ctgcgagagc tcggtgtacc tgagacgcga gtaagccctc gagtcaaata cgtagtcgtt | 7440 |
| gcaagtccgc accaggtact ggtatcccac caaaaagtgc ggcggcggct ggcggtagag | 7500 |
| gggccagcgt agggtggccg gggctccggg ggcgagatct ccaacataa ggcgatgata | 7560 |
| tccgtagatg tacctggaca tccaggtgat gccggcggcg gtggtggagg cgcgcggaaa | 7620 |
| gtcgcggacg cggttccaga tgttgcgcag cggcaaaaag tgctccatgg tcgggacgct | 7680 |
| ctggccggtc aggcgcgcgc aatcgttgac gctctaccgt gcaaaaggag agcctgtaag | 7740 |
| cgggcactct ccgtggtct ggtggataaa ttcgcaaggg tatcatggcg gacgaccggg | 7800 |
| gttcgagccc cgtatccggc cgtccgccgt gatccatgcg gttaccgccc gcgtgtcgaa | 7860 |
| cccaggtgtg cgacgtcaga aacgggggga gtgctccttt tggcttcctt ccaggcgcgg | 7920 |
| cggctgctgc gctagctttt ttggccactg gccgcgcgca gcgtaagcgg ttaggctgga | 7980 |
| aagcgaaagc attaagtggc tcgctccctg tagccggagg gttattttcc aagggttgag | 8040 |
| tcgcgggacc cccggttcga gtctcggacc ggccggactg cggcgaacgg gggtttgcct | 8100 |
| ccccgtcatg caagaccccg cttgcaaatt cctccggaaa cagggacgag cccctttttt | 8160 |
| gcttttccca gatgcatccg gtgctgcggc agatgcgccc ccctcctcag cagcggcaag | 8220 |
| agcaagagca gcggcagaca tgcagggcac cctccctcc tcctaccgcg tcaggagggg | 8280 |
| cgacatccgc ggttgacgcg gcagcagatg gtgattacga accccgcgg cgccgggccc | 8340 |
| ggcactacct ggacttggag gagggcgagg gcctggcgcg gctaggagcg ccctctcctg | 8400 |
| agcggtaccc aagggtgcag ctgaagcgtg atacgcgtga ggcgtacgtg ccgcggcaga | 8460 |
| acctgtttcg cgaccgcgag ggagaggagc ccgaggagat gcgggatcga aagttccacg | 8520 |
| cagggcgcga gctgcggcat ggcctgaatc gcgagcggtt gctgcgcgag gaggactttg | 8580 |
| agcccgacgc gcgaaccggg attagtcccg cgcgcgcaca cgtggcggcc gccgacctgg | 8640 |
| taaccgcata cgagcagacg gtgaaccagg agattaactt tcaaaaaagc tttaacaacc | 8700 |
| acgtgcgtac gcttgtggcg cgcgaggagg tggctatagg actgatgcat ctgtgggact | 8760 |
| ttgtaagcgc gctggagcaa aacccaaata gcaagccgct catggcgcag ctgttcctta | 8820 |
| tagtgcagca cagcagggac aacgaggcat tcagggatgc gctgctaaac atagtagagc | 8880 |
| ccgagggccg ctggctgctc gatttgataa acatcctgca gagcatagtg gtgcaggagc | 8940 |
| gcagcttgag cctggctgac aaggtggccg ccatcaacta ttccatgctt agcctgggca | 9000 |
| agttttacgc ccgcaagata taccataccc cttacgttcc catagacaag gaggtaaaga | 9060 |
| tcgagggggtt ctacatgcgc atggcgctga aggtgcttac cttgagcgac gacctgggcg | 9120 |
| tttatcgcaa cgacgcatc cacaaggccg tgagcgtgag ccggcggcgc gagctcagcg | 9180 |
| accgcgagct gatgcacagc ctgcaaaggg ccctggctgg cacgggcagc ggcgatagag | 9240 |
| aggccgagtc ctactttgac gcgggcgctg acctgcgctg gccccaagc cgacgcgccc | 9300 |
| tggaggcagc tggggccgga cctgggctgg cggtggcacc cgcgcgcgct ggcaacgtcg | 9360 |

```
gcggcgtgga ggaatatgac gaggacgatg agtacgagcc agaggacggc gagtactaag    9420
cggtgatgtt tctgatcaga tgatgcaaga cgcaacggac ccggcggtgc gggcggcgct    9480
gcagagccag ccgtccggcc ttaactccac ggacgactgg cgccaggtca tggaccgcat    9540
catgtcgctg actgcgcgca atcctgacgc gttccggcag cagccgcagg ccaaccggct    9600
ctccgcaatt ctggaagcgg tggtcccggc gcgcgcaaac cccacgcacg agaaggtgct    9660
ggcgatcgta aacgcgctgg ccgaaaacag ggccatccgg cccgacgaag ccggcctggt    9720
ctacgacgcg ctgcttcagc gcgtggctcg ttacaacagc ggcaacgtgc agaccaacct    9780
ggaccggctg gtgggggatg tgcgcgaggc cgtggcgcag cgtgagcgcg cgcagcagca    9840
gggcaacctg ggctccatgg ttgcactaaa cgccttcctg agtacacagc ccgccaacgt    9900
gccgcgggga caggaggact acaccaactt tgtgagcgca ctgcggctaa tggtgactga    9960
gacaccgcaa agtgaggtgt accagtctgg gccagactat ttttccaga ccagtagaca   10020 aggcctgcag accgtaaacc tgagccaggc tttcaaaaac ttgcaggggc tgtgggggt   10080 gcgggctccc acaggcgacc gcgcgaccgt gtctagcttg ctgacgccca actcgcgcct   10140
gttgctgctg ctaatagcgc ccttcacgga cagtggcagc gtgtcccggg acacatacct   10200
aggtcacttg ctgacactgt accgcgaggc cataggtcag gcgcatgtgg acgagcatac   10260
tttccaggag attacaagtg tcagccgcgc gctggggcag gaggacacgg gcagcctgga   10320
ggcaacccta aactacctgc tgaccaaccg gcggcagaag atcccctcgt tgcacagttt   10380
aaacagcgag gaggagcgca ttttgcgcta cgtgcagcag agcgtgagcc ttaacctgat   10440
gcgcgacggg gtaacgccca gcgtggcgct ggacatgacc gcgcgcaaca tggaaccggg   10500
catgtatgcc tcaaaccggc cgtttatcaa ccgcctaatg gactacttgc atcgcgcggc   10560
cgccgtgaac cccgagtatt tcaccaatgc catcttgaac ccgcactggc taccgccccc   10620
tggtttctac accgggggat tcgaggtgcc cgagggtaac gatggattcc tctgggacga   10680
catagacgac agcgtgtttt ccccgcaacc gcagaccctg ctagagttgc aacagcgcga   10740
gcaggcagag gcggcgctgc gaaaggaaag cttccgcagg ccaagcagct tgtccgatct   10800
aggcgctgcg gccccgcggt cagatgctag tagcccattt ccaagcttga tagggtctct   10860
taccagcact cgcaccaccc gcccgcgcct gctgggcgag gaggagtacc taaacaactc   10920
gctgctgcag ccgcagcgcg aaaaaaacct gcctccggca tttcccaaca acggatagga   10980
gagcctagtg gacaagatga gtagatggaa gacgtacgcg caggagcaca gggacgtgcc   11040
aggcccgcgc ccgcccaccc gtcgtcaaag gcacgaccgt cagcgggggtc tggtgtggga   11100 ggacgatgac tcggcagacg acagcagcgt cctggattg ggagggagtg caacccgtt   11160 tgcgcacctt cgccccaggc tggggagaat gttttaaaa aaaaaagca tgatgcaaaa   11220 taaaaactc accaaggcca tggcaccgag cgttggtttt cttgtattcc ccttagtatg   11280
cggcgcgcgg cgatgtatga ggaaggtcct cctccctcct acgagagtgt ggtgagcgcg   11340
gcgccagtgg cggcggcgct gggttctccc ttcgatgctc ccctggaccc gccgtttgtg   11400
cctccgcggt acctgcggcc taccgggggg agaaacagca tccgttactc tgagttggca   11460
cccctattcg acaccacccg tgtgtacctg gtggacaaca agtcaacgga tgtggcatcc   11520
ctgaactacc agaacgacca cagcaacttt ctgaccacgg tcattcaaaa caatgactac   11580
agcccggggg aggcaagcac acagaccatc aatcttgacg accggtcgca ctggggcggc   11640
gacctgaaaa ccatcctgca taccaacatg ccaaatgtga acgagttcat gtttaccaat   11700
aagtttaagg cgcgggtgat ggtgtcgcgc ttgcctacta aggacaatca ggtggagctg   11760
```

```
aaatacgagt gggtggagtt cacgctgccc gagggcaact actccgagac catgaccata   11820
gaccttatga acaacgcgat cgtggagcac tacttgaaag tgggcagaca gaacggggtt   11880
ctggaaagcg acatcgggt aaagtttgac acccgcaact tcagactggg gtttgacccc    11940
gtcactggtc ttgtcatgcc tggggtatat acaaacgaag ccttccatcc agacatcatt   12000
ttgctgccag gatgcgggt ggacttcacc cacagccgcc tgagcaactt gttgggcatc    12060
cgcaagcggc aacccttcca ggagggcttt aggatcacct acgatgatct ggagggtggt   12120
aacattcccg cactgttgga tgtggacgcc taccaggcga gcttgaaaga tgacaccgaa   12180
cagggcgggg gtggcgcagg cggcagcaac agcagtggca gcggcgcgga agagaactcc   12240
aacgcggcag ccgcggcaat gcagccggtg gaggacatga acgatcatgc cattcgcggc   12300
gacacctttg ccacacgggc tgaggagaag cgcgctgagg ccgaagcagc ggccgaagct   12360
gccgcccccg ctgcgcaacc cgaggtcgag aagcctcaga gaaaccggt gatcaaaccc     12420
ctgacagagg acagcaagaa acgcagttac aacctaataa gcaatgacag caccttcacc   12480
cagtaccgca gctggtacct tgcatacaac tacggcgacc ctcagaccgg aatccgctca   12540
tggaccctgc tttgcactcc tgacgtaacc tgcggctcgg agcaggtcta ctggtcgttg   12600
ccagacatga tgcaagaccc cgtgaccttc cgctccacgc gccagatcag caactttccg   12660
gtggtgggcg ccgagctgtt gcccgtgcac tccaagagct tctacaacga ccaggccgtc   12720
tactcccaac tcatccgcca gtttacctct ctgacccacg tgttcaatcg ctttcccgag   12780
aaccagattt tggcgcgccc gccagccccc accatcacca ccgtcagtga aaacgttcct   12840
gctctcacag atcacgggac gctaccgctg cgcaacagca tcggaggagt ccagcgagtg   12900
accattactg acgccagacg ccgcacctgc ccctacgttt acaaggccct gggcatagtc   12960
tcgccgcgcg tcctatcgag ccgcactttt tgagcaagca tgtccatcct tatatcgccc   13020
agcaataaca caggctgggg cctgcgcttc ccaagcaaga tgtttggcgg ggccaagaag   13080
cgctccgacc aacacccagt gcgcgtgcgc gggcactacc gcgcgccctg gggcgcgcac   13140
aaacgcggcc gcactgggcg caccaccgtc gatgacgcca tcgacgcggt ggtgaaggag   13200
gcgcgcaact acacgcccac gccgccacca gtgtccacag tggacgcggc cattcagacc   13260
gtggtgcgcg gagcccggcg ctatgctaaa atgaagagac ggcggaggcg cgtagcacgt   13320
cgccaccgcc gccgacccgg cactgccgcc caacgcgcgg cggcggcccct gcttaaccgc   13380
gcacgtcgca ccggccgacg ggcggccatg cgggccgctc gaaggctggc cgcgggtatt   13440
gtcactgtgc cccccaggtc caggcgacga gcggccgccg cagcagccgc ggccattagt   13500
gctatgactc agggtcgcag gggcaacgtg tattgggtgc gcgactcggt tagcggcctg   13560
cgcgtgcccg tgcgcacccg ccccccgcgc aactagattg caagaaaaaa ctacttagac   13620
tcgtactgtt gtatgtatcc agcggcggcg gcgcgcaacg aagctatgtc caagcgcaaa   13680
atcaaagaag agatgctcca ggtcatcgcg ccggagatct atggcccccc gaagaaggaa   13740
gagcaggatt acaagccccg aaagctaaag cgggtcaaaa agaaaaagaa agatgatgat   13800
gatgaacttg acgacgaggt ggaactgctg cacgctaccg cgcccaggcg acgggtacag   13860
tggaaaggtc gacgcgtaaa acgtgttttg cgacccggca ccaccgtagt ctttacgccc   13920
ggtgagcgct ccaccgcac ctacaagcgc gtgtatgatg aggtgtacgg cgacgaggac     13980
ctgcttgagc aggccaacga gcgcctcggg gagtttgcct acggaaagcg gcataaggac   14040
atgctggcgt tgccgctgga cgagggcaac ccaacaccta gcctaaagcc cgtaacactg   14100
```

```
cagcaggtgc tgcccgcgct tgcaccgtcc gaagaaaagc gcggcctaaa gcgcgagtct   14160
ggtgacttgg cacccaccgt gcagctgatg gtacccaagc gccagcgact ggaagatgtc   14220
ttggaaaaaa tgaccgtgga acctgggctg gagcccgagg tccgcgtgcg gccaatcaag   14280
caggtggcgc cgggactggg cgtgcagacc gtggacgttc agatacccac taccagtagc   14340
accagtattg ccaccgccac agagggcatg gagacacaaa cgtccccggt tgcctcagcg   14400
gtggcggatg ccgcggtgca ggcggtcgct gcggccgcgt ccaagacctc tacgaggtg   14460 caaacggacc cgtggatgtt tcgcgtttca gcccccggc gcccgcgcgg ttcgaggaag   14520 tacgcgccg ccagcgcgct actgcccgaa tatgccctac atccttccat tgcgcctacc   14580
cccggctatc gtggctacac ctaccgcccc agaagacgag caactacccg acgccgaacc   14640
accactggaa cccgccgccg ccgtcgccgt cgccagcccg tgctggcccc gatttccgtg   14700
cgcagggtgg ctcgcgaagg aggcaggacc ctggtgctgc aacagcgcg ctaccaccc   14760 agcatcgttt aaaagccggt ctttgtggtt cttgcagata tggccctcac ctgccgcctc   14820
cgtttcccgg tgccgggatt ccgaggaaga atgcaccgta ggaggggcat ggccggctac   14880
ggcctgacgg gcggcatgcg tcgtgcgcac caccggcggc ggcgcgcgtc gcaccgtcgc   14940
atgcgcggcg gtatcctgcc cctccttatt ccactgatcg ccgcggcgat tggcgccgtg   15000
cccggaattg catccgtggc cttgcaggcg cagagacact gattaaaaac aagttgcatg   15060
tggaaaaatc aaaataaaaa gtctggactc tcacgctcgc ttggtcctgt aactattttg   15120
tagaatggaa gacatcaact ttgcgtctct ggccccgcga cacggctcgc gcccgttcat   15180
gggaaactgg caagatatcg gcaccagcaa tatgagcggt ggcgccttca gctgggggctc   15240 gctgtggagc ggcattaaaa atttcggttc caccgttaag aactatggca gcaaggcctg   15300
gaacagcagc acaggccaga tgctgaggga taagttgaaa gagcaaaatt tccaacaaaa   15360
ggtggtagat ggcctggcct ctggcattag cggggtggtg gacctggcca accaggcagt   15420
gcaaaataag attaacagta agcttgatcc ccgccctccc gtagaggagc ctccaccggc   15480
cgtggagaca gtgtctccag aggggcgtgg cgaaaagcgt ccgcgccccg acagggaaga   15540
aactctggtg acgcaaatag acgagcctcc ctcgtacgag gaggcactaa agcaaggcct   15600
gcccaccacc cgtcccatcg cgcccatggc taccggagtg ctgggccagc acacacccgt   15660
aacgctggac ctgcctcccc ccgccgacac ccagcagaaa cctgtgctgc caggcccgac   15720
cgccgttgtt gtaacccgtc ctagccgcgc gtccctgcgc cgcgccgcca gcggtccgcg   15780
atcgttgcgg cccgtagcca gtggcaactg gcaaagcaca ctgaacagca tcgtgggtct   15840
gggggtgcaa tccctgaagc gccgacgatg cttctgaata gctaacgtgt cgtatgtgtg   15900
tcatgtatgc gtccatgtcg ccgccagagg agctgctgag ccgccgcgcg cccgctttcc   15960
aagatggcta cccccttcgat gatgccgcag tggtcttaca tgcacatctc gggccaggac   16020
gcctcggagt acctgagccc cgggctggtg cagtttgccc gcgccaccga dacgtacttc   16080
agcctgaata acaagtttag aaaccccacg gtggcgccta cgcacgacgt gaccacagac   16140
cggtcccagc gtttgacgct gcggttcatc cctgtggacc gtgaggatac tgcgtactcg   16200
tacaaggcgc ggttcaccct agctgtgggt gataaccgtg tgctggacat ggcttccacg   16260
tactttgaca tccgcggcgt gctggacagg ggccctactt ttaagcccta ctctggcact   16320
gcctacaacg ccctggctcc caagggtgcc ccaaatcctt gcgaatggga tgaagctgct   16380
actgctcttg aaataaacct agaagaagag gacgatgaca acgaagacga agtagacgag   16440
caagctgagc agcaaaaaac tcacgtattt gggcaggcgc cttattctgg tataaatatt   16500
```

```
acaaaggagg gtattcaaat aggtgtcgaa ggtcaaacac ctaaatatgc cgataaaaca    16560
tttcaacctg aacctcaaat aggagaatct cagtggtacg aaactgaaat taatcatgca    16620
gctgggagag tccttaaaaa gactacccca atgaaaccat gttacggttc atatgcaaaa    16680
cccacaaatg aaaatggagg gcaaggcatt cttgtaaagc aacaaaatgg aaagctagaa    16740
agtcaagtgg aaatgcaatt tttctcaact actgaggcga ccgcaggcaa tggtgataac    16800
ttgactccta aagtggtatt gtacagtgaa gatgtagata tagaaccccc agacactcat    16860
atttcttaca tgcccactat taaggaaggt aactcacgag aactaatggg ccaacaatct    16920
atgcccaaca ggcctaatta cattgctttt agggacaatt ttattggtct aatgtattac    16980
aacagcacgg gtaatatggg tgttctggcg ggccaagcat cgcagttgaa tgctgttgta    17040
gatttgcaag acagaaacac agagctttca taccagcttt tgcttgattc cattggtgat    17100
agaaccaggt acttttctat gtggaatcag gctgttgaca gctatgatcc agatgttaga    17160
attattgaaa atcatggaac tgaagatgaa cttccaaatt actgctttcc actgggaggt    17220
gtgattaata cagagactct taccaaggta aaacctaaaa caggtcagga aaatggatgg    17280
gaaaaagatg ctacagaatt ttcagataaa aatgaaataa gagttggaaa taattttgcc    17340
atggaaatca atctaaatgc caacctgtgg agaaatttcc tgtactccaa catagcgctg    17400
tatttgcccg acaagctaaa gtacagtcct tccaacgtaa aaatttctga taacccaaac    17460
acctacgact acatgaacaa gcgagtggtg gctcccgggt tagtggactg ctacattaac    17520
cttggagcac gctggtccct tgactatatg gacaacgtca acccatttaa ccaccaccgc    17580
aatgctggcc tgcgctaccg ctcaatgttg ctgggcaatg gtcgctatgt gcccttccac    17640
atccaggtgc ctcagaagtt ctttgccatt aaaaacctcc ttctcctgcc gggctcatac    17700
acctacgagt ggaacttcag gaaggatgtt aacatggttc tgcagagctc cctaggaaat    17760
gacctaaggg ttgacggagc cagcattaag tttgatagca tttgccttta cgccaccttc    17820
ttccccatgg cccacaacac cgcctccacg cttgaggcca tgcttagaaa cgacaccaac    17880
gaccagtcct ttaacgacta tctctccgcc gccaacatgc tctaccctat acccgccaac    17940
gctaccaacg tgcccatatc catcccctcc cgcaactggg cggcttttcg cggctgggcc    18000
ttcacgcgcc ttaagactaa ggaaacccca tcactgggct cgggctacga cccttattac    18060
acctactctg gctctatacc ctacctagat ggaacctttt acctcaacca caccttcaag    18120
aaggtggcca ttacctttga ctcttctgtc agctggcctg gcaatgaccg cctgcttacc    18180
cccaacgagt ttgaaattaa gcgctcagtt gacggggagg gttacaacgt tgcccagtgt    18240
aacatgacca aagactggtt cctggtacaa atgctagcta actacaacat tggctaccag    18300
ggcttctata tcccagagag ctacaaggac cgcatgtact ccttctttag aaacttccag    18360
cccatgagcc gtcaggtggt ggatgatact aaatacaagg actaccaaca ggtgggcatc    18420
ctacaccaac acaacaactc tggatttgtt ggctaccttg cccccaccat gcgcgaagga    18480
caggcctacc ctgctaactt cccctatccg cttataggca agaccgcagt tgacagcatt    18540
acccagaaaa agtttctttg cgatcgcacc ctttggcgca tcccattctc cagtaacttt    18600
atgtccatgg gcgcactcac agacctgggc caaaaccttc tctacgccaa ctccgcccac    18660
gcgctagaca tgactttga ggtggatccc atggacgagc ccaccccttct ttatgttttg    18720 tttgaagtct ttgacgtggt ccgtgtgcac cggccgcacc gcggcgtcat cgaaaccgtg    18780
tacctgcgca cgcccttctc ggccggcaac gccacaacat aaagaagcaa gcaacatcaa    18840
```

```
caacagctgc cgccatgggc tccagtgagc aggaactgaa agccattgtc aaagatcttg   18900
gttgtgggcc atattttttg ggcacctatg caagcgctt ccaggcttt gtttctccac    18960
acaagctcgc ctgcgccata gtcaatacgg ccggtcgcga gactgggggc gtacactgga   19020
tggcctttgc ctggaacccg cactcaaaaa catgctacct cttgagccc tttggctttt    19080
ctgaccagcg actcaagcag gtttaccagt ttgagtacga gtcactcctg cgccgtagcg   19140
ccattgcttc ttcccccgac cgctgtataa cgctggaaaa gtccacccaa agcgtacagg   19200
ggcccaactc ggccgcctgt ggactattct gctgcatgtt tctccacgcc tttgccaact   19260
ggccccaaac tccatggat cacaacccca ccatgaacct tattaccggg gtacccaact    19320
ccatgctcaa cagtccccag gtacagccca ccctgcgtcg caaccaggaa cagctctaca   19380
gcttcctgga gcgccactcg ccctacttcc gcagccacag tgcgcagatt aggagcgcca   19440
cttcttttg tcacttgaaa aacatgtaaa aataatgtac tagagacact ttcaataaag     19500
gcaaatgctt ttatttgtac actctcgggt gattatttac ccccacccctt gccgtctgcg   19560
ccgtttaaaa atcaaagggg ttctgccgcg catcgctatg cgccactggc agggacacgt   19620
tgcgatactg gtgtttagtg ctccacttaa actcaggcac aaccatccgc ggcagctcgg   19680
tgaagttttc actccacagg ctgcgcacca tcaccaacgc gtttagcagg tcgggcgccg   19740
atatcttgaa gtcgcagttg gggcctccgc cctgcgcgcg cgagttgcga tacacagggt   19800
tgcagcactg gaacactatc agcgccgggt ggtgcacgct ggccagcacg ctcttgtcgg   19860
agatcagatc cgcgtccagg tcctccgcgt tgctcagggc gaacggagtc aactttggta   19920
gctgccttcc caaaaagggc gcgtgcccag gctttgagtt gcactcgcac cgtagtggca   19980
tcaaaaggtg accgtgcccg gtctgggcgt taggatacag cgcctgcata aaagccttga   20040
tctgcttaaa agccacctga gcctttgcgc cttcagagaa gaacatgccg caagacttgc   20100
cggaaaactg attggccgga caggccgcgt cgtgcacgca gcaccttgcg tcggtgttgg   20160
agatctgcac cacatttcgg ccccaccggt tcttcacgat cttggccttg ctagactgct   20220
ccttcagcgc gcgctgcccg ttttcgctcg tcacatccat ttcaatcacg tgctccttat   20280
ttatcataat gcttccgtgt agacacttaa gctcgccttc gatctcagcg cagcggtgca   20340
gccacaacgc gcagcccgtg ggctcgtgat gcttgtaggt cacctctgca aacgactgca   20400
ggtacgcctg caggaatcgc cccatcatcg tcacaaaggt cttgttgctg gtgaaggtca   20460
gctgcaaccc gcggtgctcc tcgttcagcc aggtcttgca tacggccgcc agagcttcca   20520
cttggtcagg cagtagtttg aagttcgcct ttagatcgtt atccacgtgg tacttgtcca   20580
tcagcgcgcg cgcagcctcc atgcccttct cccacgcaga cacgatcggc acactcagcg   20640
ggttcatcac cgtaatttca ctttccgctt cgctgggctc ttcctcttcc tcttgcgtcc   20700
gcataccacg cgccactggg tcgtcttcat tcagccgccg cactgtgcgc ttacctcctt   20760
tgccatgctt gattagcacc ggtgggttgc tgaaacccac catttgtagc gccacatctt   20820
ctctttcttc ctcgctgtcc acgattacct ctggtgatgg cgggcgctcg gcttgggag    20880
aagggcgctt cttttctc ttgggcgcaa tggccaaatc cgccgccgag gtcgatggcc      20940
gcgggctggg tgtgcgcggc accagcgcgt cttgtgatga gtcttcctcg tcctcggact   21000
cgatacgccg cctcatccgc ttttttgggg gcgcccgggg aggcggcggc gacggggacg   21060
gggacgacac gtcctccatg gttgggggac gtcgcgccgc accgcgtccg cgctcggggg   21120
tggtttcgcg ctgctcctct tcccgactgg ccatttcctt ctcctatagg cagaaaagga   21180
tcatggagtc agtcgagaag aaggacagcc taaccgcccc ctctgagttc gccaccaccg   21240
```

```
cctccaccga tgccgccaac gcgcctacca ccttccccgt cgaggcaccc ccgcttgagg    21300
aggaggaagt gattatcgag caggacccag gttttgtaag cgaagacgac gaggaccgct    21360
cagtaccaac agaggataaa aagcaagacc aggacaacgc agaggcaaac gaggaacaag    21420
tcgggcgggg ggacgaaagg catggcgact acctagatgt gggagacgac gtgctgttga    21480
agcatctgca gcgccagtgc gccattatct gcgacgcgtt gcaagagcgc agcgatgtgc    21540
ccctcgccat agcggatgtc agccttgcct acgaacgcca cctattctca ccgcgcgtac    21600
cccccaaacg ccaagaaaac ggcacatgcg agcccaaccc gcgcctcaac ttctaccccg    21660
tatttgccgt gccagaggtg cttgccacct atcacatctt tttccaaaac tgcaagatac    21720
ccctatcctg ccgtgccaac cgcagccgag cggacaagca gctggccttg cggcagggcg    21780
ctgtcatacc tgatatcgcc tcgctcaacg aagtgccaaa aatctttgag ggtcttggac    21840
gcgacgagaa gcgcgcggca aacgctctgc aacaggaaaa cagcgaaaat gaaagtcact    21900
ctggagtgtt ggtggaactc gagggtgaca acgcgcgcct agccgtacta aaacgcagca    21960
tcgaggtcac ccactttgcc tacccggcac ttaacctacc ccccaaggtc atgagcacag    22020
tcatgagtga gctgatcgtg cgccgtgcgc agccccctgga gagggatgca aatttgcaag    22080
aacaaacaga ggagggccta cccgcagttg gcgacgagca gctagcgcgc tggcttcaaa    22140
cgcgcgagcc tgccgacttg gaggagcgac gcaaactaat gatggccgca gtgctcgtta    22200
ccgtggagct tgagtgcatg cagcggttct ttgctgaccc ggagatgcag cgcaagctag    22260
aggaaacatt gcactacacc tttcgacagg gctacgtacg ccaggcctgc aagatctcca    22320
acgtggagct ctgcaacctg gtctcctacc ttggaatttt gcacgaaaac cgccttgggc    22380
aaaacgtgct tcattccacg ctcaagggcg aggcgcgccg cgactacgtc cgcgactgcg    22440
tttacttatt tctatgctac acctggcaga cggccatggg cgtttggcag cagtgcttgg    22500
aggagtgcaa cctcaaggag ctgcagaaac tgctaaagca aacttgaag gacctatgga    22560 cggccttcaa cgagcgctcc gtggccgcgc acctggcgga catcattttc cccgaacgcc    22620
tgcttaaaac cctgcaacag ggtctgccag acttcaccag tcaaagcatg ttgcagaact    22680
ttaggaactt tatcctagag cgctcaggaa tcttgccgc cacctgctgt gcacttccta    22740
gcgactttgt gcccattaag taccgcgaat gccctccgcc gctttggggc cactgctacc    22800
ttctgcagct agccaactac cttgcctacc actctgacat aatggaagac gtgagcggtg    22860
acggtctact ggagtgtcac tgtcgctgca acctatgcac cccgcaccgc tccctggttt    22920
gcaattcgca gctgcttaac gaaagtcaaa ttatcggtac cttgagctg cagggtcct    22980 cgcctgacga aaagtccgcg gctccggggt tgaaactcac tccggggctg tggacgtcgg    23040
cttaccttcg caaatttgta cctgaggact accacgccca cgagattagg ttctacgaag    23100
accaatcccg cccgccaaat gcggagctta ccgcctgcgt cattacccag ggccacattc    23160
ttggccaatt gcaagccatc aacaaagccc gccaagagtt tctgctacga aagggacggg    23220
gggtttactt ggaccccag tccggcgagg agctcaaccc aatcccccg ccgccgcagc    23280 cctatcagca gcagccgcgg gcccttgctt cccaggatgg cacccaaaaa gaagctgcag    23340
ctgccgccgc cacccacgga cgaggaggaa tactgggaca gtcaggcaga ggaggttttg    23400
gacgaggagg aggaggacat gatggaagac tgggagagcc tagacgagga agcttccgag    23460
gtcgaagagg tgtcagacga aacaccgtca ccctcggtcg cattcccctc gccgcgcccc    23520
cagaaatcgg caaccggttc cagcatggct acaacctccg ctcctcaggc gccgccggca    23580
```

```
ctgcccgttc gccgacccaa ccgtagatgg gacaccactg gaaccagggc cggtaagtcc    23640
aagcagccgc cgccgttagc ccaagagcaa caacagcgcc aaggctaccg ctcatggcgc    23700
gggcacaaga acgccatagt tgcttgcttg caagactgtg ggggcaacat ctccttcgcc    23760
cgccgctttc ttctctacca tcacggcgtg gccttccccc gtaacatcct gcattactac    23820
cgtcatctct acagcccata ctgcaccggc ggcagcggca gcggcagcaa cagcagcggc    23880
cacacagaag caaaggcgac cggatagcaa gactctgaca aagcccaaga aatccacagc    23940
ggcggcagca gcaggaggag gagcgctgcg tctggcgccc aacgaacccg tatcgacccg    24000
cgagcttaga aacaggattt ttcccactct gtatgctata tttcaacaga gcaggggcca    24060
agaacaagag ctgaaaataa aaacaggtc tctgcgatcc ctcacccgca gctgcctgta     24120
tcacaaaagc gaagatcagc ttcggcgcac gctggaagac gcggaggctc tcttcagtaa    24180
atactgcgcg ctgactctta aggactagtt tcgcgccctt tctcaaattt aagcgcgaaa    24240
actacgtcat ctccagcggc cacacccggc gccagcacct gtcgtcagcg ccattatgag    24300
caaggaaatt cccacgccct acatgtggag ttaccagcca caaatgggac ttgcggctgg    24360
agctgcccaa gactactcaa cccgaataaa ctacatgagc gcgggacccc acatgatatc    24420
ccgggtcaac ggaatccgcg cccaccgaaa ccgaattctc ttggaacagg cggctattac    24480
caccacacct cgtaataacc ttaatccccg tagttggccc gctgccctgg tgtaccagga    24540
aagtcccgct cccaccactg tggtacttcc cagagacgcc caggccgaag ttcagatgac    24600
taactcaggg gcgcagcttg cgggcggctt tcgtcacagg gtgcggtcgc ccgggcaggg    24660
tataactcac ctgacaatca gagggcgagg tattcagctc aacgacgagt cggtgagctc    24720
ctcgcttggt ctccgtccgg acgggacatt tcagatcggc ggcgccggcc gtccttcatt    24780
cacgcctcgt caggcaatcc taactctgca gacctcgtcc tctgagccgc gctctggagg    24840
cattggaact ctgcaattta ttgaggagtt tgtgccatcg gtctacttta accccttctc    24900
gggacctccc ggccactatc cggatcaatt tattcctaac tttgacgcgg taaaggactc    24960
ggcggacggc tacgactgaa tgttaagtgg agaggcagag caactgcgcc tgaaacacct    25020
ggtccactgt cgccgccaca agtgctttgc ccgcgactcc ggtgagtttt gctactttga    25080
attgcccgag gatcatatcg agggcccggc gcacggcgtc cggcttaccg cccagggaga    25140
gcttgcccgt agcctgattc gggagtttac ccagcgcccc ctgctagttg agcgggacag    25200
gggaccctgt gttctcactg tgatttgcaa ctgtcctaac cttggattac atcaagatcc    25260
tctagttaat taacagcttg catgcctgca ggtcgacgga tcgggagatc tcggccgcat    25320
attaagtgca ttgttctcga taccgctaag tgcattgttc tcgttagctc gatggacaag    25380
tgcattgttc tcttgctgaa agctcgatgg acaagtgcat tgttctcttg ctgaaagctc    25440
gatggacaag tgcattgttc tcttgctgaa agctcagtac ccgggagtac cctcgaccgc    25500
cggagtataa atagaggcgc ttcgtctacg gagcgacaat tcaattcaaa caagcaaagt    25560
gaacacgtcg ctaagcgaaa gctaagcaaa taaacaagcg cagctgaaca agctaaacaa    25620
tctgcagtaa agtgcaagtt aaagtgaatc aattaaaagt aaccagcaac caagtaaatc    25680
aactgcaact actgaaatct gccaagaagt aattattgaa tacaagaaga gaactctgaa    25740
tactttcaac aagttaccga gaaagaagaa ctcacacaca gctagcgttt aaacttaagc    25800
ttcaccatgg tgggccctg catgctgctg ctgctgctgc tgctgggcct gaggctacag    25860 ctctcccctgg gcatcatcct agttgaggag gagaacccgg acttctggaa ccgcgaggca    25920
gccgaggccc tgggtgccgc caagaagctg cagcctgcac agacagccgc caagaacctc    25980
```

```
atcatcttcc tgggcgatgg ggtgggggtg tctacggtga cagctgccag gatcctaaaa    26040
gggcagaaga aggacaaact gggggcctgag atacccctgg ccatggaccg cttcccatat   26100
gtggctctgt ccaagacata caatgtagac aaacatgtgc cagacagtgg agccacagcc   26160
acggcctacc tgtgcggggt caagggcaac ttccagacca ttggcttgag tgcagccgcc   26220
cgctttaacc agtgcaacac gacacgcggc aacgaggtca tctccgtgat gaatcgggcc   26280
aagaaagcag ggaagtcagt gggagtggta accaccacac gagtgcagca cgcctcgcca   26340
gccggcacct acgcccacac ggtgaaccgc aactggtact cggacgccga cgtgcctgcc   26400
tcggcccgcc aggaggggtg ccaggacatc gctacgcagc tcatctccaa catggacatt   26460
gacgtgatcc taggtggggg ccgaaagtac atgtttcgca tgggaacccc agaccctgag   26520
tacccagatg actacagcca aggtgggacc aggctgacg ggaagaatct ggtgcaggaa    26580
tggctggcga agcaccaggg tgcccggtac gtgtggaacc gcactgagct catgcgggct   26640
tccctggacc cgtctgtggc ccatctcatg ggtctctttg agcctggaga catgaaatac   26700
gagatccacc gagactccac actggacccc tccctgatgg agatgacaga ggctgccctg   26760
cgcctgctga gcaggaaccc ccgcggcttc ttcctcttcg tggagggtgg tcgcatcgac   26820
catggtcatc atgaaagcag ggcttaccgg gcactgactg agacgatcat gttcgacgac   26880
gccattgaga gggcgggcca gctcaccagc gaggaggaca cgctgagcct cgtcactgcc   26940
gaccactccc acgtcttctc cttcggaggc tgccccctgc gaggggggctc catcttcggg   27000 ctggcccctg gcaaggcccg ggacaggaag gcctacacgg tcctcctata cggaaacggt   27060
ccaggctatg tgctcaagga cggcgcccgg ccggatgtta ccgagagcga gagcgggagc   27120
cccgagtatc ggcagcagtc agcagtgccc ctggacgaag agacccacgc aggcgaggac   27180
gtggcggtgt tcgcgcgcgg cccgcaggcg cacctggttc acggcgtgca ggagcagacc   27240
ttcatagcgc acgtcatggc cttcgccgcc tgcctggagc cctacaccgc tgcgacctg    27300 gcgcccccg ccggcaccac cgacgccgcg cacccggggc ggtccgtggt ccccgcgttg   27360
cttcctctgc tggccgggac cctgctgctg ctggagacgg ccactgctcc ctgagtgtcc   27420
cgtccctggg gctcctgctt ccccatcccg gagttctcct gctcccgcc tcctgtcgtc    27480 ctgcctggcc tccagcccga gtcgtcatcc ccggagtccc tatacagagg tcctgccatg   27540
gaaccttccc ctccccgtgc gctctgggga ctgagcccat gacaccaaac ctgccccttg   27600
gctgctctcg gactccctac cccaaccca gggacagatc tggccagatt tgtaaaacaa    27660
atagatttta ggcccaaaga ttatttaaag cattgcctgg aacgcagtga gttttgtta   27720 gaaaagagaa taattcaaag tggcattgct ttgcttctta tgttaatttg gtacagacct   27780
gtggctgagt ttgctcaaag tattcagagc agaattgtgg agtggaaaga gagattggac   27840
aaagagttta gtttgtcagt gtatcaaaaa atgaagttta atgtggctat gggaattgga   27900
gttttagatt ggctaagaaa cagtgatgat gatgatgaag acagccagga aaatgctgat   27960
aaaaatgaag atggtgggga aagaacatg gaagactcag ggcatgaaac aggcattgat    28020
tcacagtccc aaggctcatt tcaggcccct cagtcctcac agtctgttca tgatcataat   28080
cagccatacc acatttgtag aggttttact tgctttaaaa aacctcccac acctcccct   28140 gaacctgaaa cataaaatga atgcaattgt tgttgttaac ttgtttattg cagcttataa    28200
tggttacaaa taaagcaata gcatcacaaa tttcacaaat aaagcatttt ttcactgca   28260 ttctagttgt ggtttgtcca aactcatcaa tgtatcttat catgtctgga tccccaggaa   28320
```

```
gctcctctgt gtcctcataa accctaacct cctctacttg agaggacatt ccaatcatag    28380
gctgcccatc caccctctgt gtcctcctgt taattaggtc acttaacaaa aaggaaattg    28440
ggtaggggtt tttcacagac cgctttctaa gggtaatttt aaaatatctg ggaagtccct    28500
tccactgctg tgttccagaa gtgttggtaa acagcccaca aatgtcaaca gcagaaacat    28560
acaagctgtc agctttgcac aagggcccaa caccctgctc atcaagaagc actgtggttg    28620
ctgtgttagt aatgtgcaaa acaggaggca cattttcccc acctgtgtag gttccaaaat    28680
atctagtgtt ttcatttta cttggatcag gaacccagca ctccactgga taagcattat    28740
ccttatccaa aacagccttg tggtcagtgt tcatctgctg actgtcaact gtagcatttt    28800
ttggggttac agtttgagca ggatatttgg tcctgtagtt tgctaacaca ccctgcagct    28860 ccaaggttc cccaccaaca gcaaaaaaat gaaaatttga cccttgaatg ggttttccag    28920 caccatttc atgagttttt tgtgtccctg aatgcaagtt taacatagca gttacccaa    28980 taacctcagt tttaacagta acagcttccc acatcaaaat atttccacag gttaagtcct    29040
catttaaatt aggcaaagga attccacttc ccactgcctt gcttccgtct cccattcaaa    29100
cttttatcaa ctgacattat tctaagtaaa atcctcttca ttatgttgtc agcaatccat    29160
tgcttgaagg cctggctccc cagaacccct cgactggtat gtcttctcct agaatactcc    29220
agaagaaaag gagtgtatga agatagtgac tgcacattaa aatgactgaa accatagtaa    29280
attaggatga gattctgggc agataaacag acagctggct aggatcattt ttttatgcct    29340
tggacttctt tggcaatctg ttgaagcctg acattcctca gaataatgtt ttaaagccca    29400
acaataagac cctgtagcac atataataag tactgcagtt ttgaagtagt gataagcata    29460
aatgatattt tgatatattt attataactg taatgagatg tgtacatatc tgtgacttca    29520
taggtactga ttgtactact gtgattttt tgcctacttt caaatgaaa aggaatgctt    29580 aatttcagtt agaggttagt aaagacaaat aggtaatttt cttctccagt gaagagcatg    29640
gcgccccttg ctattcatgg acgcttgctt aaagacttgt acacaggctt gctttgtatc    29700
aacctatgac ttccccttac agccgatgat aggttttat ttgcacctcc ttcgtgtaca    29760
aagacagttt tggtggctac gccatcatta aactcattat tatcatgctt aagcctatag    29820
atgtatccag ttcttctgtt acataattga agctgtagtg aattgtctat cttaaactgc    29880
atcgctaact gactacattt cacacttcat ttgcttccaa catagactaa ccttcttgga    29940
tgtccactat tatttgaact tttgagattt ttttcctat ttctaatatc ttaaaatttc    30000
agaagactta aagttttgca actacagggc tccatataga catctagctt gaatttatac    30060
actttctttc attgatgtcc ctggactaaa aaatgttaaa tatttctaac cgctgtactt    30120
aaagtccatt acaaacgaag actactgttg ttaagttgaa taggcatctt atatatttt    30180 caccggtgca ataaataact tctattccct tctaacatct gcttgcgttg cactgagagt    30240
acactattga ttagcaatag gttcgtgatt acagcccttc tataattaat gttaggtta    30300 acatattatt cataaaatat tattttatta atttttactt gatttgctac tggatgctta    30360
gaaatagcta tgagtatatt ggtagaacca gtacttatat tttattacat ttttacattt    30420
cataaaattt aagtgatata aaaatcctga ggaagtatgc cacaaaagtg gtctcagtgg    30480 aaattaaat atgttaacat ttattttaa aatgtagcgt gaaatagaca actttaaaag    30540
ctcagcttaa aaaaaaact caaggaagct gaacttgact ttttaaagca ctgaagtgca    30600
atatttaatg taggtcaaca tgtttaaatg ggaaaatttt tttcctaatt acagccaaat    30660
ccctagctgt aattaactta aaatttgtat actatttcac aacagagtca gcatatacca    30720
```

```
ctttcttata aaattagaaa gatctaaaat tttagagctt atttggtgaa acaggcatat   30780
tgctacatct ttgtttataa attataatgt gcctttagag cccaataaca gataacaaga   30840
ttttgaaaat tcaggtgaat tagagttatc agagggaatg ttaatacact ctattcaaat   30900
actatatgag taagacattt aaaataggaa acaatacttt atatattaaa aaaaattaat   30960
cttccagtcg atttaatcca ctttatgaat tcatttaaat cgatttaaat tcgaattaat   31020
taactagagt acccggggat cttattccct ttaactaata aaaaaaaata ataaagcatc   31080
acttacttaa aatcagttag caaatttctg tccagtttat tcagcagcac ctccttgccc   31140
tcctcccagc tctggtattg cagcttcctc ctggctgcaa actttctcca caatctaaat   31200
ggaatgtcag tttcctcctg ttcctgtcca tccgcaccca ctatcttcat gttgttgcag   31260
atgaagcgcg caagaccgtc tgaagatacc ttcaaccccg tgtatccata tgacacggaa   31320
accggtcctc caactgtgcc ttttcttact cctcccttgt tatcccccaa tgggtttcaa   31380
gagagtcccc ctggggtact ctctttgcgc ctatccgaac ctctagttac ctccaatggc   31440
atgcttgcgc tcaaaatggg caacggcctc tctctggacg aggccggcaa ccttacctcc   31500
caaaatgtaa ccactgtgag cccacctctc aaaaaaacca agtcaaacat aaacctggaa   31560
atatctgcac ccctcacagt tacctcagaa gccctaactg tggctgccgc cgcacctcta   31620
atggtcgcgg gcaacacact caccatgcaa tcacaggccc cgctaaccgt gcacgactcc   31680
aaacttagca ttgccaccca aggacccctc acagtgtcag aaggaaagct agccctgcaa   31740
acatcaggcc ccctcaccac caccgatagc agtaccctta ctatcactgc ctcacccccct   31800 ctaactactg ccactggtag cttgggcatt gacttgaaag agcccatttta tacacaaaat   31860 ggaaaactag gactaagta cggggctcct ttgcatgtaa cagacgacct aaacactttg   31920
accgtagcaa ctggtccagg tgtgactatt aataatactt ccttgcaaac taaagttact   31980
ggagccttgg gttttgattc acaaggcaat atgcaactta atgtagcagg aggactaagg   32040
attgattctc aaaacagacg ccttatactt gatgttagtt atccgtttga tgctcaaaac   32100
caactaaatc taagactagg acagggcct ctttttataa actcagccca caacttggat   32160
attaactaca acaaaggcct ttacttgttt acagcttcaa acaattccaa aaagcttgag   32220
gttaacctaa gcactgccaa ggggttgatg tttgacgcta cagccatagc cattaatgca   32280
ggagatgggc ttgaatttgg ttcacctaat gcaccaaaca caaatcccct caaaacaaaa   32340
attggccatg gcctagaatt tgattcaaac aaggctatgg ttcctaaact aggaactggc   32400
cttagttttg acagcacagg tgccattaca gtaggaaaca aaaataatga taagctaact   32460
ttgtggacca caccagctcc atctcctaac tgtagactaa atgcagagaa agatgctaaa   32520
ctcactttgg tcttaacaaa atgtggcagt caaatacttg ctacagtttc agttttggct   32580
gttaaaggca gtttggctcc aatatctgga acagttcaaa gtgctcatct tattataaga   32640
tttgacgaaa atggagtgct actaaacaat tccttcctgg acccagaata ttggaacttt   32700
agaaatggag atcttactga aggcacagcc tatacaaacg ctgttggatt tatgcctaac   32760
ctatcagctt atccaaaatc tcacggtaaa actgccaaaa gtaacattgt cagtcaagtt   32820
tacttaaacg gagacaaaac taaacctgta acactaacca ttacactaaa cggtacacag   32880
gaaacaggag acacaactcc aagtgcatac tctatgtcat tttcatggga ctggtctggc   32940
cacaactaca ttaatgaaat atttgccaca tcctcttaca cttttttcata cattgcccaa   33000 gaataaagaa tcgtttgtgt tatgttcaa cgtgtttatt tttcaattgc agaaaatttc   33060
```

```
aagtcatttt tcattcagta gtatagcccc accaccacat agcttataca gatcaccgta    33120
ccttaatcaa actcacagaa ccctagtatt caacctgcca cctccctccc aacacacaga    33180
gtacacagtc ctttctcccc ggctggcctt aaaaagcatc atatcatggg taacagacat    33240
attcttaggt gttatattcc acacggtttc ctgtcgagcc aaacgctcat cagtgatatt    33300
aataaactcc ccgggcagct cacttaagtt catgtcgctg tccagctgct gagccacagg    33360
ctgctgtcca acttgcggtt gcttaacggg cggcgaagga gaagtccacg cctacatggg    33420
ggtagagtca taatcgtgca tcaggatagg gcggtggtgc tgcagcagcg cgcgaataaa    33480
ctgctgccgc cgccgctccg tcctgcagga atacaacatg gcagtggtct cctcagcgat    33540
gattcgcacc gcccgcagca taaggcgcct tgtcctccgg gcacagcagc gcaccctgat    33600
ctcacttaaa tcagcacagt aactgcagca cagcaccaca atattgttca aaatcccaca    33660
gtgcaaggcg ctgtatccaa agctcatggc ggggaccaca gaacccacgt ggccatcata    33720
ccacaagcgc aggtagatta agtggcgacc cctcataaac acgctggaca taaacattac    33780
ctcttttggc atgttgtaat tcaccactcc ccggtaccat ataaacctct gattaaacat    33840
ggcgccatcc accaccatcc taaaccagct ggccaaaacc tgcccgccgg ctatacactg    33900
cagggaaccg ggactggaac aatgacagtg gagagcccag gactcgtaac catggatcat    33960
catgctcgtc atgatatcaa tgttggcaca acacaggcac acgtgcatac acttcctcag    34020
gattacaagc tcctcccgcg ttagaaccat atcccaggga acaacccatt cctgaatcag    34080
cgtaaatccc acactgcagg gaagacctcg cacgtaactc acgttgtgca ttgtcaaagt    34140
gttacattcg ggcagcagcg gatgatcctc cagtatggta gcgcgggttt ctgtctcaaa    34200
aggaggtaga cgatccctac tgtacggagt gcgccgagac aaccgagatc gtgttggtcg    34260
tagtgtcatg ccaaatggaa cgccggacgt agtcatattt cctgaagcaa aaccaggtgc    34320
gggcgtgaca aacagatctg cgtctccggt ctcgccgctt agatcgctct gtgtagtagt    34380
tgtagtatat ccactctctc aaagcatcca ggcgcccct ggcttcgggt tctatgtaaa    34440
ctccttcatg cgccgctgcc ctgataacat ccaccaccgc agaataagcc acacccagcc    34500
aacctacaca ttcgttctgc gagtcacaca cgggaggagc gggaagagct ggaagaacca    34560
tgtttttttt tttattccaa aagattatcc aaaacctcaa aatgaagatc tattaagtga    34620
acgcgctccc ctccggtggc gtggtcaaac tctacagcca aagaacagat aatggcatt    34680 gtaagatgtt gcacaatggc ttccaaaagg caaacggccc tcacgtccaa gtggacgtaa    34740
aggctaaacc cttcagggtg aatctcctct ataaacattc cagcaccttc aaccatgccc    34800
aaataattct catctcgcca ccttctcaat atatctctaa gcaaatcccg aatattaagt    34860
ccggccattg taaaaatctg ctccagagcg ccctccacct tcagcctcaa gcagcgaatc    34920
atgattgcaa aaattcaggt tcctcacaga cctgtataag attcaaaagc ggaacattaa    34980
caaaaatacc gcgatcccgt aggtcccttc gcagggccag ctgaacataa tcgtgcaggt    35040
ctgcacggac cagcgcggcc acttccccgc caggaacctt gacaaagaa cccacactga    35100 ttatgacacg catactcgga gctatgctaa ccagcgtagc cccgatgtaa gctttgttgc    35160
atgggcggcg atataaaatg caaggtgctg ctcaaaaaat caggcaaagc ctcgcgcaaa    35220
aaagaaagca catcgtagtc atgctcatgc agataaaggc aggtaagctc cggaaccacc    35280
acagaaaaag acaccatttt tctctcaaac atgtctgcgg gtttctgcat aaacacaaaa    35340
taaaataaca aaaaaacatt taaacattag aagcctgtct tacaacagga aaacaaccc    35400 ttataagcat aagacggact acggccatgc cggcgtgacc gtaaaaaaac tggtcaccgt    35460
```

```
gattaaaaag caccaccgac agctcctcgg tcatgtccgg agtcataatg taagactcgg   35520
taaacacatc aggttgattc atcggtcagt gctaaaaagc gaccgaaata gcccggggga   35580
atacataccc gcaggcgtag agacaacatt acagccccca taggaggtat aacaaaatta   35640
ataggagaga aaaacacata aacacctgaa aaaccctcct gcctaggcaa aatagcaccc   35700
tcccgctcca gaacaacata cagcgcttca cagcggcagc ctaacagtca gccttaccag   35760
taaaaaagaa aacctattaa aaaaacacca ctcgacacgg caccagctca atcagtcaca   35820
gtgtaaaaaa gggccaagtg cagagcgagt atatatagga ctaaaaatg acgtaacggt    35880 taaagtccac aaaaaacacc cagaaaaccg cacgcgaacc tacgcccaga acgaaagcc    35940 aaaaaaccca caacttcctc aaatcgtcac ttccgttttc ccacgttacg taacttccca   36000
ttttaagaaa actacaattc ccaacacata caagttactc cgccctaaaa cctacgtcac   36060 ccgcccgtt cccacgcccc gcgccacgtc acaaactcca ccccctcatt atcatattgg    36120
cttcaatcca aaataaggta tattattgat gatg                              36154

<210> SEQ ID NO 10
<211> LENGTH: 103
<212> TYPE: DNA
<213> ORGANISM: Artificial Sequence
<220> FEATURE:
<223> OTHER INFORMATION: Synthetic

<400> SEQUENCE: 10
catcatcaat aatataccrt attttggatt gaagccaata tgataatgag ggggtggagt    60
ttgtgacgtg gcgcggggcg tgggaacggg gcgggtgacg tag                     103

<210> SEQ ID NO 11
<211> LENGTH: 73
<212> TYPE: DNA
<213> ORGANISM: Artificial Sequence
<220> FEATURE:
<223> OTHER INFORMATION: Synthetic

<400> SEQUENCE: 11
catcatcaat aatataccrt attttggatt gaagccaata tgataatgag ggggtggagt    60
ttgtgacgtg gcg                                                      73

<210> SEQ ID NO 12
<211> LENGTH: 2989
<212> TYPE: DNA
<213> ORGANISM: Artificial Sequence
<220> FEATURE:
<223> OTHER INFORMATION: Synthetic

<400> SEQUENCE: 12
ctaaattgta agcgttaata ttttgttaaa attcgcgtta aattttgtt aaatcagctc     60 attttttaac caataggccg aaatcggcaa atcccttat aaatcaaaag aatagaccga   120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttgggt cgaggtgccg taaagcacta atcggaacc ctaaagggag       300 ccccgattt agagcttgac ggggaaagcc ggcgaacgtg gcgagaaagg aagggaagaa     360
agcgaaagga gcgggcgcta gggcgctgg aagtgtagcg gtcacgctgc gcgtaaccac     420
cacacccgcc gcgcttaatg cgccgctaca gggcgcgtcc cattcgccat tcaggctgcg    480
```

```
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagcttac    660
gtattaatta aggcgccgcg gtggcggccg ctctagaact agtggatccc ccgggctgca    720
ggaattcggc cgcctaggcc acgcgtaagc ttatcgatac cgtcgacctc gaggggggc     780
ccggtaccca gcttttgttc cctttagtga gggttaattg cgcgcttggc gtaatcatgg    840
tcatagctgt ttcctgtgtg aaattgttat ccgctcacaa ttccacacaa catacgagcc    900
ggaagcataa agtgtaaagc ctggggtgcc taatgagtga gctaactcac attaattgcg    960
ttgcgctcac tgcccgcttt ccagtcggga acctgtcgt gccagctgca ttaatgaatc    1020
ggccaacgcg cggggagagg cggtttgcgt attgggcgct cttccgcttc ctcgctcact   1080
gactcgctgc gctcggtcgt tcggctgcgg cgagcggtat cagctcactc aaaggcggta   1140
atacggttat ccacagaatc agggataac gcaggaaaga acatgtgagc aaaaggccag    1200
caaaaggcca ggaaccgtaa aaaggccgcg ttgctggcgt ttttccatag gctccgcccc   1260
cctgacgagc atcacaaaaa tcgacgctca agtcagaggt ggcgaaaccc gacaggacta   1320
taaagatacc aggcgtttcc ccctggaagc tccctcgtgc gctctcctgt tccgaccctg   1380
ccgcttaccg gatacctgtc cgcctttctc ccttcgggaa gcgtggcgct ttctcatagc   1440
tcacgctgta ggtatctcag ttcggtgtag tcgttcgct ccaagctggg ctgtgtgcac   1500
gaaccccccg ttcagcccga ccgctgcgcc ttatccggta actatcgtct tgagtccaac   1560
ccggtaagac acgacttatc gccactggca gcagccactg gtaacaggat tagcagagcg   1620
aggtatgtag gcggtgctac agagttcttg aagtggtggc ctaactacgg ctacactaga   1680
aggacagtat ttggtatctg cgctctgctg aagccagtta ccttcggaaa aagagttggt   1740
agctcttgat ccggcaaaca aaccaccgct ggtagcggtg gttttttgt ttgcaagcag   1800
cagattacgc gcagaaaaaa aggatctcaa gaagatcctt tgatcttttc tacgggtct    1860
gacgctcagt ggaacgaaaa ctcacgttaa gggattttgg tcatgagatt atcaaaaagg   1920
atcttcacct agatcctttt aaattaaaaa tgaagtttta atcaatcta aagtatatat    1980
gagtaaactt ggtctgacag ttaccaatgc ttaatcagtg aggcacctat ctcagcgatc   2040
tgtctatttc gttcatccat agttgcctga ctccccgtcg tgtagataac tacgatacgg   2100
gagggcttac catctggccc cagtgctgca atgataccgc gagacccacg ctcaccggct   2160
ccagatttat cagcaataaa ccagccagcc ggaagggccg agcgcagaag tggtcctgca   2220
actttatccg cctccatcca gtctattaat tgttgccggg aagctagagt aagtagttcg   2280
ccagttaata gtttgcgcaa cgttgttgcc attgctacag gcatcgtggt gtcacgctcg   2340
tcgtttggta tggcttcatt cagctccggt tcccaacgat caaggcgagt tacatgatcc   2400
cccatgttgt gcaaaaaagc ggttagctcc ttcggtcctc cgatcgttgt cagaagtaag   2460
ttggccgcag tgttatcact catggttatg gcagcactgc ataattctct tactgtcatg   2520
ccatccgtaa gatgcttttc tgtgactggt gagtactcaa ccaagtcatt ctgagaatag   2580
tgtatgcggc gaccgagttg ctcttgcccg gcgtcaatac gggataatac cgcgccacat   2640
agcagaactt taaaagtgct catcattgga aaacgttctt cggggcgaaa actctcaagg   2700
atcttaccgc tgttgagatc cagttcgatg taacccactc gtgcacccaa ctgatcttca   2760
gcatctttta ctttcaccag cgtttctggg tgagcaaaaa caggaaggca aaatgccgca   2820
aaaaagggaa taagggcgac acggaaatgt tgaatactca tactcttcct ttttcaatat   2880
```

```
tattgaagca tttatcaggg ttattgtctc atgagcggat acatatttga atgtatttag   2940
aaaaataaac aaatagggt tccgcgcaca tttccccgaa aagtgccac                2989

<210> SEQ ID NO 13
<211> LENGTH: 38041
<212> TYPE: DNA
<213> ORGANISM: Artificial Sequence
<220> FEATURE:
<223> OTHER INFORMATION: Synthetic

<400> SEQUENCE: 13
ctaaattgta agcgttaata ttttgttaaa attcggccgg ccatcatcaa taatatacct     60 tatttttggat tgaagccaat atgataatga gggggtggag tttgtgacgt ggcgcggggc   120
gtgggaacgg ggcgggtgac gtagtagtgt ggcggaagtg tgatgttgca agtgtggcgg   180
aacacatgta taacttcgta taatgtatgc tatacgaagt tatacatgta agcgacggat   240
gtggcaaaag tgacgttttt ggtgtgcgcc ggtgtacaca ggaagtgaca attttcgcgc   300
ggttttaggc ggatgttgta gtaaatttgg gcgtaaccga gtaagatttg gccattttcg   360
cgggaaaact gaataagagg aagtgaaatc tgaataattt tgtgttactc atagcgcgta   420
atatttgtct agggagatct ataacttcgt ataatgtatg ctatacgaag ttattaccga   480
agaaatggct cgagatctgg aaggtgctga ggtacgatga gacccgcacc aggtgcagac   540
cctgcgagtg tggcggtaaa catattagga accagcctgt gatgctggat gtgaccgagg   600
agctgaggcc cgatcacttg gtgctggcct gcacccgcgc tgagtttggc tctagcgatg   660
aagatacaga ttgaggtact gaaatgtgtg ggcgtggctt aagggtggga agaatatat   720 aaggtggggg tcttatgtag ttttgtatct gttttgcagc agccgccgcc gccatgagca   780
ccaactcgtt tgatggaagc attgtgagct catatttgac aacgcgcatg cccccatggg   840
ccggggtgcg tcagaatgtg atgggctcca gcattgatgg tcgccccgtc ctgcccgcaa   900
actctactac cttgacctac gagaccgtgt ctggaacgcc gttggagact gcagcctccg   960
ccgccgcttc agccgctgca gccaccgccc gcgggattgt gactgacttt gctttcctga  1020
gcccgcttgc aagcagtgca gcttcccgtt catccgcccg cgatgacaag ttgacggctc  1080
ttttggcaca attggattct ttgacccggg aacttaatgt cgtttctcag cagctgttgg  1140
atctgcgcca gcaggtttct gccctgaagg cttcctcccc tcccaatgcg gtttaaaaca  1200
taaataaaaa accagactct gtttggattt ggatcaagca agtgtcttgc tgtctttatt  1260 tagggggtttt gcgcgcgcgg taggcccggg accagcggtc tcggtcgttg agggtcctgt  1320 gtatttttttc caggacgtgg taaaggtgac tctggatgtt cagatacatg gcataagcc   1380 cgtctctggg gtggaggtag caccactgca gagcttcatg ctgcggggtg gtgttgtaga  1440
tgatccagtc gtagcaggag cgctgggcgt ggtgcctaaa aatgtctttc agtagcaagc  1500
tgattgccag gggcaggccc ttggtgtaag tgtttacaaa gcggttaagc tgggatgggt  1560
gcatacgtgg ggatatgaga tgcatcttgg actgtatttt taggttggct atgttcccag  1620
ccatatccct ccggggattc atgttgtgca gaaccaccag cacagtgtat ccggtgcact  1680
tgggaaattt gtcatgtagc ttagaaggaa atgcgtggaa gaacttggag acgcccttgt  1740
gacctccaag attttccatg cattcgtcca taatgatggc aatgggccca cgggcggcgg  1800
cctgggcgaa gatatttctg ggatcactaa cgtcatagtt gtgttccagg atgagatcgt  1860
cataggccat ttttacaaag cgcgggcgga gggtgccaga ctgcggtata atggttccat  1920
```

```
ccggcccagg ggcgtagtta ccctcacaga tttgcatttc ccacgctttg agttcagatg    1980
gggggatcat gtctacctgc ggggcgatga agaaaacggt ttccgggta ggggagatca     2040 gctgggaaga aagcaggttc ctgagcagct gcgacttacc gcagccggtg ggcccgtaaa    2100
tcacacctat taccgggtgc aactggtagt taagagagct gcagctgccg tcatccctga    2160 gcagggggc cacttcgtta agcatgtccc tgactcgcat gttttccctg accaaatccg     2220
ccagaaggcg ctcgccgccc agcgatagca gttcttgcaa ggaagcaaag ttttcaacg     2280 gtttgagacc gtccgccgta ggcatgcttt tgagcgtttg accaagcagt ccaggcggt    2340 cccacagctc ggtcacctgc tctacggcat ctcgatccag catatctcct cgtttcgcgg    2400 gttgggcgg ctttcgctgt acggcagtag tcggtgctcg tccagacggg ccagggtcat    2460
gtctttccac gggcgcaggg tcctcgtcag cgtagtctgg gtcacggtga aggggtgcgc    2520
tccgggctgc gcgctggcca gggtgcgctt gaggctggtc ctgctggtgc tgaagcgctg    2580
ccggtcttcg ccctgcgcgt cggccaggta gcatttgacc atggtgtcat agtccagccc    2640
ctccgcggcg tggcccttgg cgcgcagctt gcccttggag gaggcgccgc acgagggca    2700 gtgcagactt tgagggcgt agagcttggg cgcgagaaat accgattccg gggagtaggc     2760
atccgcgccg caggccccgc agacggtctc gcattccacg agccaggtga gctctggccg    2820
ttcggggtca aaaaccaggt ttccccatg cttttgatg cgtttcttac ctctggtttc      2880
catgagccgg tgtccacgct cggtgacgaa aaggctgtcc gtgtcccgt atacagactt    2940 gagaggcctg tcctcgagcg tgttccgcg gtcctcctcg tatagaaact cggaccactc     3000
tgagacaaag gctcgcgtcc aggccagcac gaaggaggct aagtgggagg ggtagcggtc    3060
gttgtccact aggggtcca ctcgctccag ggtgtgaaga cacatgtcgc cctcttcggc     3120
atcaaggaag gtgattggtt tgtaggtgta ggccacgtga ccgggtgttc ctgaagggg     3180 gctataaag ggggtgggg gcgttcgtc ctcactctct tccgcatcgc tgtctgcgag       3240
ggccagctgt tggggtgagt actccctctg aaaagcgggc atgacttctg cgctaagatt    3300
gtcagttccc aaaaacgagg aggatttgat attcacctgg cccgcggtga tgcctttgag    3360
ggtggccgca tccatctggt cagaaaagac aatcttttg ttgtcaagct tggtggcaaa    3420
cgacccgtag agggcgttgg acagcaactt ggcgatggag cgcagggttt ggttttgtc     3480 gcgatcggcg cgctccttgg ccgcgatgtt tagctgcacg tattcgcgcg caacgcaccg    3540
ccattcggga aagacggtgg tgcgctcgtc gggcaccagg tgcacgcgcc aaccgcggtt    3600
gtgcagggtg acaaggtcaa cgctggtggc tacctctccg cgtaggcgct cgttggtcca    3660
gcagaggcgg ccgcccttgc gcgagcagaa tggcggtagg gggtctagct gcgtctcgtc    3720
cggggggtct gcgtccacgg taaagacccc gggcagcagg cgcgcgtcga agtagtctat    3780
cttgcatcct tgcaagtcta gcgcctgctg ccatgcgcgg gcgcaagcg cgcgctcgta     3840 tgggttgagt gggggacccc atggcatggg gtgggtgagc gcggaggcgt acatgccgca    3900
aatgtcgtaa acgtagaggg gctctctgag tattccaaga tatgtagggt agcatcttcc    3960
accgcggatg ctggcgcgca cgtaatcgta tagttcgtgc gagggagcga ggaggtcggg    4020
accgaggttg ctacgggcgg gctgctctgc tcggaagact atctgcctga agatggcatg    4080
tgagttggat gatatggttg gacgctggaa gacgttgaag ctggcgtctg tgagacctac    4140
cgcgtcacgc acgaaggagg cgtaggagtc gcgcagcttg ttgaccagct cggcggtgac    4200
ctgcacgtct agggcgcagt agtccagggt ttccttgatg atgtcatact tatcctgtcc    4260
cttttttttc cacagctcgc ggttgaggac aaactcttcg cggtctttcc agtactcttg    4320
```

```
gatcggaaac ccgtcggcct ccgaacggta agagcctagc atgtagaact ggttgacggc   4380
ctggtaggcg cagcatccct tttctacggg tagcgcgtat gcctgcgcgg ccttccggag   4440
cgaggtgtgg gtgagcgcaa aggtgtccct gaccatgact ttgaggtact ggtatttgaa   4500
gtcagtgtcg tcgcatccgc cctgctccca gagcaaaaag tccgtgcgct ttttggaacg   4560
cggatttggc agggcgaagg tgacatcgtt gaagagtatc tttcccgcgc gaggcataaa   4620
gttgcgtgtg atgcgaagg gtcccggcac ctcggaacgg ttgttaatta cctgggcggc   4680
gagcacgatc tcgtcaaagc cgttgatgtt gtgcccaca atgtaaagtt ccaagaagcg   4740
cgggatgccc ttgatggaag gcaattttt aagttcctcg taggtgagct cttcagggga   4800
gctgagcccg tgctctgaaa gggcccagtc tgcaagatga gggttggaag cgacgaatga   4860
gctccacagg tcacgggcca ttagcatttg caggtggtcg cgaaaggtcc taaactggcg   4920
acctatggcc atttttctg gggtgatgca gtagaaggta agcgggtctt gttcccagcg   4980
gtcccatcca aggttcgcgg ctaggtctcg cgcggcagtc actagaggct catctccgcc   5040
gaacttcatg accagcatga agggcacgag ctgcttccca aaggccccca tccaagtata   5100
ggtctctaca tcgtaggtga caaagagacg ctcggtgcga ggatgcgagc cgatcgggaa   5160
gaactggatc tcccgccacc aattggagga gtggctattg atgtggtgaa agtagaagtc   5220
cctgcgacgg gccgaacact cgtgctggct tttgtaaaaa cgtgcgcagt actggcagcg   5280
gtgcacgggc tgtacatcct gcacgaggtt gacctgacga ccgcgcacaa ggaagcagag   5340
tgggaatttg agcccctcgc ctggcggtt tggctggtgg tcttctactt cggctgcttg   5400
tccttgaccg tctggctgct cgaggggagt tacggtggat cggaccacca cgccgcgcga   5460
gcccaaagtc cagatgtccg cgcgcggcg tcggagcttg atgacaacat cgcgcagatg   5520
ggagctgtcc atggtctgga gctcccgcgg cgtcaggtca ggcgggagct cctgcaggtt   5580
tacctcgcat agacgggtca gggcgcgggc tagatccagg tgataccta tttccagggg   5640 ctggttggtg gcggcgtcga tggcttgcaa gaggccgcat ccccgcggcg cgactacggt   5700
accgcgcggc gggcggtggg ccgcgggggt gtccttggat gatgcatcta aaagcggtga   5760
cgcgggcgag cccccggagg tagggggggc tccggacccg ccgggagagg gggcaggggc   5820
acgtcggcgc cgcgcgcggg caggagctgg tgctgcgcgc gtaggttgct ggcgaacgcg   5880
acgacgcggc ggttgatctc ctgaatctgg cgcctctgcg tgaagacgac gggcccggtg   5940
agcttgagcc tgaaagagag ttcgacagaa tcaatttcgg tgtcgttgac ggcggcctgg   6000
cgcaaaatct cctgcacgtc tcctgagttg tcttgatagg cgatctcggc catgaactgc   6060
tcgatctctt cctcctggag atctccgcgt ccggctcgct ccacggtggc ggcgaggtcg   6120
ttggaaatgc gggccatgag ctgcgagaag gcgttgaggc ctccctcgtt ccagacgcgg   6180
ctgtagacca cgccccttc ggcatcgcgg gcgcgcatga ccacctgcgc gagattgagc   6240
tccacgtgcc gggcgaagac ggcgtagttt cgcaggcgct gaaagaggta gttgagggtg   6300
gtggcggtgt gttctgccac gaagaagtac ataacccagc gtcgcaacgt ggattcgttg   6360
atatccccca aggcctcaag gcgctccatg gcctcgtaga agtccacggc gaagttgaaa   6420
aactgggagt tgcgcgccga cacggttaac tcctcctcca gaagacggat gagctcggcg   6480
acagtgtcgc gcacctcgcg ctcaaaggct acaggggcct cttcttcttc ttcaatctcc   6540
tcttccataa gggcctcccc ttcttcttct tctggcggcg gtggggagg ggggacacgg   6600 cggcgacgac ggcgcaccgg gaggcggtcg acaaagcgct cgatcatctc cccgcggcga   6660
```

```
cggcgcatgg tctcggtgac ggcgcggccg ttctcgcggg ggcgcagttg gaagacgccg    6720
cccgtcatgt cccggttatg ggttggcggg gggctgccat gcggcaggga tacggcgcta    6780
acgatgcatc tcaacaattg ttgtgtaggt actccgccgc cgagggacct gagcgagtcc    6840
gcatcgaccg gatcggaaaa cctctcgaga aaggcgtcta accagtcaca gtcgcaaggt    6900
aggctgagca ccgtggcggg cggcagcggg cggcggtcgg ggttgtttct ggcggaggtg    6960
ctgctgatga tgtaattaaa gtaggcggtc ttgagacggc ggatggtcga cagaagcacc    7020
atgtccttgg gtccggcctg ctgaatgcgc aggcggtcgg ccatgcccca ggcttcgttt    7080
tgacatcggc gcaggtcttt gtagtagtct tgcatgagcc tttctaccgg cacttcttct    7140
tctccttcct cttgtcctgc atctcttgca tctatcgctg cggcggcggc ggagtttggc    7200
cgtaggtggc gccctcttcc tcccatgcgt gtgaccccga agcccctcat cggctgaagc    7260
agggctaggt cggcgacaac gcgctcggct aatatggcct gctgcacctg cgtgagggta    7320
gactggaagt catccatgtc cacaaagcgg tggtatgcgc ccgtgttgat ggtgtaagtg    7380
cagttggcca taacggacca gttaacgtc tggtgacccg gctgcgagag ctcggtgtac    7440
ctgagacgcg agtaagccct cgagtcaaat acgtagtcgt tgcaagtccg caccaggtac    7500
tggtatccca ccaaaaagtg cggcggcggc tggcggtaga ggggcagcg tagggtggcc    7560 ggggctccgg gggcgagatc ttccaacata aggcgatgat atccgtagat gtacctggac    7620
atccaggtga tgccggcggc ggtggtggag gcgcgcggaa agtcgcggac gcggttccag    7680
atgttgcgca gcggcaaaaa gtgctccatg gtcgggacgc tctggccggt caggcgcgcg    7740
caatcgttga cgctctaccg tgcaaaagga gagcctgtaa gcgggcactc ttccgtggtc    7800
tggtggataa attcgcaagg gtatcatggc ggacgaccgg ggttcgagcc ccgtatccgg    7860
ccgtccgccg tgatccatgc ggttaccgcc gcgtgtcga acccaggtgt gcgacgtcag    7920
acaacggggg agtgctcctt ttggcttcct tccaggcgcg gcggctgctg cgctagcttt    7980
tttggccact ggccgcgcgc agcgtaagcg gttaggctgg aaagcgaaag cattaagtgg    8040
ctcgctccct gtagccggag ggttatttttc caagggttga gtcgcgggac ccccggttcg    8100
agtctcggac cggccggact gcggcgaacg ggggtttgcc tccccgtcat gcaagacccc    8160
gcttgcaaat tcctccggaa acagggacga gccccttttt tgcttttccc agatgcatcc    8220
ggtgctgcgg cagatgcgcc cccctcctca gcagcggcaa gagcaagagc agcggcagac    8280
atgcagggca ccctcccctc ctcctaccgc gtcaggaggg gcgacatccg cggttgacgc    8340
ggcagcagat ggtgattacg aaccccccgcg gcgccgggcc cggcactacc tggacttgga    8400
ggagggcgag ggcctggcgc ggctaggagc gccctctcct gagcggtacc caagggtgca    8460
gctgaagcgt gatacgcgtg aggcgtacgt gccgcggcag aacctgtttc gcgaccgcga    8520
gggagaggag cccgaggaga tgcgggatcg aaagttccac gcagggcgcg agctgcggca    8580
tggcctgaat cgcgagcggt tgctgcgcga ggaggacttt gagcccgacg cgcgaaccgg    8640
gattagtccc gcgcgcgcac acgtggcggc cgccgacctg gtaaccgcat acgagcagac    8700
ggtgaaccag gagattaact ttcaaaaaag ctttaacaac cacgtgcgta cgcttgtggc    8760
gcgcgaggag gtggctatag gactgatgca tctgtgggac tttgtaagcg cgctggagca    8820
aaacccaaat agcaagccgc tcatggcgca gctgttcctt atagtgcagc acagcaggga    8880
caacgaggca ttcagggatg cgctgctaaa catagtagag cccgagggcc gctggctgct    8940
cgatttgata aacatcctgc agagcatagt ggtgcaggag cgcagcttga gcctggctga    9000
caaggtggcc gccatcaact attccatgct tagcctgggc aagttttacg cccgcaagat    9060
```

```
ataccatacc ccttacgttc ccatagacaa ggaggtaaag atcgagggt  tctacatgcg   9120
catggcgctg aaggtgctta ccttgagcga cgacctgggc gtttatcgca acgagcgcat   9180
ccacaaggcc gtgagcgtga gccggcggcg cgagctcagc gaccgcgagc tgatgcacag   9240
cctgcaaagg gccctggctg cacgggcag  cggcgataga gaggccgagt cctactttga   9300
cgcgggcgct gacctgcgct gggccccaag ccgacgcgcc ctggaggcag ctggggccgg   9360
acctgggctg gcggtggcac ccgcgcgcgc tggcaacgtc ggcggcgtgg aggaatatga   9420
cgaggacgat gagtacgagc cagaggacgg cgagtactaa gcggtgatgt ttctgatcag   9480
atgatgcaag acgcaacgga cccggcgtg  cgggcggcgc tgcagagcca gccgtccggc   9540
cttaactcca cggacgactg gcgccaggtc atggaccgca tcatgtcgct gactgcgcgc   9600
aatcctgacg cgttccggca gcagccgcag gccaaccggc tctccgcaat tctggaagcg   9660
gtggtcccgg cgcgcgcaaa ccccacgcac gagaaggtgc tggcgatcgt aaacgcgctg   9720
gccgaaaaca gggccatccg gcccgacgaa gccggcctgg tctacgacgc gctgcttcag   9780
cgcgtggctc gttacaacag cggcaacgtg cagaccaacc tggaccggct ggtggggat   9840
gtgcgcgagg ccgtggcgca gcgtgagcgc gcgcagcagc agggcaaccct gggctccatg   9900
gttgcactaa acgccttcct gagtacacag cccgccaacg tgccgcgggg acaggaggac   9960
tacaccaact ttgtgagcgc actgcggcta atggtgactg agacaccgca aagtgaggtg  10020
taccagtctg ggccagacta ttttttccag accagtagac aaggcctgca gaccgtaaac  10080
ctgagccagg ctttcaaaaa cttgcagggg ctgtgggggg tgcgggctcc cacaggcgac  10140
cgcgcgaccg tgtctagctt gctgacgccc aactcgcgcc tgttgctgct gctaatagcg  10200
cccttcacgg acagtggcag cgtgtcccgg gacacatacc taggtcactt gctgacactg  10260
taccgcgagg ccataggtca ggcgcatgtg gacgagcata ctttccagga gattacaagt  10320
gtcagccgcg cgctggggca ggaggacacg ggcagcctgg aggcaaccct aaactacctg  10380
ctgaccaacc ggcggcagaa gatccccctg ttgcacagtt taaacagcga ggaggagcgc  10440
attttgcgct acgtgcagca gagcgtgagc cttaacctga tgcgcgacgg ggtaacgccc  10500
agcgtggcgc tggacatgac cgcgcgcaac atggaaccgg gcatgtatgc ctcaaaccgg  10560
ccgtttatca accgcctaat ggactacttg catcgcgcgg ccgccgtgaa ccccgagtat  10620
ttcaccaatg ccatcttgaa cccgcactgg ctaccgcccc ctggttccta caccggggga  10680
ttcgaggtgc ccgagggtaa cgatggattc ctctgggacg acatagacga cagcgtgttt  10740
tcccccgcaac cgcagaccct gctagagttg caacagcgcg agcaggcaga ggcggcgctg  10800
cgaaaggaaa gcttccgcag gccaagcagc ttgtccgatc taggcgctgc ggccccgcgg  10860
tcagatgcta gtagcccatt tccaagcttg ataggtctc ttaccagcac tcgcaccacc  10920
cgcccgcgcc tgctgggcga ggaggagtac ctaaacaact cgctgctgca gccgcagcgc  10980
gaaaaaaacc tgcctccggc atttcccaac aacgggatag agagcctagt ggacaagatg  11040
agtagatgga agacgtacgc gcaggagcac agggacgtgc caggcccgcg cccgcccacc  11100
cgtcgtcaaa ggcacgaccg tcagcggggt ctggtgtggg aggacgatga ctcggcagac  11160
gacagcagcg tcctggattt gggagggagt ggcaacccgt ttgcgcacct tcgccccagg  11220
ctggggagaa tgttttaaaa aaaaaaagc  atgatgcaaa ataaaaaact caccaaggcc  11280
atggcaccga gcgttggttt tcttgtattc cccttagtat gcggcgcgcg gcgatgtatg  11340
aggaaggtcc tcctccctcc tacgagagtg tggtgagcgc ggcgccagtg gcggcggcgc  11400
```

```
tgggttctcc cttcgatgct cccctggacc cgccgtttgt gcctccgcgg tacctgcggc    11460
ctaccggggg gagaaacagc atccgttact ctgagttggc acccctattc gacaccaccc    11520
gtgtgtacct ggtggacaac aagtcaacgg atgtggcatc cctgaactac agaacgacc     11580 acagcaactt tctgaccacg gtcattcaaa acaatgacta cagcccgggg gaggcaagca    11640
cacagaccat caatcttgac gaccggtcgc actggggcgg cgacctgaaa accatcctgc    11700
ataccaacat gccaaatgtg aacgagttca tgtttaccaa taagtttaag gcgcgggtga    11760
tggtgtcgcg cttgcctact aaggacaatc aggtggagct gaaatacgag tgggtggagt    11820
tcacgctgcc cgagggcaac tactccgaga ccatgaccat agaccttatg aacaacgcga    11880
tcgtggagca ctacttgaaa gtgggcagac agaacggggt tctggaaagc gacatcgggg    11940
taaagtttga cacccgcaac ttcagactgg ggtttgaccc cgtcactggt cttgtcatgc    12000
ctggggtata tacaaacgaa gccttccatc cagacatcat tttgctgcca ggatgcgggg    12060
tggacttcac ccacagccgc ctgagcaact tgttgggcat ccgcaagcgg caaccccttcc   12120 aggagggctt taggatcacc tacgatgatc tggagggtgg taacattccc gcactgttgg    12180
atgtggacgc ctaccaggcg agcttgaaag atgacaccga acagggcggg ggtggcgcag    12240
gcggcagcaa cagcagtggc agcggcgcgg aagagaactc caacgcggca gccgcggcaa    12300
tgcagccggt ggaggacatg aacgatcatg ccattcgcgg cgacaccttt gccacacggg    12360
ctgaggagaa gcgcgctgag gccgaagcag cggccgaagc tgccgccccc gctgcgcaac    12420
ccgaggtcga gaagcctcag aagaaaccgg tgatcaaacc cctgacagag gacagcaaga    12480
aacgcagtta caacctaata agcaatgaca gcaccttcac ccagtaccgc agctggtacc    12540
ttgcatacaa ctacggcgac cctcagaccg gaatccgctc atggaccctg ctttgcactc    12600
ctgacgtaac ctgcggctcg gagcaggtct actggtcgtt gccagacatg atgcaagacc    12660
ccgtgacctt ccgctccacg cgccagatca gcaactttcc ggtggtgggc gccgagctgt    12720
tgcccgtgca ctccaagagc ttctacaacg accaggccgt ctactcccaa ctcatccgcc    12780
agtttacctc tctgacccac gtgttcaatc gctttcccga aaccagatt ttggcgcgcc     12840 cgccagcccc caccatcacc accgtcagtg aaaacgttcc tgctctcaca gatcacggga    12900
cgctaccgct gcgcaacagc atcggaggag tccagcgagt gaccattact gacgccagac    12960
gccgcacctg cccctacgtt tacaaggccc tgggcatagt ctcgccgcgc gtcctatcga    13020
gccgcacttt ttgagcaagc atgtccatcc ttatatcgcc cagcaataac acaggctggg    13080
gcctgcgctt cccaagcaag atgtttggcg gggccaagaa gcgctccgac caacacccag    13140
tgcgcgtgcg cgggcactac cgcgcgccct ggggcgcgca caaacgcggc cgcactgggc    13200
gcaccaccgt cgatgacgcc atcgacgcgg tggtggagga ggcgcgcaac tacacgcccg    13260
cgccgccacc agtgtccaca gtggacgcgg ccattcagac cgtggtgcgc ggagcccggc    13320
gctatgctaa aatgaagaga cggcggaggc gcgtagcacg tcgccaccgc cgccgacccg    13380
gcactgccgc ccaacgcgcg gcggcggccc tgcttaaccg cgcacgtcgc accggccgac    13440
gggcggccat gcgggccgct cgaaggctgg ccgcgggtat tgtcactgtg ccccccaggt    13500
ccaggcgacg agcggccgcc gcagcagccg cggccattag tgctatgact cagggtcgca    13560
ggggcaacgt gtattgggtg cgcgactcgg ttagcggcct gcgcgtgccc gtgcgcaccc    13620 gcccccgcg caactagatt gcaagaaaaa actacttaga ctcgtactgt tgtatgtatc     13680
cagcggcggc ggcgcgcaac gaagctatgt ccaagcgcaa aatcaaagaa gagatgctcc    13740
aggtcatcgc gccggagatc tatggccccc cgaagaagga agagcaggat tacaagcccc    13800
```

```
gaaagctaaa gcgggtcaaa aagaaaaaga aagatgatga tgatgaactt gacgacgagg   13860
tggaactgct gcacgctacc gcgcccaggc gacgggtaca gtggaaaggt cgacgcgtaa   13920
aacgtgtttt gcgacccggc accaccgtag tctttacgcc cggtgagcgc tccacccgca   13980
cctacaagcg cgtgtatgat gaggtgtacg gcgacgagga cctgcttgag caggccaacg   14040
agcgcctcgg ggagtttgcc tacggaaagc ggcataagga catgctggcg ttgccgctgg   14100
acgagggcaa cccaacacct agcctaaagc ccgtaacact gcagcaggtg ctgcccgcgc   14160
ttgcaccgtc cgaagaaaag cgcggcctaa agcgcgagtc tggtgacttg gcacccaccg   14220
tgcagctgat ggtacccaag cgccagcgac tggaagatgt cttggaaaaa atgaccgtgg   14280
aacctgggct ggagcccgag gtccgcgtgc ggccaatcaa gcaggtggcg ccgggactgg   14340
gcgtgcagac cgtggacgtt cagataccca ctaccagtag caccagtatt gccaccgcca   14400
cagagggcat ggagacacaa acgtccccgg ttgcctcagc ggtggcggat gccgcggtgc   14460
aggcggtcgc tgcggccgcg tccaagacct ctacggaggt gcaaacggac ccgtggatgt   14520
ttcgcgtttc agccccccgg cgcccgcgcg gttcgaggaa gtacggcgcc gccagcgcgc   14580
tactgcccga atatgcccta catccttcca ttgcgcctac ccccggctat cgtggctaca   14640
cctaccgccc cagaagacga gcaactaccc gacgccgaac caccactgga acccgccgcc   14700
gccgtcgccg tcgccagccc gtgctggccc cgatttccgt gcgcagggtg gctcgcgaag   14760
gaggcaggac cctggtgctg ccaacagcgc gctaccaccc cagcatcgtt taaaagccgg   14820
tctttgtggt tcttgcagat atggccctca cctgccgcct ccgtttcccg gtgccgggat   14880
tccgaggaag aatgcaccgt aggaggggca tggccggcta cggcctgacg ggcggcatgc   14940
gtcgtgcgca ccaccggcgg cggcgcgcgt cgcaccgtcg catgcgcggc ggtatcctgc   15000
ccctccttat tccactgatc gccgcggcga ttggcgccgt gcccggaatt gcatccgtgg   15060
ccttgcaggc gcagagacac tgattaaaaa caagttgcat gtggaaaaat caaaataaaa   15120
agtctggact ctcacgctcg cttggtcctg taactatttt gtagaatgga agacatcaac   15180
tttgcgtctc tggccccgcg cacacggctcg cgcccgttca tgggaaactg gcaagatatc   15240
ggcaccagca atatgagcgg tggcgccttc agctggggct cgctgtggag cggcattaaa   15300
aatttcggtt ccaccgttaa gaactatggc agcaaggcct ggaacagcag cacaggccag   15360
atgctgaggg ataagttgaa agagcaaaat ttccaacaaa aggtggtaga tggcctggcc   15420
tctggcatta gcggggtggt ggacctggcc aaccaggcag tgcaaaataa gattaacagt   15480
aagcttgatc cccgccctcc cgtagaggag cctccaccgg ccgtggagac agtgtctcca   15540
gaggggcgtg gcgaaaagcg tccgcgcccc gacagggaag aaactctggt gacgcaaata   15600
gacgagcctc cctcgtacga ggaggcacta agcaaggcc tgcccaccac ccgtcccatc   15660
gcgcccatgg ctaccggagt gctgggccag cacacacccg taacgctgga cctgcctccc   15720
cccgccgaca cccagcagaa acctgtgctg ccaggcccga ccgccgttgt tgtaacccgt   15780
cctagccgcg cgtccctgcg ccgcgccgcc agcggtccgc gatcgttgcg gcccgtagcc   15840
agtggcaact ggcaaagcac actgaacagc atcgtgggtc tgggggtgca atccctgaag   15900
cgccgacgat gcttctgaat agctaacgtg tcgtatgtgt gtcatgtatg cgtccatgtc   15960
gccgccagag gagctgctga ccgccgcgc gcccgctttc caagatggct accccttcga   16020
tgatgccgca gtggtcttac atgcacatct cggggccagga cgcctcggag tacctgagcc   16080 ccggggctggt gcagtttgcc cgcgccaccg agacgtactt cagcctgaat aacaagttta   16140
```

```
gaaaccccac ggtggcgcct acgcacgacg tgaccacaga ccggtcccag cgtttgacgc    16200
tgcggttcat ccctgtggac cgtgaggata ctgcgtactc gtacaaggcg cggttcaccc    16260
tagctgtggg tgataaccgt gtgctggaca tggcttccac gtactttgac atccgcggcg    16320
tgctggacag gggccctact tttaagccct actctggcac tgcctacaac gccctggctc    16380
ccaagggtgc cccaaatcct tgcgaatggg atgaagctgc tactgctctt gaaataaacc    16440
tagaagaaga ggacgatgac aacgaagacg aagtagacga gcaagctgag cagcaaaaaa    16500
ctcacgtatt tgggcaggcg ccttattctg gtataaatat tacaaaggag ggtattcaaa    16560
taggtgtcga aggtcaaaca cctaaatatg ccgataaaac atttcaacct gaacctcaaa    16620
taggagaatc tcagtggtac gaaactgaaa ttaatcatgc agctgggaga gtccttaaaa    16680
agactacccc aatgaaacca tgttacggtt catatgcaaa acccacaaat gaaaatggag    16740
ggcaaggcat tcttgtaaag caacaaaatg gaaagctaga aagtcaagtg gaaatgcaat    16800
ttttctcaac tactgaggcg accgcaggca atggtgataa cttgactcct aaagtggtat    16860
tgtacagtga agatgtagat atagaaaccc cagacactca tatttcttac atgcccacta    16920
ttaaggaagg taactcacga gaactaatgg gccaacaatc tatgcccaac aggcctaatt    16980
acattgcttt tagggacaat tttattggtc taatgtatta caacagcacg ggtaatatgg    17040
gtgttctggc gggccaagca tcgcagttga atgctgttgt agatttgcaa gacagaaaca    17100
cagagctttc ataccagctt ttgcttgatt ccattggtga tagaaccagg tacttttcta    17160
tgtggaatca ggctgttgac agctatgatc agatgttag aattattgaa aatcatggaa    17220
ctgaagatga acttccaaat tactgctttc cactgggagg tgtgattaat acagagactc    17280
ttaccaaggt aaaacctaaa acaggtcagg aaaatggatg ggaaaaagat gctacagaat    17340
tttcagataa aaatgaaata agagttggaa ataattttgc catggaaatc aatctaaatg    17400
ccaacctgtg gagaaatttc ctgtactcca acatagcgct gtatttgccc gacaagctaa    17460
agtacagtcc ttccaacgta aaaatttctg ataacccaaa cacctacgac tacatgaaca    17520
agcgagtggt ggctcccggg ttagtggact gctacattaa ccttggagca cgctggtccc    17580
ttgactatat ggacaacgtc aacccattta accaccaccg caatgctggc ctgcgctacc    17640
gctcaatgtt gctgggcaat ggtcgctatg tgcccttcca catccaggtg cctcagaagt    17700
tctttgccat taaaaacctc cttctcctgc cgggctcata cacctacgag tggaacttca    17760
ggaaggatgt taacatggtt ctgcagagct ccctaggaaa tgacctaagg gttgacggag    17820
ccagcattaa gtttgatagc atttgccttt acgccaccct cttccccatg cccacaaca    17880 ccgcctccac gcttgaggcc atgcttagaa acgacaccaa cgaccagtcc tttaacgact    17940
atctctccgc cgccaacatg ctctacccta tacccgccaa cgctaccaac gtgcccatat    18000
ccatcccctc ccgcaactgg cgggctttcc gcggctgggc cttcacgcgc cttaagacta    18060
aggaaacccc atcactgggc tcgggctacg acccttatta cacctactct ggctctatac    18120
cctacctaga tggaacctt tacctcaacc acacctttaa gaaggtggcc attaccttg    18180 actcttctgt cagctggcct ggcaatgacc gcctgcttac ccccaacgag tttgaaatta    18240
agcgctcagt tgacggggag ggttacaacg ttgcccagtg taacatgacc aaagactggt    18300
tcctggtaca aatgctagct aactacaaca ttggctacca gggcttctat atcccagaga    18360
gctacaagga ccgcatgtac tccttcttta gaaacttcca gcccatgagc cgtcaggtgg    18420
tggatgatac taaatacaag gactaccaac aggtgggcat cctacaccaa cacaacaact    18480
ctggatttgt tggctacctt gcccccacca tgcgcgaagg acaggcctac cctgctaact    18540
```

```
tcccctatcc gcttataggc aagaccgcag ttgacagcat tacccagaaa aagtttcttt    18600
gcgatcgcac cctttggcgc atcccattct ccagtaactt tatgtccatg ggcgcactca    18660
cagacctggg ccaaaacctt ctctacgcca actccgccca cgcgctagac atgacttttg    18720
aggtggatcc catggacgag cccacccttc tttatgtttt gtttgaagtc tttgacgtgg    18780
tccgtgtgca ccggccgcac cgcggcgtca tcgaaaccgt gtacctgcgc acgcccttct    18840
cggccggcaa cgccacaaca taaagaagca agcaacatca acaacagctg ccgccatggg    18900
ctccagtgag caggaactga aagccattgt caaagatctt ggttgtgggc catatttttt    18960
gggcacctat gacaagcgct ttccaggctt tgtttctcca cacaagctcg cctgcgccat    19020
agtcaatacg gccggtcgcg agactggggg cgtacactgg atggcctttg cctggaaccc    19080
gcactcaaaa acatgctacc tctttgagcc ctttggcttt tctgaccagc gactcaagca    19140
ggtttaccag tttgagtacg agtcactcct gcgccgtagc gccattgctt cttccccga    19200 ccgctgtata acgctggaaa agtccaccca aagcgtacag gggcccaact cggccgcctg    19260
tggactattc tgctgcatgt ttctccacgc ctttgccaac tggccccaaa ctcccatgga    19320 tcacaaccc accatgaacc ttattaccgg ggtacccaac tccatgctca acagtccca    19380 ggtacagccc accctgcgtc gcaaccagga acagctctac agcttcctgg agcgccactc    19440
gccctacttc cgcagccaca gtgcgcagat taggagcgcc acttcttttt gtcacttgaa    19500
aaacatgtaa aaataatgta ctagagacac tttcaataaa ggcaaatgct tttatttgta    19560
cactctcggg tgattattta cccccaccct tgccgtctgc gccgtttaaa aatcaaaggg    19620
gttctgccgc gcatcgctat gcgccactgg cagggacacg ttgcgatact ggtgtttagt    19680
gctccactta aactcaggca caaccatccg cggcagctcg gtgaagtttt cactccacag    19740
gctgcgcacc atcaccaacg cgtttagcag gtcgggcgcc gatatcttga agtcgcagtt    19800
ggggcctccg ccctgcgcgc gcgagttgcg atacacaggg ttgcagcact ggaacactat    19860
cagcgccggg tggtgcacgc tggccagcac gctcttgtcg gagatcagat ccgcgtccag    19920
gtcctccgcg ttgctcaggg cgaacggagt caactttggt agctgccttc ccaaaaaggg    19980
cgcgtgccca ggctttgagt tgcactcgca ccgtagtggc atcaaaaggt gaccgtgccc    20040
ggtctgggcg ttaggataca gcgcctgcat aaaagccttg atctgcttaa aagccacctg    20100
agcctttgcg ccttcagaga agaacatgcc gcaagacttg ccggaaaact gattggccgg    20160
acaggccgcg tcgtgcacgc agcaccttgc gtcggtgttg gagatctgca ccacatttcg    20220
gccccaccgg ttcttcacga tcttggcctt gctagactgc tccttcagcg cgcgctgccc    20280
gttttcgctc gtcacatcca tttcaatcac gtgctcctta tttatcataa tgcttccgtg    20340
tagacactta agctcgcctt cgatctcagc gcagcggtgc agccacaacg cgcagcccgt    20400
gggctcgtga tgcttgtagg tcacctctgc aaacgactgc aggtacgcct gcaggaatcg    20460
ccccatcatc gtcacaaagg tcttgttgct ggtgaaggtc agctgcaacc cgcggtgctc    20520
ctcgttcagc caggtcttgc atacggccgc cagagcttcc acttggtcag gcagtagttt    20580
gaagttcgcc tttagatcgt tatccacgtg gtacttgtcc atcagcgcgc gcgcagcctc    20640
catgcccttc tcccacgcag acacgatcgg cacactcagc gggttcatca ccgtaatttc    20700
actttccgct tcgctgggct cttcctcttc ctcttgcgtc cgcataccac gcgccactgg    20760
gtcgtcttca ttcagccgcc gcactgtgcg cttacctcct ttgccatgct tgattagcac    20820
cggtgggttg ctgaaaccca ccatttgtag cgccacatct tctctttctt cctcgctgtc    20880
```

```
cacgattacc tctggtgatg gcgggcgctc gggcttggga aagggcgct tcttttttctt    20940
cttgggcgca atggccaaat ccgccgccga ggtcgatggc cgcgggctgg gtgtgcgcgg    21000
caccagcgcg tcttgtgatg agtcttcctc gtcctcggac tcgatacgcc gcctcatccg    21060
cttttttggg ggcgcccggg gaggcggcgg cgacggggac ggggacgaca cgtcctccat    21120
ggttggggga cgtcgcgccg caccgcgtcc gcgctcgggg gtggtttcgc gctgctcctc    21180
ttcccgactg gccatttcct tctcctatag gcagaaaaag atcatggagt cagtcgagaa    21240
gaaggacagc ctaaccgccc cctctgagtt cgccaccacc gcctccaccg atgccgccaa    21300
cgcgcctacc accttccccg tcgaggcacc cccgcttgag gaggaggaag tgattatcga    21360
gcaggaccca ggttttgtaa gcgaagacga cgaggaccgc tcagtaccaa cagaggataa    21420
aaagcaagac caggacaacg cagaggcaaa cgaggaacaa gtcgggcggg gggacgaaag    21480
gcatggcgac tacctagatg tgggagacga cgtgctgttg aagcatctgc agcgccagtg    21540
cgccattatc tgcgacgcgt tgcaagagcg cagcgatgtg ccccctcgcca tagcggatgt    21600
cagccttgcc tacgaacgcc acctattctc accgcgcgta ccccccaaac gccaagaaaa    21660
cggcacatgc gagcccaacc cgcgcctcaa cttctacccc gtatttgccg tgccagaggt    21720
gcttgccacc tatcacatct ttttccaaaa ctgcaagata cccctatcct gccgtgccaa    21780
ccgcagccga gcggacaagc agctggcctt gcggcagggc gctgtcatac ctgatatcgc    21840
ctcgctcaac gaagtgccaa aaatctttga gggtcttgga cgcgacgaga gcgcgcggc    21900
aaacgctctg caacaggaaa acagcgaaaa tgaaagtcac tctggagtgt tggtggaact    21960
cgagggtgac aacgcgcgcc tagccgtact aaaacgcagc atcgaggtca cccactttgc    22020
ctacccggca cttaacctac cccccaaggt catgagcaca gtcatgagtg agctgatcgt    22080
gcgccgtgcg cagcccctgg agagggatgc aaatttgcaa gaacaaacag aggagggcct    22140
acccgcagtt ggcgacgagc agctagcgcg ctggcttcaa acgcgcgagc ctgccgactt    22200
ggaggagcga cgcaaactaa tgatggccgc agtgctcgtt accgtggagc ttgagtgcat    22260
gcagcggttc tttgctgacc cggagatgca gcgcaagcta gaggaaacat gcactacac    22320
cttttcgacag ggctacgtac gccaggcctg caagatctcc aacgtggagc tctgcaacct    22380
ggtctcctac cttggaattt tgcacgaaaa ccgccttggg caaaacgtgc ttcattccac    22440
gctcaagggc gaggcgcgcc gcgactacgt ccgcgactgc gtttacttat ttctatgcta    22500
cacctggcag acggccatgg gcgtttggca gcagtgcttg gaggagtgca acctcaagga    22560
gctgcagaaa ctgctaaagc aaaacttgaa ggacctatgg acggccttca acgagcgctc    22620
cgtggccgcg cacctggcgg acatcatttt ccccgaacgc ctgcttaaaa ccctgcaaca    22680
gggtctgcca gacttcacca gtcaaagcat gttgcagaac tttaggaact ttatcctaga    22740
gcgctcagga atcttgccg ccacctgctg tgcacttcct agcgactttg tgcccattaa    22800
gtaccgcgaa tgccctccgc cgctttgggg ccactgctac cttctgcagc tagccaacta    22860
ccttgcctac cactctgaca taatggaaga cgtgagcggt gacggtctac tggagtgtca    22920
ctgtcgctgc aacctatgca cccgcaccg ctccctggtt tgcaattcgc agctgcttaa    22980
cgaaagtcaa attatcggta cctttgagct gcagggtccc tcgcctgacg aaaagtccgc    23040
ggctccgggg ttgaaactca ctccgggct gtggacgtcg gcttaccttc gcaaatttgt    23100
acctgaggac taccacgccc acgagattag gttctacgaa gaccaatccc gcccgccaaa    23160
tgcggagctt accgctgcg tcattaccca gggccacatt cttggccaat gcaagccat    23220
caacaaagcc cgccaagagt ttctgctacg aaagggacgg ggggtttact tggaccccca    23280
```

```
gtccggcgag gagctcaacc caatcccccc gccgccgcag ccctatcagc agcagccgcg   23340
ggcccttgct tcccaggatg gcacccaaaa agaagctgca gctgccgccg ccacccacgg   23400
acgaggagga atactgggac agtcaggcag aggaggtttt ggacgaggag gaggaggaca   23460
tgatggaaga ctgggagagc ctagacgagg aagcttccga ggtcgaagag gtgtcagacg   23520
aaacaccgtc accctcggtc gcattcccct cgccggcgcc ccagaaatcg caaccggtt    23580 ccagcatggc tacaacctcc gctcctcagg cgccgccggc actgcccgtt cgccgaccca   23640
accgtagatg ggacaccact ggaaccaggg ccggtaagtc caagcagccg ccgccgttag   23700
cccaagagca caacagcgc caaggctacc gctcatggcg cgggcacaag aacgccatag    23760
ttgcttgctt gcaagactgt gggggcaaca tctccttcgc ccgccgcttt cttctctacc   23820
atcacggcgt ggccttcccc cgtaacatcc tgcattacta ccgtcatctc tacagcccat   23880
actgcaccgg cggcagcggc agcggcagca acagcagcgg ccacacagaa gcaaaggcga   23940
ccggatagca agactctgac aaagcccaag aaatccacag cggcggcagc agcaggagga   24000
ggagcgctgc gtctggcgcc caacgaaccc gtatcgaccc gcgagcttag aaacaggatt   24060
tttcccactc tgtatgctat atttcaacag agcaggggcc aagaacaaga gctgaaaata   24120
aaaaacaggt ctctgcgatc cctcacccgc agctgcctgt atcacaaaag cgaagatcag   24180
cttcggcgca cgctggaaga gcggaggct ctcttcagta aatactgcgc gctgactctt     24240
aaggactagt ttcgcgccct ttctcaaatt taagcgcgaa aactacgtca tctccagcgg   24300
ccacacccgg cgccagcacc tgtcgtcagc gccattatga gcaaggaaat tcccacgccc   24360
tacatgtgga gttaccagcc acaaatggga cttgcggctg gagctgccca agactactca   24420
acccgaataa actacatgag cgcgggaccc cacatgatat cccgggtcaa cggaatccgc   24480
gcccaccgaa accgaattct cttggaacag gcggctatta ccaccacacc tcgtaataac   24540
cttaatcccc gtagttggcc cgctgccctg gtgtaccagg aaagtcccgc tcccaccact   24600
gtggtacttc ccagagacgc ccaggccgaa gttcagatga ctaactcagg ggcgcagctt   24660
gcgggcggct ttcgtcacag ggtgcggtcg cccgggcagg gtataactca cctgacaatc   24720
agagggcgag gtattcagct caacgacgag tcggtgagct cctcgcttgg tctccgtccg   24780
gacgggacat ttcagatcgg cggcgccggc cgtccttcat tcacgcctcg tcaggcaatc   24840
ctaactctgc agacctcgtc ctctgagccg cgctctggag gcattggaac tctgcaattt   24900
attgaggagt ttgtgccatc ggtctacttt aaccccttct cgggacctcc cggccactat   24960
ccggatcaat ttattcctaa ctttgacgcg gtaaaggact cggcggacgg ctacgactga   25020
atgttaagtg gagaggcaga gcaactgcgc ctgaaacacc tggtccactg tcgccgccac   25080
aagtgctttg cccgcgactc cggtgagttt tgctactttg aattgcccga ggatcatatc   25140
gagggcccgg cgcacggcgt ccggcttacc gcccagggag agcttgcccg tagcctgatt   25200
cgggagttta cccagcgccc cctgctagtt gagcgggaca ggggaccctg tgttctcact   25260
gtgatttgca actgtcctaa ccttggatta catcaagatc tctagttaa ttaacagctt     25320 gcatgcctgc aggtcgacgg atcgggagat ctcggccgca tattaagtgc attgttctcg   25380
ataccgctaa gtgcattgtt ctcgttagct cgatggacaa gtgcattgtt ctcttgctga   25440
aagctcgatg gacaagtgca ttgttctctt gctgaaagct cgatggacaa gtgcattgtt   25500
ctcttgctga aagctcagta cccggggagta ccctcgaccg ccggagtata aatagaggcg   25560
cttcgtctac ggagcgacaa ttcaattcaa acaagcaaag tgaacacgtc gctaagcgaa   25620
```

```
agctaagcaa ataaacaagc gcagctgaac aagctaaaca atctgcagta aagtgcaagt   25680
taaagtgaat caattaaaag taaccagcaa ccaagtaaat caactgcaac tactgaaatc   25740
tgccaagaag taattattga atacaagaag agaactctga atactttcaa caagttaccg   25800
agaaagaaga actcacacac agctagcgtt taaacttaag cttcaccatg gtggggccct   25860
gcatgctgct gctgctgctg ctgctgggcc tgaggctaca gctctccctg gcatcatcc    25920 tagttgagga ggagaacccg gacttctgga accgcgaggc agccgaggcc ctgggtgccg   25980
ccaagaagct gcagcctgca cagacagccg ccaagaacct catcatcttc ctgggcgatg   26040
gggtgggggt gtctacggtg acagctgcca ggatcctaaa agggcagaag aaggacaaac   26100
tggggcctga gatacccctg gccatggacc gcttcccata tgtggctctg tccaagacat   26160
acaatgtaga caaacatgtg ccagacagtg gagccacagc cacggcctac ctgtgcgggg   26220
tcaagggcaa cttccagacc attggcttga gtgcagccgc ccgctttaac cagtgcaaca   26280
cgacacgcgg caacgaggtc atctccgtga tgaatcgggc caagaaagca gggaagtcag   26340
tgggagtggt aaccaccaca cgagtgcagc acgcctcgcc agccggcacc tacgcccaca   26400
cggtgaaccg caactggtac tcggacgccg acgtgcctgc ctcggcccgc caggaggggt   26460
gccaggacat cgctacgcag ctcatctcca acatggacat tgacgtgatc ctaggtgggg   26520
gccgaaagta catgtttcgc atgggaaccc cagaccctga gtacccagat gactacagcc   26580
aaggtgggac caggctggac gggaagaatc tggtgcagga tggctggcg aagcaccagg   26640 gtgcccggta cgtgtggaac cgcactgagc tcatgcgggc ttccctggac cgtctgtgg    26700 cccatctcat gggtctcttt gagcctggag acatgaaata cgagatccac cgagactcca   26760
cactggaccc ctccctgatg gagatgacag aggctgccct gcgcctgctg agcaggaacc   26820
cccgcggctt cttcctcttc gtggagggtg gtcgcatcga ccatggtcat catgaaagca   26880
gggcttaccg ggcactgact gagacgatca tgttcgacga cgccattgag agggcgggcc   26940
agctcaccag cgaggaggac acgctgagcc tcgtcactgc cgaccactcc cacgtcttct   27000
ccttcggagg ctgccccctg cgagggggct ccatcttcgg gctggcccct ggcaaggccc   27060
gggacaggaa ggcctacacg gtcctcctat acggaaacgg tccaggctat gtgctcaagg   27120
acggcgcccg gccggatgtt accgagagcg agagcgggag ccccgagtat cggcagcagt   27180
cagcagtgcc cctggacgaa gagacccacg caggcgagga cgtggcggtg ttcgcgcgcg   27240
gcccgcaggc gcacctggtt cacggcgtgc aggagcagac cttcatagcg cacgtcatgg   27300
ccttcgccgc ctgcctggag ccctacaccg cctgcgacct ggcgcccccc gccggcacca   27360
ccgacgccgc gcacccgggg cggtccgtgg tccccgcgtt gcttcctctg ctggccggga   27420
ccctgctgct gctggagacg gccactgctc cctgagtgtc ccgtccctgg gctcctgct    27480 tccccatccc ggagttctcc tgctccccgc ctcctgtcgt cctgcctggc ctccagcccg   27540
agtcgtcatc cccggagtcc ctatacagag gtcctgccat ggaaccttcc cctccccgtg   27600
cgctctgggg actgagccca tgacaccaaa cctgcccctt ggctgctctc ggactcccta   27660
cccaaccccc agggacagat ctggccagat ttgtaaaaca aatagatttt aggcccaaag   27720
attatttaaa gcattgcctg gaacgcagtg agttttgtt agaaaagaga ataattcaaa     27780
gtggcattgc tttgcttctt atgttaattt ggtacagacc tgtggctgag tttgctcaaa   27840
gtattcagag cagaattgtg gagtggaaag agagattgga caaagagttt agtttgtcag   27900
tgtatcaaaa aatgaagttt aatgtggcta tgggaattgg agttttagat tggctaagaa   27960
acagtgatga tgatgatgaa gacagccagg aaaatgctga taaaaatgaa gatggtgggg   28020
```

```
agaagaacat ggaagactca gggcatgaaa caggcattga ttcacagtcc caaggctcat   28080
ttcaggcccc tcagtcctca cagtctgttc atgatcataa tcagccatac cacatttgta   28140
gaggttttac ttgctttaaa aaacctccca cacctccccc tgaacctgaa acataaaatg   28200
aatgcaattg ttgttgttaa cttgtttatt gcagcttata atggttacaa ataaagcaat   28260
agcatcacaa atttcacaaa taaagcattt ttttcactgc attctagttg tggtttgtcc   28320
aaactcatca atgtatctta tcatgtctgg atccccagga agctcctctg tgtcctcata   28380
aaccctaacc tcctctactt gagaggacat tccaatcata ggctgcccat ccaccctctg   28440
tgtcctcctg ttaattaggt cacttaacaa aaaggaaatt gggtagtggg ttttcacaga   28500
ccgctttcta agggtaattt taaaatatct gggaagtccc ttccactgct gtgttccaga   28560
agtgttggta aacagcccac aaatgtcaac agcagaaaca taaagctgt cagctttgca   28620 caagggccca acaccctgct catcaagaag cactgtggtt gctgtgttag taatgtgcaa   28680
aacaggaggc acatttttcc cacctgtgta ggttccaaaa tatctagtgt tttcattttt   28740
acttggatca ggaacccagc actccactgg ataagcatta tccttatcca aaacagcctt   28800
gtggtcagtg ttcatctgct gactgtcaac tgtagcattt tttggggtta cagtttgagc   28860
aggatatttg gtcctgtagt ttgctaacac accctgcagc tccaaaggtt ccccaccaac   28920
agcaaaaaaa tgaaaatttg acccttgaat gggttttcca gcaccatttt catgagtttt   28980
ttgtgtccct gaatgcaagt ttaacatagc agttacccca ataacctcag ttttaacagt   29040
aacagcttcc cacatcaaaa tatttccaca ggttaagtcc tcatttaaat taggcaaagg   29100
aattccactt cccactgcct tgcttccgtc tcccattcaa acttttatca actgacatta   29160
ttctaagtaa aatcctcttc attatgttgt cagcaatcca ttgcttgaag gcctggctcc   29220
ccagaaccCC tcgactggta tgtcttctcc tagaatactc cagaagaaaa ggagtgtatg   29280
aagatagtga ctgcacatta aaatgactga aaccatagta aattaggatg agattctggg   29340
cagataaaca gacagctggc taggatcatt ttttttatgcc ttggacttct ttggcaatct   29400
gttgaagcct gacattcctc agaataatgt tttaaagccc aacaataaga ccctgtagca   29460
catataataa gtactgcagt tttgaagtag tgataagcat aaatgatatt ttgatatatt   29520
tattataact gtaatgagat gtgtacatat ctgtgacttc ataggtactg attgtactac   29580
tgtgattttt ttgcctactt tcaaaatgaa aaggaatgct taatttcagt tagaggttag   29640
taaagacaaa taggtaattt tcttctccag tgaagagcat ggcgcccctt gctattcatg   29700
gacgcttgct taaagacttg tacacaggct tgctttgtat caacctatga cttcccctta   29760
cagccgatga taggttttta tttgcacctc cttcgtgtac aaagacagtt ttggtggcta   29820
cgccatcatt aaactcatta ttatcatgct taagcctata gatgtatcca gttcttctgt   29880
tacataattg aagctgtagt gaattgtcta tcttaaactg catcgctaac tgactacatt   29940
tcacacttca tttgcttcca acatagacta accttcttgg atgtccacta ttatttgaac   30000
ttttgagatt ttttttccta tttctaatat cttaaaattt cagaagactt aaagttttgc   30060
aactacaggg ctccatatag acatctagct tgaatttata cactttcttt cattgatgtc   30120
cctggactaa aaaatgttaa atatttctaa ccgctgtact taaagtccat tacaaacgaa   30180
gactactgtt gttaagttga ataggcatct tatatatttt tcaccggtgc aataaataac   30240
ttctattccc ttctaacatc tgcttgcgtt gcactgagag tacactattg attagcaata   30300
ggttcgtgat tacagcccct ctataattaa ttgttaggtt aacatattat tcataaaata   30360
```

| | |
|---|---|
| ttatttatt aatttttact tgatttgcta ctggatgctt agaaatagct atgagtatat | 30420 |
| tggtagaacc agtacttata ttttattaca tttttacatt tcataaaatt taagtgatat | 30480 |
| aaaaatcctg aggaagtatg ccacaaaagt ggtctcagtg gaaatttaaa tatgttaaca | 30540 |
| tttatttta aaatgtagcg tgaaatagac aactttaaaa gctcagctta aaaaaaaaac | 30600 |
| tcaaggaagc tgaacttgac ttttttaaagc actgaagtgc aatatttaat gtaggtcaac | 30660 |
| atgtttaaat gggaaaattt ttttcctaat tacagccaaa tccctagctg taattaactt | 30720 |
| aaaatttgta tactatttca caacagagtc agcatatacc actttcttat aaaattagaa | 30780 |
| agatctaaaa ttttagagct tatttggtga acaggcata ttgctacatc tttgttata | 30840 |
| aattataatg tgcctttaga gcccaataac agataacaag attttgaaaa ttcaggtgaa | 30900 |
| ttagagttat cagagggaat gttaatacac tctattcaaa tactatatga gtaagacatt | 30960 |
| taaaatagga acaatactt tatatattaa aaaaaattaa tcttccagtc gatttaatcc | 31020 |
| actttatgaa ttcatttaaa tcgatttaaa ttcgaattaa ttaactagag tacccgggga | 31080 |
| tcttattccc tttaactaat aaaaaaaaat aataaagcat cacttactta aaatcagtta | 31140 |
| gcaaatttct gtccagttta ttcagcagca cctccttgcc ctcctcccag ctctggtatt | 31200 |
| gcagcttcct cctggctgca aactttctcc acaatctaaa tggaatgtca gtttcctcct | 31260 |
| gttcctgtcc atccgcaccc actatcttca tgttgttgca gatgaagcgc gcaagaccgt | 31320 |
| ctgaagatac cttcaacccc gtgtatccat atgacacgga aaccggtcct ccaactgtgc | 31380 |
| cttttcttac tcctccctt gtatccccca atgggtttca agagagtccc cctggggtac | 31440 |
| tctctttgcg cctatccgaa cctctagtta cctccaatgg catgcttgcg ctcaaaatgg | 31500 |
| gcaacggcct ctctctggac gaggccggca accttacctc ccaaaatgta accactgtga | 31560 |
| gcccacctct caaaaaaacc aagtcaaaca taaacctgga aatatctgca cccctcacag | 31620 |
| ttacctcaga agccctaact gtggctgccg ccgcacctct aatggtcgcg ggcaacacac | 31680 |
| tcaccatgca atcacaggcc ccgctaaccg tgcacgactc caaacttagc attgccaccc | 31740 |
| aaggacccct cacagtgtca gaaggaaagc tagccctgca acatcaggc cccctcacca | 31800 |
| ccaccgatag cagtacccct actatcactg cctcacccc tctaactact gccactggta | 31860 |
| gcttgggcat tgacttgaaa gagcccattt atacacaaaa tggaaaacta ggactaaagt | 31920 |
| acggggctcc tttgcatgta acagacgacc taaacacttt gaccgtagca actggtccag | 31980 |
| gtgtgactat taataatact tccttgcaaa ctaaagttac tggagccttg ggttttgatt | 32040 |
| cacaaggcaa tatgcaactt aatgtagcag gaggactaag gattgattct caaaacagac | 32100 |
| gccttatact tgatgttagt tatccgttg atgctcaaaa ccaactaaat ctaagactag | 32160 |
| gacagggccc tcttttttata aactcagccc acaacttgga tattaactac aacaaaggcc | 32220 |
| tttacttgtt tacagcttca aacaattcca aaagcttga ggttaaccta agcactgcca | 32280 |
| aggggttgat gtttgacgct acagccatag ccattaatgc aggagatggg cttgaatttg | 32340 |
| gttcacctaa tgcaccaaac acaaatcccc tcaaacaaa aattggccat ggcctagaat | 32400 |
| ttgattcaaa caaggctatg gttcctaaac taggaactgg ccttagtttt gacagcacag | 32460 |
| gtgccattac agtaggaaac aaaaataatg ataagctaac tttgtggacc acaccagctc | 32520 |
| catctcctaa ctgtagacta aatgcagaga aagatgctaa actcactttg gtcttaacaa | 32580 |
| aatgtggcag tcaaatactt gctacagttt cagttttggc tgttaaaggc agtttggctc | 32640 |
| caatatctgg aacagttcaa agtgctcatc ttattataag atttgacgaa aatggagtgc | 32700 |
| tactaaacaa ttccttcctg gacccagaat attggaactt tagaaatgga gatcttactg | 32760 |

```
aaggcacagc ctatacaaac gctgttggat ttatgcctaa cctatcagct tatccaaaat  32820
ctcacggtaa aactgccaaa agtaacattg tcagtcaagt ttacttaaac ggagacaaaa  32880
ctaaacctgt aacactaacc attacactaa acggtacaca ggaaacagga gacacaactc  32940
caagtgcata ctctatgtca tttttcatggg actggtctgg ccacaactac attaatgaaa  33000
tatttgccac atcctcttac acttttcat acattgccca agaataaaga atcgtttgtg  33060
ttatgtttca acgtgtttat ttttcaattg cagaaaattt caagtcattt ttcattcagt  33120
agtatagccc caccaccaca tagcttatac agatcaccgt accttaatca aactcacaga  33180
accctagtat tcaacctgcc acctccctcc caacacacag agtacacagt cctttctccc  33240
cggctggcct taaaaagcat catatcatgg gtaacagaca tattcttagg tgttatattc  33300
cacacggttt cctgtcgagc caaacgctca tcagtgatat taataaactc cccgggcagc  33360
tcacttaagt tcatgtcgct gtccagctgc tgagccacag gctgctgtcc aacttgcggt  33420
tgcttaacgg gcggcgaagg agaagtccac gcctacatgg gggtagagtc ataatcgtgc  33480
atcaggatag ggcggtggtg ctgcagcagc gcgcgaataa actgctgccg ccgccgctcc  33540
gtcctgcagg aatacaacat ggcagtggtc tcctcagcga tgattcgcac cgcccgcagc  33600
ataaggcgcc ttgtcctccg ggcacagcag cgcaccctga tctcacttaa atcagcacag  33660
taactgcagc acagcaccac aatattgttc aaaatcccac agtgcaaggc gctgtatcca  33720
aagctcatgg cggggaccac agaacccacg tggccatcat accacaagcg caggtagatt  33780
aagtggcgac ccctcataaa cacgctggac ataaacatta cctctttgg catgttgtaa  33840 ttcaccacct cccggtacca tataaacctc tgattaaaca tggcgccatc caccaccatc  33900
ctaaaccagc tggccaaaac ctgcccgccg gctatacact gcagggaacc gggactggaa  33960
caatgacagt ggagagccca ggactcgtaa ccatggatca tcatgctcgt catgatatca  34020
atgttggcac aacacaggca cacgtgcata cacttcctca ggattacaag ctcctcccgc  34080
gttagaacca tatcccaggg aacaacccat tcctgaatca gcgtaaatcc cacactgcag  34140
ggaagacctc gcacgtaact cacgttgtgc attgtcaaag tgttacattc gggcagcagc  34200
ggatgatcct ccagtatggt agcgcgggtt tctgtctcaa aaggaggtag acgatcccta  34260
ctgtacggag tgcgccgaga caaccgagat cgtgttggtc gtagtgtcat gccaaatgga  34320
acgccggacg tagtcatatt tcctgaagca aaaccaggtg cgggcgtgac aaacagatct  34380
gcgtctccgg tctcgccgct tagatcgctc tgtgtagtag ttgtagtata tccactctct  34440
caaagcatcc aggcgccccc tggcttcggg ttctatgtaa actccttcat gcgccgctgc  34500
cctgataaca tccaccaccg cagaataagc cacacccagc caacctacac attcgttctg  34560
cgagtcacac acgggaggag cgggaagagc tggaagaacc atgttttttt ttttattcca  34620
aaagattatc caaaacctca aaatgaagat ctattaagtg aacgcgctcc cctccggtgg  34680
cgtggtcaaa ctctacagcc aaagaacaga taatggcatt tgtaagatgt tgcacaatgg  34740
cttccaaaag gcaaacggcc ctcacgtcca agtggacgta aaggctaaac ccttcagggt  34800
gaatctcctc tataaacatt ccagcacctt caaccatgcc caaataattc tcatctcgcc  34860
accttctcaa tatatctcta agcaaatccc gaatattaag tccggccatt gtaaaaatct  34920
gctccagagc gccctccacc ttcagcctca agcagcgaat catgattgca aaaattcagg  34980
ttcctcacag acctgtataa gattcaaaag cggaacatta acaaaaatac cgcgatcccg  35040 taggtcccctt cgcagggcca gctgaacata atcgtgcagg tctgcacgga ccagcgcggc  35100
```

```
cacttccccg ccaggaacct tgacaaaaga acccacactg attatgacac gcatactcgg    35160
agctatgcta accagcgtag ccccgatgta agctttgttg catgggcggc gatataaaat    35220
gcaaggtgct gctcaaaaaa tcaggcaaag cctcgcgcaa aaagaaagc acatcgtagt    35280
catgctcatg cagataaagg caggtaagct ccggaaccac cacagaaaaa gacaccattt    35340
ttctctcaaa catgtctgcg ggtttctgca taaacacaaa ataaaataac aaaaaaacat    35400
ttaaacatta gaagcctgtc ttacaacagg aaaaacaacc cttataagca taagacggac    35460
tacggccatg ccggcgtgac cgtaaaaaaa ctggtcaccg tgattaaaaa gcaccaccga    35520
cagctcctcg gtcatgtccg gagtcataat gtaagactcg gtaaacacat caggttgatt    35580
catcggtcag tgctaaaaag cgaccgaaat agcccggggg aatacatacc cgcaggcgta    35640
gagacaacat tacagccccc ataggaggta taacaaaatt aataggagag aaaaacacat    35700
aaacacctga aaaaccctcc tgcctaggca aaatagcacc ctcccgctcc agaacaacat    35760
acagcgcttc acagcggcag cctaacagtc agccttacca gtaaaaaaga aaacctatta    35820
aaaaaacacc actcgacacg gcaccagctc aatcagtcac agtgtaaaaa agggccaagt    35880
gcagagcgag tatatatagg actaaaaaat gacgtaacgg ttaaagtcca caaaaaacac    35940
ccagaaaacc gcacgcgaac ctacgcccag aaacgaaagc caaaaaaccc acaacttcct    36000
caaatcgtca cttccgtttt cccacgttac gtaacttccc attttaagaa aactacaatt    36060
cccaacacat acaagttact ccgccctaaa acctacgtca cccgcccgt tcccacgccc    36120
cgcgccacgt cacaaactcc accccctcat tatcatattg gcttcaatcc aaaataaggt    36180
atattattga tgatggccgg ccgaattgaa tcagggata acgcaggaaa gaacatgtga    36240
gcaaaaggcc agcaaaaggc caggaaccgt aaaaaggccg cgttgctggc gttttttccat    36300
aggctccgcc cccctgacga gcatcacaaa atcgacgct caagtcagag gtggcgaaac    36360
ccgacaggac tataaagata ccaggcgttt cccctggaa gctccctcgt gcgctctcct    36420
gttccgaccc tgccgcttac cggatacctg tccgcctttc tcccttcggg aagcgtggcg    36480
cttctctcata gctcacgctg taggtatctc agttcggtgt aggtcgttcg ctccaagctg    36540
ggctgtgtgc acgaaccccc cgttcagccc gaccgctgcg ccttatccgg taactatcgt    36600
cttgagtcca acccggtaag acacgactta tcgccactgg cagcagccac tggtaacagg    36660
attagcagag cgaggtatgt aggcggtgct acagagttct tgaagtggtg gcctaactac    36720
ggctacacta gaaggacagt atttggtatc tgcgctctgc tgaagccagt taccttcgga    36780
aaaagagttg gtagctcttg atccggcaaa caaaccaccg ctggtagcgg tggttttttt    36840
gtttgcaagc agcagattac gcgcagaaaa aaaggatctc aagaagatcc tttgatcttt    36900
tctacggggt ctgacgctca gtggaacgaa aactcacgtt aagggatttt ggtcatgaga    36960
ttatcaaaaa ggatcttcac ctagatcctt ttaaattaaa aatgaagttt taaatcaatc    37020
taaagtatat atgagtaaac ttggtctgac agttaccaat gcttaatcag tgaggcacct    37080
atctcagcga tctgtctatt tcgttcatcc atagttgcct gactccccgt cgtgtagata    37140
actacgatac gggagggctt accatctggc cccagtgctg caatgatacc gcgagaccca    37200
cgctcaccgg ctccagattt atcagcaata aaccagccag ccgaagggc cgagcgcaga    37260
agtggtcctg caactttatc cgcctccatc cagtctatta attgttgccg ggaagctaga    37320
gtaagtagtt cgccagttaa tagtttgcgc aacgttgttg ccattgctac aggcatcgtg    37380
gtgtcacgct cgtcgtttgg tatggcttca ttcagctccg gttcccaacg atcaaggcga    37440
gttacatgat cccccatgtt gtgcaaaaaa gcggttagct ccttcggtcc tccgatcgtt    37500
```

```
gtcagaagta agttggccgc agtgttatca ctcatggtta tggcagcact gcataattct    37560
cttactgtca tgccatccgt aagatgcttt tctgtgactg gtgagtactc aaccaagtca    37620
ttctgagaat agtgtatgcg gcgaccgagt tgctcttgcc cggcgtcaat acgggataat    37680
accgcgccac atagcagaac tttaaaagtg ctcatcattg gaaaacgttc ttcggggcga    37740
aaactctcaa ggatcttacc gctgttgaga tccagttcga tgtaacccac tcgtgcaccc    37800
aactgatctt cagcatcttt tactttcacc agcgtttctg ggtgagcaaa aacaggaagg    37860
caaaatgccg caaaaaaggg aataagggcg acacggaaat gttgaatact catactcttc    37920
ctttttcaat attattgaag catttatcag ggttattgtc tcatgagcgg atacatattt    37980
gaatgtattt agaaaaataa acaaataggg gttccgcgca catttccccg aaaagtgcca    38040
c                                                                   38041

<210> SEQ ID NO 14
<211> LENGTH: 7180
<212> TYPE: DNA
<213> ORGANISM: Artificial Sequence
<220> FEATURE:
<223> OTHER INFORMATION: Synthetic

<400> SEQUENCE: 14
tctagagtcg accggtcatg gctgcgcccc gacacccgcc aacacccgct gacgcgccct      60
gacgggcttg tctgctcccg gcatccgctt acagacaagc tgtgaccgtc tccgggagct     120
gcatgtgtca gaggttttca ccgtcatcac cgaaacgcgc gaggcagccg gatcataatc     180
agccatacca catttgtaga ggttttactt gctttaaaaa acctcccac ctcccctga      240 acctgaaaca taaatgaat gcaattgttg ttgttaactt gtttattgca gcttataatg     300
gttacaaata aagcaatagc atcacaaatt tcacaaataa agcatttttt tcactgcatt     360
ctagttgtgg tttgtccaaa ctcatcaatg tatcttatca tgtctggatc cagttcgatg     420
taacccactc gtgcacccaa ctgatcttca gcatctttta ctttcaccag cgtttctggg     480
tgagcaaaaa caggaaggca aaatgccgca aaaaagggaa taagggcgac acggaaatgt     540
tgaatactca tactcttcct ttttcaatat tattgaagca tttatcaggg ttattgtctc     600
atgagcggat acatatttga atgtatttag aaaaataaac aataggggt tccgcgcaca     660 tttccccgaa aagtgccacc tgacgtccat tgttcattcc acggacaaaa acagagaaag     720
gaaacgacag aggccaaaaa gcctcgcttt cagcacctgt cgtttccttt cttttcagag     780
ggtattttaa ataaaaacat taagttatga cgaagaagaa cggaaacgcc ttaaaccgga     840 aaatttttcat aaatagcgaa aacccgcgag gtcgccgccc cgtaacctgt cggatcaccg     900
gaaaggaccc gtaaagtgat aatgattatc atctagacta catcgatggg tcgtgcgctc     960
ctttcggtcg gcgctgcgg gtcgtggggc gggcgtcagg caccgggctt gcgggtcatg    1020
caccaggtcg cgcggtcctt cgggcactcg acgtcggcgg tgacggtgaa gccgagccgc    1080
tcgtagaagg ggaggttgcg gggcgcggag gtctccagga aggcgggcac ccggcgcgc    1140 tcggccgcct ccactccggg gagcacgacg gcgctgccca gaccccttgcc ctggtggtcg    1200 ggcgagacgc cgacggtggc caggaaccac gcgggctcct tgggcggtg cggcgccagg    1260 aggccttcca tctgttgctg cgcggccagc cggaaccgc tcaactcggc catgcgcggg    1320
ccgatctcgg cgaacaccgc cccgcttcg acgctctccg gcgtggtcca gaccgccacc    1380
gcggcgccgt cgtccgcgac ccacaccttg ccgatgtcga gccgacgcg cgtgaggaag    1440
```

```
agttcttgca gctcggtgac ccgctcgatg tggcggtccg gatcgacggt gtggcgcgtg    1500
gcggggtagt cggcgaacgc ggcggcgagg gtgcgtacgg ccctggggac gtcgtcgcgg    1560
gtggcgaggc gcaccgtggg cttgtactcg gtcatggtaa gcttgctagc agctggtacc    1620
cagcttctag agatctgacg gttcactaaa cgagctctgc ttatatagac ctcccaccgt    1680
acacgcctac cgcccatttg cgtcaacggg gcggggttat tacgacattt tggaaagtcc    1740
cgttgatttt ggtgccaaaa caaactccca ttgacgtcaa tggggtggag acttggaaat    1800
ccccgtgagt caaaccgcta ccacgcccca ttggtgtact gccaaaaccg catcaccatg    1860
gtaatagcga tgactaatac gtagatgtac tgccaagtag aaagtcccg taaggtcatg     1920
tactgggcat aatgccaggc gggccattta ccgtcattga cgtcaatagg gggcggactt    1980
ggcatatgat acacttgatg tactgccaag tgggcagttt accgtaaata ctccacccat    2040
tgacgtcaat ggaaagtccc tattggcgtt actatgggaa catacgtcat tattgacgtc    2100
aatgggcggg ggtcgttggg cggtcagcca ggcgggccat ttaccgtaag ttatgtaacg    2160
cggaactcca tatatgggct atgaactaat gaccccgtaa ttgattacta ttaataacta    2220
gtcaataatc aatgtcaaca tggcggtcat attggacatg agccaatata aatgtacata    2280
ttatgatata gatacaacgt atgcaatggc caatagccaa tattgattta tgctatataa    2340
ccaatgacta atatggctaa ttgccaatat tgattcaatg tatagatctt ccatacctac    2400
cagttctgcg cctgcagcaa tgcaacaacg ttgcccggat ctgcgatgat aagctgtcaa    2460
acatgagaat tggtcgacta gcttggcacg ccagaaatcc gcgcggtggt ttttggggt     2520
cgggggtgtt tggcagccac agacgcccgg tgttcgtgtc gcgccagtac atgcggtcca    2580
tgcccaggcc atccaaaaac catgggtctg tctgctcagt ccagtcgtgg accagacccc    2640
acgcaacgcc caaaataata accccacga accataaacc attccccatg ggggaccccg     2700
tccctaaccc acggggccag tggctatggc agggcctgcc gccccgacgt tggctgcgag    2760
ccctgggcct tcacccgaac ttgggggggtg gggtggggaa aaggaagaaa cgcgggcgta    2820
ttggccccaa tggggtctcg gtggggtatc gacagagtgc cagccctggg accgaacccc    2880
gcgtttatga acaaacgacc caacacccgt gcgttttatt ctgtcttttt attgccgtca    2940
tagcgcgggt tccttccggt attgtctcct tccgtgtttc agttagcctc ccccatctcc    3000
cctattcctt tgccctcgga cgagtgctgg ggcgtcggtt ccactatcg gcgagtactt     3060
ctacacagcc atcggtccag acggccgcgc ttctgcgggc gatttgtgta cgcccgacag    3120
tcccggctcc ggatcggacg attgcgtcgc atcgaccctg cgcccaagct gcatcatcga    3180
aattgccgtc aaccaagctc tgatagagtt ggtcaagacc aatgcggagc atatacgccc    3240
ggagccgcgg cgatcctgca agctccggat gcctccgctc gaagtagcgc gtctgctgct    3300
ccatacaagc caaccacggc ctccagaaga agatgttggc gacctcgtat tgggaatccc    3360
cgaacatcgc ctcgctccag tcaatgaccg ctgttatgcg gccattgtcc gtcaggacat    3420
tgttggagcc gaaatccgcg tgcacgaggt gccggacttc ggggcagtcc tcggcccaaa    3480
gcatcagctc atcgagagcc tgcgcgacgg acgcactgac ggtgtcgtcc atcacagttt    3540
gccagtgata cacatgggga tcagcaatcg cgcatatgaa atcacgccat gtagtgtatt    3600
gaccgattcc ttgcggtccg aatgggccga accgctcgt ctggctaaga tcggccgcag     3660
cgcgcgcaaa accctaaat aaagacagca agacacttgc ttgatccaaa tccaaacaga     3720
gtctggtttt ttatttatgt tttaaaccgc attgggaggg gaggaagcct tcagggcaga    3780
aacctgctgg cgcagatcca acagctgctg agaaacgaca ttaagttccc gggtcaaaga    3840
```

```
atccaattgt gccaaaagag ccgtcaactt gtcatcgcgg gcggatgaac gggaagctgc   3900
actgcttgca agcgggctca ggaaagcaaa gtcagtcaca atcccgcggg cggtggctgc   3960
agcggctgaa gcggcggcgg aggctgcagt ctccaacggc gttccagaca cggtctcgta   4020
ggtcaaggta gtagagtttg cgggcaggac ggggcgacca tcaatgctgg agcccatcac   4080
attctgacgc accccggccc atggggcat gcgcgttgtc aaatatgagc tcacaatgct    4140
tccatcaaac gagttggtgc tcatggcggc ggcggctgct gcaaaacaga tacaaaacta   4200
cataagaccc ccaccttata tattctttcc cacccgggat ctgcggcacg ctgttgacgc   4260
tgttaagcgg gtcgctgcag ggtcgctcgg tgttcgaggc cacacgcgtc accttaatat   4320
gcgaagtgga cctgggaccg cgccgccccg actgcatctg cgtgttcgaa ttcgccaatg   4380
acaagacgct gggcggggtt tgtgtcatca tagaactaaa gacatgcaaa tatatttctt   4440
ccggggacac cgccagcaaa cgcgagcaac gggccacggg gatgaagcag gcatggcgg    4500
ccgacgcgct gggctacgtc ttgctggcgt tcgcgacgcg aggctggatg gccttcccca   4560
ttatgattct tctcgcttcc ggcggcatcg ggatgcccgc gttgcaggcc atgctgtcca   4620
ggcaggtaga tgacgaccat cagggacagc ttcaaggatc gctcgcggct cttaccagcc   4680
taacttcgat cactggaccg ctgatcgtca cggcgattta tgccgcctcg gcgagcacat   4740
ggaacgggtt ggcatggatt gtaggcgccg ccctatacct tgtctgcctc cccgcgttgc   4800
gtcgcggtgc atggagccgg gccacctcga cctgaatgga agccggcggc acctcgctaa   4860
cggattcacc actccaagaa ttggagccaa tcaattcttg cggagaactg tgaatgcgca   4920
aaccaaccct tggcagaaca tatccatcgc gtccgccatc tccagcagcc gcacgcggcg   4980
cagcaaaagg ccaggaaccg taaaaaggcc gcgttgctgg cgttttttcca taggctccgc   5040
cccctgacg agcatcacaa aaatcgacgc tcaagtcaga ggtggcgaaa cccgacagga   5100
ctataaagat accaggcgtt tccccctgga agctccctcg tgcgctctcc tgttccgacc   5160
ctgccgctta ccggatacct gtccgccttt ctcccttcgg gaagcgtggc gctttctcat   5220
agctcacgct gtaggtatct cagttcggtg taggtcgttc gctccaagct gggctgtgtg   5280
cacgaacccc ccgttcagcc cgaccgctgc gccttatccg gtaactatcg tcttgagtcc   5340
aacccggtaa gacacgactt atcgccactg gcagcagcca ctggtaacag gattagcaga   5400
gcgaggtatg taggcggtgc tacagagttc ttgaagtggt ggcctaacta cggctacact   5460
agaaggacag tatttggtat ctgcgctctg ctgaagccag ttaccttcgg aaaaagagtt   5520
ggtagctctt gatccggcaa acaaaccacc gctggtagcg gtggtttttt tgtttgcaag   5580
cagcagatta cgcgcagaaa aaaggatctc aagaagatc ctttgatctt ttctacgggg    5640
tctgacgctc agtggaacga aaactcacgt taagggattt tggtcatgag attatcaaaa   5700
aggatcttca cctagatcct tttaaattaa aaatgaagtt ttaaatcaat ctaaagtata   5760
tatgagtaaa cttggtctga cagttaccaa tgcttaatca gtgaggcacc tatctcagcg   5820
atctgtctat ttcgttcatc catagttgcc tgactccccg tcgtgtagat aactacgata   5880
cgggagggct taccatctgg ccccagtgct gcaatgatac cgcgagaccc acgctcaccg   5940
gctccagatt tatcagcaat aaaccagcca gccggaaggg ccgagcgcag aagtggtcct   6000
gcaactttat ccgcctccat ccagtctatt aattgttgcc gggaagctag agtaagtagt   6060
tcgccagtta atagtttgcg caacgttgtt gccattgctg caggcatcgt ggtgtcacgc   6120
tcgtcgtttg gtatggcttc attcagctcc ggttcccaac gatcaaggcg agttacatga   6180
```

```
tcccccatgt tgtgcaaaaa agcggttagc tccttcggtc ctccgatcgt tgtcagaagt      6240
aagttggccg cagtgttatc actcatggtt atggcagcac tgcataattc tcttactgtc      6300
atgccatccg taagatgctt ttctgtgact ggtgagtact caaccaagtc attctgagaa      6360
tagtgtatgc ggcgaccgag ttgctcttgc ccggcgtcaa cacgggataa taccgcgcca      6420
catagcagaa ctttaaaagt gctcatcatt ggaaaacgtt cttcggggcg aaaactctca      6480
aggatcttac cgctgttgag atccagttcg atgtaaccca ctcgtgcacc caactgatct      6540
tcagcatctt ttactttcac cagcgtttct gggtgagcaa aaacaggaag gcaaaatgcc      6600
gcaaaaaagg gaataagggc gacacggaaa tgttgaatac tcatactctt ccttttcaa       6660 tattattgaa gcatttatca gggttattgt ctcatgagcg gatacatatt tgaatgtatt      6720
tagaaaaata aacaaatagg ggttccgcgc acatttcccc gaaaagtgcc acctgacgtc      6780
taagaaacca ttattatcat gacattaacc tataaaaata ggcgtatcac gaggcccttc      6840
ccgtagtctt cctgggcccc tgggaggtac atgtccccca gcattggtgt aagagcttca      6900
gccaagagtt acacataaag gcaatgttgt gttgcagtcc acagactgca aagtctgctc      6960
caggatgaaa gccactcagt gttggcaaat gtgcacatcc atttataagg atgtcaacta      7020
cagtcagaga accccttttgt gtttggtccc cccccgtgtc acatgtggaa cagggcccag      7080
ttggcaagtt gtaccaacca actgaaggga ttacatgcac tgccccgcga agaaggggca      7140
gagatgccgt agtcaggttt agttcgtccg gcggcggggc                            7180

<210> SEQ ID NO 15
<211> LENGTH: 37391
<212> TYPE: DNA
<213> ORGANISM: Artificial Sequence
<220> FEATURE:
<223> OTHER INFORMATION: Synthetic

<400> SEQUENCE: 15
ctaaattgta agcgttaata ttttgttaaa attcggccgg ccatcatcaa taatataccct       60 tattttggat tgaagccaat atgataatga gggggtggag tttgtgacgt ggcgcggggc      120
gtgggaacgg ggcgggtgac gtagtagtgt ggcggaagtg tgatgttgca agtgtggcgg      180
aacacatgta taacttcgta taatgtatgc tatacgaagt tatacatgta agcgacggat      240
gtggcaaaag tgacgttttt ggtgtgcgcc ggtgtacaca ggaagtgaca attttcgcgc      300
ggttttaggc ggatgttgta gtaaatttgg gcgtaaccga gtaagatttg gccattttcg      360
cgggaaaact gaataagagg aagtgaaatc tgaataattt tgtgttactc atagcgcgta      420
atatttgtct agggagatca attggattct ttgacccggg aacttaatgt cgtttctcag      480
cagctgttgg atctgcgcca gcaggtttct gccctgaagg cttcctcccc tcccaatgcg      540
gtttaaaaca taaataaaaa accagactct gtttggattt ggatcaagca agtgtcttgc      600
tgtctttatt taggggtttt gcgcgcgcgg taggcccggg accagcggtc tcggtcgttg      660
agggtcctgt gtattttttc caggacgtgg taaaggtgac tctggatgtt cagatacatg      720
ggcataagcc cgtctctggg gtggaggtag caccactgca gagcttcatg ctgcggggtg      780
gtgttgtaga tgatccagtc gtagcaggag cgctgggcgt ggtgcctaaa aatgtctttc      840
agtagcaagc tgattgccag gggcaggccc ttggtgtaag tgtttacaaa gcggttaagc      900
tgggatgggt gcatacgtgg ggatatgaga tgcatcttgg actgtatttt taggttggct      960
atgttcccag cctatatccct ccggggattc atgttgtgca gaaccaccag cacagtgtat     1020
ccggtgcact tgggaaattt gtcatgtagc ttagaaggaa atgcgtggaa gaacttggag     1080
```

```
acgcccttgt gacctccaag attttccatg cattcgtcca taatgatggc aatgggccca   1140
cgggcggcgg cctgggcgaa gatatttctg ggatcactaa cgtcatagtt gtgttccagg   1200
atgagatcgt cataggccat ttttacaaag cgcggcgga gggtgccaga ctgcggtata    1260
atggttccat ccggcccagg ggcgtagtta ccctcacaga tttgcatttc ccacgctttg   1320
agttcagatg gggggatcat gtctacctgc ggggcgatga agaaaacggt ttccggggta   1380
ggggagatca gctgggaaga aagcaggttc ctgagcagct gcgacttacc gcagccggtg   1440
ggcccgtaaa tcacacctat taccgggtgc aactggtagt taagagagct gcagctgccg   1500
tcatccctga gcaggggggc cacttcgtta agcatgtccc tgactcgcat gttttccctg   1560
accaaatccg ccagaaggcg ctcgccgccc agcgatagca gttcttgcaa ggaagcaaag   1620
tttttcaacg gtttgagacc gtccgccgta ggcatgcttt tgagcgtttg accaagcagt   1680
tccaggcggt cccacagctc ggtcacctgc tctacggcat ctcgatccag catatctcct   1740
cgtttcgcgg gttggggcgg ctttcgctgt acggcagtag tcggtgctcg tccagacggg   1800
ccagggtcat gtcttccac gggcgcaggg tcctcgtcag cgtagtctgg gtcacggtga    1860
aggggtgcgc tccgggctgc gcgctggcca gggtgcgctt gaggctggtc ctgctggtgc   1920
tgaagcgctg ccggtcttcg ccctgcgcgt cggccaggta gcatttgacc atggtgtcat   1980
agtccagccc ctccgcggcg tggcccttgg cgcgcagctt gcccttggag gaggcgccgc   2040
acgaggggca gtgcagactt tgagggcgt agagcttggg cgcgagaaat accgattccg    2100
gggagtaggc atccgcgccg caggccccgc agacggtctc gcattccacg agccaggtga   2160
gctctggccg ttcggggtca aaaccaggt ttccccatg cttttttgatg cgtttcttac    2220
ctctggtttc catgagccgg tgtccacgct cggtgacgaa aaggctgtcc gtgtccccgt   2280
atacagactt gagaggcctg tcctcgagcg tgttccgcg gtcctcctcg tatagaaact    2340
cggaccactc tgagacaaag gctcgcgtcc aggccagcac gaaggaggct aagtgggagg   2400
ggtagcggtc gttgtccact aggggggtcca ctcgctccag ggtgtgaaga cacatgtcgc   2460
cctcttcggc atcaaggaag gtgattggtt tgtaggtgta ggccacgtga ccgggtgttc   2520
ctgaaggggg gctataaaag ggggtggggg cgcgttcgtc ctcactctct tccgcatcgc   2580
tgtctgcgag ggccagctgt tggggtgagt actccctctg aaaagcgggc atgacttctg   2640
cgctaagatt gtcagtttcc aaaaacgagg aggatttgat attcacctgg cccgcggtga   2700
tgcctttgag ggtggccgca tccatctggt cagaaaagac aatcttttg ttgtcaagct    2760
tggtggcaaa cgaccgtag agggcgttgg acagcaactt ggcgatggag cgcagggttt    2820
ggttttgtc gcgatcggcg cgctccttgg ccgcgatgtt tagctgcacg tattcgcgcg    2880
caacgcaccg ccattcggga aagacggtgg tgcgctcgtc gggcaccagg tgcacgcgcc   2940
aaccgcggtt gtgcagggtg acaaggtcaa cgctggtggc tacctctccg cgtaggcgct   3000
cgttggtcca gcagaggcgg ccgcccttgc gcgagcagaa tggcggtagg gggtctagct   3060
gcgtctcgtc cgggggtct gcgtccacgg taaagacccc gggcagcagg cgcgcgtcga    3120
agtagtctat cttgcatcct tgcaagtcta gcgcctgctg ccatgcgcgg gcggcaagcg   3180
cgcgctcgta tgggttgagt gggggacccc atggcatggg gtgggtgagc gcggaggcgt   3240
acatgccgca aatgtcgtaa acgtagaggg gctctctgag tattccaaga tatgtagggt   3300
agcatcttcc accgcggatg ctggcgcgca cgtaatcgta tagttcgtgc gagggagcga   3360
ggaggtcggg accgaggttg ctacgggcgg gctgctctgc tcggaagact atctgcctga   3420
```

```
agatggcatg tgagttggat gatatggttg gacgctggaa gacgttgaag ctggcgtctg    3480
tgagacctac cgcgtcacgc acgaaggagg cgtaggagtc gcgcagcttg ttgaccagct    3540
cggcggtgac ctgcacgtct agggcgcagt agtccagggt ttccttgatg atgtcatact    3600
tatcctgtcc ctttttttc cacagctcgc ggttgaggac aaactcttcg cggtctttcc     3660
agtactcttg gatcggaaac ccgtcggcct ccgaacggta agagcctagc atgtagaact    3720
ggttgacggc ctggtaggcg cagcatccct tttctacggg tagcgcgtat gcctgcgcgg    3780
ccttccggag cgaggtgtgg gtgagcgcaa aggtgtccct gaccatgact ttgaggtact    3840
ggtatttgaa gtcagtgtcg tcgcatccgc cctgctccca gagcaaaaag tccgtgcgct    3900
ttttggaacg cggatttggc agggcgaagg tgacatcgtt gaagagtatc tttcccgcgc    3960
gaggcataaa gttgcgtgtg atgcggaagg gtcccggcac ctcggaacgg ttgttaatta    4020
cctgggcggc gagcacgatc tcgtcaaagc cgttgatgtt gtggcccaca atgtaaagtt    4080
ccaagaagcg cgggatgccc ttgatggaag gcaattttt aagttcctcg taggtgagct      4140
cttcagggga gctgagcccg tgctctgaaa gggcccagtc tgcaagatga gggttggaag    4200
cgacgaatga gctccacagg tcacgggcca ttagcatttg caggtggtcg cgaaaggtcc    4260
taaactggcg acctatggcc attttttctg gggtgatgca gtagaaggta agcgggtctt    4320
gttcccagcg gtcccatcca aggttcgcgg ctaggtctcg cgcggcagtc actagaggct    4380
catctccgcc gaacttcatg accagcatga agggcacgag ctgcttccca aggcccccca    4440
tccaagtata ggtctctaca tcgtaggtga caaagagacg ctcggtgcga ggatgcgagc    4500
cgatcgggaa gaactggatc tcccgccacc aattggagga gtggctattg atgtggtgaa    4560
agtagaagtc cctgcgacgg gccgaacact cgtgctggct tttgtaaaaa cgtgcgcagt    4620
actggcagcg gtgcacgggc tgtacatcct gcacgaggtt gacctgacga ccgcgcacaa    4680
ggaagcagag tgggaatttg agcccctcgc ctggcgggtt tggctggtgg tcttctactt    4740
cggctgcttg tccttgaccg tctggctgct cgaggggagt tacggtggat cggaccacca    4800
cgccgcgcga gcccaaagtc cagatgtccg cgcgcggcgg tcggagcttg atgacaacat    4860
cgcgcagatg ggagctgtcc atggtctgga gctcccgcgg cgtcaggtca ggcgggagct    4920
cctgcaggtt tacctcgcat agacgggtca gggcgcgggc tagatccagg tgatacctaa    4980
tttccagggg ctggttggtg gcggcgtcga tggcttgcaa gaggccgcat ccccgcggcg    5040
cgactacggt accgcgcggc gggcggtggg ccgcggggt gtccttggat gatgcatcta     5100
aaagcggtga cgcggggcgag ccccggagg tagggggggc tccggacccg ccgggagagg    5160
gggcaggggc acgtcggcgc cgcgcgcggg caggagctgg tgctgcgcgc gtaggttgct    5220
ggcgaacgcg acgacgcggc ggttgatctc ctgaatctgg cgcctctgcg tgaagacgac    5280
gggcccggtg agcttgagcc tgaaagagag ttcgacagaa tcaatttcgg tgtcgttgac    5340
ggcggcctgg cgcaaaatct cctgcacgtc cctgagttg tcttgatagg cgatctcggc     5400
catgaactgc tcgatctctt cctcctggag atctccgcgt ccggctcgct ccacggtggc    5460
ggcgaggtcg ttggaaatgc gggccatgag ctgcgagaag gcgttgaggc ctccctcgtt    5520
ccagacgcgc ctgtagacca cgccccttc ggcatcgcgg gcgcgcatga ccacctgcgc     5580
gagattgagc tccacgtgcc gggcgaagac ggcgtagttt cgcaggcgct gaaagaggta    5640
gttgaggtg tggcggtgt gttctgccac gaagaagtac ataacccagc gtcgcaacgt      5700
ggattcgttt atatcccca aggcctcaag gcgctccatg gcctcgtaga agtccacggc     5760
gaagttgaaa aactgggagt tgcgcgccga cacggttaac tcctcctcca gaagacggat    5820
```

```
gagctcggcg acagtgtcgc gcacctcgcg ctcaaaggct acaggggcct cttcttcttc   5880
ttcaatctcc tcttccataa gggcctcccc ttcttcttct tctggcggcg gtggggagg    5940
gggacacgg cggcgacgac ggcgcaccgg gaggcggtcg acaaagcgct cgatcatctc    6000
cccgcggcga cggcgcatgg tctcggtgac ggcgcggccg ttctcgcggg ggcgcagttg   6060
gaagacgccg cccgtcatgt cccggttatg ggttggcggg gggctgccat gcggcaggga   6120
tacgcgcta acgatgcatc tcaacaattg ttgtgtaggt actccgccgc cgagggacct    6180
gagcgagtcc gcatcgaccg gatcggaaaa cctctcgaga aaggcgtcta accagtcaca   6240
gtcgcaaggt aggctgagca ccgtggcggg cggcagcggg cggcggtcgg ggttgtttct   6300
ggcggaggtg ctgctgatga tgtaattaaa gtaggcggtc ttgagacggc ggatggtcga   6360
cagaagcacc atgtccttgg gtccggcctg ctgaatgcgc aggcggtcgg ccatgcccca   6420
ggcttcgttt tgacatcggc gcaggtcttt gtagtagtct tgcatgagcc tttctaccgg   6480
cacttcttct tctccttcct cttgtcctgc atctcttgca tctatcgctg cggcggcggc   6540
ggagtttggc cgtaggtggc gccctcttcc tcccatgcgt gtgaccccga agcccctcat   6600
cggctgaagc agggctaggt cggcgacaac gcgctcggct aatatggcct gctgcacctg   6660
cgtgagggta gactggaagt catccatgtc cacaaagcgg tggtatgcgc ccgtgttgat   6720
ggtgtaagtg cagttggcca taacggacca gttaacggtc tggtgacccg gctgcgagag   6780
ctcggtgtac ctgagacgcg agtaagccct cgagtcaaat acgtagtcgt tgcaagtccg   6840
caccaggtac tggtatccca ccaaaaagtg cggcggcggc tggcggtaga ggggccagcg   6900
tagggtggcc ggggctccgg gggcgagatc ttccaacata aggcgatgat atccgtagat   6960
gtacctggac atccaggtga tgccggcggc ggtggtggag gcgcgcggaa agtcgcggac   7020
gcggttccag atgttgcgca gcggcaaaaa gtgctccatg gtcgggacgc tctggccggt   7080
caggcgcgcg caatcgttga cgctctaccg tgcaaaagga gagcctgtaa gcgggcactc   7140
ttccgtggtc tggtggataa attcgcaagg gtatcatggc ggacgaccgg ggttcgagcc   7200
ccgtatccgg ccgtccgccg tgatccatgc ggttaccgcc cgcgtgtcga acccaggtgt   7260
gcgacgtcag acaacggggg agtgctcctt ttggcttcct tccaggcgcg gcggctgctg   7320
cgctagcttt tttggccact ggccgcgcgc agcgtaagcg gttaggctgg aaagcgaaag   7380
cattaagtgg ctcgctccct gtagccgag ggttattttc caagggttga gtcgcggac    7440
ccccggttcg agtctcggac cggccggact gcggcgaacg ggggtttgcc tccccgtcat   7500
gcaagacccc gcttgcaaat tcctccggaa acagggacga gcccctttt tgcttttccc    7560
agatgcatcc ggtgctgcgg cagatgcgcc cccctcctca gcagcggcaa gagcaagagc   7620
agcggcagac atgcagggca ccctcccctc ctcctaccgc gtcaggaggg gcgacatccg   7680
cggttgacgc ggcagcagat ggtgattacg aaccccgcg gcgccgggcc cggcactacc    7740
tggacttgga ggagggcgag ggcctggcgc ggctaggagc gccctctcct gagcggtacc   7800
caagggtgca gctgaagcgt gatacgcgtg aggcgtacgt gccgcggcag aacctgtttc   7860
gcgaccgcga gggagaggag cccgaggaga tgcgggatcg aaagttccac gcagggcgcg   7920
agctgcggca tggcctgaat cgcgagcggt tgctgcgcga ggaggacttt gagcccgacg   7980
cgcgaaccgg gattagtccc gcgcgcgcac acgtggcggc cgccgacctg gtaaccgcat   8040
acgagcagac ggtgaaccag gagattaact ttcaaaaaag ctttaacaac cacgtgcgta   8100
cgcttgtggc gcgcgaggag gtggctatag gactgatgca tctgtgggac tttgtaagcg   8160
```

```
cgctggagca aaacccaaat agcaagccgc tcatggcgca gctgttcctt atagtgcagc   8220
acagcaggga caacgaggca ttcagggatg cgctgctaaa catagtagag cccgagggcc   8280
gctggctgct cgatttgata acatcctgc agagcatagt ggtgcaggag cgcagcttga    8340
gcctggctga caaggtggcc gccatcaact attccatgct tagcctgggc aagttttacg   8400
cccgcaagat ataccatacc ccttacgttc ccatagacaa ggaggtaaag atcgagggg    8460
tctacatgcg catggcgctg aaggtgctta ccttgagcga cgacctgggc gtttatcgca   8520
acgagcgcat ccacaaggcc gtgagcgtga gccggcggcg cgagctcagc gaccgcgagc   8580
tgatgcacag cctgcaaagg gccctggctg cacgggcag cggcgataga gaggccgagt    8640
cctactttga cgcgggcgct gacctgcgct gggccccaag ccgacgcgcc ctggaggcag   8700
ctggggccgg acctgggctg gcggtggcac ccgcgcgcgc tggcaacgtc ggcggcgtgg   8760
aggaatatga cgaggacgat gagtacgagc cagaggacgg cgagtactaa gcggtgatgt   8820
ttctgatcag atgatgcaag acgcaacgga cccggcggtg cgggcggcgc tgcagagcca   8880
gccgtccggc cttaactcca cggacgactg gcgccaggtc atggaccgca tcatgtcgct   8940
gactgcgcgc aatcctgacg cgttccggca gcagccgcag gccaaccggc tctccgcaat   9000
tctggaagcg gtggtcccgg cgcgcgcaaa ccccacgcac gagaaggtgc tggcgatcgt   9060
aaacgcgctg gccgaaaaca gggccatccg gcccgacgaa gccggcctgg tctacgacgc   9120
gctgcttcag cgcgtggctc gttacaacag cggcaacgtg cagaccaacc tggaccggct   9180
ggtgggggat gtgcgcgagg ccgtggcgca gcgtgagcgc gcgcagcagc agggcaacct   9240
gggctccatg gttgcactaa acgccttcct gagtacacag cccgccaacg tgccgcgggg   9300
acaggaggac tacaccaact ttgtgagcgc actgcggcta atggtgactg agacaccgca   9360
aagtgaggtg taccagtctg ggccagacta ttttttccag accagtagac aaggcctgca   9420
gaccgtaaac ctgagccagg ctttcaaaaa cttgcagggg ctgtgggggg tgcgggctcc   9480
cacaggcgac cgcgcgaccg tgtctagctt gctgacgccc aactcgcgcc tgttgctgct   9540
gctaatagcg cccttcacgg acagtggcag cgtgtcccgg gacacatacc taggtcactt   9600
gctgacactg taccgcgagg ccataggtca ggcgcatgtg gacgagcata ctttccagga   9660
gattacaagt gtcagccgcg cgctggggca ggaggacacg ggcagcctgg aggcaaccct   9720
aaactacctg ctgaccaacc ggcggcagaa gatcccctcg ttgcacagtt taaacagcga   9780
ggaggagcgc atttttgcgct acgtgcagca gagcgtgagc cttaacctga tgcgcgacgg   9840
ggtaacgccc agcgtggcgc tggacatgac cgcgcgcaac atggaaccgg gcatgtatgc   9900
ctcaaaccgg ccgtttatca accgcctaat ggactacttg catcgcgcgg ccgccgtgaa   9960
ccccgagtat ttcaccaatg ccatcttgaa cccgcactgg ctaccgcccc tggtttctcta 10020
caccggggga ttcgaggtgc ccgagggtaa cgatggattc ctctgggacg acatagacga  10080
cagcgtgttt tccccgcaac cgcagaccct gctagagttg caacagcgcg agcaggcaga  10140
ggcggcgctg cgaaaggaaa gcttccgcag gccaagcagc ttgtccgatc taggcgctgc  10200
ggccccgcgg tcagatgcta gtagcccatt tccaagcttg atagggtctc ttaccagcac  10260
tcgcaccacc cgcccgcgcc tgctgggcga ggaggagtac ctaaacaact cgctgctgca  10320
gccgcagcgc gaaaaaaacc tgcctccggc atttcccaac aacgggatag agagcctagt  10380
ggacaagatg agtagatgga agacgtacgc gcaggagcac agggacgtgc caggcccgcg  10440
cccgcccacc cgtcgtcaaa ggcacgaccg tcagcggggt ctggtgtggg aggacgatga  10500
ctcggcagac gacagcagcg tcctggattt gggagggagt ggcaacccgt tgcgcacct   10560
```

```
tcgccccagg ctggggagaa tgttttaaaa aaaaaaaagc atgatgcaaa ataaaaaact    10620
caccaaggcc atggcaccga gcgttggttt tcttgtattc cccttagtat gcggcgcgcg    10680
gcgatgtatg aggaaggtcc tcctccctcc tacgagagtg tggtgagcgc ggcgccagtg    10740
gcggcggcgc tgggttctcc cttcgatgct cccctggacc cgccgtttgt gcctccgcgg    10800
tacctgcggc ctaccggggg agaaacagc atccgttact ctgagttggc acccctattc     10860
gacaccaccc gtgtgtacct ggtggacaac aagtcaacgg atgtggcatc cctgaactac    10920
cagaacgacc acagcaactt tctgaccacg gtcattcaaa acaatgacta cagcccgggg    10980
gaggcaagca cacagaccat caatcttgac gaccggtcgc actggggcgg cgacctgaaa    11040
accatcctgc ataccaacat gccaaatgtg aacgagttca tgtttaccaa taagtttaag    11100
gcgcgggtga tggtgtcgcg cttgcctact aaggacaatc aggtgagct gaaatacgag     11160 tgggtggagt tcacgctgcc cgagggcaac tactccgaga ccatgaccat agaccttatg    11220
aacaacgcga tcgtggagca ctacttgaaa gtgggcagac agaacggggt tctggaaagc    11280
gacatcgggg taaagtttga cacccgcaac ttcagactgg ggtttgaccc cgtcactggt    11340
cttgtcatgc tgggtata tacaaacgaa gccttccatc cagacatcat tttgctgcca      11400
ggatgcgggg tggacttcac ccacagccgc ctgagcaact tgttgggcat ccgcaagcgg    11460 caaccttcc aggagggctt taggatcacc tacgatgatc tggagggtgg taacattccc     11520
gcactgttgg atgtggacgc ctaccaggcg agcttgaaag atgacaccga acagggcggg    11580
ggtggcgcag gcggcagcaa cagcagtggc agcggcgcgg aagagaactc caacgcggca    11640
gccgcggcaa tgcagccggt ggaggacatg aacgatcatg ccattcgcgg cgacaccttt    11700
gccacacggg ctgaggagaa gcgcgctgag gccgaagcag cggccgaagc tgccgccccc    11760
gctgcgcaac ccgaggtcga gaagcctcag aagaaaccgg tgatcaaacc cctgacagag    11820
gacagcaaga aacgcagtta caacctaata agcaatgaca gcaccttcac ccagtaccgc    11880
agctggtacc ttgcatacaa ctacggcgac cctcagaccg gaatccgctc atggaccctg    11940
ctttgcactc ctgacgtaac ctgcggctcg gagcaggtct actggtcgtt gccagacatg    12000
atgcaagacc ccgtgacctt ccgctccacg cgccagatca gcaactttcc ggtggtgggc    12060
gccgagctgt tgcccgtgca ctccaagagc ttctacaacg accaggccgt ctactcccaa    12120
ctcatccgcc agtttacctc tctgacccac gtgttcaatc gctttcccga gaaccagatt    12180
ttggcgcgcc cgccagcccc caccatcacc accgtcagtg aaaacgttcc tgctctcaca    12240
gatcacggga cgctaccgct gcgcaacagc atcggaggag tccagcgagt gaccattact    12300
gacgccagac gccgcacctg cccctacgtt tacaaggccc tgggcatagt ctcgccgcgc    12360
gtcctatcga gccgcacttt ttgagcaagc atgtccatcc ttatatcgcc cagcaataac    12420
acaggctggg gcctgcgctt cccaagcaag atgtttggcg gggccaagaa gcgctccgac    12480
caacacccag tgcgcgtgcg cgggcactac cgcgcgccct ggggcgcgca caaacgcggc    12540
cgcactgggc gcaccaccgt cgatgacgcc atcgacgcgg tggtggagga ggcgcgcaac    12600
tacacgccca cgccgccacc agtgtccaca gtggacgcgg ccattcagac cgtggtgcgc    12660
ggagcccggc gctatgctaa aatgaagaga cggcggaggc gcgtagcacg tcgccaccgc    12720
cgccgacccg gcactgccgc ccaacgcgcg gcggcggccc tgcttaaccg cgcacgtcgc    12780 accgccgac gggcggccat gcgggccgct cgaaggctgg ccgcgggtat tgtcactgtg    12840 cccccaggt ccaggcgacg agcggccgcc gcagcagccg cggccattag tgctatgact    12900
```

| | |
|---|---|
| cagggtcgca ggggcaacgt gtattgggtg cgcgactcgg ttagcggcct gcgcgtgccc | 12960 |
| gtgcgcaccc gccccccgcg caactagatt gcaagaaaaa actacttaga ctcgtactgt | 13020 |
| tgtatgtatc cagcggcggc ggcgcgcaac gaagctatgt ccaagcgcaa aatcaaagaa | 13080 |
| gagatgctcc aggtcatcgc gccggagatc tatggccccc cgaagaagga agagcaggat | 13140 |
| tacaagcccc gaaagctaaa gcgggtcaaa aagaaaaaga aagatgatga tgatgaactt | 13200 |
| gacgacgagg tggaactgct gcacgctacc gcgcccaggc gacgggtaca gtggaaaggt | 13260 |
| cgacgcgtaa aacgtgtttt gcgacccggc accaccgtag tctttacgcc cggtgagcgc | 13320 |
| tccacccgca cctacaagcg cgtgtatgat gaggtgtacg gcgacgagga cctgcttgag | 13380 |
| caggccaacg agcgcctcgg ggagtttgcc tacgaaaagc ggcataagga catgctggcg | 13440 |
| ttgccgctgg acgagggcaa cccaacacct agcctaaagc ccgtaacact gcagcaggtg | 13500 |
| ctgcccgcgc ttgcaccgtc cgaagaaaag cgcggcctaa agcgcgagtc tggtgacttg | 13560 |
| gcacccaccg tgcagctgat ggtacccaag cgccagcgac tggaagatgt cttggaaaaa | 13620 |
| atgaccgtgg aacctgggct ggagcccgag gtccgcgtgc ggccaatcaa gcaggtggcg | 13680 |
| ccgggactgg gcgtgcagac cgtggacgtt cagataccca ctaccagtag caccagtatt | 13740 |
| gccaccgcca cagagggcat ggagacacaa acgtccccgg ttgcctcagc ggtggcggat | 13800 |
| gccgcggtgc aggcggtcgc tgcggccgcg tccaagacct ctacggaggt gcaaacggac | 13860 |
| ccgtggatgt ttcgcgtttc agccccccgg cgcccgcgcg gttcgaggaa gtacggcgcc | 13920 |
| gccagcgcgc tactgcccga atatgcccta catccttcca ttgcgcctac ccccggctat | 13980 |
| cgtggctaca cctaccgccc cagaagacga gcaactaccc gacgccgaac caccactgga | 14040 |
| acccgccgcc gccgtcgccg tcgccagccc gtgctggccc cgatttccgt gcgcagggtg | 14100 |
| gctcgcgaag gaggcaggac cctggtgctg ccaacagcgc gctaccaccc cagcatcgtt | 14160 |
| taaaagccgg tctttgtggt tcttgcagat atggccctca cctgccgcct ccgtttcccg | 14220 |
| gtgccgggat tccgaggaag aatgcaccgt aggaggggca tggccggcta cggcctgacg | 14280 |
| ggcggcatgc gtcgtgcgca ccaccggcgg cggcgcgcgt cgcaccgtcg catgcgcggc | 14340 |
| ggtatcctgc ccctccttat tccactgatc gccgcggcga ttggcgccgt gcccggaatt | 14400 |
| gcatccgtgg ccttgcaggc gcagagacac tgattaaaaa caagttgcat gtggaaaaat | 14460 |
| caaaataaaa agtctggact ctcacgctcg cttggtcctg taactatttt gtagaatgga | 14520 |
| agacatcaac tttgcgtctc tggccccgcg acacggctcg cgcccgttca tgggaaactg | 14580 |
| gcaagatatc ggcaccagca atatgagcgg tggcgccttc agctgggggct cgctgtggag | 14640 |
| cggcattaaa aatttcggtt ccaccgttaa gaactatggc agcaaggcct ggaacagcag | 14700 |
| cacaggccag atgctgaggg ataagttgaa agagcaaaat ttccaacaaa aggtggtaga | 14760 |
| tggcctggcc tctggcatta gcggggtggt ggacctggcc aaccaggcag tgcaaaataa | 14820 |
| gattaacagt aagcttgatc cccgccctcc cgtagaggag cctccaccgg ccgtggagac | 14880 |
| agtgtctcca gaggggcgtg gcgaaaagcg tccgcgcccc gacagggaag aaactctggt | 14940 |
| gacgcaaata gacgagcctc cctcgtacga ggaggcacta aagcaaggcc tgcccaccac | 15000 |
| ccgtcccatc gcgcccatgg ctaccggagt gctgggccag cacacacccg taacgctgga | 15060 |
| cctgcctccc cccgccgaca cccagcagaa acctgtgctg ccaggcccga ccgccgttgt | 15120 |
| tgtaacccgt cctagccgcg cgtccctgcg ccgcgccgcc agcggtccgc gatcgttgcg | 15180 |
| gcccgtagcc agtggcaact ggcaaagcac actgaacagc atcgtgggtc tgggggtgca | 15240 |
| atccctgaag cgccgacgat gcttctgaat agctaacgtg tcgtatgtgt gtcatgtatg | 15300 |

```
cgtccatgtc gccgccagag gagctgctga gccgccgcgc gcccgctttc caagatggct    15360
accccttcga tgatgccgca gtggtcttac atgcacatct cgggccagga cgcctcggag    15420
tacctgagcc ccgggctggt gcagtttgcc cgcgccaccg agacgtactt cagcctgaat    15480
aacaagttta gaaaccccac ggtggcgcct acgcacgacg tgaccacaga ccggtcccag    15540
cgtttgacgc tgcggttcat ccctgtggac cgtgaggata ctgcgtactc gtacaaggcg    15600
cggttcaccc tagctgtggg tgataaccgt gtgctggaca tggcttccac gtactttgac    15660
atccgcggcg tgctggacag gggccctact tttaagccct actctggcac tgcctacaac    15720
gccctggctc ccaagggtgc cccaaatcct tgcgaatggg atgaagctgc tactgctctt    15780
gaaataaacc tagaagaaga ggacgatgac aacgaagacg aagtagacga gcaagctgag    15840
cagcaaaaaa ctcacgtatt tgggcaggcg ccttattctg gtataaatat tacaaaggag    15900
ggtattcaaa taggtgtcga aggtcaaaca cctaaatatg ccgataaaac atttcaacct    15960
gaacctcaaa taggagaatc tcagtggtac gaaactgaaa ttaatcatgc agctgggaga    16020
gtccttaaaa agactacccc aatgaaacca tgttacggtt catatgcaaa acccacaaat    16080
gaaaatggag ggcaaggcat tcttgtaaag caacaaaatg gaaagctaga aagtcaagtg    16140
gaaatgcaat ttttctcaac tactgaggcg accgcaggca atggtgataa cttgactcct    16200
aaagtggtat tgtacagtga agatgtagat atagaaaccc cagacactca tatttcttac    16260
atgcccacta ttaaggaagg taactcacga gaactaatgg gccaacaatc tatgcccaac    16320
aggcctaatt acattgcttt tagggacaat tttattggtc taatgtatta caacagcacg    16380
ggtaatatgg gtgttctggc gggccaagca tcgcagttga atgctgttgt agatttgcaa    16440
gacagaaaca cagagctttc ataccagctt ttgcttgatt ccattggtga tagaaccagg    16500
tacttttcta tgtggaatca ggctgttgac agctatgatc cagatgttag aattattgaa    16560
aatcatggaa ctgaagatga acttccaaat tactgctttc cactgggagg tgtgattaat    16620
acagagactc ttaccaaggt aaaacctaaa acaggtcagg aaaatggatg ggaaaaagat    16680
gctacagaat tttcagataa aaatgaaata agagttggaa ataattttgc catggaaatc    16740
aatctaaatg ccaacctgtg gagaaatttc ctgtactcca acatagcgct gtatttgccc    16800
gacaagctaa agtacagtcc ttccaacgta aaaatttctg ataacccaaa cacctacgac    16860
tacatgaaca agcgagtggt ggctcccggg ttagtggact gctacattaa ccttggagca    16920
cgctggtccc ttgactatat ggacaacgtc aacccattta accaccaccg caatgctggc    16980
ctgcgctacc gctcaatgtt gctgggcaat ggtcgctatg tgcccttcca catccaggtg    17040
cctcagaagt tctttgccat taaaaacctc cttctcctgc cgggctcata cacctacgag    17100
tggaacttca ggaaggatgt taacatggtt ctgcagagct ccctaggaaa tgacctaagg    17160
gttgacggag ccagcattaa gtttgatagc atttgccttt acgccacctt cttccccatg    17220
gcccacaaca ccgcctccac gcttgaggcc atgcttagaa acgacaccaa cgaccagtcc    17280
tttaacgact atctctccgc cgccaacatg ctctacccta tacccgccaa cgctaccaac    17340
gtgcccatat ccatcccctc ccgcaactgg gcggctttcc gcggctgggc cttcacgcgc    17400
cttaagacta aggaaacccc atcactgggc tcgggctacg acccttatta cacctactct    17460
ggctctatac cctacctaga tggaaccttt tacctcaacc acaccttaaa gaaggtggcc    17520 attaccttg actcttctgt cagctggcct ggcaatgacc gcctgcttac ccccaacgag    17580
tttgaaatta gcgctcagt tgacggggag ggttacaacg ttgcccagtg taacatgacc    17640
```

```
aaagactggt tcctggtaca aatgctagct aactacaaca ttggctacca gggcttctat  17700
atcccagaga gctacaagga ccgcatgtac tccttcttta gaaacttcca gcccatgagc  17760
cgtcaggtgg tggatgatac taaatacaag gactaccaac aggtgggcat cctacaccaa  17820
cacaacaact ctggatttgt tggctaccct gcccccacca tgcgcgaagg acaggcctac  17880
cctgctaact tcccctatcc gcttataggc aagaccgcag ttgacagcat tacccagaaa  17940
aagtttcttt gcgatcgcac cctttggcgc atcccattct ccagtaactt tatgtccatg  18000
ggcgcactca cagacctggg ccaaaacctt ctctacgcca actccgccca cgcgctagac  18060
atgacttttg aggtggatcc catggacgag cccacccttc tttatgtttt gtttgaagtc  18120
tttgacgtgg tccgtgtgca ccggccgcac cgcggcgtca tcgaaaccgt gtacctgcgc  18180
acgcccttct cggccggcaa cgccacaaca taaagaagca agcaacatca acaacagctg  18240
ccgccatggg ctccagtgag caggaactga agccattgt caaagatctt ggttgtgggc  18300
catatttttt gggcacctat gacaagcgct ttccaggctt tgtttctcca cacaagctcg  18360
cctgcgccat agtcaatacg gccggtcgcg agactggggg cgtacactgg atggcctttg  18420
cctggaaccc gcactcaaaa acatgctacc tctttgagcc cttttggcttt tctgaccagc  18480
gactcaagca ggtttaccag tttgagtacg agtcactcct gcgccgtagc gccattgctt  18540
cttcccccga ccgctgtata acgctggaaa agtccaccca aagcgtacag gggcccaact  18600
cggccgcctg tggactattc tgctgcatgt ttctccacgc ctttgccaac tggccccaaa  18660
ctcccatgga tcacaacccc accatgaacc ttattaccgg ggtacccaac tccatgctca  18720
acagtcccca ggtacagccc accctgcgtc gcaaccagga acagctctac agcttcctgg  18780
agcgccactc gccctacttc cgcagccaca gtgcgcagat taggagcgcc acttcttttt  18840
gtcacttgaa aaacatgtaa aaataatgta ctagagacac tttcaataaa ggcaaatgct  18900
tttatttgta cactctcggg tgattattta cccccaccct tgccgtctgc gccgtttaaa  18960
aatcaaaggg gttctgccgc gcatcgctat gcgccactgg cagggacacg ttgcgatact  19020
ggtgtttagt gctccactta aactcaggca caaccatccg cggcagctcg gtgaagtttt  19080
cactccacag gctgcgcacc atcaccaacg cgtttagcag gtcgggcgcc gatatcttga  19140
agtcgcagtt ggggcctccg ccctgcgcgc gcgagttgcg atacacaggg ttgcagcact  19200
ggaacactat cagcgccggg tggtgcacgc tggccagcac gctcttgtcg gagatcagat  19260
ccgcgtccag gtcctccgcg ttgctcaggg cgaacggagt caactttggt agctgccttc  19320
ccaaaaaggg cgcgtgccca ggctttgagt tgcactcgca ccgtagtggc atcaaaaggt  19380
gaccgtgccc ggtctgggcg ttaggataca gcgcctgcat aaaagccttg atctgcttaa  19440
aagccacctg agccttttgcg ccttcagaga agaacatgcc gcaagacttg ccggaaaact  19500
gattggccgg acaggccgcg tcgtgcacgc agcaccttgc gtcggtgttg agatctgca  19560
ccacatttcg gccccaccgg ttcttcacga tcttggcctt gctagactgc tccttcagcg  19620
cgcgctgccc gttttcgctc gtcacatcca tttcaatcac gtgctcctta tttatcataa  19680
tgcttccgtg tagacactta agctcgcctt cgatctcagc gcagcggtgc agccacaacg  19740
cgcagcccgt gggctcgtga tgcttgtagg tcacctctgc aaacgactgc aggtacgcct  19800
gcaggaatcg ccccatcatc gtcacaaagg tcttgttgct ggtgaaggtc agctgcaacc  19860
cgcggtgctc ctcgttcagc caggtcttgc atacggccgc cagagcttcc acttggtcag  19920
gcagtagttt gaagttcgcc tttagatcgt tatccacgtg gtacttgtcc atcagcgcgc  19980
gcgcagcctc catgcccttc tcccacgcag acacgatcgg cacactcagc gggttcatca  20040
```

```
ccgtaatttc actttccgct tcgctgggct cttcctcttc ctcttgcgtc cgcataccac   20100
gcgccactgg gtcgtcttca ttcagccgcc gcactgtgcg cttacctcct ttgccatgct   20160
tgattagcac cggtgggttg ctgaaaccca ccatttgtag cgccacatct tctctttctt   20220
cctcgctgtc cacgattacc tctggtgatg gcgggcgctc gggcttggga gaagggcgct   20280
tcttttcctt cttgggcgca atggccaaat ccgccgccga ggtcgatggc cgcgggctgg   20340
gtgtgcgcgg caccagcgcg tcttgtgatg agtcttcctc gtcctcggac tcgatacgcc   20400
gcctcatccg cttttttggg ggcgcccggg gaggcggcgg cgacggggac ggggacgaca   20460
cgtcctccat ggttggggga cgtcgcgccg caccgcgtcc gcgctcgggg gtggtttcgc   20520
gctgctcctc ttcccgactg gccatttcct tctcctatag gcagaaaaag atcatggagt   20580
cagtcgagaa gaaggacagc ctaaccgccc cctctgagtt cgccaccacc gcctccaccg   20640
atgccgccaa cgcgcctacc accttccccg tcgaggcacc cccgcttgag gaggaggaag   20700
tgattatcga gcaggaccca ggttttgtaa gcgaagacga cgaggaccgc tcagtaccaa   20760
cagaggataa aaagcaagac caggacaacg cagaggcaaa cgaggaacaa gtcgggcggg   20820
gggacgaaag gcatggcgac tacctagatg tgggagacga cgtgctgttg aagcatctgc   20880
agcgccagtg cgccattatc tgcgacgcgt tgcaagagcg cagcgatgtg cccctcgcca   20940
tagcggatgt cagccttgcc tacgaacgcc acctattctc accgcgcgta ccccccaaac   21000
gccaagaaaa cggcacatgc gagcccaacc cgcgcctcaa cttctacccc gtatttgccg   21060
tgccagaggt gcttgccacc tatcacatct ttttccaaaa ctgcaagata cccctatcct   21120
gccgtgccaa ccgcagccga gcggacaagc agctggcctt gcggcagggc gctgtcatac   21180
ctgatatcgc ctcgctcaac gaagtgccaa aaatctttga gggtcttgga cgcgacgaga   21240
agcgcgcggc aaacgctctg caacaggaaa acagcgaaaa tgaaagtcac tctggagtgt   21300
tggtggaact cgagggtgac aacgcgcgcc tagccgtact aaaacgcagc atcgaggtca   21360
cccactttgc ctacccggca cttaacctac cccccaaggt catgagcaca gtcatgagtg   21420
agctgatcgt gcgccgtgcg cagccccctgg agagggatgc aaatttgcaa gaacaaacag   21480
aggagggcct acccgcagtt ggcgacgagc agctagcgcg ctggcttcaa acgcgcgagc   21540
ctgccgactt ggaggagcga cgcaaactaa tgatggccgc agtgctcgtt accgtggagc   21600
ttgagtgcat gcagcggttc tttgctgacc cggagatgca cgcaagcta gaggaaacat   21660
tgcactacac cttcgacag ggctacgtac gccaggcctg caagatctcc aacgtggagc   21720
tctgcaacct ggtctcctac cttggaattt tgcacgaaaa ccgccttggg caaaacgtgc   21780
ttcattccac gctcaagggc gaggcgcgcc gcgactacgt ccgcgactgc gtttacttat   21840
ttctatgcta cacctggcag acggccatgg gcgtttggca gcagtgcttg gaggagtgca   21900
acctcaagga gctgcagaaa ctgctaaagc aaaacttgaa ggacctatgg acggccttca   21960
acgagcgctc cgtggccgcg cacctggcgg acatcatttt ccccgaacgc ctgcttaaaa   22020
ccctgcaaca gggtctgcca gacttcacca gtcaaagcat gttgcagaac tttaggaact   22080
ttatcctaga gcgctcagga atcttgcccg ccacctgctg tgcacttcct agcgactttg   22140
tgcccattaa gtaccgcgaa tgccctccgc cgctttgggg ccactgctac cttctgcagc   22200
tagccaacta ccttgcctac cactctgaca taatggaaga cgtgagcggt gacggtctac   22260
tggagtgtca ctgtcgctgc aacctatgca ccccgcaccg ctccctggtt tgcaattcgc   22320
agctgcttaa cgaaagtcaa attatcggta cctttgagct gcagggtccc tcgcctgacg   22380
```

```
aaaagtccgc ggctccgggg ttgaaactca ctccggggct gtggacgtcg gcttaccttc   22440
gcaaatttgt acctgaggac taccacgccc acgagattag gttctacgaa gaccaatccc   22500
gcccgccaaa tgcggagctt accgcctgcg tcattaccca gggccacatt cttggccaat   22560
tgcaagccat caacaaagcc cgccaagagt ttctgctacg aaagggacgg ggggtttact   22620
tggaccccca gtccggcgag gagctcaacc caatcccccc gccgccgcag ccctatcagc   22680
agcagccgcg ggcccttgct tcccaggatg gcacccaaaa agaagctgca gctgccgccg   22740
ccacccacgg acgaggagga atactgggac agtcaggcag aggaggtttt ggacgaggag   22800
gaggaggaca tgatggaaga ctgggagagc ctagacgagg aagcttccga ggtcgaagag   22860
gtgtcagacg aaacaccgtc accctcggtc gcattcccct cgccggcgcc ccagaaatcg   22920
gcaaccggtt ccagcatggc tacaacctcc gctcctcagg cgccgccggc actgcccgtt   22980
cgccgaccca accgtagatg ggacaccact ggaaccaggg ccggtaagtc caagcagccg   23040
ccgccgttag cccaagagca acaacagcgc caaggctacc gctcatggcg cgggcacaag   23100
aacgccatag ttgcttgctt gcaagactgt ggggcaaca tctccttcgc ccgccgcttt    23160
cttctctacc atcacggcgt ggccttcccc cgtaacatcc tgcattacta ccgtcatctc   23220
tacagcccat actgcaccgg cggcagcggc agcggcagca acagcagcgg ccacacagaa   23280
gcaaaggcga ccggatagca agactctgac aaagcccaag aaatccacag cggcggcagc   23340
agcaggagga ggagcgctgc gtctggcgcc caacgaaccc gtatcgaccc gcgagcttag   23400
aaacaggatt tttcccactc tgtatgctat atttcaacag agcaggggcc aagaacaaga   23460
gctgaaaata aaaaacaggt ctctgcgatc cctcacccgc agctgcctgt atcacaaaag   23520
cgaagatcag cttcggcgca cgctggaaga cgcggaggct ctcttcagta aatactgcgc   23580
gctgactctt aaggactagt ttcgcgccct ttctcaaatt taagcgcgaa aactacgtca   23640
tctccagcgg ccacacccgg cgccagcacc tgtcgtcagc gccattatga gcaaggaaat   23700
tcccacgccc tacatgtgga gttaccagcc acaaatggga cttgcggctg gagctgccca   23760
agactactca acccgaataa actacatgag cgcgggaccc cacatgatat cccgggtcaa   23820
cggaatccgc gcccaccgaa accgaattct cttggaacag gcggctatta ccaccacacc   23880
tcgtaataac cttaatcccc gtagttggcc cgctgccctg gtgtaccagg aaagtcccgc   23940
tcccaccact gtggtacttc ccagagacgc ccaggccgaa gttcagatga ctaactcagg   24000
ggcgcagctt gcgggcggct ttcgtcacag ggtgcggtcg cccgggcagg gtataactca   24060
cctgacaatc agagggcgag gtattcagct caacgacgag tcggtgagct cctcgcttgg   24120
tctccgtccg gacgggacat ttcagatcgg cggcgccggc cgtccttcat tcacgcctcg   24180
tcaggcaatc ctaactctgc agacctcgtc ctctgagccg cgctctggag gcattggaac   24240
tctgcaattt attgaggagt ttgtgccatc ggtctacttt aaccccttct cgggacctcc   24300
cggccactat ccggatcaat ttattcctaa cttttgacgcg gtaaaggact cggcggacgg   24360
ctacgactga atgttaagtg gagaggcaga gcaactgcgc ctgaaacacc tggtccactg   24420
tcgccgccac aagtgctttg cccgcgactc cggtgagttt tgctactttg aattgcccga   24480
ggatcatatc gagggcccgg cgcacggcgt ccggcttacc gcccagggag agcttgcccg   24540
tagcctgatt cgggagttta cccagcgccc cctgctagtt gagcgggaca ggggaccctg   24600
tgttctcact gtgatttgca actgtcctaa ccttggatta catcaagatc tctagttaa   24660 ttaacagctt gcatgcctgc aggtcgacgg atcgggagat ctcggccgca tattaagtgc   24720
attgttctcg ataccgctaa gtgcattgtt ctcgttagct cgatggacaa gtgcattgtt   24780
```

```
ctcttgctga aagctcgatg gacaagtgca ttgttctctt gctgaaagct cgatggacaa   24840
gtgcattgtt ctcttgctga aagctcagta cccgggagta ccctcgaccg ccggagtata   24900
aatagaggcg cttcgtctac ggagcgacaa ttcaattcaa acaagcaaag tgaacacgtc   24960
gctaagcgaa agctaagcaa ataaacaagc gcagctgaac aagctaaaca atctgcagta   25020
aagtgcaagt taaagtgaat caattaaaag taaccagcaa ccaagtaaat caactgcaac   25080
tactgaaatc tgccaagaag taattattga atacaagaag agaactctga atactttcaa   25140
caagttaccg agaaagaaga actcacacac agctagcgtt taaacttaag cttcaccatg   25200
gtggggccct gcatgctgct gctgctgctg ctgctgggcc tgaggctaca gctctccctg   25260
ggcatcatcc tagttgagga ggagaacccg gacttctgga accgcgaggc agccgaggcc   25320
ctgggtgccg ccaagaagct gcagcctgca cagacagccg ccaagaacct catcatcttc   25380
ctgggcgatg gggtggggt gtctacggtg acagctgcca ggatcctaaa agggcagaag   25440
aaggacaaac tggggcctga gatacccctg ccatggacc gcttcccata tgtggctctg   25500
tccaagacat acaatgtaga caaacatgtg ccagacagtg gagccacagc cacggcctac   25560
ctgtgcgggt tcaagggcaa cttccagacc attggcttga gtgcagccgc ccgctttaac   25620
cagtgcaaca cgacacgcgg caacgaggtc atctccgtga tgaatcgggc caagaaagca   25680
gggaagtcag tgggagtggt aaccaccaca cgagtgcagc acgcctcgcc agccggcacc   25740
tacgcccaca cggtgaaccg caactggtac tcggacgccg acgtgcctgc ctcggcccgc   25800
caggaggggt gccaggacat cgctacgcag ctcatctcca acatggacat tgacgtgatc   25860
ctaggtgggg gccgaaagta catgtttcgc atgggaaccc cagaccctga gtacccagat   25920
gactacagcc aagtgggac caggctggac gggaagaatc tggtgcagga atggctggcg   25980
aagcaccagg gtgcccggta cgtgtggaac cgcactgagc tcatgcgggc ttccctggac   26040
ccgtctgtgg cccatctcat gggtctcttt gagcctggag acatgaaata cgagatccac   26100
cgagactcca cactggaccc ctccctgatg gagatgacag aggctgccct gcgcctgctg   26160
agcaggaacc cccgcggctt cttcctcttc gtggagggtg gtcgcatcga ccatggtcat   26220
catgaaagca gggcttaccg ggcactgact gagacgatca tgttcgacga cgccattgag   26280
agggcgggcc agctcaccag cgaggaggac acgctgagcc tcgtcactgc cgaccactcc   26340
cacgtcttct ccttcggagg ctgccccctg cgagggggct ccatcttcgg gctgccccct   26400
ggcaaggccc gggacaggaa ggcctacacg gtcctcctat acggaaacgg tccaggctat   26460
gtgctcaagg acgcgcccg gccggatgtt accgagagcg agagcgggag ccccgagtat   26520
cggcagcagt cagcagtgcc cctggacgaa gagacccacg caggcgagga cgtggcggtg   26580
ttcgcgcgcg gcccgcaggc gcacctggtt cacggcgtgc aggagcagac cttcatagcg   26640
cacgtcatgg ccttcgccgc ctgcctggag ccctacaccg cctgcgacct ggcgcccccc   26700
gccggcacca ccgacgccgc gcaccgggg cggtccgtgg tccccgcgtt gcttcctctg   26760
ctggccggga ccctgctgct gctggagacg gccactgctc cctgagtgtc ccgtccctgg   26820
ggctcctgct tccccatccc ggagttctcc tgctccccgc ctcctgtcgt cctgcctggc   26880
ctccagcccg agtcgtcatc cccggagtcc ctatacagag gtcctgccat ggaaccttcc   26940
cctccccgtg cgctctgggg actgagccca tgacaccaaa cctgccccct ggctgctctc   27000
ggactcccta ccccaacccc agggacagat ctggccagat ttgtaaaaca aatagatttt   27060
aggcccaaag attatttaaa gcattgcctg gaacgcagtg agttttttgtt agaaaagaga   27120
```

```
ataattcaaa gtggcattgc tttgcttctt atgttaattt ggtacagacc tgtggctgag   27180
tttgctcaaa gtattcagag cagaattgtg gagtggaaag agagattgga caaagagttt   27240
agtttgtcag tgtatcaaaa aatgaagttt aatgtggcta tgggaattgg agttttagat   27300
tggctaagaa acagtgatga tgatgatgaa gacagccagg aaaatgctga taaaaatgaa   27360
gatggtgggg agaagaacat ggaagactca gggcatgaaa caggcattga ttcacagtcc   27420
caaggctcat ttcaggcccc tcagtcctca cagtctgttc atgatcataa tcagccatac   27480
cacatttgta gaggttttac ttgctttaaa aaacctccca cacctccccc tgaacctgaa   27540
acataaaatg aatgcaattg ttgttgttaa cttgtttatt gcagcttata atggttacaa   27600
ataaagcaat agcatcacaa atttcacaaa taaagcattt ttttcactgc attctagttg   27660
tggtttgtcc aaactcatca atgtatctta tcatgtctgg atccccagga agctcctctg   27720
tgtcctcata acccctaacc tcctctactt gagaggacat tccaatcata ggctgcccat   27780
ccaccctctg tgtcctcctg ttaattaggt cacttaacaa aaaggaaatt gggtaggggt   27840
ttttcacaga ccgctttcta agggtaattt taaaatatct gggaagtccc ttccactgct   27900
gtgttccaga agtgttggta aacagcccac aaatgtcaac agcagaaaca tacaagctgt   27960
cagctttgca caagggccca acaccctgct catcaagaag cactgtggtt gctgtgttag   28020
taatgtgcaa aacaggaggc acattttccc cacctgtgta ggttccaaaa tatctagtgt   28080 tttcatttttt acttggatca ggaacccagc actccactgg ataagcatta tccttatcca   28140
aaacagcctt gtggtcagtg ttcatctgct gactgtcaac tgtagcattt tttggggtta   28200
cagtttgagc aggatatttg gtcctgtagt ttgctaacac accctgcagc tccaaaggtt   28260
ccccaccaac agcaaaaaaa tgaaaatttg acccttgaat gggttttcca gcaccatttt   28320
catgagtttt ttgtgtccct gaatgcaagt ttaacatagc agttacccca ataacctcag   28380
ttttaacagt aacagcttcc cacatcaaaa tatttccaca ggttaagtcc tcatttaaat   28440
taggcaaagg aattccactt cccactgcct tgcttccgtc tcccattcaa acttttatca   28500
actgacatta ttctaagtaa aatcctcttc attatgttgt cagcaatcca ttgcttgaag   28560
gcctggctcc ccagaacccc tcgactggta tgtcttctcc tagaatactc cagaagaaaa   28620
ggagtgtatg aagatagtga ctgcacatta aaatgactga aaccatagta aattaggatg   28680
agattctggg cagataaaca gacagctggc taggatcatt tttttatgcc ttggacttct   28740
ttggcaatct gttgaagcct gacattcctc agaataatgt tttaaagccc aacaataaga   28800
ccctgtagca catataataa gtactgcagt tttgaagtag tgataagcat aaatgatatt   28860
ttgatatatt tattataact gtaatgagat gtgtacatat ctgtgacttc ataggtactg   28920
attgtactac tgtgattttt ttgcctactt tcaaaatgaa aaggaatgct taatttcagt   28980
tagaggttag taaagacaaa taggtaattt tcttctccag tgaagagcat ggcgcccctt   29040
gctattcatg gacgcttgct taaagacttg tacacaggct tgctttgtat caacctatga   29100 cttccccttta cagccgatga taggttttta tttgcacctc cttcgtgtac aaagacagtt   29160
ttggtggcta cgccatcatt aaactcatta ttatcatgct taagcctata gatgtatcca   29220
gttcttctgt tacataattg aagctgtagt gaattgtcta tcttaaactg catcgctaac   29280
tgactacatt tcacacttca tttgcttcca acatagacta accttcttgg atgtccacta   29340
ttatttgaac ttttgagatt tttttttccta tttctaatat cttaaaattt cagaagactt   29400
aaagttttgc aactacaggg ctccatatag acatctagct tgaatttata cacttttcttt   29460 cattgatgtc cctggactaa aaaatgttaa atatttctaa ccgctgtact taaagtccat   29520
```

```
tacaaacgaa gactactgtt gttaagttga ataggcatct tatatatttt tcaccggtgc  29580
aataaataac ttctattccc ttctaacatc tgcttgcgtt gcactgagag tacactattg  29640
attagcaata ggttcgtgat tacagcccti ctataattaa ttgttaggtt aacatattat  29700
tcataaaata ttattttatt aattttract tgatttgcta ctggatgctt agaaatagct  29760
atgagtatat tggtagaacc agtacttata ttttattaca tttttacatt tcataaaatt  29820
taagtgatat aaaaatcctg aggaagtatg ccacaaaagt ggtctcagtg gaaatttaaa  29880
tatgttaaca tttattttta aaatgtagcg tgaaatagac aactttaaaa gctcagctta  29940
aaaaaaaaac tcaaggaagc tgaacttgac tttttaaagc actgaagtgc aatatttaat  30000
gtaggtcaac atgtttaaat gggaaaattt ttttcctaat tacagccaaa tccctagctg  30060
taattaactt aaaatttgta tactatttca caacagagtc agcatatacc actttcttat  30120
aaaattagaa agatctaaaa ttttagagct tatttggtga aacaggcata ttgctacatc  30180
tttgtttata aattataatg tgcctttaga gcccaataac agataacaag attttgaaaa  30240
ttcaggtgaa ttagagttat cagagggaat gttaatacac tctattcaaa tactatatga  30300
gtaagacatt taaatagga aacaatactt tatatattaa aaaaaattaa tcttccagtc  30360
gatttaatcc actttatgaa ttcatttaaa tcgatttaaa ttcgaattaa ttaactagag  30420
tacccgggga tcttattccc tttaactaat aaaaaaaaat aataaagcat cacttactta  30480
aaatcagtta gcaaatttct gtccagttta ttcagcagca cctccttgcc ctcctcccag  30540
ctctggtatt gcagcttcct cctggctgca aactttctcc acaatctaaa tggaatgtca  30600
gtttcctcct gttcctgtcc atccgcaccc actatcttca tgttgttgca gatgaagcgc  30660
gcaagaccgt ctgaagatac cttcaacccc gtgtatccat atgacacgga aaccggtcct  30720
ccaactgtgc cttttcttac tcctcccttt gtatccccca atgggtttca agagagtccc  30780 cctgggtac tctctttgcg cctatccgaa cctctagtta cctccaatgg catgcttgcg  30840
ctcaaaatgg gcaacggcct ctctctggac gaggccggca accttacctc ccaaaatgta  30900
accactgtga gcccacctct caaaaaaacc aagtcaaaca taaacctgga atatctgca   30960 cccctcacag ttacctcaga agccctaact gtggctgccg ccgcacctct aatggtcgcg  31020
ggcaacacac tcaccatgca atcacaggcc ccgctaaccg tgcacgactc caaacttagc  31080
attgccaccc aaggaccccct cacagtgtca gaaggaaagc tagccctgca aacatcaggc  31140
cccctcacca ccaccgatag cagtacccct actatcactg cctcacccccc tctaactact  31200 gccactggta gcttgggcat tgacttgaaa gagcccattt atacacaaaa tggaaaacta  31260
ggactaaagt acggggctcc tttgcatgta acagacgacc taaacacttt gaccgtagca  31320
actggtccag gtgtgactat taataatact tccttgcaaa ctaaagttac tggagccttg  31380
ggttttgatt cacaaggcaa tatgcaactt aatgtagcag gaggactaag gattgattct  31440 caaacagac gccttatact tgatgttagt tatccgtttg atgctcaaaa ccaactaaat  31500
ctaagactag gacagggccc tctttttata aactcagccc acaacttgga tattaactac  31560
aacaaaggcc tttacttgtt tacagcttca aacaattcca aaaagcttga ggttaaccta  31620
agcactgcca aggggttgat gtttgacgct acagccatag ccattaatgc aggagatggg  31680
cttgaatttg gttcacctaa tgcaccaaac acaaatcccc tcaaaacaaa aattggccat  31740
ggcctagaat ttgattcaaa caaggctatg gttcctaaac taggaactgg ccttagtttt  31800
gacagcacag gtgccattac agtaggaaac aaaaataatg ataagctaac tttgtggacc  31860
```

```
acaccagctc catctcctaa ctgtagacta aatgcagaga aagatgctaa actcactttg    31920
gtcttaacaa aatgtggcag tcaaatactt gctacagttt cagttttggc tgttaaaggc    31980
agtttggctc caatatctgg aacagttcaa agtgctcatc ttattataag atttgacgaa    32040
aatggagtgc tactaaacaa ttccttcctg gacccagaat attggaactt tagaaatgga    32100
gatcttactg aaggcacagc ctatacaaac gctgttggat ttatgcctaa cctatcagct    32160
tatccaaaat ctcacggtaa aactgccaaa agtaacattg tcagtcaagt ttacttaaac    32220
ggagacaaaa ctaaacctgt aacactaacc attacactaa acggtacaca ggaaacagga    32280
gacacaactc caagtgcata ctctatgtca ttttcatggg actggtctgg ccacaactac    32340
attaatgaaa tatttgccac atcctcttac acttttcat acattgccca agaataaaga     32400
atcgtttgtg ttatgtttca acgtgtttat ttttcaattg cagaaaattt caagtcatt     32460 ttcattcagt agtatagccc caccaccaca tagcttatac agatcaccgt accttaatca    32520
aactcacaga accctagtat tcaacctgcc acctccctcc caacacacag agtacacagt    32580
cctttctccc cggctggcct taaaaagcat catatcatgg gtaacagaca tattcttagg    32640
tgttatattc cacacggttt cctgtcgagc caaacgctca tcagtgatat taataaactc    32700
cccgggcagc tcacttaagt tcatgtcgct gtccagctgc tgagccacag gctgctgtcc    32760
aacttgcggt tgcttaacgg gcggcgaagg agaagtccac gcctacatgg gggtagagtc    32820
ataatcgtgc atcaggatag ggcggtggtg ctgcagcagc gcgcgaataa actgctgccg    32880
ccgccgctcc gtcctgcagg aatacaacat ggcagtggtc tcctcagcga tgattcgcac    32940
cgcccgcagc ataaggcgcc ttgtcctccg ggcacagcag cgcaccctga tctcacttaa    33000
atcagcacag taactgcagc acagcaccac aatattgttc aaaatcccac agtgcaaggc    33060
gctgtatcca aagctcatgg cggggaccac agaacccacg tggccatcat accacaagcg    33120
caggtagatt aagtggcgac ccctcataaa cacgctggac ataaacatta cctcttttgg    33180
catgttgtaa ttcaccacct cccgtacca tataaacctc tgattaaaca tggcgccatc     33240
caccaccatc ctaaaccagc tggccaaaac ctgcccgccg gctatacact gcagggaacc    33300
gggactggaa caatgacagt ggagagccca ggactcgtaa ccatggatca tcatgctcgt    33360
catgatatca atgttggcac aacacaggca cacgtgcata cacttcctca ggattacaag    33420
ctcctcccgc gttagaacca tatcccaggg aacaacccat tcctgaatca gcgtaaatcc    33480
cacactgcag ggaagacctc gcacgtaact cacgttgtgc attgtcaaag tgttacattc    33540
gggcagcagc ggatgatcct ccagtatggt agcgcgggtt tctgtctcaa aaggaggtag    33600
acgatcccta ctgtacggag tgcgccgaga caaccgagat cgtgttggtc gtagtgtcat    33660
gccaaatgga acgccggacg tagtcatatt tcctgaagca aaaccaggtg cgggcgtgac    33720
aaacagatct gcgtctccgg tctcgccgct tagatcgctc tgtgtagtag ttgtagtata    33780
tccactctct caaagcatcc aggcgccccc tggcttcggg ttctatgtaa actccttcat    33840
gcgccgctgc cctgataaca tccaccaccg cagaataagc cacacccagc caacctacac    33900
attcgttctg cgagtcacac acgggaggag cgggaagagc tggaagaacc atgttttttt    33960
ttttattcca aaagattatc caaaacctca aaatgaagat ctattaagtg aacgcgctcc    34020
cctccggtgg cgtggtcaaa ctctacagcc aaagaacaga taatggcatt tgtaagatgt    34080
tgcacaatgg cttccaaaag gcaaacggcc ctcacgtcca agtggacgta aaggctaaac    34140
ccttcagggt gaatctcctc tataaacatt ccagcacctt caaccatgcc caaataattc    34200
tcatctcgcc accttctcaa tatatctcta agcaaatccc gaatattaag tccggccatt    34260
```

```
gtaaaaatct gctccagagc gccctccacc ttcagcctca agcagcgaat catgattgca    34320
aaaattcagg ttcctcacag acctgtataa gattcaaaag cggaacatta acaaaaatac    34380
cgcgatcccg taggtccctt cgcagggcca gctgaacata atcgtgcagg tctgcacgga    34440
ccagcgcggc cacttccccg ccaggaacct tgacaaaaga acccacactg attatgacac    34500
gcatactcgg agctatgcta accagcgtag ccccgatgta agctttgttg catgggcggc    34560
gatataaaat gcaaggtgct gctcaaaaaa tcaggcaaag cctcgcgcaa aaagaaagc    34620 acatcgtagt catgctcatg cagataaagg caggtaagct ccggaaccac cacagaaaaa    34680
gacaccattt ttctctcaaa catgtctgcg ggtttctgca taaacacaaa ataaaataac    34740
aaaaaaacat ttaaacatta gaagcctgtc ttacaacagg aaaaacaacc cttataagca    34800
taagacggac tacggccatg ccggcgtgac cgtaaaaaaa ctggtcaccg tgattaaaaa    34860
gcaccaccga cagctcctcg gtcatgtccg gagtcataat gtaagactcg gtaaacacat    34920
caggttgatt catcggtcag tgctaaaaag cgaccgaaat agcccggggg aatacatacc    34980
cgcaggcgta gagacaacat tacagccccc ataggaggta taacaaaatt aataggagag    35040
aaaaacacat aaacacctga aaaccctcc tgcctaggca aaatagcacc ctcccgctcc    35100
agaacaacat acagcgcttc acagcggcag cctaacagtc agccttacca gtaaaaaaga    35160
aaacctatta aaaaaacacc actcgacacg gcaccagctc aatcagtcac agtgtaaaaa    35220
agggccaagt gcagagcgag tatatatagg actaaaaat gacgtaacgg ttaaagtcca    35280
caaaaaacac ccagaaaacc gcacgcgaac ctacgcccag aaacgaaagc caaaaaccc    35340 acaacttcct caaatcgtca cttccgtttt cccacgttac gtaacttccc attttaagaa    35400
aactacaatt cccaacacat acaagttact ccgccctaaa acctacgtca cccgccccgt    35460
tcccacgccc cgcgccacgt cacaaactcc acccctcat tatcatattg gcttcaatcc    35520
aaaataaggt atattattga tgatggccgg ccgaattgaa tcaggggata acgcaggaaa    35580
gaacatgtga gcaaaaggcc agcaaaaggc caggaaccgt aaaaaggccg cgttgctggc    35640
gtttttccat aggctccgcc cccctgacga gcatcacaaa aatcgacgct caagtcagag    35700
gtggcgaaac ccgacaggac tataaagata ccaggcgttt ccccctggaa gctccctcgt    35760
gcgctctcct gttccgaccc tgccgcttac cggatacctg tccgcctttc tcccttcggg    35820
aagcgtggcg ctttctcata gctcacgctg taggtatctc agttcggtgt aggtcgttcg    35880
ctccaagctg ggctgtgtgc acgaaccccc cgttcagccc gaccgctgcg ccttatccgg    35940
taactatcgt cttgagtcca acccggtaag acacgactta tcgccactgg cagcagccac    36000
tggtaacagg attagcagag cgaggtatgt aggcggtgct acagagttct tgaagtggtg    36060
gcctaactac ggctacacta aggacagt atttggtatc tgcgctctgc tgaagccagt    36120
taccttcgga aaagagttg gtagctcttg atccggcaaa caaaccaccg ctggtagcgg    36180
tggttttttt gtttgcaagc agcagattac gcgcagaaaa aaggatctc aagaagatcc    36240 tttgatcttt tctacggggt ctgacgctca gtggaacgaa aactcacgtt aagggatttt    36300
ggtcatgaga ttatcaaaaa ggatcttcac ctagatcctt ttaaattaaa aatgaagttt    36360
taaatcaatc taaagtatat atgagtaaac ttggtctgac agttaccaat gcttaatcag    36420
tgaggcacct atctcagcga tctgtctatt tcgttcatcc atagttgcct gactccccgt    36480
cgtgtagata actacgatac gggagggctt accatctggc cccagtgctg caatgatacc    36540
gcgagaccca cgctcaccgg ctccagattt atcagcaata aaccagccag ccggaagggc    36600
```

```
cgagcgcaga agtggtcctg caactttatc cgcctccatc cagtctatta attgttgccg    36660
ggaagctaga gtaagtagtt cgccagttaa tagtttgcgc aacgttgttg ccattgctac    36720
aggcatcgtg gtgtcacgct cgtcgtttgg tatggcttca ttcagctccg gttcccaacg    36780
atcaaggcga gttacatgat cccccatgtt gtgcaaaaaa gcggttagct ccttcggtcc    36840
tccgatcgtt gtcagaagta agttggccgc agtgttatca ctcatggtta tggcagcact    36900
gcataattct cttactgtca tgccatccgt aagatgcttt tctgtgactg gtgagtactc    36960
aaccaagtca ttctgagaat agtgtatgcg gcgaccgagt tgctcttgcc cggcgtcaat    37020
acgggataat accgcgccac atagcagaac tttaaaagtg ctcatcattg gaaaacgttc    37080
ttcgggcga aaactctcaa ggatcttacc gctgttgaga tccagttcga tgtaacccac    37140
tcgtgcaccc aactgatctt cagcatcttt tactttcacc agcgtttctg ggtgagcaaa    37200
aacaggaagg caaaatgccg caaaaaaggg aataagggcg acacggaaat gttgaatact    37260
catactcttc ctttttcaat attattgaag catttatcag ggttattgtc tcatgagcgg    37320
atacatattt gaatgtattt agaaaaataa acaaataggg gttccgcgca catttccccg    37380
aaaagtgcca c                                                         37391
```

<210> SEQ ID NO 16

<400> SEQUENCE: 16

000

<210> SEQ ID NO 17
<211> LENGTH: 671
<212> TYPE: PRT
<213> ORGANISM: Homo sapiens

<400> SEQUENCE: 17

```
Met Ala Leu Ser Val Asn Asp Cys Ala Arg Leu Thr Gly Gln Ser Val
1               5                   10                  15

Pro Thr Met Glu His Phe Leu Pro Leu Arg Asn Ile Trp Asn Arg Val
            20                  25                  30

Arg Asp Phe Pro Arg Ala Ser Thr Ala Ala Gly Ile Thr Trp Met
        35                  40                  45

Ser Arg Tyr Ile Tyr Gly Tyr His Arg Leu Met Leu Glu Asp Leu Ala
    50                  55                  60

Pro Gly Ala Pro Ala Thr Leu Arg Trp Pro Leu Tyr Arg Gln Pro Pro
65                  70                  75                  80

Pro His Phe Leu Val Gly Tyr Gln Tyr Leu Val Arg Thr Cys Asn Asp
                85                  90                  95

Tyr Val Phe Asp Ser Arg Ala Tyr Ser Arg Leu Arg Tyr Thr Glu Leu
            100                 105                 110

Ser Gln Pro Gly His Gln Thr Val Asn Trp Ser Val Met Ala Asn Cys
        115                 120                 125

Thr Tyr Thr Ile Asn Thr Gly Ala Tyr His Arg Phe Val Asp Met Asp
    130                 135                 140

Asp Phe Gln Ser Thr Leu Thr Gln Val Gln Gln Ala Ile Leu Ala Glu
145                 150                 155                 160

Arg Val Val Ala Asp Leu Ala Leu Leu Gln Pro Met Arg Gly Phe Gly
                165                 170                 175

Val Thr Arg Met Gly Gly Arg Gly Arg His Leu Arg Pro Asn Ser Ala
            180                 185                 190
```

-continued

Ala Ala Val Ala Ile Asp Ala Arg Asp Ala Gly Gln Glu Gly Glu
            195             200             205
Glu Glu Val Pro Val Glu Arg Leu Met Gln Asp Tyr Tyr Lys Asp Leu
    210             215             220
Arg Arg Cys Gln Asn Glu Ala Trp Gly Met Ala Asp Arg Leu Arg Ile
225             230             235             240
Gln Gln Ala Gly Pro Lys Asp Met Val Leu Leu Ser Thr Ile Arg Arg
                245             250             255
Leu Lys Thr Ala Tyr Phe Asn Tyr Ile Ile Ser Ser Thr Ser Ala Arg
            260             265             270
Asn Asn Pro Asp Arg His Pro Leu Pro Pro Ala Thr Val Leu Ser Leu
        275             280             285
Pro Cys Asp Cys Asp Trp Leu Asp Ala Phe Leu Glu Arg Phe Ser Asp
    290             295             300
Pro Val Asp Ala Asp Ser Leu Arg Ser Leu Gly Gly Val Pro Thr
305             310             315             320
Gln Gln Leu Leu Arg Cys Ile Val Ser Ala Val Ser Leu Pro His Gly
                325             330             335
Ser Pro Pro Pro Thr His Asn Arg Asp Met Thr Gly Gly Val Phe Gln
            340             345             350
Leu Arg Pro Arg Glu Asn Gly Arg Ala Val Thr Glu Thr Met Arg Arg
        355             360             365
Arg Arg Gly Glu Met Ile Glu Arg Phe Val Asp Arg Leu Pro Val Arg
    370             375             380
Arg Arg Arg Arg Arg Val Pro Pro Pro Pro Pro Glu Glu
385             390             395             400
Glu Glu Gly Glu Ala Leu Met Glu Glu Glu Ile Glu Glu Glu Ala
                405             410             415
Pro Val Ala Phe Glu Arg Glu Val Arg Asp Thr Val Ala Glu Leu Ile
            420             425             430
Arg Leu Leu Glu Glu Leu Thr Val Ser Ala Arg Asn Ser Gln Phe
        435             440             445
Phe Asn Phe Ala Val Asp Phe Tyr Glu Ala Met Glu Arg Leu Glu Ala
450             455             460
Leu Gly Asp Ile Asn Glu Ser Thr Leu Arg Arg Trp Val Met Tyr Phe
465             470             475             480
Phe Val Ala Glu His Thr Ala Thr Thr Leu Asn Tyr Leu Phe Gln Arg
                485             490             495
Leu Arg Asn Tyr Ala Val Phe Ala Arg His Val Glu Leu Asn Leu Ala
            500             505             510
Gln Val Val Met Arg Ala Arg Asp Ala Glu Gly Gly Val Val Tyr Ser
        515             520             525
Arg Val Trp Asn Glu Gly Gly Leu Asn Ala Phe Ser Gln Leu Met Ala
    530             535             540
Arg Ile Ser Asn Asp Leu Ala Ala Thr Val Glu Arg Ala Gly Arg Gly
545             550             555             560
Asp Leu Gln Glu Glu Glu Ile Glu Gln Phe Met Ala Glu Ile Ala Tyr
                565             570             575
Gln Asp Asn Ser Gly Asp Val Gln Glu Ile Leu Arg Gln Ala Ala Val
            580             585             590
Asn Asp Thr Glu Ile Asp Ser Val Glu Leu Ser Phe Arg Phe Lys Leu
        595             600             605
Thr Gly Pro Val Val Phe Thr Gln Arg Arg Gln Ile Gln Glu Ile Asn

```
            610                 615                 620
Arg Arg Val Val Ala Phe Ala Ser Asn Leu Arg Ala Gln His Gln Leu
625                 630                 635                 640

Leu Pro Ala Arg Gly Ala Asp Val Pro Leu Pro Pro Leu Pro Ala Gly
                645                 650                 655

Pro Glu Pro Pro Leu Pro Pro Gly Ala Arg Pro Arg His Arg Phe
                660                 665                 670

<210> SEQ ID NO 18
<211> LENGTH: 322
<212> TYPE: PRT
<213> ORGANISM: Homo sapiens

<400> SEQUENCE: 18

Val Phe Gln Leu Arg Pro Arg Glu Asn Gly Arg Ala Val Thr Glu Thr
1               5                   10                  15

Met Arg Arg Arg Arg Gly Glu Met Ile Glu Arg Phe Val Asp Arg Leu
                20                  25                  30

Pro Val Arg Arg Arg Arg Arg Val Pro Pro Pro Pro Pro Pro Pro Pro
                35                  40                  45

Glu Glu Glu Glu Glu Gly Glu Ala Leu Met Glu Glu Ile Glu Glu Glu
            50                  55                  60

Glu Glu Ala Pro Val Ala Phe Glu Arg Glu Val Arg Asp Thr Val Ala
65                  70                  75                  80

Glu Leu Ile Arg Leu Leu Glu Glu Leu Thr Val Ser Ala Arg Arg Asn
                85                  90                  95

Ser Gln Phe Phe Asn Phe Ala Val Asp Phe Tyr Glu Ala Met Glu Arg
                100                 105                 110

Leu Glu Ala Leu Gly Asp Ile Asn Glu Ser Thr Leu Arg Arg Trp Val
            115                 120                 125

Met Tyr Phe Phe Val Ala Glu His Thr Ala Thr Thr Leu Asn Tyr Leu
130                 135                 140

Phe Gln Arg Leu Arg Asn Tyr Ala Val Phe Ala Arg His Val Glu Leu
145                 150                 155                 160

Asn Leu Ala Gln Val Val Met Arg Ala Arg Asp Ala Glu Gly Gly Val
                165                 170                 175

Val Tyr Ser Arg Val Trp Asn Glu Gly Gly Leu Asn Ala Phe Ser Gln
            180                 185                 190

Leu Met Ala Arg Ile Ser Asn Asp Leu Ala Ala Thr Val Glu Arg Ala
            195                 200                 205

Gly Arg Gly Asp Leu Gln Glu Glu Ile Glu Gln Phe Met Ala Glu
            210                 215                 220

Ile Ala Tyr Gln Asp Asn Ser Gly Asp Val Gln Glu Ile Leu Arg Gln
225                 230                 235                 240

Ala Ala Val Asn Asp Thr Glu Ile Asp Ser Val Glu Leu Ser Phe Arg
                245                 250                 255

Phe Lys Leu Thr Gly Pro Val Val Phe Thr Gln Arg Gln Ile Gln
                260                 265                 270

Glu Ile Asn Arg Arg Val Val Ala Phe Ala Ser Asn Leu Arg Ala Gln
            275                 280                 285

His Gln Leu Leu Pro Ala Arg Gly Ala Asp Val Pro Leu Pro Pro Leu
            290                 295                 300

Pro Ala Gly Pro Glu Pro Pro Leu Pro Pro Gly Ala Arg Pro Arg His
305                 310                 315                 320
```

Arg Phe

<210> SEQ ID NO 19
<211> LENGTH: 671
<212> TYPE: PRT
<213> ORGANISM: Homo sapiens

<400> SEQUENCE: 19

Met Ala Leu Ser Val Asn Asp Cys Ala Arg Leu Thr Gly Gln Ser Val
1               5                   10                  15

Pro Thr Met Glu His Phe Leu Pro Leu Arg Asn Ile Trp Asn Arg Val
            20                  25                  30

Arg Asp Phe Pro Arg Ala Ser Thr Thr Ala Ala Gly Ile Thr Trp Met
        35                  40                  45

Ser Arg Tyr Ile Tyr Gly Tyr His Arg Leu Met Leu Glu Asp Leu Ala
    50                  55                  60

Pro Gly Ala Pro Ala Thr Leu Arg Trp Pro Leu Tyr Arg Gln Pro Pro
65                  70                  75                  80

Pro His Phe Leu Val Gly Tyr Gln Tyr Leu Val Arg Thr Cys Asn Asp
                85                  90                  95

Tyr Val Phe Asp Ser Arg Ala Tyr Ser Arg Leu Arg Tyr Thr Glu Leu
            100                 105                 110

Ser Gln Pro Gly His Gln Thr Val Asn Trp Ser Val Met Ala Asn Cys
        115                 120                 125

Thr Tyr Thr Ile Asn Thr Gly Ala Tyr His Arg Phe Val Asp Met Asp
130                 135                 140

Asp Phe Gln Ser Thr Leu Thr Gln Val Gln Gln Ala Ile Leu Ala Glu
145                 150                 155                 160

Arg Val Val Ala Asp Leu Ala Leu Leu Gln Pro Met Arg Gly Phe Gly
                165                 170                 175

Val Thr Arg Met Gly Gly Arg Gly Arg His Leu Arg Pro Asn Ser Ala
            180                 185                 190

Ala Ala Ala Ala Ile Asp Ala Arg Asp Ala Gly Gln Glu Glu Gly Glu
        195                 200                 205

Glu Glu Val Pro Val Glu Arg Leu Met Gln Asp Tyr Tyr Lys Asp Leu
    210                 215                 220

Arg Arg Cys Gln Asn Glu Ala Trp Gly Met Ala Asp Arg Leu Arg Ile
225                 230                 235                 240

Gln Gln Ala Gly Pro Lys Asp Met Val Leu Leu Ser Thr Ile Arg Arg
                245                 250                 255

Leu Lys Thr Ala Tyr Phe Asn Tyr Ile Ile Ser Ser Thr Ser Ala Arg
            260                 265                 270

Asn Asn Pro Asp Arg Arg Pro Leu Pro Pro Ala Thr Val Leu Ser Leu
        275                 280                 285

Pro Cys Asp Cys Asp Trp Leu Asp Ala Phe Leu Glu Arg Phe Ser Asp
    290                 295                 300

Pro Val Asp Ala Asp Ser Leu Arg Ser Leu Gly Gly Val Pro Thr
305                 310                 315                 320

Gln Gln Leu Leu Arg Cys Ile Val Ser Ala Val Ser Leu Pro His Gly
                325                 330                 335

Ser Pro Pro Pro Thr His Asn Arg Asp Met Thr Gly Gly Val Phe Gln
            340                 345                 350

Leu Arg Pro Arg Glu Asn Gly Arg Ala Val Thr Glu Thr Met Arg Arg
        355                 360                 365

```
Arg Arg Gly Glu Met Ile Glu Arg Phe Val Asp Arg Leu Pro Val Arg
        370                 375                 380

Arg Arg Arg Arg Arg Val Pro Pro Pro Pro Pro Pro Glu Glu
385                 390                 395                 400

Glu Gly Glu Ala Leu Met Glu Glu Ile Glu Glu Glu Glu Ala
                405                 410                 415

Pro Val Ala Phe Glu Arg Glu Val Arg Asp Thr Val Ala Glu Leu Ile
                420                 425                 430

Arg Leu Leu Glu Glu Leu Thr Val Ser Ala Arg Asn Ser Gln Phe
            435                 440                 445

Phe Asn Phe Ala Val Asp Phe Tyr Glu Ala Met Glu Arg Leu Glu Ala
        450                 455                 460

Leu Gly Asp Ile Asn Glu Ser Thr Leu Arg Arg Trp Val Met Tyr Phe
465                 470                 475                 480

Phe Val Ala Glu His Thr Ala Thr Thr Leu Asn Tyr Leu Phe Gln Arg
                485                 490                 495

Leu Arg Asn Tyr Ala Val Phe Ala Arg His Val Glu Leu Asn Leu Ala
                500                 505                 510

Gln Val Val Met Arg Ala Arg Asp Ala Glu Gly Gly Val Val Tyr Ser
            515                 520                 525

Arg Val Trp Asn Glu Gly Leu Asn Ala Phe Ser Gln Leu Met Ala
        530                 535                 540

Arg Ile Ser Asn Asp Leu Ala Ala Thr Val Glu Arg Ala Gly Arg Gly
545                 550                 555                 560

Asp Leu Gln Glu Glu Glu Ile Glu Gln Phe Met Ala Glu Ile Ala Tyr
                565                 570                 575

Gln Asp Asn Ser Gly Asp Val Gln Glu Ile Leu Arg Gln Ala Ala Val
                580                 585                 590

Asn Asp Thr Glu Ile Asp Ser Val Glu Leu Ser Phe Arg Leu Lys Leu
            595                 600                 605

Thr Gly Pro Val Val Phe Thr Gln Arg Arg Gln Ile Gln Glu Ile Asn
        610                 615                 620

Arg Arg Val Val Ala Phe Ala Ser Asn Leu Arg Ala Gln His Gln Leu
625                 630                 635                 640

Leu Pro Ala Arg Gly Ala Asp Val Pro Leu Pro Pro Leu Pro Ala Gly
                645                 650                 655

Pro Glu Pro Pro Leu Pro Pro Gly Ala Arg Pro Arg His Arg Phe
                660                 665                 670

<210> SEQ ID NO 20
<211> LENGTH: 322
<212> TYPE: PRT
<213> ORGANISM: Homo sapiens

<400> SEQUENCE: 20

Val Phe Gln Leu Arg Pro Arg Glu Asn Gly Arg Ala Val Thr Glu Thr
1               5                   10                  15

Met Arg Arg Arg Arg Gly Glu Met Ile Glu Arg Phe Val Asp Arg Leu
                20                  25                  30

Pro Val Arg Arg Arg Arg Arg Val Pro Pro Pro Pro Pro Pro
            35                  40                  45

Glu Glu Glu Glu Gly Glu Ala Leu Met Glu Glu Ile Glu Glu Glu
        50                  55                  60

Glu Glu Ala Pro Val Ala Phe Glu Arg Glu Val Arg Asp Thr Val Ala
65                  70                  75                  80
```

```
Glu Leu Ile Arg Leu Leu Glu Glu Leu Thr Val Ser Ala Arg Asn
             85                  90                  95

Ser Gln Phe Phe Asn Phe Ala Val Asp Phe Tyr Glu Ala Met Glu Arg
            100                 105                 110

Leu Glu Ala Leu Gly Asp Ile Asn Glu Ser Thr Leu Arg Arg Trp Val
            115                 120                 125

Met Tyr Phe Phe Val Ala Glu His Thr Ala Thr Thr Leu Asn Tyr Leu
130                 135                 140

Phe Gln Arg Leu Arg Asn Tyr Ala Val Phe Ala Arg His Val Glu Leu
145                 150                 155                 160

Asn Leu Ala Gln Val Val Met Arg Ala Arg Asp Ala Glu Gly Gly Val
            165                 170                 175

Val Tyr Ser Arg Val Trp Asn Glu Gly Gly Leu Asn Ala Phe Ser Gln
            180                 185                 190

Leu Met Ala Arg Ile Ser Asn Asp Leu Ala Ala Thr Val Glu Arg Ala
            195                 200                 205

Gly Arg Gly Asp Leu Gln Glu Glu Ile Glu Gln Phe Met Ala Glu
            210                 215                 220

Ile Ala Tyr Gln Asp Asn Ser Gly Asp Val Gln Glu Ile Leu Arg Gln
225                 230                 235                 240

Ala Ala Val Asn Asp Thr Glu Ile Asp Ser Val Glu Leu Ser Phe Arg
            245                 250                 255

Leu Lys Leu Thr Gly Pro Val Val Phe Thr Gln Arg Arg Gln Ile Gln
            260                 265                 270

Glu Ile Asn Arg Arg Val Val Ala Phe Ala Ser Asn Leu Arg Ala Gln
            275                 280                 285

His Gln Leu Leu Pro Ala Arg Gly Ala Asp Val Pro Leu Pro Pro Leu
            290                 295                 300

Pro Ala Gly Pro Glu Pro Pro Leu Pro Pro Gly Ala Arg Pro Arg His
305                 310                 315                 320

Arg Phe

<210> SEQ ID NO 21
<211> LENGTH: 12
<212> TYPE: DNA
<213> ORGANISM: Artificial Sequence
<220> FEATURE:
<223> OTHER INFORMATION: Synthetic

<400> SEQUENCE: 21
catcatcaat aa                                                          12

<210> SEQ ID NO 22
<211> LENGTH: 12
<212> TYPE: DNA
<213> ORGANISM: Artificial Sequence
<220> FEATURE:
<223> OTHER INFORMATION: Synthetic

<400> SEQUENCE: 22
gtagtagtta tt                                                          12

<210> SEQ ID NO 23
<211> LENGTH: 15
<212> TYPE: DNA
<213> ORGANISM: Artificial Sequence
<220> FEATURE:
<223> OTHER INFORMATION: Synthetic
```

```
<400> SEQUENCE: 23
taacatcatc aataa                                                   15

<210> SEQ ID NO 24
<211> LENGTH: 17
<212> TYPE: DNA
<213> ORGANISM: Artificial Sequence
<220> FEATURE:
<223> OTHER INFORMATION: Synthetic

<400> SEQUENCE: 24
taattgtagt agttatt                                                 17

<210> SEQ ID NO 25
<211> LENGTH: 13
<212> TYPE: DNA
<213> ORGANISM: Artificial Sequence
<220> FEATURE:
<223> OTHER INFORMATION: Synthetic

<400> SEQUENCE: 25
ccatcatcaa taa                                                     13

<210> SEQ ID NO 26
<211> LENGTH: 17
<212> TYPE: DNA
<213> ORGANISM: Artificial Sequence
<220> FEATURE:
<223> OTHER INFORMATION: Synthetic

<400> SEQUENCE: 26
ggccggtagt agttatt                                                 17

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
gacgaggccg gcctggtc                                                18

<210> SEQ ID NO 28
<211> LENGTH: 18
<212> TYPE: DNA
<213> ORGANISM: Artificial Sequence
<220> FEATURE:
<223> OTHER INFORMATION: Synthetic

<400> SEQUENCE: 28
ggcatggccg gccacggc                                                18

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
gacgaagccg gcctggtc                                                18

<210> SEQ ID NO 30
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 30
ggcatggccg gctacggc                                                 18

<210> SEQ ID NO 31
<211> LENGTH: 13
<212> TYPE: DNA
<213> ORGANISM: Artificial Sequence
<220> FEATURE:
<223> OTHER INFORMATION: Synthetic

<400> SEQUENCE: 31
ccatcatcaa taa                                                      13

<210> SEQ ID NO 32
<211> LENGTH: 17
<212> TYPE: DNA
<213> ORGANISM: Artificial Sequence
<220> FEATURE:
<223> OTHER INFORMATION: Synthetic

<400> SEQUENCE: 32
ggccggtagt agttatt                                                  17

<210> SEQ ID NO 33
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: n is a, c, g, or t

<400> SEQUENCE: 33
nnnnnggccg gtagtagtta tt                                            22

<210> SEQ ID NO 34
<211> LENGTH: 13
<212> TYPE: DNA
<213> ORGANISM: Artificial Sequence
<220> FEATURE:
<223> OTHER INFORMATION: Synthetic

<400> SEQUENCE: 34
ggtagtagtt att                                                      13
```

PRODUCTION OF VIRAL VECTORS

CROSS-REFERENCE

The present Application claims the benefit of U.S. application Ser. No. 14/163,331, now U.S. Pat. No. 9,453,240, filed Jan. 24, 2014, which claims the benefit of U.S. application Ser. No. 12/884,027, now U.S. Pat. No. 8,637,313, filed Sep. 16, 2010, which claims the benefit of U.S. application Ser. No. 10/381,153, now U.S. Pat. No. 7,820,441, filed Oct. 9, 2003, which is a National Stage Entry of International Application Number PCT/US01/29496, filed Sep. 21, 2001, which claims priority to U.S. Provisional Application Ser. No. 60/235,060, filed Sep. 25, 2000, each of which claims priority to U.S. Provisional Application Ser. No. 60/235,060, filed Sep. 25, 2000, each of which applications are hereby incorporated by reference in their entirety.

STATEMENT AS TO FEDERALLY SPONSORED RESEARCH

This invention was made with Government support under contract NIH P01A6015434. The government has certain rights in this invention.

REFERENCE TO A SEQUENCE LISTING

The instant application contains a Sequence Listing which has been submitted in ASCII format via EFS-Web and is hereby incorporated by reference in its entirety. Said ASCII copy created on Jan. 23, 2014, is named "39891_704_302_07763ST25_raw.txt" and is 217 kilobytes in size.

FIELD OF THE INVENTION

The present invention relates to methods and compositions for the production of viral vectors. In particular, the present invention provides methods and compositions for faster, higher titer and higher purity production of adenovirus vectors.

BACKGROUND OF THE INVENTION

Conventional adenovirus (Ad) gene-delivery vectors are based on replacement of early regions of the viral genome with an expression cassette coding for a gene of interest. Unfortunately, Ad vectors have drawbacks that limit their usefulness for many applications. First, the cloning capacity of these vectors is limited to 8-10 kb. Second, despite deletion of the E1 region, leaky expression of immunogenic viral proteins occurs in vivo, which leads to a host immune response and elimination of gene expression from transduced tissues. Gutted, or helper-dependent, adenoviral vectors may overcome these drawbacks. Gutted vectors contain cis-acting DNA sequences necessary for viral replication and packaging, but usually do not contain viral coding sequences (See U.S. Pat. No. 6,083,750, incorporated by reference). These vectors can accommodate up to 36 kb of exogenous DNA and are unable to express viral proteins. Gutted vectors are produced by replication in the presence of a helper virus, which provides all necessary viral proteins in trans. Since the viral proteins act to replicate both gutted and helper genomes, gutted adenovirus particles are prepared as a mixture with helper virions, though selection against helper virus packaging can reduce this contamination. Particles containing gutted viral genomes, rather than helper genomes, are subsequently purified on the basis of their lower density.

Generally, the starting point for production of a gutted virus is plasmid DNA. The plasmid contains the viral inverted terminal repeats (ITRs), the viral packaging signal, and exogenous DNA to be carried by the gutted virus. To increase production of gutted virus, most investigators linearize the gutted viral plasmid (some systems require the ligation of viral ITRs after linearization). The plasmid DNA is co-introduced with helper sequences into a cell line that can replicate the helper virus, normally 293 cells. Replication of the helper virus eventually causes lysis of the cells with the lysate containing a large number of helper virions and a comparatively small number of gutted virions.

To increase the number and proportion of gutted virions in the lysate, the initial mixture is generally serially passaged. Helper-dependent Ad vectors are usually propagated with constant selective pressure against helper virus packaging. During early passages, selection allows for gradual improvement in the ratio of gutted to helper virus. At the last passage selection removes the majority of helper virus before further purification. Unfortunately, growth of vector stocks under selective pressure can lead to rearrangement of helper and gutted viruses.

The production of gutted virus particles from plasmid DNA in the first step of gutted vector production is so inefficient that titers of less than 100 particles per milliliter have been reported. In some cases no gutted virions can be detected until at least one serial passage has been performed. What is needed is methods and compositions for faster, higher titer and higher purity production of adenovirus vectors.

SUMMARY OF THE INVENTION

The present invention relates to methods and compositions for the production of viral vectors. In particular, the present invention provides methods and compositions for faster, higher titer and higher purity production of viral vectors (e.g. adenoviral vectors). In some embodiments, the present invention provides gutted and helper viruses with corresponding termini. In other embodiments, the present invention provides terminal protein linked adenoviral DNA. In other embodiments, the present invention provides template extended adenoviral DNA (e.g. for increased viral production/recovery and plaquing efficiency). In additional embodiments, the present invention provides methods and compositions for culturing gutted and helper adenoviruses (e.g. with similar or identical termini). For example, the present invention provides compositions and methods for regulated expression of site specific recombinases. In another example, the present invention provides compositions (e.g. cell lines) and methods for culturing adenoviral vectors with adenoviral protein IX.

In some embodiments, the present invention provides methods for producing helper-dependent viral vectors comprising: a) providing; i) helper-dependent viral DNA comprising a first origin of replication, ii) helper viral DNA comprising a second origin of replication, wherein the second origin of replication has similar activity level in a replication assay as the first origin of replication, and iii) target cells; and b) transfecting the target cells with the helper-dependent viral DNA and the helper viral DNA under conditions such that helper-dependent viral vectors are produced. In particular embodiments, the present invention provides compositions comprising the helper-dependent viral vectors produced with the methods of the present invention. In certain embodiments, the helper-dependent viral DNA comprises adenoviral DNA. In particular embodiments, the helper-dependent viral DNA comprises a heterologous gene sequence. In some embodiments, the helper-dependent viral DNA comprises the left and right inverted terminal repeats (ITRs) of adenovirus, the adenoviral packaging sequence (e.g. linked to one of the ITRs), and a heterologous gene sequence.

In preferred embodiments, the first origin of replication and the second origin of replication have nucleic acid sequences that are identical. In some embodiments, the first and/or second origin of replication lie near the terminus of the viral DNA. In other embodiments, the helper-dependent viral DNA has been released from a plasmid backbone by restriction enzyme digestion. In some embodiments, the helper viral DNA has been released from a plasmid backbone. In preferred embodiments, the helper-dependent viral DNA is at least partially linear (in some cases, entirely linear). In other embodiments, the helper viral DNA is at least partially linear (in some cases, entirely linear). In certain embodiments, both the helper-viral DNA and the helper viral DNA lack internal FseI restriction sites (e.g. so plasmids containing both kinds of viral DNA may be digested with FseI to release the viral DNA without cutting viral coding sequences).

In certain embodiments, the first origin of replication and the second origin of replication have nucleic acid sequences that are similar (e.g. they differ by one base, two bases, or three bases). In additional embodiments, the origins are similar and one of the origins is the natural origin and the other is unnatural (e.g. it has additional sequences attached). In some embodiments, the helper viral DNA is adenoviral helper viral DNA. In preferred embodiments, the first origin of replication and the second origin of replication are not linked to terminal protein or any terminal protein remnant.

In some embodiments, the helper viral DNA comprises a crippling sequence. In preferred embodiments, the crippling sequence comprises recognition sites for site-specific recombinases (e.g. loxP and Frt). In some embodiments, the target cells express adenoviral DNA polymerase and preterminal protein. In other embodiments, the target cells express adenoviral factor IX.

In some embodiments, the present invention provides methods for producing helper-dependent viral vectors comprising: a) providing; i) helper-dependent viral DNA comprising a first origin of replication, ii) helper viral DNA comprising a crippling sequence and a second origin of replication, wherein the second origin of replication has similar activity level in a replication assay as the first origin of replication, iii) target cells, and iv) a vector encoding a site-specific recombinase; and b) transfecting the target cells with the helper-dependent viral DNA, the helper viral DNA, and the vector encoding a site-specific recombinase under conditions such that helper-dependent viral vectors are produced. In preferred embodiments, the transfection of the helper-dependent viral DNA, the helper viral DNA, and the vector encoding a site-specific recombinase all occur at approximately the same time. In particularly preferred embodiments, the transfection of the helper-dependent viral DNA, the helper viral DNA, and the vector encoding a site-specific recombinase all occur at approximately the same time such that the vector expresses the recombinase in a regulated manner (e.g. the amount of recombinase in the transfected cells builds up slowly over time). In some embodiments, the transfection of the helper-dependent viral DNA, the helper viral DNA, and the vector encoding a site-specific recombinase occur at different time (e.g. the helper-dependent viral DNA is transfected before the helper viral DNA, or vice versa). In particular embodiments, the transfecting is accomplished by a method selected from calcium phosphate-DNA co-precipitation, DEAE-dextran-mediated transfection, polybrene-mediated transfection, electroporation, microinjection, liposome fusion, lipofection, and biolistics.

In some embodiments, the present invention provides methods for producing helper-dependent viral vectors comprising: a) providing; i) helper-dependent viral DNA comprising a first origin of replication, ii) helper viral DNA comprising a second origin of replication, wherein the second origin of replication has a similar activity level in a replication assay as the first origin of replication, and iii) target cells; b) transfecting the target cells with the helper-dependent viral DNA and the helper viral DNA under conditions such that helper-dependent viral vectors are produced; and c) recovering the helper-dependent vectors. In preferred embodiments, the recovering step yields a helper-dependent titer of up to approximately 30 fold increase compared to transfection/infection protocols in cells expressing adenoviral DNA polymerase and preterminal protein (e.g., at least a 10 fold, at least a 15 fold, at least a 20 fold, or at least 25 fold increase). In particularly preferred embodiments, the recovering step yields a helper-dependent titer of up to approximately 60 fold increase compared to transfection/infection protocols in cells expressing adenoviral DNA polymerase and preterminal protein (e.g., at least 40 fold, at least 50 fold, or at least 55 fold increase).

In some embodiments, the present invention provides compositions comprising; a) helper-dependent viral DNA comprising a first origin of replication, and b) helper viral DNA comprising a second origin of replication, wherein the second origin of replication has a similar activity level in a replication assay as the first origin of replication. In certain embodiments, the helper-dependent viral DNA comprises adenoviral DNA. In particular embodiments, the helper-dependent viral DNA comprises a heterologous gene sequence. In some embodiments, the helper-dependent viral DNA comprises the left and right inverted terminal repeats (ITRs) of adenovirus, the adenoviral packaging sequence (e.g. linked to one of the ITRs), and a heterologous gene sequence. In preferred embodiments, the first origin of replication and the second origin of replication have nucleic acid sequences that are identical. In certain embodiments, the first origin of replication and the second origin of replication have nucleic acid sequences that are similar (e.g. they differ by one base, two bases, or three bases). In additional embodiments, the origins are similar and one of the origins is the natural origin and the other is unnatural (e.g. it has additional sequences attached). In some embodiments, the helper viral DNA is adenoviral helper viral DNA. In preferred embodiments, the first origin of replication and the second origin of replication are not linked to terminal protein or any terminal protein remnant.

In some embodiments, the present invention provides kits and systems comprising; i) helper-dependent viral DNA comprising a first origin of replication, and ii) helper viral DNA comprising a second origin of replication, wherein the second origin of replication has similar activity level in a replication assay as the first origin of replication. In preferred embodiments, the kits and systems of the present invention further comprise target cells (e.g., cells expressing adenoviral DNA polymerase and preterminal protein). In other embodiments, the kits and systems of the present invention comprise the helper-dependent viral vectors produced by the methods of the present invention, and one additional component (e.g., an insert component with written instructions for using the components of the kit and system). The kits and systems of the present invention may comprise any of the components listed herein (e.g., helper-dependent viral DNA, helper viral DNA, target cells, insert component, etc.). In particular embodiments, the kits and systems of the present invention comprise a host cell and one additional component, wherein the host cell comprises a) helper-dependent viral DNA comprising a first origin of replication, and b) helper viral DNA comprising a second origin of replication, wherein the second origin of replication has a similar activity level in a replication assay as the first origin of replication.

In some embodiments, the present invention provides methods for producing helper-dependent viral vectors comprising: a) providing; i) helper-dependent viral DNA comprising an origin of replication linked to a replication-promoting agent, and ii) target cells; and b) transfecting the target cells with the helper-dependent viral DNA under conditions such that helper-dependent viral vectors are produced. In particular embodiments, the present invention provides methods for producing helper-dependent viral vectors comprising: a) providing; i) helper-dependent viral DNA comprising an origin of replication linked to a replication-promoting agent, ii) helper viral DNA, and iii) target cells; and b) transfecting the target cells with the helper-dependent viral DNA and the helper viral DNA under conditions such that helper-dependent viral vectors are produced. In certain embodiments, the present invention provides compositions comprising the helper-dependent viral vectors produced with the methods of the present invention. In preferred embodiments, the replication-promoting agent is selected from Ad2 preterminal protein, Ad2 terminal protein, Ad5 preterminal protein, and Ad5 terminal protein. In other embodiments, replication-promoting agent is selected from at least a portion of Ad2 preterminal protein, Ad2 terminal protein, Ad5 preterminal protein, and Ad5 terminal protein. In preferred embodiments, the replication-promoting agent is Ad5 terminal protein.

In some embodiments, the helper-dependent viral DNA comprises adenoviral DNA. In other embodiments, the helper-dependent viral DNA comprises a heterologous gene sequence. In some embodiments, the helper-dependent viral DNA comprises the left and right inverted terminal repeats (ITRs) of adenovirus, the adenoviral packaging sequence (e.g. linked to one of the ITRs), and a heterologous gene sequence. In some embodiments, the helper viral DNA is linked to adenoviral terminal protein. In additional embodiments, the helper viral DNA is adenoviral helper viral DNA. In preferred embodiments, the helper viral DNA comprises a crippling sequence (e.g. loxP). In particular embodiments, the helper viral DNA comprises recognition sites for site-specific recombinases. In certain embodiments, the target cells express adenoviral DNA polymerase and preterminal protein. In other embodiments, the target cells express adenoviral protein IX. In certain embodiments, the target cells express adenoviral DNA polymerase, preterminal protein, and adenoviral protein IX. In some embodiments, the method further comprises recovering the helper-dependent vectors. In particular embodiments, the recovering yields a helper-dependent titer of up to approximately 85 fold increase compared to transfection/infection protocols in cells expressing adenoviral DNA polymerase and preterminal protein (e.g., at least a 40 fold, 55 fold, 70 fold, or 80 fold increase). In preferred embodiments, the recovering yields a helper-dependent titer of up to 170 fold increase compared to transfection/infection protocols in cells expressing adenoviral DNA polymerase and preterminal protein (e.g., at least 100 fold, 120 fold, 140 fold, 150 fold, or 160 fold increase).

In particular embodiments, the present invention provides methods for producing helper-dependent viral vectors comprising: a) providing; i) helper-dependent viral DNA comprising an origin of replication linked to a replication-promoting agent, ii) helper viral DNA comprising a crippling sequence, and iii) target cells; and b) transfecting the target cells with the helper-dependent viral DNA and the helper viral DNA under conditions such that helper-dependent viral vectors are produced. In preferred embodiments, the transfection of the helper-dependent viral DNA, the helper viral DNA, and the vector encoding a site-specific recombinase all occur at approximately the same time. In particularly preferred embodiments, the transfection of the helper-dependent viral DNA, the helper viral DNA, and the vector encoding a site-specific recombinase all occur at approximately the same time such that the vector expresses the recombinase in a regulated manner (e.g. the amount of recombinase in the transfected cells builds up slowly over time). In some embodiments, the transfection of the helper-dependent viral DNA, the helper viral DNA, and the vector encoding a site-specific recombinase occur at different time (e.g. the helper-dependent viral DNA is transfected before the helper viral DNA, or vice versa). In particular embodiments, the transfecting is accomplished by a method selected from calcium phosphate-DNA co-precipitation, DEAE-dextran-mediated transfection, polybrene-mediated transfection, electroporation, microinjection, liposome fusion, lipofection, and biolistics.

In some embodiments, the present invention provides compositions comprising helper-dependent viral DNA comprising an origin of replication linked a replication-promoting agent. In preferred embodiments, the replication-promoting agent is selected from Ad2 preterminal protein, Ad2 terminal protein, Ad5 preterminal protein, and Ad5 terminal protein. In other embodiments, replication-promoting agent is selected from at least a portion of Ad2 preterminal protein, Ad2 terminal protein, Ad5 preterminal protein, and Ad5 terminal protein. In preferred embodiments, the replication-promoting agent is Ad5 terminal protein.

In some embodiments, the present invention provides kits and systems comprising i) helper-dependent viral DNA comprising an origin of replication linked to a replication-promoting agent, and ii) target cells. In preferred embodiments, the kits and systems of the present invention further comprise helper viral DNA. In other embodiments, the kits and systems of the present invention comprise the helper-dependent viral vectors produced by the methods of the present invention, and one additional component (e.g., an insert component with written instructions). The kits and systems of the present invention may comprise any of the components listed herein (e.g., helper-dependent viral DNA, helper viral DNA, target cells, insert component, etc.).

In certain embodiments, the present invention provides methods comprising: a) providing; i) a first helper-dependent viral DNA comprising a first origin of replication capable of promoting a first activity level in a replication assay, ii) an agent capable of extending the first origin of replication, and b) contacting the helper-dependent viral DNA with the agent for a period of time sufficient to generate a second helper-dependent viral DNA with an second origin of replication capable of promoting a second activity level in a replication assay, wherein the second activity level in a replication assay is greater than the first activity level in a replication assay. In other embodiments, the present invention provides methods comprising: a) providing; i) a first helper-dependent viral DNA comprising a first origin of replication capable of promoting a first activity level in a replication assay, ii) an agent capable of extending the first origin of replication, iii) helper viral DNA, and iv) target cells; b) contacting the helper-dependent viral DNA with the agent for a period of time sufficient to generate a second helper-dependent viral DNA with an second origin of replication capable of promoting a second activity level in a replication assay, wherein the second activity level in a replication assay is greater than the first activity level in a replication assay; and c) transfecting the target cells with the second helper-dependent viral DNA and the helper viral DNA under conditions such that helper-dependent viral vectors are produced.

In certain embodiments, the first origin of replication is natural. In some embodiments, the first origin of replication is non-natural (e.g. it has one, two, or three bases added onto the natural origin of replication). In other embodiments, the agent is selected from the group of terminal transferase, T4 DNA ligase, and T4 RNA ligase. In preferred embodiments, the agent is terminal transferase. In some embodiments, the helper-dependent viral DNA comprises adenoviral DNA. In other embodiments, the helper-dependent viral DNA comprises a heterologous gene sequence. In still other embodiments, the helper-dependent viral DNA comprises the left and right inverted terminal repeats (ITRs) of adenovirus, the adenoviral packaging sequence (e.g. linked to of the ITRs), and a heterologous gene sequence. In particular embodiments, the helper viral DNA is adenoviral helper viral DNA. In preferred embodiments, the helper viral DNA comprises a crippling sequence (e.g. a site specific recombinase). In some embodiments, the crippling sequence is loxP. In some embodiments, the target cells express adenoviral DNA polymerase and preterminal protein. In other embodiments, the target cells express adenoviral factor IX. In certain embodiments, the method further comprises recovering the helper-dependent vectors. In preferred embodiments, the second activity level in a replication assay is approximately 2-2.5 fold greater than the first activity level in a replication assay.

In other embodiments, the present invention provides methods comprising: a) providing; i) a first helper-dependent viral DNA comprising a first origin of replication capable of promoting a first activity level in a replication assay, ii) an agent capable of extending the first origin of replication, iii) helper viral DNA, iv) target cells and v) a vector encoding a site-specific recombinase; b) contacting the helper-dependent viral DNA with the agent for a period of time sufficient to generate a second helper-dependent viral DNA with an second origin of replication capable of promoting a second activity level in a replication assay, wherein the second activity level in a replication assay is greater than the first activity level in a replication assay; and c) transfecting the target cells with the second helper-dependent viral DNA, the helper viral DNA, and the vector encoding a site-specific recombinase under conditions such that helper-dependent viral vectors are produced. In certain embodiments, the present invention provides compositions comprising the helper-dependent viral vectors produced with the methods of the present invention. In preferred embodiments, the transfection of the helper-dependent viral DNA, the helper viral DNA, and the vector encoding a site-specific recombinase all occur at approximately the same time. In particularly preferred embodiments, the transfection of the helper-dependent viral DNA, the helper viral DNA, and the vector encoding a site-specific recombinase all occur at approximately the same time such that the vector expresses the recombinase in a regulated manner (e.g. the amount of recombinase in the transfected cells builds up slowly over time). In some embodiments, the transfection of the helper-dependent viral DNA, the helper viral DNA, and the vector encoding a site-specific recombinase occur at different time (e.g. the helper-dependent viral DNA is transfected before the helper viral DNA, or vice versa). In particular embodiments, the transfecting is accomplished by a method selected from calcium phosphate-DNA co-precipitation, DEAE-dextran-mediated transfection, polybrene-mediated transfection, electroporation, microinjection, liposome fusion, lipofection, retroviral infection and biolistics.

In some embodiments, the present invention provides kits and systems comprising i) a first helper-dependent viral DNA comprising a first origin of replication capable of promoting a first activity level in a replication assay, and an agent capable of extending the first origin of replication. In other embodiments, the kits and systems further comprise helper viral DNA and/or target cells. In other embodiments, the kits and systems of the present invention comprise the helper-dependent viral vectors produced by the methods of the present invention, and one additional component (e.g., an insert component with written instructions). The kits and systems of the present invention may comprise any of the components listed herein (e.g., helper-dependent viral DNA, helper viral DNA, target cells, insert component, etc.). In particular embodiments, the kits and systems of the present invention comprise a host cell and one additional component, wherein the host cell (e.g., mammalian) stably and constitutively expresses adenovirus preterminal protein, adenovirus DNA polymerase, and adenovirus protein IX.

In some embodiments the present invention provides mammalian cell lines stably and constitutively expressing adenovirus preterminal protein, adenovirus DNA polymerase, and adenovirus protein IX. In some embodiments, the cell line is D2104#10.

DESCRIPTION OF THE FIGURES

FIG. 1 shows: A) (SEQ ID NOS:21-26) the structure of viral origins of replication (both natural and non-natural origins that result when particular restriction enzymes are employed); B) points where viral genome is mutated to remove FseI restriction sites; and C) partial structure of pD1940#3 and pD1940#6.

FIG. 3 shows a method for conversion of plasmid-derived Ad origins to natural form (creating TP-primer and ligating it to plasmid derived viral DNA).

FIG. 4 shows that conversion of plasmid-derived gutted virus to a natural, TP-linked structure facilitates gutted virus rescue.

FIG. 8 shows the nucleic acid sequence of (+)lox(+)pol helper virus (SEQ ID NO:1).

FIG. 9 shows the nucleic acid sequence of pBSX (SEQ ID NO:12).

FIG. 11 shows the nucleic acid sequence of ΔFseI.4 helper virus (SEQ ID NO:9).

FIG. 13 shows TP-DNA complex from (+)lox(+)pol helper viral DNA; deproteinized Hirt prep DNA from ΔFseI.4; and pD1940#3 and pD1940#6.

FIG. 14 shows the nucleic acid sequence of pD1940 (SEQ ID NO:13).

FIG. 15 shows the nucleic acid sequence of pD1962delBbsI-pIX (SEQ ID NO:14).

FIG. 17 shows the nucleic acid sequence of ΔHIX#3 (SEQ ID NO:15).

FIG. 18 shows the nucleic acid sequence for: Ad2 preterminal protein (SEQ ID NO:17); Ad2 terminal protein (SEQ ID NO:18); Ad5 preterminal protein (SEQ ID NO:19); and Ad5 terminal protein (SEQ ID NO:20).

DEFINITIONS

Figure 2:
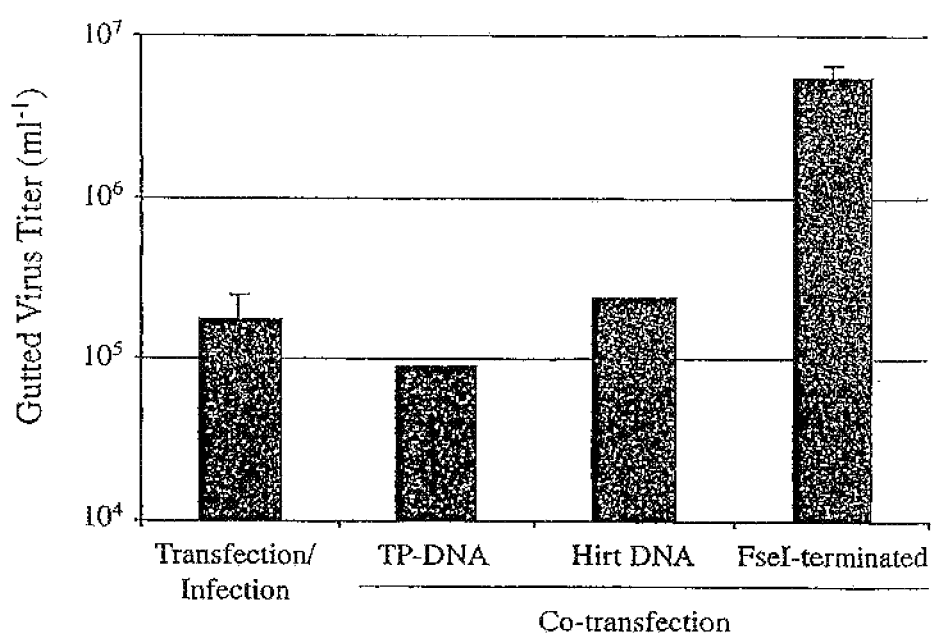
FIG. 2 shows improved gutted virus rescue that is achieved by co-transfection of matching plasmid-derived gutted and helper virus DNAs.

To facilitate an understanding of the present invention, a number of terms and phrases are defined below:

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. Oligonucleotide may be generated in any manner, including chemical synthesis, DNA replication, reverse transcription, or a combination thereof.

As used herein, the term "helper dependent viral DNA" or "gutted viral DNA" refers to viral DNA that codes for viral vectors that contain cis-acting DNA sequences necessary for viral replication and packaging, but generally no viral coding sequences (See U.S. Pat. No. 6,083,750, incorporated by reference). These vectors can accommodate up to about 36 kb of exogenous DNA and are unable to express viral proteins sufficient for replication. Helper-dependent viral vectors are produced by replication of the helper dependent viral DNA in the presence of a helper adenovirus, which alone or with a packaging cell line, supplies necessary viral proteins in trans such that the helper-dependent viral DNA is able to be replicated. Gutted vectors may be constructed as described in U.S. Pat. No. 6,083,750.

As used herein the term "helper viral DNA" refers to viral DNA encoding helper viral vectors, that are capable of providing, alone or with a packaging cell line, viral proteins in trans such that a gutted virus is able to replicate. A "helper adenovirus" or "helper virus" refers to an adenovirus which is replication-competent in a particular host cell. The host may provide, for example, Ad gene products such as E1 proteins. The 'helper virus' is used to supply in trans functions (e.g., proteins) which are lacking in a second replication-incompetent virus (e.g. a gutted viral vector). Therefore, the first replication-competent virus is said to "help" the second replication-incompetent virus thereby permitting the propagation of the second viral genome in the cell containing the helper and second viruses. Helper virus may include a sequence capable of crippling helper virus replication in the presence of certain crippling agents. An example of a helper virus with a crippling sequence is the (+)lox(+)pol helper virus (SEQ ID NO:1). The (+)lox(+)pol helper virus is an E1-, E3-deleted virus that can be negatively selected using Cre recombinase and carries an alkaline phosphatase reporter gene in its E3 region. The packaging signal, which consists of packaging elements I-V, is flanked by loxP sites in direct repeat orientation, allowing removal of the packaging signal in the presence of Cre (a crippling agent).

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery). Adenoviruses are double-stranded DNA viruses. The left and right inverted terminal repeats (ITRs) are short elements located at the 5' and 3' termini of the linear Ad genome, respectively, and are required for replication of the viral DNA. The left ITR is located between 1-130 bp in the Ad genome (also referred to as 0-0.5 mu). The right ITR is located from +35,800 bp to the end of the genome (also referred to as 99.5-100 mu). The two ITRs are inverted repeats of each other.

The term "transfection" as used herein refers to the introduction of foreign DNA into eukaryotic cells. Transfection may be accomplished by a variety of means known to the art including, but not limited to, calcium phosphate-DNA co-precipitation, DEAE-dextran-mediated transfection, polybrene-mediated transfection, electroporation, microinjection, liposome fusion, lipofection and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

As used herein, the term "gene of interest" or "heterologous gene sequence" refers to a gene inserted into a vector or plasmid whose expression is desired in a host cell. Genes of interest include genes having therapeutic value as well as reporter genes. A variety of such genes are contemplated, including genes of interest encoding proteins which provide a therapeutic function (such as the dystrophin gene, which is capable of correcting the defect seen in the muscle of MD patients), the utrophin gene, the CFTR gene (capable of correcting the defect seen in cystic fibrosis patients), etc.

The term "reporter gene" indicates a gene sequence that encodes a reporter molecule (including an enzyme). A "reporter molecule" is detectable in detection systems, including, but not limited to enzyme (e.g., ELISA, as well as enzyme-based histochemical assays), fluorescent, radioactive, and luminescent systems. Examples of reporter molecules include, but are not limited to, beta-galactosidase gene (available from Pharmacia Biotech, Pistacataway, N.J.), green fluorescent protein (GFP) (commercially available from Clontech, Palo Alto, Calif.), the human placental alkaline phosphatase gene, and the chloramphenicol acetyltransferase (CAT) gene. Other reporter genes are known to the art and may be employed.

As used herein, the term "activity level in a replication assay" refers to the level of activity observed for a particular type of viral origin of replication as measured in a replication assay. Examples of replication assays include, but are not limited to, plaque assays, rate of initiation of DNA replication assays, and replication factor affinity assays.

As used herein, the term "plaque assay" refers to a means for measuring the frequency with which virus or viral DNA can replicate productively (See, Graham, F. L. and Prevec, L. *Manipulation of Adenovirus Vectors in Gene Transfer and Expression Protocols*, Clifton: The Humana Press, Inc., 1991, hereby incorporated by reference). The assay may be performed, for example, by using either virus (by infection) or viral DNA (by transfection). For purposes of measuring the activity of an origin of replication the assay is performed using viral DNA. When viral DNA is introduced into cells by transfection, some transfected cells allow replication of the genome and progeny virions are produced. If the cells have been overlayed with agarose, the progeny virions diffuse to and infect only nearby cells. Thus, after several rounds of replication, foci of dead cells are observed (e.g. their presence may be highlighted through use of dyes like neutral red). These foci of dead cells are referred to as "plaques". To measure the activity of an origin of replication in this assay, the origin is linked to helper-independent viral DNA and transfected into cells which support growth of the virus. The cells are overlayed with agarose, and the investigator waits for the appearance of plaques (e.g. 3-14 days). After plaques have appeared, their appearance may be highlighted with dye, and their number counted. The higher the number of plaques, the more often the viral DNA has been converted into replicating virus, and the higher the activity of the origin of replication is found to be. The number of plaques observed is also correlated with the amount of DNA transfected, so the results of a plaque assay may be expressed as "specific activity"; that is, the number of plaques observed per weight of DNA transfected. An origin of replication that is more active than a second origin will tend to display more plaques in the plaque assay.

As used herein, the term "rate of initiation of DNA replication assays" refers to methods for determining the rate of initiation of DNA replication on a given origin (See, Challberg M D., Rawlins Dr., *P.N.A.S.*, 81(1):100-4, 1984, herein incorporated by reference). The rate of initiation of DNA replication on a given origin may be measured, for example, by incubating the origin together with all the viral and cellular factors required for initiation, and then noting the rate with which new copies of the non-template strand appear. Generally, the steps in such an assay include: isolation of cellular and viral factors from infected cells; incubation of the isolated factors with origin fragments and radioactive nucleotides; observation of new DNA copies using an assay method such as gel electrophoresis followed by autoradiography. For each origin, the analysis is usually performed at several time points, so that the appearance of new DNA copies may be charted over time. Using this information, the rate of their appearance can be calculated. An origin of replication that is more active than a second origin will tend to cause the rate of appearance of new DNA copies to be more rapid in this assay.

As used herein, the term "replication factor affinity assays" refers to methods for determining the ability of viral DNA to attract viral replication factors (e.g. adenovirus DNA polymerase, adenovirus preterminal protein, NFI, and NFIII, See Pronk et al., *Nucleic Acids Research*, 25(10): 2293-300, 1993, herein incorporated by reference). The affinity of a replication factor for an origin of replication may be measured, for example, by incubating the two together at a variety of concentrations and then determining, at each concentration, the amount of origin DNA that was bound by factor. One example of a method used to determine the amount of bound origin DNA is an "electrophoretic mobility shift assay" (EMSA). In this assay, the presence of factor bound to DNA causes the mobility of the origin-containing DNA to be reduced in polyacrylamide gels. Using radioactive origin DNA, the amount of DNA bound by factor can therefore be determined by measuring the amount of radioactivity found in an electrophoretic band of reduced mobility—the larger the amount of radioactivity, the larger the amount of DNA bound by factor. The affinity of an origin of replication for a replication factor is indicated by the concentration levels at which substantial binding can occur: the lower the concentration at which binding occurs, the higher the affinity is said to be. The relative affinities of two origins for a replication factor could be compared by incubating radioactive samples of each origin together with different concentrations of replication factor, usually in the presence of random DNA fragments to inhibit non-specific interactions. If the first origin has a higher affinity for factor than the second origin, a lesser concentration of factor will be required to bind a given amount of origin DNA. For example, a lesser concentration of factor will be required to retard the migration of a certain proportion of DNA sequences containing the first origin than DNA sequences containing the second, as determined by EMSA.

As used herein, the term "target cells" refers to any cells that may be transfected with viral DNA. Target cells include, but are not limited to, bacterial cells, mammalian cells, and insect cells. Target cells may from any source including, but not limited to, bacterial colonies, cell lines, tissue samples, and blood samples.

As used herein the term "expresses said recombinase in a regulated manner" refers to the expression of recombinase in a target cell such that the level of recombinase in the cell gradually increases over time. This gradual increase in expression allows the helper viral DNA to replicate at a greater rate initially after transfection (when the level of recombinase is lower), and slows the replication rate of the helper virus as the level of recombinase increases. One example expression of recombinase in a regulated manner is provided in Example 6.

As used herein, the term "similar activity level in a replication assay" refers to the situation where two origins of replication have about the same activity level in a replication assay (e.g. plaque assay, replication factor affinity assay, or rate of initiation of DNA replication assay). For example, similar activity level includes a difference of 20 fold or less, preferably 10 fold or less, more preferably 5 fold or less, and most preferably 2 fold or less.

As used herein, the phrase "wherein said second activity level in a replication assay is greater than said first activity level in a replication assay" refers to a second activity level of at least 5% greater, preferably 10%, more preferably 20% greater, most preferably 50% greater, than said first activity level.

As used herein the phrase "at about the same time" refers to transfection steps that occur within approximately one hour of each other.

As used herein, the term "under conditions such that helper-dependent viral vectors are produced" refers to conditions such that help dependent viral DNA is able to replicate inside a cell (e.g. may require helper viral DNA) such that helper-dependent viral vectors (particles) are produced.

As used herein, the term "origin of replication" refers to the DNA sequence elements that are necessary and sufficient to direct replication of a DNA molecule to which they are attached. Generally, the sequence elements include binding sites for replication factors and usually span the points at which the synthesis of new DNA strand begin. Origins of replication can often be identified by the fact that their mutation or removal prevents replication of DNA molecules to which they had been attached and which had formerly replicated in a given system. In addition, the attachment of an origin of replication to a formerly inert molecule should be sufficient to cause its replication in a given system. For example, the origin of replication for adenoviral DNA has been identified as including at least the first 50 base pairs of the adenoviral genome and commonly refers to approximately the first 100 base pairs of the adenoviral genome also known as the inverted terminal repeat (ITR). Removal of the ITRs from adenoviral genome prevents its replication; the addition of ITRs to most DNA molecules is sufficient to allow their replication in cells that have been infected by helper independent adenovirals, which provides viral replication factors.

As used herein the term "viral recovery" refers to collection and storage of progeny virions produced by cells (e.g. infected by helper-dependent and helper viral DNA). This can be accomplished with or without purification of the virions to remove cellular contaminants. For example, a simple method for viral recovery is to collect lysed cells and store them in the freezer. The presence of virions may be revealed through an examination of the lysate by any of several methods including, but not limited to, plaque assay, a transduction assay that reveals the presence of a marker genes like beta-galactosidase, or physical methods such as chromatography followed by spectroscopy.

As used herein, the term "transfection/infection protocol" refers to the standard protocol where helper-dependent viral DNA is introduced into cells by a transfection method at approximately the same time (e.g. plus or minus 24 hours) that intact helper independent viral particles (e.g. contain adenoviral terminal protein linked to the origin of replication) are allowed to contact the cells and infect them. After a variable period of time the cells lyse due to replication of the virus. At that point, the progeny viral particles are collected.

As used herein, the term "replication-promoting agent" refers to a compound or molecule that may be ligated to viral DNA terminus such that the activity level in a replication assay of such viral DNA is increased (compared to not having the replication-promoting agent ligated to the viral terminus). Examples of replication-promoting agents include, but are not limited to, Ad5 adnenoviral preterminal protein, Ad5 adenoviral protein, Ad2 preterminal protein, and Ad2 terminal protein.

As used herein, the term "agent capable of extending said first origin of replication" refers to any agent that is capable of adding single nucleotides, or oligonucleotides (e.g. 10 mers) to the terminal end of viral DNA. Examples of such agents include, but are not limited to, terminal transferase, T4 DNA ligase, and T4 RNA ligase.

As used herein, the phrase "contacting said helper-dependent viral DNA with said agent for a period of time sufficient to generate", in regards to time, refers to the length of time required to expose viral DNA origins (natural or un-natural) to an agent capable of extending such origins, such that the activity level in a replication assay of such extended origin is increased (as compared to not extended origins). This time period may vary according to the agent employed and other conditions (e.g. type and concentrations of nucleotides). One example of determining the appropriate length of time is provided in Example 5.

As used herein, the phrase "said first origin of replication and said second origin of replication have nucleic acid sequences that are substantially similar" refers to the situation where the first and second origins, while not identical, have origins of replication that are similar in nature (e.g. they both have additional nucleotides added to the natural origin of replication such that the ability). One example of substantially similar origins is provided in FIG. 1A, comparing the structure of the PacI digested viral DNA origin to the FseI digested viral DNA origin.

DESCRIPTION OF THE INVENTION

The present invention relates to methods and compositions for the production of viral vectors. In particular, the present invention provides methods and compositions for faster, higher titer and higher purity production of viral vectors (e.g. adenoviral vectors). In some embodiments, the present invention provides gutted and helper viruses with corresponding termini. In other embodiments, the present invention provides terminal protein linked adenoviral DNA. In other embodiments, the present invention provides template extended adenoviral DNA (e.g. for increased viral production/recovery and plaquing efficiency). In additional embodiments, the present invention provides methods and compositions for culturing gutted and helper adenoviruses (e.g. with similar or identical termini). For example, the present invention provides compositions and methods for regulated expression of site specific recombinases. In another example, the present invention provides compositions (e.g. cell lines) and methods for culturing adenoviral vectors with adenoviral protein IX.

I. Gutted and Helper Viruses with Similar or Identical Termini

In typical gutted virus-helper virus rescue production methods, the helper virus eventually comes to dominate the contents of the packaging cell (to the detriment of the gutted adenovirus). The number and proportion of gutted virions is small because plasmid DNA, whether circular (with fused ITRs) or linear, is a poor substrate for initiation of adenoviral DNA replication. As a result, replication of the helper virus occurs in many cells without concomitant production of gutted virus, despite the presence of gutted viral plasmid substrate.

As mentioned above, to increase the number and proportion of gutted virions in the lysate, the initial mixture is generally serially passaged. Helper-dependent Ad vectors are usually propagated with constant selective pressure against helper virus packaging. During early passages, selection allows for gradual improvement in the ratio of gutted to helper virus. Unfortunately, growth of vector stocks under selective pressure can lead to rearrangement of helper and gutted viruses. In addition, serial passage is time consuming.

Published protocols for rescue of helper-dependent Ad vectors employ gutted viral DNA derived from plasmids and helper viral DNA derived from replicating virus. Most investigators transfect gutted viral DNA and then infect with replication-competent helper virus the "transfection/infection" protocol. Others have compared transfection/infection to co-transfection of gutted viral DNA from plasmids and helper viral DNA prepared from replicating virus and found that co-transfection is more efficient. In these protocols, the helper and gutted viral DNAs have different structures at their origins of replication.

The present invention provides gutted and helper viral DNA with similar corresponding termini or linked to terminal protein, thus alleviating some of the problems of normal viral rescue protocols. While not limited to any mechanism, providing gutted and viral DNA that are substantially similar at the origin of replication allows parallel amplification of both types of vectors, thus preventing the helper viruses production from dominating over gutted virus production. Again, while not limited to any mechanism, it is believed that substantially similar termini or origins of replication (or identical termini or origins of replication) allow parallel amplification of both types of vectors because neither type of virus has a competitive advantage for attracting replication factors (such as adenoviral polymerase, transcription factors, etc.).

The present invention provides gutted and helper viruses with corresponding termini, and methods of employing such vectors for increased production yields (and faster production) of adenoviral vectors (which, may then be used, for example, for gene therapy applications). In some embodiments, gutted adenoviral DNA and helper adenoviral DNA (e.g. both located on plasmids) are released from their plasmids with the same restriction enzyme (cutting at the termini) such that the termini of the linearized DNA are the same (i.e. the gutted and helper adenoviral DNA have corresponding termini). Any type of restriction enzyme (or other enzyme that will cut DNA) may be used, as long as at least one viral terminus is released from its host vector or the ends of the DNA are able to be cut, leaving corresponding termini on both the gutted and helper DNA. In particular embodiments, different restriction enzymes are employed. In such embodiments, the ends of the viral DNA may not be identical, but the ability of the ends to promote replication in cells is approximately the same (e.g. neither type of DNA has a substantial competitive advantage after transfection, such that replication of both types of viruses proceeds at approximately the same pace). In preferred embodiments, the same restriction enzyme is used to generate the termini of both the gutted and helper viral DNA.

Preferably, restriction enzymes are employed that cut close to or at the termini of helper and gutted viral DNA. In some embodiments, creating gutted and helper adenoviral DNA with identical or similar termini requires that particular restriction sites be removed from one or both types of DNA (to prevent the digestion of the viral DNA). An example of removing unwanted restriction sites (FseI sites) from viral DNA (the Ad5 genome) is provided in Example 1. A similar procedure can be employed to remove other types of unwanted restriction sites from viral DNA. In this regard, any restriction enzyme could be employed to create identical (or similar) termini if the suitable modification are made (if necessary) in the viral DNA.

To confirm that the restriction enzyme employed is capable of releasing replication-competent viral DNA from flanking DNA sequences (e.g. plasmid DNA), an assay similar to Example 2 may be employed (transfecting gutted and helper DNA into cells known to replicate adenoviral DNA). Such a technique may also be employed to test the relative efficiency of production of viral particles from viral DNA with various termini.

In certain embodiments, neither the gutted or the helper viral DNA contain terminal protein, and both types are transfected into a cell line as DNA (e.g. the helper DNA is transfected as DNA, instead of a viral particle). In such embodiments, the identity of the termini of the helper and gutted viral DNA is not critical, as long as the termini both do not contain terminal protein or any terminal protein remnant (e.g. one serine residue). In certain embodiments, the gutted and helper viral DNA are co-transfected into a packaging cell line.

II. Replication-Promoting Agent Linked Adenoviral DNA

Another method for increasing viral production is linking gutted adenoviral DNA (e.g. the adenoviral origin) to a replication-promoting agent (e.g. adenoviral preterminal protein or adenoviral terminal protein). The normal substrate for initiation of adenoviral DNA replication is terminal protein-DNA complex. Plasmid-based substrates propagated in, for example, *E. coli*, normally lack terminal protein. As such, replication is greatly increased by linking gutted adenoviral DNA (and, in some embodiments, helper viral DNA) to adenoviral terminal protein.

In the transfection/infection protocol, or when helper virus terminal protein-DNA complex is used for co-transfection, the helper virus DNA is already attached to adenoviral terminal protein. While not limited to any mechanism, it is believed that linking the gutted adenoviral DNA termini to a replication-promoting agent (e.g. adenoviral terminal protein) reduces the competitive advantage helper virus has when supplied as viral particles (or DNA) that is already attached to terminal protein. In this regard, both types of viral DNA have a similar ability to attract replication factors and replicate into viral particles. Again, while not limited to any mechanism, it is believed that the presence of a replication-promoting agent (e.g. adenoviral preterminal protein) bound to the template confers higher affinity for incoming Ad polymerase-preterminal protein complex, an essential viral replication factor.

One method for preparing gutted viral genomes linked to adenoviral terminal protein (i.e. terminal protein serves as the replication-promoting agent) involves purifying terminal protein-containing fragments. Terminal protein-containing fragments (e.g. isolated from intact virus), can be purified away from other viral DNA fragments before ligation. It is desired that such purification be employed as the presence of other viral fragments would tend to inhibit the desired ligation reaction, since both partners in the desired ligation (gutted viral genomes and terminal protein-containing fragments) would likely be ligated to contaminating, more numerous random viral fragments in a mixed reaction. A second purification step may be performed after ligation, when unligated terminal protein-DNA fragments are removed. As these fragments contain natural Ad origins, failure to remove them could reduce the yield of gutted virus by inhibiting viral replication. Another method for obtaining terminal protein is purification of terminal protein-gutted genome complex from gutted virus preparations.

In a preferred embodiments, gutted Ad genomes are linked to normal Ad origins (FIG. 4). This method requires relatively small amounts of terminal protein DNA-complex (e.g. 2-4 moles of terminal protein-DNA complex are sufficient to convert approximately 1 mole of gutted viral genomes to the natural, terminal protein-containing form). Conveniently, the reaction can be performed without purification of the terminal protein-DNA reagent either before or after origin conversion (See Example 3).

In some embodiments, the compound used in the conversion process is terminal protein linked to single-stranded DNA (e.g. from the non-template strand of an Ad ITR). Another term for terminal protein linked to single-stranded DNA is "TP-primer". Example 3 provides one example of the preparation of TP-primer, employing a restriction enzyme digest of viral TP-DNA complex (employing Bsh1236I, AluI, and HinfI) followed by λ exonuclease treatment. Other restriction enzymes may be employed in this process. Preferably, restriction enzymes are chosen that leave a substantial length of nucleic acid (i.e. 'primer') on the TP-primer reagent. For example, Bsh1236I, employed in Example 3, is known to cut between base pairs 73 and 74 of the Ad5 ITR, so this type of digestion results in terminal protein linked to a 73-bp, double stranded DNA molecule. This method may also employ other exonucleases (i.e. besides λ exonuclease), preferably 5' to 3' exonucleases (e.g. T7 gene 6 exonuclease).

In some embodiments, the TP-primer reagent is purified after it is constructed (e.g. to remove any mononucleotides or oligonucleotides created as a result of the enzyme digests). For example, as the TP-primer contains single-stranded DNA, any type of solid-phase purification strategy may be used (e.g. paramagnetic beads linked to single-stranded DNA that is complementary to the DNA in the TP-primer reagent—after binding of TP-primer to the beads, the beads could be collected and the TP-primer reagent released through heating). Other suitable purification/collection techniques are known in the art.

TP-primer may also be constructed synthetically. Such a synthetic reagent would contain, for example, a peptide fragment (or entire protein) of the Ad terminal protein linked to any number of bases from an adenovirus ITR. Synthesis techniques for polypeptides and nucleic acid are well known in the art.

A natural or synthetic "primer" sequence, for generating a TP-primer molecule, is selected to be substantially or completely complementary to a strand of specific sequence of the gutted viral template. A primer must be sufficiently complementary to hybridize with a template strand (e.g. such that primer elongation can occur). A primer sequence need not reflect the exact sequence of the template. Non-complementary bases or longer sequences can be interspersed into the primer, provided that the primer sequence has sufficient complementarity with the sequence of the template to hybridize and thereby form a template primer complex. Complementarity need not be perfect, stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

TP-primer molecules (or similar molecules) are used to convert viral origins to "natural" viral origins of replication. In a preferred embodiment, TP-primer is used to convert plasmid derived gutted viral genomes to natural adenoviral origins by attaching TP-primer to the terminus of adenoviral DNA. Any type of method may be employed. For example, gutted viral genomic DNA (flanked by restriction enzyme sites) may be digested with the appropriate restriction enzyme to release the gutted viral DNA. The products of this are then subjected to limited digestion with a 5' to 3' exonuclease (limited digestion with this type of enzyme exposes single-stranded regions near the gutted vector genomic termini, see FIG. 3B). Any type of 5' to 3' exonuclease may be employed (e.g. T7-gene-6 exonuclease, λ exonuclease, etc.). Digestion with the 5' to 3' nuclease is for a limited time (e.g. about 1-2 minutes), such that enough single strand template is exposed to hybridize to the nucleic acid in the TP-primer, but not so much that the entire strand is digested. The longer the single-stranded nucleic acid is on the TP-primer compound, the more 5' to 3' digestion is needed to expose a single-stranded template for hybridization. The exonuclease is preferably inactivated (e.g. by heating) prior to the introduction of the TP-primer.

TP-primer is then added to the digested product that is created after exonuclease digestion. The nucleic acid portion of the TP-primer (i.e. the 'primer' portion) will hybridize to its complement on the partially digested viral DNA. In preferred embodiments, the nucleic acid portion of the TP-primer is relatively long (e.g. 25 or more bases) such that the TP-primer reagent can bind efficiently to the exonuclease digest gutted DNA, even at low molar ratios. However, any length of 'primer' nucleic acid capable of hybridizing to the exonuclease digested viral DNA may be employed (see discussion above). Once the TP-primer reagent is added to the digested viral DNA, the mixture may be subjected to conditions that promote rapid hybridization. For example, the temperature of the mixture may be raised (e.g. to 75° C.) and allowed to cool (e.g. the temperature is allowed to fall slowly over 2-3 hours to room temperature).

Hybridized TP-primer molecules are then extended (e.g. using T4 DNA polymerase, Taq polymerase, etc.) and nicks are repaired (e.g. using T4 DNA ligase) in the presence of dNTPs. In some embodiments, products of the extension and nick repair are incubated for a period of time (e.g. 5 minutes) at 0°, then a period of time (e.g. 5 minutes) at room temperature, and then a period of time (e.g. 2 hours) at 37° C. In certain embodiments, EDTA is then added to this mixture, and the mixture is stored on ice. In particular embodiments, the reaction products are dialyzed against transfection buffer before being used (e.g. before being used to transfect cells).

In particular embodiments, the successful addition of TP-primer to the origin of replication (e.g. of gutted adenoviral DNA) is confirmed. Confirmation may be performed by any method. For example, a restriction digestion may be performed on the TP-primer-viral DNA molecules followed by agarose gel electrophoresis (See FIG. 4A, and Example 3). Another example of a method that may be employed to confirm the successful addition of TP-primer to the origin of replication is determining if these molecules have increased specific activity of these molecules (e.g. Example 4).

Linking gutted viral DNA to adenoviral terminal protein (e.g. by attaching TP-primer) increased the yield of gutted virus produced in a gutted viral rescue procedure. In some embodiments, co-transfection of terminal protein linked gutted DNA with terminal protein DNA complex from helper virus results in an 85 fold increase in virus production, when compared to transfection/infection protocols using C7 cells without linking the gutted viral DNA to adenoviral terminal protein. In other embodiments, co-transfection of adenoviral terminal linked gutted and helper adenoviral DNA results in greater than a 2.5 fold increase in adenoviral production (e.g. 2.7 fold increase), compared to not linking either viral DNA to adenoviral terminal protein.

The replication-promoting agent may be adenoviral terminal protein. Viral DNA may also be linked to adenoviral preterminal protein. Any source of terminal or preterminal protein (e.g. natural or synthetic) from any type of adenovirus (e.g. Ad5 and Ad2). The terminal protein or preterminal protein may be made synthetically by, for example, transfecting cells with an expression vector (e.g. plasmid) with a gene sequence encoding a least a portion of adenoviral terminal, or preterminal, protein. Examples of such nucleic acid sequences that may be express in such a recombinant fashion include, but are not limited to, SEQ ID NO:18 (Ad2 terminal protein, FIG. 18) and SEQ ID NO:20 (Ad5 terminal protein, FIG. 18). Examples of preterminal protein nucleic acid sequences include, but are not limited to, SEQ ID NO:17 (Ad2 preterminal protein, FIG. 18) and SEQ ID NO:19 (Ad5 preterminal protein). The sequences, or portions thereof, may linked to viral DNA as described above. The present invention also contemplates other replication promoting agents, including lipids, other proteins, carbohydrates, and nucleic acids, as long as they are capable of promoting the replication of viral DNA when linked to the origin of the viral DNA.

Another method for creating terminal protein-linked viral DNA is by the use of Cre recombinase to transfer a segment of DNA linked to terminal protein. For example, gutted viral plasmid DNA containing a loxP site near at least one terminus is incubated with terminal protein-DNA complex from a helper virus whose genome contains a loxP site. Cre is then added to the reaction to facilitate intermolecular exchange.

The present invention contemplates terminal protein linked gutted adenoviral DNA that is transfected with helper viral DNA that is either linked to terminal protein (e.g. natural adenoviral DNA), or not linked to helper viral DNA (e.g. deproteinized helper viral DNA). For example, terminal protein linked gutted viral DNA may be used in conjunction with adenovirus (e.g. transfection/infection protocol), deproteinized viral DNA or terminal transferase treated (see below) helper viral DNA. In some embodiments, the helper virus does not contain terminal protein. In other embodiments, the helper virus does not contain terminal protein and is used at a higher concentration than the gutted viral DNA. These sequence may also be mutated (e.g. directed evolution) to increase their ability to promote replication (See, e.g. U.S. Pat. No. 5,811,238, hereby incorporated by reference).

III. Template Strand Extended Adenoviral DNA

Figure 5:
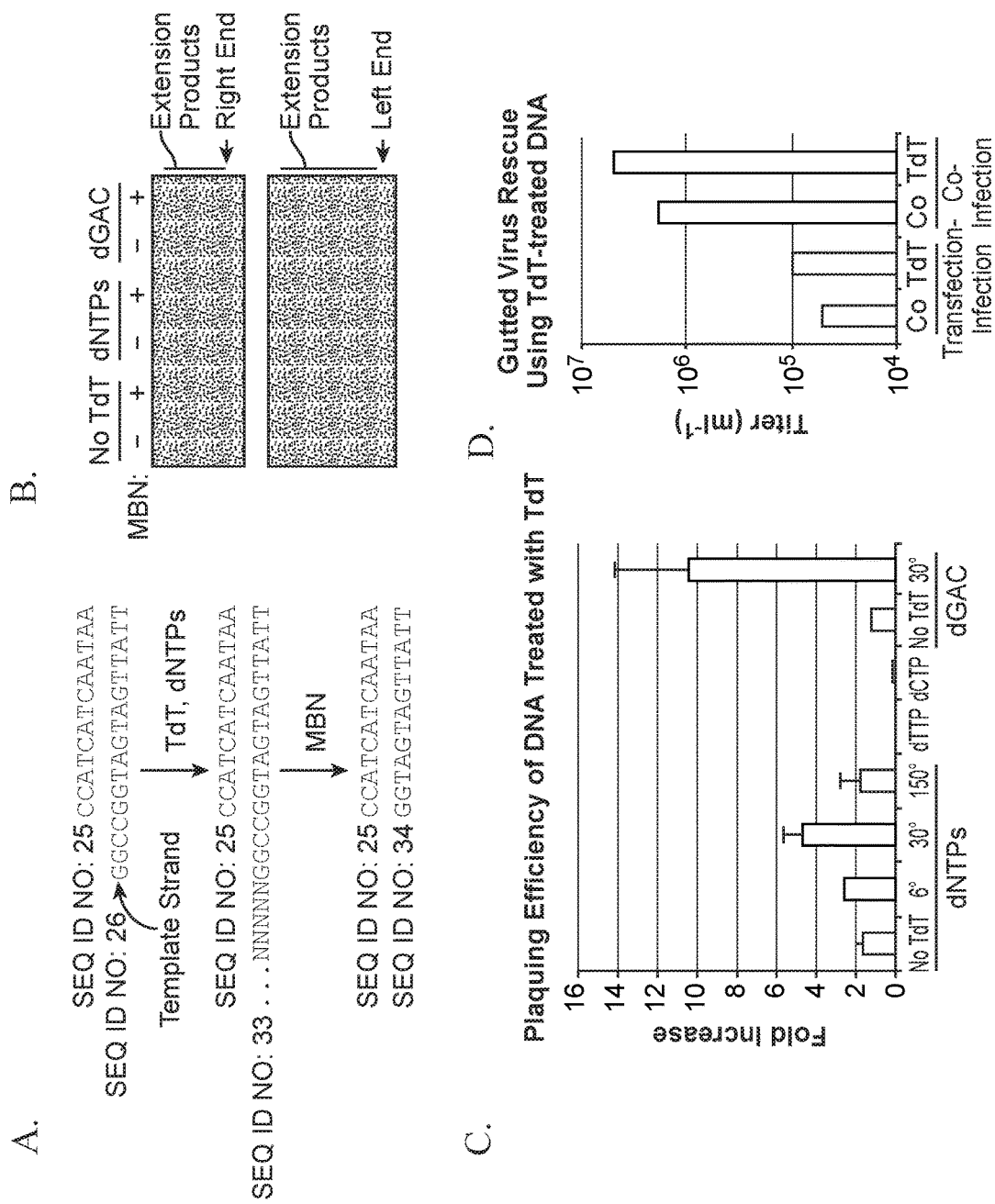
FIG. 5 (SEQ ID NOS:31-34) shows limited extension of template strand of the Ad origin increases plaquing efficiency and gutted virus recovery.

The present invention provides a further method for increasing gutted virus production (and recovery), as well as methods for increasing the plaquing efficiency of adenoviral DNA after transfection into cells. In particular, limited extension of adenoviral DNA termini (e.g. gutted adenoviral termini) increases plaquing efficiency (e.g. approximately 10 fold increase in efficiency, see Example 5 and FIG. 5) as well as increasing gutted virus recovery (e.g. an increase of 2.5 fold gutted viral recovery).

In preferred embodiments, the terminus of an adenoviral DNA is extended for a time sufficient to allow increased plaquing efficiency and/or gutted virus recovery. As demonstrated in Example 5, various time points may be tested to determine the appropriate limited template extension (e.g. in Example 5, approximately 30 minutes of extension in the presence of terminal transferase was optimal, with 6 minutes being less than optimal and 150 minutes being worse than no template extension). In some embodiments, adenoviral template DNA is extended from approximately 6 minutes to approximately 100 minutes. In preferred embodiments, the adenoviral DNA is extended for approximately 20 minutes to approximately 40 minutes. In particularly preferred embodiments, the adenoviral DNA is extended for approximately 30 minutes (e.g. 25-35 minutes). The time required to achieve a successful limited extension may be determined empirically employing methods similar to Example 5 and will vary depending on the conditions used (e.g. extending enzymes employed, concentrations of dNTPs, etc.).

Any type of enzyme capable of extending viral template DNA may be employed. For example, Taq polymerase, T4 polymerase, T4 DNA or RNA ligase, or terminal transferase may be used. In preferred embodiments, terminal transferase is employed. In some embodiments, the viral template DNA sequence is linearized by digesting with restriction enzyme(s) before template strand extension.

Template strand extension of viral DNA templates (e.g. gutted adenoviral DNA) employs molecule(s) capable of adding deoxyribonucleotide triphosphates (dNTPs) to the viral template DNA. In some embodiments, all four dNTPs are provided in the reaction mixture (i.e guanine, cytosine, adenine, thymine). In other embodiments, only two or three of the dNTPs are provided (e.g. guanine and adenine, or guanine, adenine, and cytosine). In preferred embodiments, only guanine, adenine, and cytosine are supplied to the reaction mixture (i.e. not thymine).

Limited template extension of viral DNA increases plaquing efficiency and gutted virus recovery. In certain embodiments, the plaquing efficiency is increased two fold (i.e. the plaquing efficiency is double compared to controls that do not have limited extension of the template DNA). In preferred embodiments, the plaquing efficiency is more than doubled (e.g. 3 fold, 4 fold, and 5 fold increased efficiency). In particularly preferred embodiments, the plaquing efficiency is increased approximately 10 fold. In some embodiments, the recovery of gutted virus is increased two fold. In preferred embodiments, the recovery of gutted virus is increased more than two fold (e.g. 2.5 fold). In some embodiments, template extended gutted viral DNA is transfected into cells, followed later by infection by helper virus (i.e. a transfection/infection protocol is employed). In preferred embodiments, helper and gutted viral DNA are co-transfected into cells (See Example 5, and FIG. 5D).

Extensions of viral DNA may also be accomplished by ligating various length oligos to the viral origin (i.e. ligation of oligonucleotides is employed instead of or in addition to the methods described above). For example, T4 DNA ligase may be used to ligate various oligonucleotides (e.g. ranging from 2-100 base pairs in length, and mixtures of various lengths) to viral origins in order to increase the activity of these origins. Again, assays may be employed to determine the optimal length of oligonucleotides to employ and the amount of time ligation is allowed to proceed.

IV. Culturing Gutted and Helper Adenoviruses

Methods and compositions are also provided by the present invention to increase viral recovery. In particular, improved selection strategies are provided (particularly well suited for gutted and helper adenoviral DNA with identical or similar termini). The present invention also provides cells lines expressing protein IX (and methods for allowing cells to express factor IX) to increase viral recovery.

A. Regulated Expression of Site-Specific Recombinases

Site-specific recombinases have been used to reduce helper contamination and improve gutted virus titer during serial passage. In these systems, the packaging element of the helper virus is flanked by recognition sites for site-specific recombinases like Cre or Flp. In these systems, the yield of gutted virus after rescue from plasmid is low, so improvement in gutted virus titer during serial passage is paramount. Use of a site-specific recombinase improves gutted virus titer by improving the gutted:helper ratio after lysis of a plate, so that a higher percentage of particles produced contain gutted viral genomes. This method results in a higher gutted virus titer at the following passage, since each infected cell contains a higher proportion of gutted genomes.

Such systems are typically designed for infection of each producer cell by at least one helper virus particle. This protocol typically allows for complete lysis of the plate despite the action of recombinase, which acts to prevent packaging and spread of helper virus, but does not prevent death of infected cells. In these systems, high-level production of the site-specific recombinase is desirable. Since each cell is infected by helper virus, viral spread is not necessary; higher production of recombinase leads to lower contamination with helper virus but does not compromise gutted virus production.

As described above, gutted virus rescue is most efficient when gutted and helper viral genomes with identical origin structure are co-transfected into producer cells (see also, Example 2). Employing gutted and helper viral genomes with identical (or similar) origin structure, however, a smaller fraction of transfected cells convert the helper virus DNA into replicating virus. This fact is confirmed by the observation that lysis of transfected plates takes about a week, although the time for a single round of viral replication is on the order of 24 hours. Virus produced by those few cells that converted transfected DNA to replicating virus must spread through the plate before complete lysis occurs. Under these conditions, constitutive, high-level expression of recombinase is not appropriate (See Example 6). In the presence of high levels of recombinase, the few cells that can produce virus produce very little, which often is not sufficient to lyse the plate, typically a requirement for high titers of gutted virus.

Regulated expression of site specific recombinase is provided by the present invention in order to take advantage of the beneficial activity of site specific recombinases, yet avoid the detrimental results evidenced in cells expressing site specific recombinase constitutively. Site specific recombinase may be regulated in time, with minimal to no expression at early times after transfection and high expression at later time points. While not limited to any mechanism, it is believed that the expression of a site-specific recombinase is detrimental at early times after transfection, when transfected helper genomes are being converted to replicating virus, thus providing helper particles that should spread through the plate. At later time points, however, when helper and gutted virus particles are replicating in tandem, expression of site-specific recombinase could increase the proportion of viral particles that contain gutted genomes, thereby assisting in gutted virus recovery. One example of providing such temporal expression employs co-transfection of site specific expression vectors (e.g. Cre recombinase expression vector) with viral genomes (e.g. gutted and helper viral genomes with identical origins of replication) (See Example 6). In this manner, transfected cells are not expressing Cre at the time of transfection, and after transfection, some time will pass before the appearance of the first molecules of Cre protein, since RNA and then protein must be synthesized. Finally, the level of Cre will increase to some equilibrium level on a time scale that depends on the half life of the RNA, the half life of the protein, and the strength of the promoter used to drive Cre recombinase expression.

The amount of the recombinase expression vector employed will depend on many factors. Importantly, transfecting cells with a level of recombinase expression vector that is too high to allow the helper virus DNA to replicate at a high enough level to infect most of the cells, and lyse the plate is to be avoided (See Example 6, where 176 ng of pOG231 is less effective than providing no Cre at all). Likewise, transfecting cells with a level of recombinase expression vector that is too low to prevent the helper virus from dominating the type of virus being expressed is also to be avoided (See Example 6, where 1.41 ng of pOG231 was no more effective than providing no Cre at all). Determining the appropriate level of recombinase expression level to employ for a given type of cell type, recombinase, promoters employed, etc., is within the skill in the art. For example, a concentration type assay may be employed as exemplified in Example 6. As demonstrated in this example, various levels of recombinase expression vector may be tested to determine the optimal levels of starting recombinase expression vector that should be employed. Examples of appropriate levels of recombinase expression level are provided in Example 6 (for the types of conditions employed in this assay). For example, appropriate levels of pOG231, as determined in example 6 include approximately 5-37 ng of expression vector, preferably 7-36 ng of expression vector, more preferably 16-35 ng of expression vector. Of course, altering the type of vector, cells, conditions, etc., may change the appropriate level as described above.

B. Culturing Adenovirus in Cells Expressing Adenoviral Protein IX

In order to improve production, gutted and helper adenovirus are co-transfected in cells expressing adenoviral protein IX (pIX). The protein IX gene of the adenoviruses encodes a minor component of the outer adenoviral capsid which stabilizes the group-of-nine hexons which compose the majority of the viral capsid (See U.S. Pat. Nos. 5,932,210 and 5,824,544, hereby incorporated by reference). Based upon study of adenovirus deletion mutants, protein IX initially was thought to be a non-essential component of the adenovirus, although its absence was associated with greater heat lability than observed with wild-type virus. More recently it was discovered that protein IX is essential for packaging full length viral DNA into capsids and that in the absence of protein IX, only genomes at least 1 kb smaller than wild-type could be propagated as recombinant viruses.

In one embodiment, an expression vector encoding protein IX is co-transfected with the gutted and helper adenovirus. In some embodiments, gutted and helper adenovirus are transfected in a cell line that expresses adenoviral protein IX. In preferred embodiments, the cell stably and constitutively expresses adenoviral protein IX. In particularly preferred embodiments, the cell line also expresses E2B proteins. One example of a cell line expressing E2B proteins (adenoviral DNA polymerase and preterminal protein) is the C7 cell line (See, U.S. Pat. No. 6,083,750). Creating a cell line that stably and constitutively expresses adenoviral protein IX, in addition to adenoviral DNA polymerase and preterminal protein, may be accomplished, for example by stably transfecting C7 cells (or other cells expressing E2B proteins) with a vector expressing adenoviral protein IX (See Example 7, creating the D2104#10 cell line).

Additional cell lines that stably and constitutely expresses adenoviral protein IX, in addition to adenoviral DNA polymerase and preterminal protein are contemplated. For example, any type of cell known to effectively allow adenoviral replication may be transfected with an expression vector encoding adenoviral protein IX (preferably with a selectable marker). Preferably, the cells also express preterminal protein and adenoviral DNA polymerase. Transfected cells may be grown on selective media. Clones are then screened for expression by transfection with an adenoviral protein IX negative genome, and clones producing virus after transfection are isolated.

V. Heterologous Gene Sequences

As described above, the present invention is useful for the production of adenoviral vectors (e.g. helper-dependent adenoviral vectors). The adenoviral vectors produced, in preferred embodiments, comprise a heterologous gene sequence, such that the vectors may be useful for various applications (protein expression in vitro, therapeutic applications, etc). Suitable heterologous DNA sequences include, for example, nucleic acid sequences that encode a protein that is defective or missing in a recipient subject, or a heterologous gene that encodes a protein having a desired biological or therapeutic effect (e.g. an antibacterial, antiviral, or antitumor function). Other suitable heterologous nucleic acids include, but are not limited to, those encoding for proteins used for the treatment of endocrine, metaloic, hematologic, cardiovascular, neurologic, musculoskeletal, urologic, pulmonary, and immune disorders, including such disorders as inflammatory diseases, autoimmune disease, chronic and infectious diseases, such as AIDS, cancer, hypercholestemia, insulin disorders such as diabetes, growth disorders, various blood disorders including various enemias, thalassemias, and hemophilia; genetic defects such as cystic fibrosis, Gaucher's disease, Hurler's disease, adenosine deaminase (ADA) deficiency, and emphysema.

The therapeutic or diagnostic nucleic acid sequence, in some embodiments, will code for a protein antigen. The antigen may include a native protein or protein fragment, or a synthetic protein or protein fragment or peptide. Examples of antigens include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, hemophilus influenza type b, chlamydia, varicella-zoster virus or rabies. The nucleic acid sequence may also be a normal muscle gene that is effected in a muscle disease (e.g. muscular dystrophies like Duchenne muscular dystrophy, limb-girdle muscular dystrophy, Landouzy-Dejerine muscular dystrophy, Becker's muscular dystrophy, ocular myopathy, and myotonic muscular dystrophy). For such muscular dystrophies, the nucleic acid may be a heterologous gene encoding the full length dystrophin gene (or cDNA sequence), BMD-minigene, ΔH2-R19 minigene, Laminin-α2, utrophin, α-sarcoglycan, and emerin. BMD mini-gene refers to dystrophin cDNAs containing internal truncations corresponding to specific exons of the gene, in particular, a deletion of the sequences encoded on exons 17-48 [Amalfitano et al., in Lucy J, and Brown S. (eds): Dystrophin: Gene, Protein, and Cell Biology (Cambridge University Press, 1997), Chpt. 1, 1-26, herein incorporated by reference]. ΔH2-R19 refers to a specific dystrophin eDNA containing internal deletions corresponding to specific functional domains of the gene, in particular, a deletion of the sequences that encode 'hinge 2' through 'spectrin-like repeat' 19 [See Amalfitano et al.].

Nucleic acid sequences may also be antisense molecules (e.g. for blocking the expression of an abnormal muscle gene). The nucleic acid sequence may also code for proteins that circulate in mammalian blood or lymphatic systems. Examples of circulating proteins include, but are not limited to, insulin, peptide hormones, hemoglobin, growth factors, liver enzymes, clotting factors and enzymes, complement factors, cytokines, tissue necrosis factor and erythropoietin. Heterologous genes may also include gene encoding proteins that are to be produced (e.g. commercially produced) in muscle cells in vitro or in vivo. For example, the improved expressions systems of the present invention may be applied to preexisting, working muscle expression systems to improve the level of expression of protein product from a gene of interest. The present invention also contemplates employing any gene of interest (heterologous or endogenous).

VI. Using Adenoviral Vectors

The adenoviral vectors produced as described above may be used, for example, in drug screen or in gene therapy methods. In one screening method, an adenoviral vector (e.g. helper-dependent adenoviral vector, produced according to the above methods) contain adenoviral DNA operably linked to a heterologous gene encoding an factor (e.g. enzyme, protein, antisense molecule) with a known function (e.g. alcohol dehydrogenase), is contacted in vitro with a tissue culture sample (e.g. a muscle cell containing tissue culture) such that the heterologous gene is expressed. A candidate compound is added along with a substrate for the enzyme (e.g. ethanol), and a parallel assay is run without the candidate compound. The level of enzyme activity is detected (e.g. amount of substrate remaining over time) in each assay. The results of both assays are compared in order to determine the affect of the candidate compound on the activity of the enzyme. In other embodiments, the candidate compound many comprise a factor suspected of altering gene expression of the heterologous gene and the assay detects that degree and/or ability of the candidate compound to reduce the activity of the expressed factor. One of ordinary skill in the art will appreciate that many other screening methods can be used. The adenoviral vectors may also be used advantageously in gene therapy to replace a defective gene in subject with a heterologous gene.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nn (nanometers); ° C. (degrees Centigrade); Sigma (Sigma Chemical Co., St. Louis, Mo.); and Example 1

Generating Gutted and Helper Virus with Identical Termini

This example describes the deletion of internal FseI sites in the nucleic acid sequence of an Ad5-based helper virus, and insertion of this nucleic acid sequence into a plasmid such that it is removable with FseI.

The FseI recognition sequence, "GGCCGGCC", contains cytosine residues and can be arranged to overlap with the first nucleotide of viral DNA so that only one additional base pair is attached to viral DNA removed from plasmid vectors with this enzyme (FIG. 1A). In addition, FseI is rare in cloning vector polylinkers and mammalian sequences, so it is ideal for removal of gutted viral genomes from plasmid vectors. FseI has been used previously for linearization of viral shuttle vectors, which contain a portion of the Ad genome; however, it could not be used to liberate the entire Ad5 genome from plasmid DNA, because the Ad5 genome contains two FseI sites.

Figure 8:
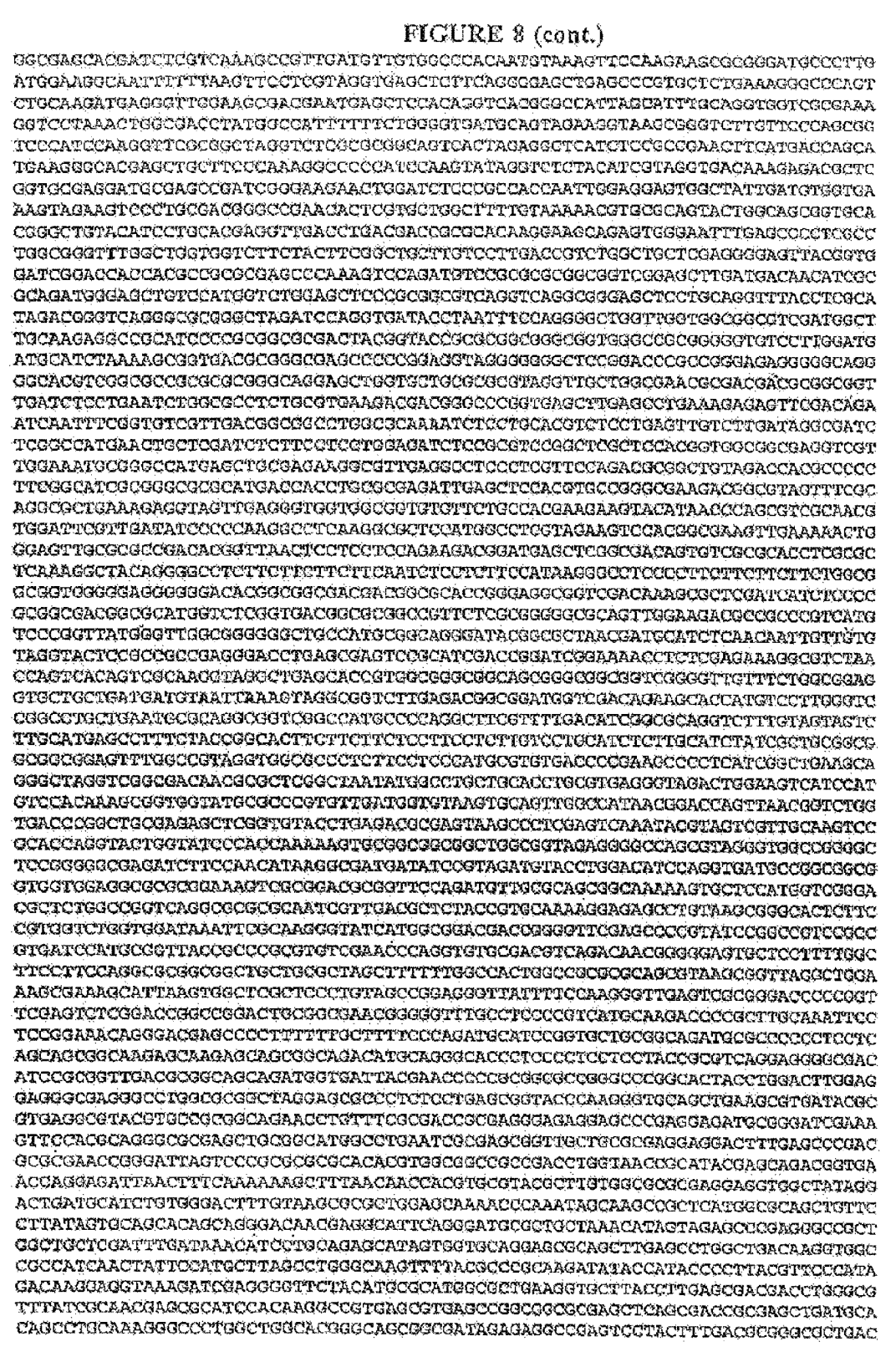
Figure 10:
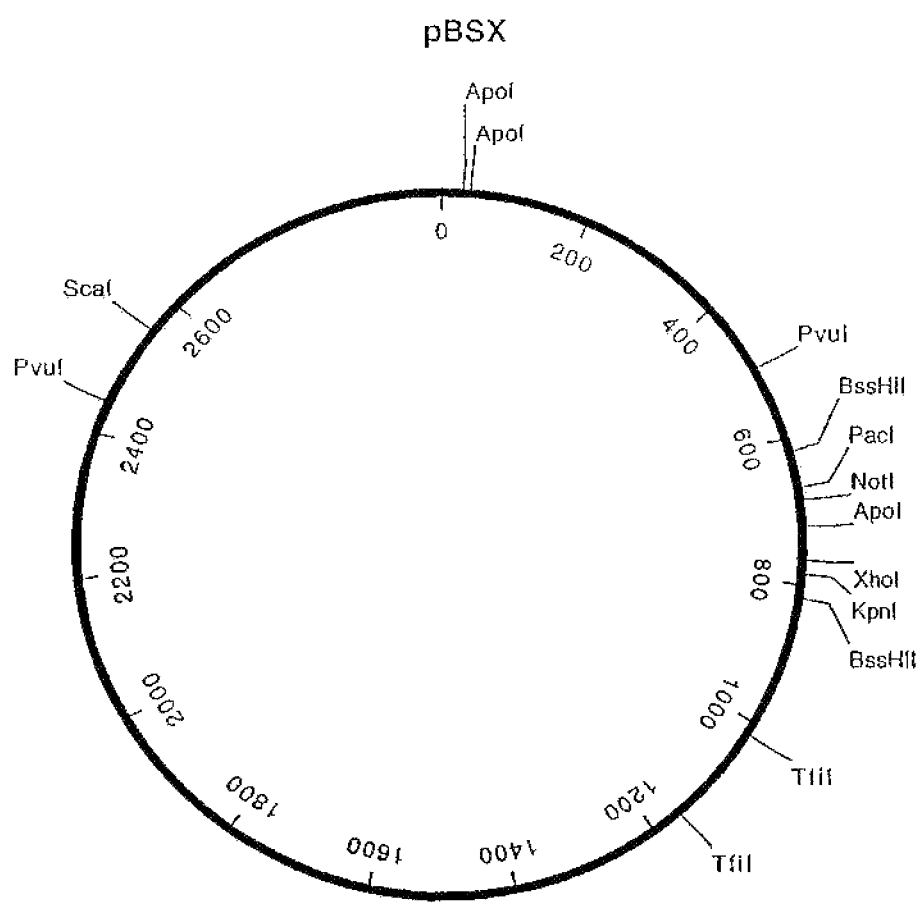
FIG. 10 show a restriction map of pBSX.

In order to remove the FseI sites in the (+)lox(+)pol helper virus DNA sequence (SEQ ID NO:1), mutations were created that destroy both FseI sites while maintaining the ability of the virus to replicate (transitions were made at nucleotides 12587 and 17756, creating SEQ ID NO:9, FIG. 11, see also FIG. 1B). The mutation at nucleotide 12587 was chosen so as to preserve the amino acid sequence of capsid protein Ma. Primers 92521, CGGAATTCGGATCCAGCGACCGCGA GCTGAT (SEQ ID NO:2) and 92531, CGGAATTCAGC-CGGCTTCGTCGGGCCGGATGGC (SEQ ID NO:3) were used in a PCR reaction to simultaneously amplify approximately 540 base pairs of the Ad5 sequence, to introduce the G to A transition at nucleotide 12587, and to flank the resulting DNA sequence with EcoRI sites. The product was digested with EcoRI and ligated to the large, approximately 2.2 kb ApoI fragment of pBSX (pBSX—SEQ ID NO:12, FIG. 9, which is a minor modification of a Bluescript vector, with alterations to the polylinker sequence, See FIG. 10) to yield pD1858#7. Primers 92541, CGCGGATCCGCCGGC-TACGGCCTGACGGGCGG (SEQ ID NO:4) and 92551, CGGAATTCACACACATACGACACGTTAG (SEQ ID NO:5) were used to amplify approximately 1 kb of Ad5 sequence, to introduce the C to T transition at nucleotide 17756, and to append an EcoRI site to the rightmost end of the resulting DNA fragment. The product was digested with EcoRI and NgoMI, then ligated to EcoRI-, NgoMI-digested pD1858#7 to yield pD1863#4. This plasmid was digested with NgoMI and ligated to the 5162-bp NgoMI fragment from the Ad5 genome, resulting in pD1866#17, which contains both transitions mentioned above. To create a virus lacking FseI sites, pD1866#17 was digested with EcoRI and co-transfected with FseI-digested terminal protein-DNA complex from (+)lox(+)pol Ecd-AP helper virus. The sequence for (+)lox(+)pol Ecd-AP is SEQ ID NO:1, FIG. 8. After one week of incubation, the transfected cells showed evidence of viral cytopathic effect, indicating that they contained replicating virus, designated ΔFseI.4 (SEQ ID NO:9, FIG. 1B). The DNA was extracted from these cells by Hirt prep (DNA episomal extraction method employing lysis in 0.6% SDS/10 mM EDTA, followed by addition of salt, incubation at 4° C., and centrifugation to remove contaminants, Hirt, B., J. Mol. Biol. 26:365 [1967]) and shown not to contain FseI sites by restriction digest.

To confirm that FseI could be used to release replication-competent viral DNA from flanking DNA sequences, ΔFseI.4 genomic DNA was cloned into a plasmid vector, where it was flanked by FseI sites (FIG. 1C). Primers 82701, CGGAATTCGGCCGGCCATCATCAAT AATATAC (SEQ ID NO:6) and 82741, CGGTCGATTCAATTGCTG-GCAAGCTTCGG CCCTAGACAAATAT (SEQ ID NO:7) were used in a PCR reaction to amplify approximately 400 bp from the left end of (+)lox(+)pol Ecd-AP helper virus and to introduce flanking restriction sites: EcoRI and FseI at the left end of the fragment and HindIII, MfeI, and TfiI at the right end. The product was digested with EcoRI and TfiI and cloned into the 1.86 kb ApoI/TfiI fragment of pBSX (See, FIG. 9), generating pD1812#1. Primers 82701 (SEQ ID NO:6) and 82731, CTATGCTAACCAGCGTAGC (SEQ ID NO:8) were used to amplify approximately 1 kb from the right end of (+)lox(+)pol Ecd-AP helper virus and to add FseI and EcoRI sites at the right end of the fragment. The product was digested with HindIII and EcoRI and cloned into HindIII-, MfeI-digested pD1812#1, generating pD1821#8. To clone ΔFseI.4 viral genomic DNA into pD1821#8, the plasmid was digested with HindIII and recombined with ΔFseI.4 Hirt prep DNA in BJ5183 bacterial cells (BJ5183 bacterial cells, see Hanahan, D., *J. Mol. Biol.*, 166:557 [1983]). The resulting plasmids, including pD1940#3 and pD1940#6, were shown by restriction digest to contain the entire ΔFseI.4 genome flanked by FseI sites (FIG. 1C). No internal FseI sites were detected, confirming that virus ΔFseI.4 contains mutations that destroy these sites.

To show that FseI digestion could release replication-competent Ad DNA from plasmids, pD1940#3 and pD1940#6 were digested with FseI and transfected into C7 cells (C7 cells express both Ad DNA polymerase and preterminal protein, see U.S. Pat. No. 6,083,750, hereby incorporated by reference). Plasmid pFG140 [See, Graham, F. L., *The EMBO J.*, 3:2917 (1984)] known to produce replicating adenovirus after transfection, was used as a control. Both sets of transfected cells were overlaid with agarose after transfection and stained with neutral red 10 days after overlay. It was determined that FseI-digested pD1940#3 and pD1940#6 produced 36 and 56 plaques per microgram, respectively; pFG140 produced 38 plaques per microgram. This result indicates that mutation of internal FseI sites did not prevent replication of adenovirus and that FseI is an appropriate enzyme for release of viral DNA from plasmids.

Example 2

Figure 12:
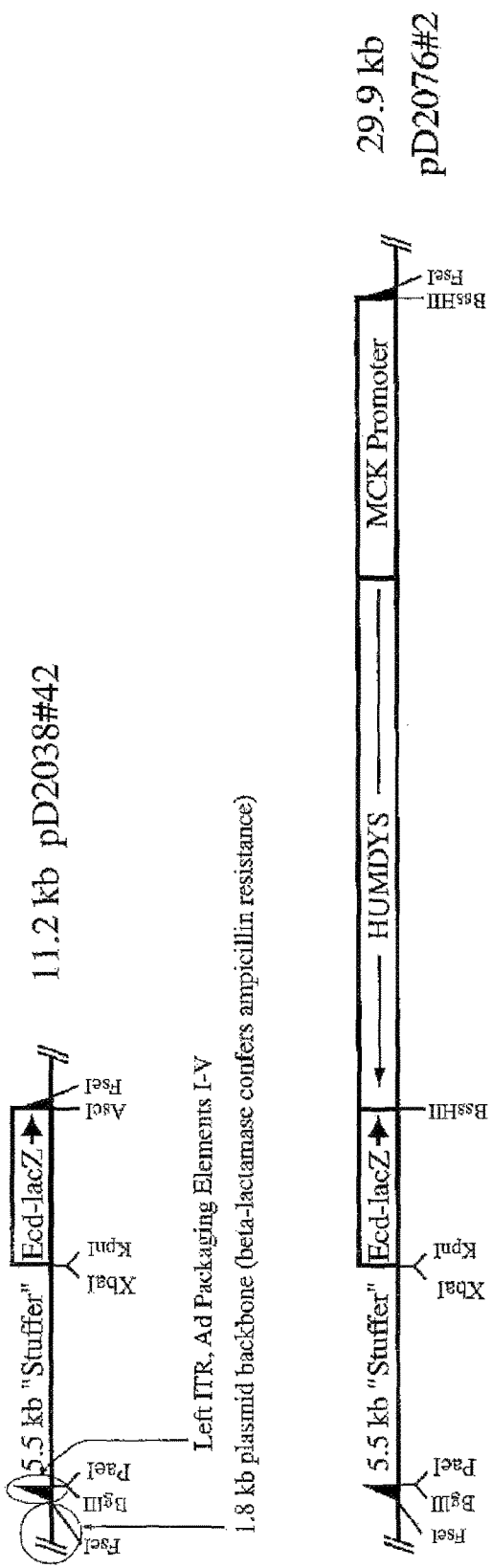
FIG. 12 shows pD2076#2.

Rescue of Helper-Dependent Ad Vectors Using Plasmid-Derived Substrates with Corresponding Termini This example describes the rescue of helper-dependent Ad vectors using plasmid-derived substrates with corresponding termini. To demonstrate that efficient gutted virus rescue depends on the relative specific activities of gutted and helper viral DNA, a FseI-terminated gutted virus was co-transfected with various forms of helper virus DNA or transfection/infection was performed (FIG. 2). The gutted adenovirus DNA employed was pD2076#2, which contains a gutted Ad genome flanked by FseI recognition sites and carries an inducible beta-galactosidase expression cassette (FIG. 12). This plasmid was digested with FseI, and 4.4 micrograms of digested DNA were transfected into C7 cells.

For co-transfection assays, 4.4. micrograms of helper viral DNA (either TP-DNA, Hirt DNA, or FseI-terminated DNA) were co-transfected with pD2076#2 DNA. For transfection/infection, helper virus particles were added immediately following transfection at an MOI of 10 transducing units per cell. For the TP-DNA complex co-transfection, terminal protein-DNA complex was isolated from (+)lox(+)pol helper virus (SEQ ID NO:1) was isolated and transfected into cells to provide helper activity (FIG. 13). For the Hirt DNA samples, ΔFseI.4 DNA (SEQ ID NO:9) was isolated from infected cells and deproteinized (FIG. 13). For FseI-terminated samples, pD1940#3 or pD1940#6 (See FIG. 13) was digested with FseI and the released DNA was used to provide helper activity (SEQ ID NO:13, FIG. 14). Digestion with FseI releases what is essentially ΔFseI.4 (SEQ ID NO:9), except with a couple of extra nucleotides at the end (as shown in FIG. 1).

Transfection/infection was found to be very inefficient (See FIG. 2), although it is the method most frequently reported in the literature. In co-transfections, an inverse correlation was observed between the specific activity of the helper virus DNA from and the yield of gutted virus produced. Co-transfection of gutted viral DNA with plasmid-derived helper viral DNA, carrying a physically identical origin of replication (constructed as described in Example 1), was by far the most efficient method for rescue of gutted adenovirus (See, FIG. 2). After co-transfection of plasmid-derived, FseI-terminated genomes, the average gutted viral titer observed was $5.6 \times 10^6$ ml$^{-1}$. This yield represents an improvement of approximately 30 fold over typical titers obtained by transfection/infection into C7 cells and 300 fold over typical titers obtained by transfection/infection into 293 cells.

Example 3

Conversion of Plasmid-Derived Viral Replication Origins to Natural, Terminal Protein-Linked Origins This example describes the conversion of plasmid derived viral replication origins to natural, terminal protein-linked origins. This conversion employs "TP-primer", which is terminal protein DNA linked to single-stranded DNA from the non-template strand of an Ad ITR (FIG. 3A). TP Primer was prepared in the following manner. Terminal protein-DNA complex prepared from (+)lox(+)pol Ecd-AP virus was digested for at least 16 hours at 37° C. with 2.5 U/μg Bsh1236I, 1.33 U/μg AluI, and 0.69 U/μg HinfI. Bsh1236I cuts between base pairs 73 and 74 of the Ad5 ITR (CAT-CATCAATAATATACCTTATTTTGGATTGAAGC-CAATATGATAATGAGGG GGTGGAGTTTGTGACGTG-GCGCGGGGCGTGGGAACGGGGCGGGTGACGTAG, SEQ ID NO:10), so this digestion results in terminal protein linked to a 73-bp, double-stranded DNA molecule (one of the two strands is as follows, CATCATCAATAATATACCT-TATTTTGGATTGAAGCCAATATGATAATGAGGG GGTGGAGTTTGTGACGTGGCG, SEQ ID NO:11). The products of restriction digestion were then treated with 2.5 U/μg DNA of lambda exonuclease for 20 minutes at 37° C. This enzyme catalyzes the removal of 5' mononucleotides from duplex DNA. Since the enzyme acts in a 5' to 3' direction, strands linked to terminal protein are not degraded; all other strands are degraded until a single-stranded region is reached.

The products of this digestion, therefore, include: 1) terminal protein linked to 73 unpaired bases (SEQ ID NO:11) of the non-template strand of the Ad5 ITR (TP-primer); 2) many random, small, single-stranded DNA molecules resulting from the degradation of approximately half of the restriction fragments present in the reaction; and 3) mononucleotides. The first of these is the desired and useful product; however, the other products do not interfere with subsequent steps. The enzymes in the reaction were then inactivated by incubation at 75° C. for 20 minutes.

TP-primer was then used to convert plasmid-derived gutted viral genomes to natural Ad origins by the following method (FIG. 3B). First, a plasmid containing gutted viral genomic DNA (pD2076#2), flanked by FseI sites, was digested with FseI to release gutted viral DNA. The products were subjected to very limited digestion with T7 gene 6 exonuclease (0.76 U/μg for 1 minute, 40 seconds) and the exonuclease was inactivated by incubation at 80° C. for 15 minutes. T7 gene 6 exonuclease, like lambda exonuclease, is a 5' to 3' exonuclease, so limited digestion with this enzyme exposes single-stranded regions near the gutted vector genomic termini. These regions are complementary to the single-stranded DNA found in the TP-primer reagent. Due to the long (73 bp) stretch of complementary DNA sequence and the absence of competing binding partners, the TP-primer reagent can bind efficiently to T7 gene 6-digested gutted DNA even at low molar ratios.

We added TP-primer reagent, prepared as described above, to the digested gutted DNA, raised the temperature of the mixture to 75° C., and allowed the temperature to fall slowly (over 2-3 hours) to room temperature. Hybridized TP-primer molecules were then extended using T4 DNA polymerase and nicks were repaired using T4 DNA ligase. This was accomplished by addition of 0.5 mM each dNTP, 1 mM ATP, 2.5 units T4 polymerase per μg DNA, and 2 Weiss units T4 ligase per μg DNA. A small amount of buffer (10 mM Tris-HCl, 10 mM $MgCl_2$, 50 mM NaCl, and 1 mM DTT, pH 7.9 at 25 C) was also added such that the final concentration of gutted vector genomic DNA was 0.04 μg/μL, when a 2:1 (TP-primer:gutted genome) ratio was used or 0.029 μg/μL, when a 4:1 ratio was used. The reaction was then incubated for 5 minutes at 0° C., 5 minutes at room temperature, and 2 hours at 37° C. EDTA was added to a final concentration of 15 mM and the reaction was stored on ice.

An assay was performed to confirm the successful addition of terminal protein to the origin of replication of the gutted virus. Specifically, a restriction digest employing NotI was performed on circular pD2076#2, the TP-primer linked pD2076#2 (FseI digested), and FseI digested pD2076#2 (negative control). This digestion was followed by agarose gel electrophoresis (FIG. 4A). The results confirmed the successful addition of the TP-primer as approximately two-thirds of the gutted DNA terminal fragments were retained in the wells of the agarose gel, behavior that is typical of protein-linked DNA (FIG. 4A).

Example 4

TP-Primer Increases the Specific Activity of Plasmid-Derived Ad DNA

This example describes the ability of TP-primer to increase the specific activity of plasmid derived Ad DNA. In particular, replication-competent helper virus genomes were excised from plasmids pD1940#3 or pD1940#6 and the origins of DNA replication were modified as described above (See Example 3, adding TP-primer to Ad DNA). Reaction mixtures were then diluted into 0.1×TE such that transfection mixtures contained either one microgram or 0.1 micrograms of modified plasmid DNA. Parallel transfection mixtures were prepared using unmodified FseI-digested pD1940 plasmid (SEQ ID NO:13, FIG. 14). The DNA was co-precipitated with calcium phosphate, and added to plates of C7 cells. Plates were washed 16 hours after addition of precipitates and overlayed with noble agar (See, Graham, F. L. and Prevec, L. *Manipulation of Adenovirus Vectors in Gene Transfer and Expression Protocols*, Clifton: The Humana Press, Inc., 1991). Eight to ten days after overlay, the plates were stained with neutral red and plaques were counted. Specific activity was calculated as the number of plaques observed divided by the weight of transfected DNA.

It was found that the specific activity of treated genomes was increased by an average of 24 or 27 fold after treatment with a 2:1 or 4:1 molar ratio of TP-primer, respectively. We also examined the effect of TP-primer treatment on the rescue of gutted Ad vectors from their plasmid-derived precursors. For these experiments, since large amounts of DNA were transfected, reaction mixtures were dialyzed against 1×HBS to avoid dilution. Conversion of gutted vector origins to natural, TP-linked form resulted in improved competition with helper virus DNA (FIG. 4B). Strikingly, co-transfection of TP-gutted DNA and untreated, FseI-terminated helper virus DNA prevented lysis of the transfected cells, indicating that the specific activity of TP-gutted DNA is high enough to prevent robust helper replication.

Co-transfection of TP-gutted DNA with terminal protein-DNA complex from helper virus resulted in an average gutted viral titer of $1.5 \times 10^7$ per nil. This titer represents an improvement of approximately 85 fold over typical titers obtained by transfection/infection into C7 cells, 850 fold over titers obtained by transfection/infection into 293 cells, and 2.7 fold over titers obtained by co-transfection of plasmid-derived, FseI-liberated gutted and helper genomes (See FIG. 4B).

Example 5

Terminal Transferase Template Strand Extension of Adenoviral DNA

This example describes terminal transferase (TdT) template strand extension of adenoviral DNA, and how limited extensions increase the specific activity in plaque assays and allow for more efficient recovery of gutted adenovirus.

pD1940#3 or pD1940#6 viral DNA was digested to completion with FseI. The restriction enzyme reaction was diluted 3.125-fold into 1×TdT reaction buffer (Promega, Madison, Wis.) and supplemented with 80 micromolar dNTPs and 10 units TdT per picomole DNA termini. The reaction was mixed well, incubated for a variable length of time at 37° C., and the TdT was inactivated by incubation at 75° C. for 10 minutes. The reaction mixture was extracted with 0.5 volumes of phenol-chloroform and DNA was precipitated. Samples were resuspended in 0.1×TE and transfected into C7 cells using the calcium phosphate co-precipitation method.

To determine whether TdT treatment had improved the ability of viral DNA to replicate in cells, the specific activity of treated and untreated DNA in transfected cells was measured ('specific activity' was defined as the number of viral plaques observed per microgram of DNA transfected; higher specific activity indicates that a lesser weight of viral DNA must be transfected to produce actively replicating virus). The results of the this assay indicate that the specific activity of pD1940 DNA was increased by approximately 5 fold after 30 minutes of treatment but less so after 6 minutes or 2.5 hours (FIG. 5C). Control reactions lacking the TdT enzyme showed no evidence of increased plaquing efficiency (FIG. 5C).

To test whether the identity of added nucleotides is important for the observed effect, we supplemented individual TdT reactions with various single and mixed nucleotides. The various reactions were precipitated individually, transfected into cells, and developing viral plaques were counted after 7-10 days. The effectiveness of TdT treatment was found to vary with the identity of the nucleotides included in the reaction (FIG. 5C). It was determined that the addition of single nucleotides was not effective; in fact, addition of thymidine or cytosine residues alone markedly reduced plaquing efficiency. It was also determined that the most effective combination was addition of guanine, adenine, and cytosine (dGAC), which increased plaquing efficiency by approximately 10 fold (FIG. 5C and data not shown).

An assay was also conducted involving TdT treatment of gutted Ad virus, and rescue from bacterial plasmids. In this example, gutted Ad genomes excised from pD2076#2 with the restriction enzyme FseI were employed. These excised genomes were treated with the combination of guanine, adenine, and cytosine as described above. 8.8 micrograms of treated DNA were transfected into approximately 2 million C7 cells in a 60-mm plate. 16 hours later the cells were washed and then infected with 20 million transducing units of ΔFseI.4 helper virus (SEQ ID NO:9). Two to three days after this procedure, the plates displayed viral cytopathic effect and lysates were harvested. By measuring the titer of gutted virus in the recovered lysates, it was determined that TdT treatment of the gutted vector doubled the amount of gutted virus produced by the cells after rescue (FIG. 5D). By co-transfecting plasmid-derived helper and gutted DNAs, as described above, the baseline titer obtained without TdT treatment was increased (FIG. 5D). After treatment of gutted plasmid DNA with TdT, a further 2.5-fold increase in gutted virus titer was obtained (FIG. 5D).

Example 6

Regulated Expression of Site-Specific Recombinase Improves Gutted Virus Rescue

This example describes the use of regulated expression of Cre recombinase to improve gutted virus rescue when gutted and helper virus with identical ends are co-transfected. Initially, the effect of constitutive expression of Cre recombinase in packing cells co-transfected with gutted and helper viruses with identical ends was examined. ΔFseI.4 helper virus (SEQ ID NO:9) is an E1-, E3-deleted virus that can be negatively selected using Cre recombinase and carries an alkaline phosphatase reporter gene in its E3 region. The packaging signal, which consists of packaging elements I-V, is flanked by loxP sites in direct repeat orientation, allowing removal of the packaging signal in the presence of Cre. The E1 region (map units 1-9.2) has been removed. The E3 region (map units 78.3-85.8) has also been removed and replaced with an expression cassette, oriented from left to right in the viral genome, that consists of the inducible ecdysone promoter, the coding region for human placental alkaline phosphatase, polyadenylation sequences from SV40, and approximately 2 kb of "stuffer" DNA derived from an intron of the human dystrophin gene. For these experiments, ΔFseI.4 genomes were released from pD1940#3 or pD1940#6 by digestion with FseI.

Figure 6:
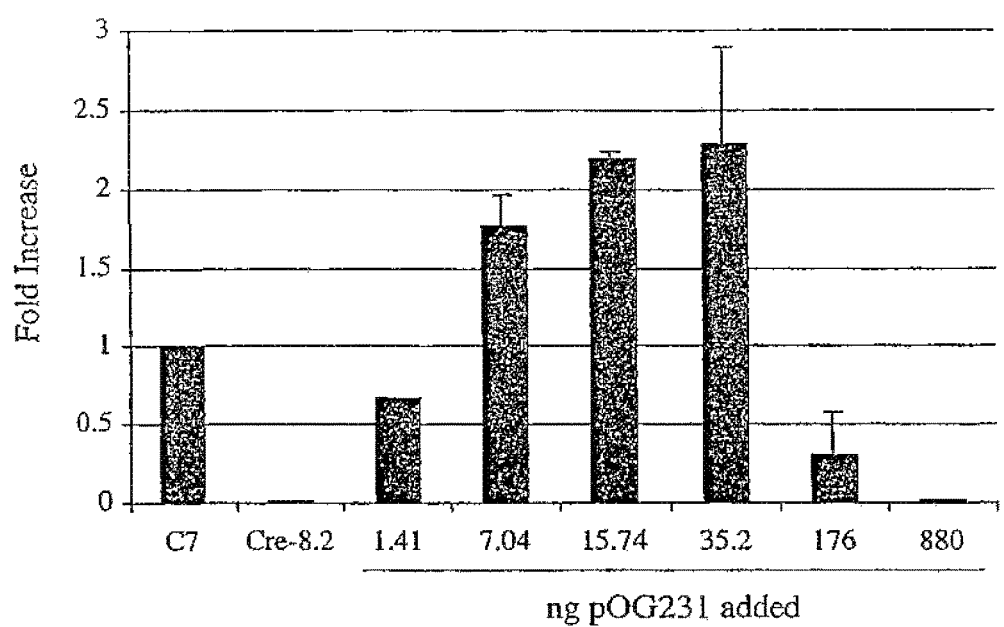
FIG. 6 shows that the regulated expression of Cre recombinase improves gutted virus recovery.

Specifically, FseI-terminated gutted and helper viral genomes were co-transfected into either C7 cells or C7-Cre-8.2 cells, which constitutively express Cre recombinase. The plate of transfected C7-Cre-8.2 cells showed no signs of lysis even after 12 days of incubation and the resulting titer of gutted virus was approximately 100 times lower than that observed in C7 cells (FIG. 6). This result indicates that when gutted and helper viral genomes with identical origin structures are co-transfected, constitutive expression Cre recombinase in the packaging cells is not desirable.

Cre recombinase, however, may still be employed to improve gutted virus recovery. Instead of constitutive expression of Cre recombinase, the recombinase expression is regulated over time. This was accomplished by co-transfection of a Cre recombinase expression vector (the level of Cre recombinase will increase gradually over time). Specifically, C7 cells were transfected with FseI-terminated gutted virus, FseI-terminated helper virus, and varying amounts of a Cre recombinase expression vector (pOG231). The results of this experiment show very low amounts of pOG231 had minimal effects on gutted virus production, with increasing amounts of pOG231, gutted virus production was improved (FIG. 6). The results also indicate that using the highest amounts of pOG231, little viral replication was observed and gutted virus titers were reduced (indicating that Cre protein levels increased to a level beyond which lysis could not proceed). Maximal improvement in gutted virus titers was observed using 16-35 ng of Cre expression vector, at which level average gutted titers more than doubled, to $1.3 \times 10^7$ ml-1 (FIG. 6). High levels of gutted virus were also observed using 7.04 ng of the Cre expression vector.

This selection strategy was also shown to be effective for gutted virus rescue from TdT-modified and TP-primer-modified genomes. For TdT-modified genomes, co-transfection with 35.2 ng Cre increased gutted virus production by an average of 3 fold. For TP-primer-modified genomes, use of 0.88 μg Cre approximately doubled gutted virus production, to $2.5 \times 10^7$ ml-1.

Example 7

Generating an Adenoviral Protein IX Expressing Cell Line

Figure 16:
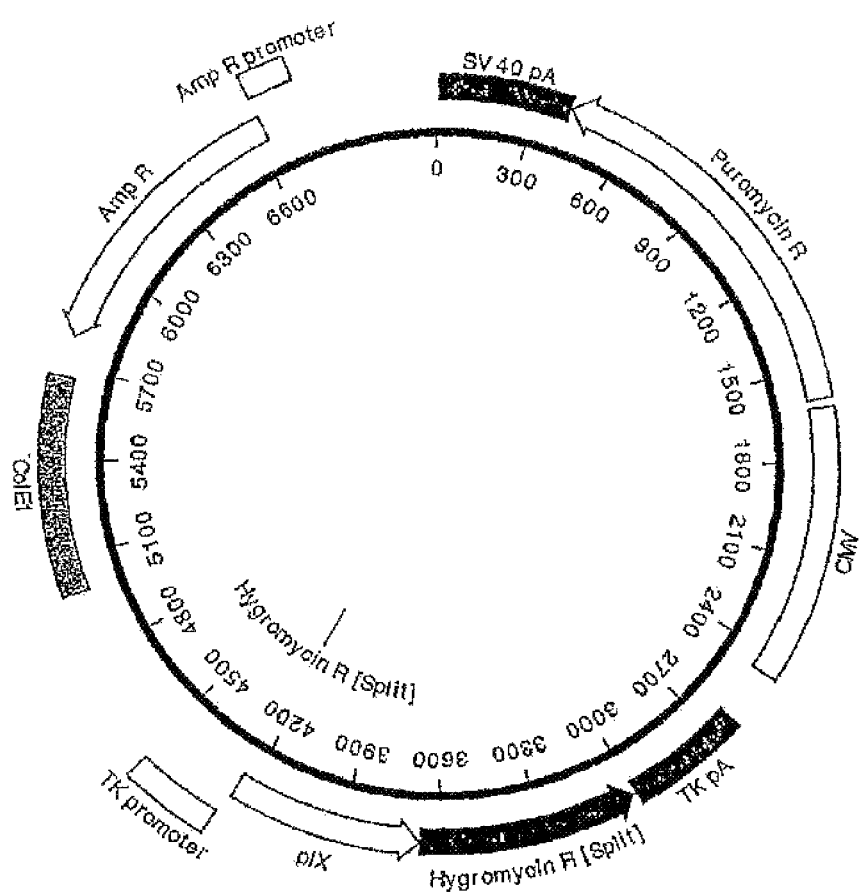
FIG. 16 shows a restriction map of pD1962delBsI.

This example describes the generation of a cell line expressing adenoviral protein IX (pIX), in addition to E2B proteins (adenoviral DNA polymerase and preterminal protein). C7 cells (that already express adenoviral DNA polymerase and preterminal protein) were transfected with PvuI-linearized pD1962delBbsI-pIX (SEQ ID NO:14, FIG. 15), a plasmid that contains expression cassettes directing expression of adenoviral protein IX and puromycin N-acetyl transferase (See FIG. 16). Positive clones were selected in the presence of 2 micrograms puromycin per milliliter of medium. Clones were screened for expression of pIX by transfection with FseI-digested HΔIX#3 (SEQ ID NO:15, FIG. 17), a plasmid that contains an E1-, E3-, and pIX-negative Ad genome of approximately 35.6 kb in size. Clone pD2104#10 produced virus after transfection with HΔIX#3.

Figure 7:
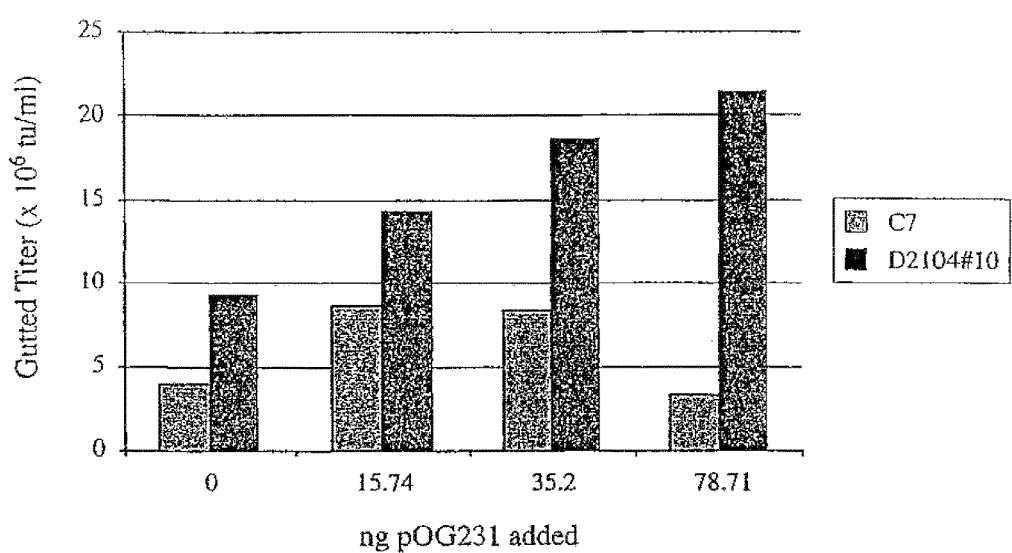
FIG. 7 shows the recovery of gutted virus in D2104#10 cells.

D2104#10 cells and C7 cells were then transfected with FseI-digested pD1940#6, which contains a pIX-positive Ad genome. The cells were then overlayed with agarose to allow for counting of plaques, each representing the successful conversion of a transfected genome to a replicating virus. It was determined that D2104#10 cells displayed three times as many plaques as C7 cells (FIG. 7). Additionally, plaques formed on D2104#10 cells were larger than those formed on C7 cells.

D2104#10 cells were then tested for the ability to rescue gutted virus from a plasmid-based precursor, either in the presence or absence of regulated Cre expression (FIG. 7). Plates of each cell type were transfected with FseI-terminated gutted and helper genomes at a 1:1 ratio, together with varying amounts (15.74 ng, 35.2 ng, and 78.71 ng) of the Cre expression plasmid pOG231. Plates of D2104#10 cells were found to lyse before plates of C7 cells that had been transfected under the same conditions, reflecting the higher proportion of transfected cells that initiated replication of the helper. The co-transfection of C7 cells in the presence of 79 ng of pOG231 failed to produce lysis even after 13 days, whereas D2104#10 cells lysed within 10 days. More gutted virus was produced in D2104#10 cells under all the conditions tested (FIG. 7). In the absence of Cre selection, D2104#10 cells produced twice as much virus as C7 cells. Examining the highest level of selection tested (79 ng), D2104#10 cells produced twice as much virus as C7 cells did under their highest selection conditions (16 ng).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

We claim:

1. A method for producing helper-dependent adenoviral vectors comprising:
   a) providing:
      a helper-dependent adenoviral DNA comprising a first origin of replication, a helper viral DNA comprising a second origin of replication, wherein said first origin of replication and said second origin of replication are not linked to terminal protein or any terminal protein remnant,
      a vector comprising a nucleic acid encoding an adenoviral protein IX operably linked to a heterologous promoter, and
      target cells; and
   b) transfecting said target cells with said helper-dependent adenoviral DNA, said helper viral DNA, and said vector comprising a nucleic acid encoding an adenoviral protein IX operably linked to a heterologous promoter under conditions such that helper-dependent adenoviral vectors are produced.

2. The method of claim 1, wherein said helper-dependent adenoviral DNA comprises a heterologous gene sequence.

3. The method of claim 1, wherein said first origin of replication and second origin of replication have nucleic acid sequences that are substantially similar.

4. The method of claim 1, wherein said helper viral DNA is adenoviral helper viral DNA.

5. The method of claim 1, wherein said helper viral DNA comprises a crippling sequence.

6. The method of claim 1, wherein said helper viral DNA comprises recognition sites for site-specific recombinases.

7. The method of claim 6, further comprising: providing a vector encoding a site-specific recombinase, and step c) transfecting said target cells with said vector encoding a site-specific recombinase.

8. The method of claim 7, further comprising recovering said helper-dependent vectors.

9. The method of claim 5, wherein the crippling sequence comprises recognition sites for a site-specific recombinase.

10. The method of claim 9, wherein the site-specific recombinase comprises loxP or Frt.

11. The method of claim 7, wherein the transfecting said target cells with said helper-dependent adenoviral DNA, said helper viral DNA, and said vector comprising a nucleic acid encoding an adenoviral protein IX operably linked to a heterologous promoter and the transfecting said target cells with said vector encoding a site-specific recombinase all occur at approximately the same time.

12. The method of claim 7, wherein the transfecting said target cells with said helper-dependent adenoviral DNA, said helper viral DNA, and said vector comprising a nucleic acid encoding an adenoviral protein IX operably linked to a heterologous promoter and the transfecting said target cells with said vector encoding a site-specific recombinase is not simultaneous.

13. The method of claim 7, wherein the transfecting said target cells with said vector encoding a site-specific recombinase is accomplished by a method comprising calcium phosphate-DNA co-precipitation, DEAE-dextran-mediated transfection, polybrene-mediated transfection, electroporation, microinjection, liposome fusion, lipofection, or biolistics.

14. The method of claim 1, wherein said target cells express adenoviral DNA polymerase and preterminal protein.

15. The method of claim 1, wherein the helper-dependent adenoviral DNA comprises a left and a right inverted terminal repeats (ITRs) of adenovirus.

16. The method of claim 1, wherein the helper-dependent adenoviral DNA further comprises the adenoviral packaging sequence linked to a left or a right ITR and a heterologous gene sequence.

17. The method of claim 1, wherein the first origin of replication, the second origin of replication, or a combination thereof, lies near a terminus of the helper-dependent adenoviral DNA or the helper viral DNA.

18. The method of claim 1, wherein the helper-dependent adenoviral DNA has been released from a plasmid backbone by restriction enzyme digestion.

19. The method of claim 1, wherein the helper-dependent adenoviral DNA is linear.

20. The method of claim 1, wherein the helper-dependent adenoviral DNA, the helper viral DNA, or a combination thereof lack internal FseI restriction sites.

21. The method of claim 1, wherein the transfecting is accomplished by a method comprising calcium phosphate-DNA co-precipitation, DEAE-dextran-mediated transfection, polybrene-mediated transfection, electroporation, microinjection, liposome fusion, lipofection, or biolistics.

* * * * *